United States Patent
Oh et al.

(10) Patent No.: US 11,296,279 B2
(45) Date of Patent: Apr. 5, 2022

(54) COMPOUND FOR ORGANIC ELECTRIC ELEMENT, ORGANIC ELECTRIC ELEMENT COMPRISING THE SAME AND ELECTRONIC DEVICE THEREOF

(71) Applicant: DUK SAN NEOLUX CO., LTD., Cheonan-si (KR)

(72) Inventors: Dae Hwan Oh, Cheonan-si (KR); Jeongkeun Park, Seoul (KR); Hyemin Cho, Goyang-si (KR); Ga-Eun Lee, Chungcheongbuk-do (KR); Daesung Kim, Yongin-si (KR); Junghwan Park, Hwaseong-si (KR); Sun-Hee Lee, Hwaseong-si (KR); Sunpil Hwang, Ansan-si (KR)

(73) Assignee: DUK SAN NEOLUX CO., LTD., Cheonan-si (KR)

( * ) Notice: Subject to any disclaimer, the term of this patent is extended or adjusted under 35 U.S.C. 154(b) by 492 days.

(21) Appl. No.: 16/326,438

(22) PCT Filed: Jul. 27, 2017

(86) PCT No.: PCT/KR2017/008092
§ 371 (c)(1),
(2) Date: Feb. 19, 2019

(87) PCT Pub. No.: WO2018/034444
PCT Pub. Date: Feb. 22, 2018

(65) Prior Publication Data
US 2021/0288262 A1 Sep. 16, 2021

(30) Foreign Application Priority Data
Aug. 17, 2016 (KR) .................. 10-2016-0104137

(51) Int. Cl.
*C07D 491/048* (2006.01)
*C07D 495/04* (2006.01)
(Continued)

(52) U.S. Cl.
CPC ...... *H01L 51/0061* (2013.01); *C07D 491/048* (2013.01); *C07D 495/04* (2013.01);
(Continued)

(58) Field of Classification Search
CPC . C07D 491/048; C07D 495/04; H01L 51/006; H01L 51/0061
See application file for complete search history.

(56) References Cited

U.S. PATENT DOCUMENTS

| 5,843,607 A | 12/1998 | Hu et al. |
| 10,428,084 B2 * | 10/2019 | Park ............ H01L 27/3211 |
| 2010/0187977 A1 | 7/2010 | Kai et al. |

FOREIGN PATENT DOCUMENTS

| JP | 11-162650 A | 6/1999 |
| KR | 10-2008-0085000 A | 9/2008 |

(Continued)

*Primary Examiner* — Vu A Nguyen
(74) *Attorney, Agent, or Firm* — The PL Law Group, PLLC

(57) ABSTRACT

Provided is the compound represented by Formula 1, an organic electric element comprising a first electrode, a second electrode, and an organic material layer formed between the first electrode and the second electrode, and electronic device thereof, and by comprising the compound represented by Formula 1 in the organic material layer, the driving voltage of the organic electronic device can be lowered, and the luminous efficiency and life time of the organic electronic device can be improved.

11 Claims, 1 Drawing Sheet

(51) Int. Cl.
*C09K 11/06* (2006.01)
*H01L 51/00* (2006.01)
*H01L 51/50* (2006.01)

(52) U.S. Cl.
CPC ............ *C09K 11/06* (2013.01); *H01L 51/006* (2013.01); *C07B 2200/05* (2013.01); *C09K 2211/1018* (2013.01); *H01L 51/0052* (2013.01); *H01L 51/0056* (2013.01); *H01L 51/0067* (2013.01); *H01L 51/0071* (2013.01); *H01L 51/0072* (2013.01); *H01L 51/0073* (2013.01); *H01L 51/0074* (2013.01); *H01L 51/5016* (2013.01); *H01L 51/5056* (2013.01); *H01L 51/5072* (2013.01); *H01L 51/5088* (2013.01); *H01L 51/5092* (2013.01)

(56) References Cited

FOREIGN PATENT DOCUMENTS

| | | | |
|---|---|---|---|
| KR | 10-2009-0057711 A | 6/2009 | |
| KR | 10-2011-0018340 A | 2/2011 | |
| KR | 10-2013-0093195 A | 8/2013 | |
| KR | 10-2014-0011093 A | 1/2014 | |
| KR | 10-1555680 B1 | 9/2015 | |
| KR | 10-2015-0115033 A | 10/2015 | |
| WO | 2016/153198 A1 | 9/2016 | |
| WO | WO-2016153198 A1 * | 9/2016 | ......... H01L 51/0052 |

* cited by examiner

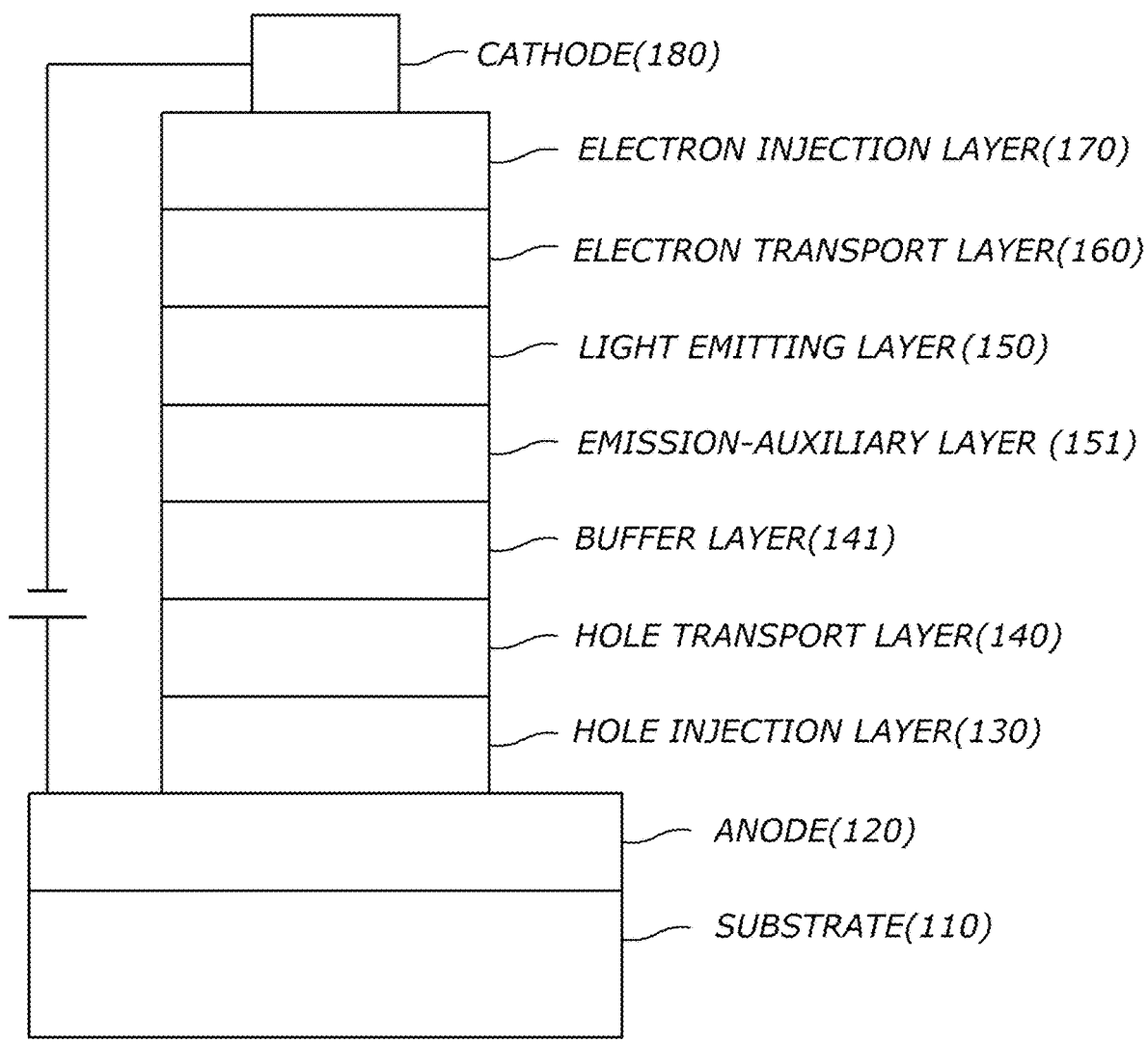

COMPOUND FOR ORGANIC ELECTRIC ELEMENT, ORGANIC ELECTRIC ELEMENT COMPRISING THE SAME AND ELECTRONIC DEVICE THEREOF

CROSS-REFERENCE TO RELATED APPLICATION

This patent application claims priority from and the benefit under 35 U.S.C. § 119 to § 121, and § 365 of Korean Patent Application No. 10-2016-0104137, filed on Aug. 17, 2016, which is hereby incorporated by reference for all purposes as if fully set forth herein. Further, this application claims the benefit of priority in countries other than U.S., which is hereby incorporated by reference herein.

BACKGROUND

Technical Field

The present invention relates to compounds for organic electric elements, organic electric elements comprising the same, and electronic devices thereof.

Background Art

In general, an organic light emitting phenomenon refers to a phenomenon in which electric energy is converted into light energy of an organic material. An organic electric element utilizing the organic light emitting phenomenon usually has a structure including an anode, a cathode, and an organic material layer interposed therebetween. In many cases, the organic material layer has a multi-layered structure having respectively different materials in order to improve efficiency and stability of an organic electric element, and for example, may include a hole injection layer, a hole transport layer, a light emitting layer, an electron transport layer, an electron injection layer, or the like.

Materials used as an organic material layer in an organic electric element may be classified into a light emitting material and a charge transport material, for example, a hole injection material, a hole transport material, an electron transport material, an electron injection material, and the like according to its function.

Currently, the power consumption is required more and more as size of display becomes larger and larger in the portable display market. Therefore, the power consumption is a very important factor in the portable display with a limited power source of the battery, and efficiency and life span issue also must be solved.

Efficiency, life span, driving voltage, and the like are correlated with each other. For example, if efficiency is increased, then driving voltage is relatively lowered, and the crystallization of an organic material due to Joule heating generated during operation is reduced as driving voltage is lowered, as a result of which life span shows a tendency to increase. However, efficiency cannot be maximized only by simply improving the organic material layer. This is because long life span and high efficiency can be simultaneously achieved when energy levels and T1 values among the respective layers included in the organic material layer, inherent material properties (mobility, interfacial properties, etc.) and the like are optimal combination.

In addition, an emission-auxiliary layer must be present between the hole transport layer and the light emitting layer in order to solve the problem of luminescence in the hole transport layer of recent organic electroluminescent devices, and it is time to develop different emission-auxiliary layers according to respective light emitting layers (R, G, B).

In general, an electron is transferred from an electron transport layer to a light emitting layer and a hole is transferred from a hole transport layer to the light emitting layer, as a result, an exciton is formed by the recombination of the electron and hole. However, material used in a hole transport layer has a low T1 value because the material should have a low HOMO value. As a result, the exciton generated in the light emitting layer is transferred to the interface of the hole transport layer or the hole transport layer, and thereby emitting light at the interface of the hole transport layer or a charge unbalance in the light-emitting layer.

When light is emitted from the interface of the hole transporting layer, the color purity and efficiency of the organic electronic element are lowered and the lifetime is shortened. Therefore, it is strongly desired to develop materials for the emission-auxiliary layer having a HOMO level between the HOMO energy level of the hole transporting layer and the HOMO energy level of the light emitting layer, a high T1 energy value and a hole mobility within a suitable driving voltage range (within a driving voltage range of blue element of a full device).

However, this cannot be achieved simply by the structural properties of the core of the emission-auxiliary layer material. An element having a high efficiency and a long life span can be realized when the characteristics of core and sub-substituents of the emission-auxiliary layer material, the proper combination of the emission-auxiliary layer and the hole transport layer, and the proper combination of the emission-auxiliary layer and the light emitting layer.

On the other hand, it is also necessary to develop a hole injection/transport layer materials and an emission-auxiliary layer material having stable characteristics against Joule heat generated, that is, a high glass transition temperature when the element is driven.

It has been reported that the low glass transition temperature of the hole transporting layer and the emission-auxiliary layer material lowers the uniformity of the surface when the device is driven and causes the material to deform due to heat generated when the device is driven, as a result, the life span of the device is greatly affected.

Polycyclic ring compound comprising heteroatoms applies to various layers as material of an organic material layer since it is very different in properties depending on the material structure. Particularly, the polycyclic ring compound has different characteristics in band gap (HOMO, LUMO), electrical property, chemical property and physical property depending on the number of rings and fused position, the type and arrangement of heteroatoms. Therefore, research and development have been carried out to apply it as a material for various layers of the organic electronic devices.

As a representative example, the following Patent Documents 1 to 4 disclose the performance of the five-ring of an polycyclic ring compound depending on the type and arrangement of heteroatoms, the type of substituents, the fused position and the like.

1. U.S. Pat. No. 5,843,607
2. Japanese Patent Laid-Open No. 1999-162650
3. Korean Patent Laid-Open No. 2008-0085000
4. US Patent Laid-Open No. 2010-0187977
5. Korean Patent Laid-Open No. 2011-0018340
6. Korean Patent Laid-Open No. 2009-0057711

Patent Documents 1 and 2 disclose an embodiment using an indolocarbazole core in which hetero atoms in the five-ring cyclic compound are composed only of nitrogen (N) and a substituted or unsubstituted aryl group is bonded to N of indolocarbazole. However, Patent Document 1 discloses only an aryl group substituted with an alkyl group, an amino group, an alkoxy group, or the like or an unsubstituted aryl group, and thus Patent Document 1 does not sufficiently disclose the substituent effect of a polycyclic ring compound. In addition, it discloses only the use as a hole transport material, and does not disclose the use as a phosphorescent host material or an emission-auxiliary layer material.

Patent Documents 3 and 4 disclose the compounds of which core is the same indolocarbazole having hetero-atom Ns in a five-membered ring compound as in the above Patent Documents 1 and 2, wherein an aryl group and pyridine, pyrimidine, triazine, and the like comprising N are bonded to each N of the indolocarbazole core. However, Patent Documents 3 and 4 describe only the use examples for phosphorescent green host materials and do not disclose the performance for other heterocyclic compounds substituted for indolocarbazole core.

Patent Document 5 discloses the compounds comprising nitrogen (N), oxygen (O), sulfur (S), and the like as a hetero atom in a five-ring cyclic compound. However, Patent Document 5 discloses only performance evaluation data of examples using the compound comprising the same heteroatoms, and thus the performance characteristics of a five-ring cyclic compound comprising different heteroatoms cannot be confirmed.

Therefore, the above patent document does not disclose a solution for low charge carrier mobility and low oxidation stability of a five-ring cyclic compound comprising the same heteroatoms.

When molecules of a five-ring cyclic compound are stacked, they have a strong electrical interaction as the number of adjacent π-electrons increases. This is closely related to the charge carrier mobility. Particularly, when five-ring cyclic compounds being N—N type of are stacked, they are arranged in an edge-to-face. On the other hand, the five-ring cyclic compound comprising different heteroatoms is packed in antiparallelcofacial π-stacking structure in which molecules face each other in the opposite direction, so that the arrangement order of the molecules becomes face-to-face. As a result, it is reported that carrier mobility and oxidation stability are relatively increased due to the steric effect of the substituent bonding to heteroatom N arranged asymmetrically, which is the cause of this stacking structure (*Org. Lett.* 2008, 10, 1199).

Patent Document 6 discloses an example of using a variety of polycyclic ring compounds having 7 or more rings as a fluorescent host material.

As described above, the characteristics of the polycyclic ring compound depending on the fused position, the number of rings, and the arrangement and type of heteroatoms have not yet been sufficiently developed. Particularly, the compounds for an emission-auxiliary layer are not sufficiently developed.

PATENT PRIOR ART

1. U.S. Pat. No. 5,843,607
2. Japanese Patent Laid-Open No. 1999-162650
3. Korean Patent Laid-Open No. 2008-0085000
4. US Patent Laid-Open No. 2010-0187977
5. Korean Patent Laid-Open No. 2011-0018340
6. Korean Patent Laid-Open No. 2009-0057711

Non-Patent Prior Art

1. *Org. Letters.* 2008, Vol. 10, No. 6, p. 1199-1202 (published on 16 February, 2008 through Web)

Object, Technical Solution and Effects of the Invention

The object of the present invention is to provide a compound capable of lowering driving voltage of the device, and capable of improving luminous efficiency, color purity and lifespan, an organic electric element comprising the same, and an electronic device thereof.

In accordance with an aspect of the present invention, the compound represented by the following formula is provided.

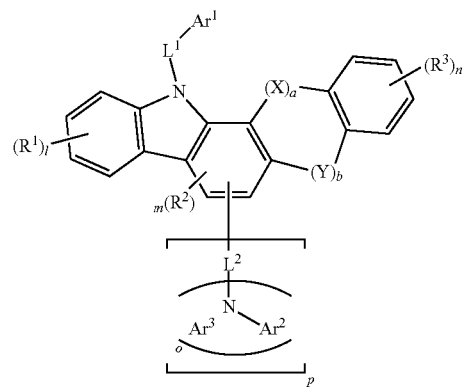

In another aspect of the present invention, organic electric element comprising the compound represented by the above formula and an electronic device including the organic electric element are provided.

According to the present invention, by using a compound according to one embodiment of the present invention, the driving voltage of a device can be lowered, and the luminous efficiency, color purity and lifespan of a device can be improved.

BRIEF DESCRIPTION OF THE DRAWINGS

The FIGURE illustrates an example of an organic light emitting diode according to an embodiment of the present invention: 100 is organic electric element, 110 is substrate, 120 is first electrode, 130 is hole injection layer, 140 is hole transport layer, 141 is buffer layer, 150 is light emitting layer, 151 is emission-auxiliary layer, 160 is electron transport layer, 170 is electron injection layer, and 180 is second electrode.

DETAILED DESCRIPTION

Hereinafter, some embodiments of the present invention will be described in detail with reference to the accompanying illustrative drawings.

In designation of reference numerals to components in respective drawings, it should be noted that the same elements will be designated by the same reference numerals although they are shown in different drawings. Further, in the following description of the present invention, a detailed description of known functions and configurations incorporated herein will be omitted when it may make the subject matter of the present invention rather unclear.

In addition, terms, such as first, second, A, B, (a), (b) or the like may be used herein when describing components of the present invention. Each of these terminologies is not used for defining an essence, order or sequence of a corresponding component but used merely to distinguish the corresponding component from other component(s). It should be noted that if it is described in the specification that one component is "connected," "coupled" or "joined" to another component, a third component may be "connected," "coupled," and "joined" between the first and second components, although the first component may be directly connected, coupled or joined to the second component.

In addition, it will be understood that when an element such as a layer, film, region or substrate is referred to as being "on" or "over" another element, it can be directly on the other element or intervening elements may also be present. In contrast, when an element is referred to as being "directly on" another element, there are no intervening elements present.

As used in the specification and the accompanying claims, unless otherwise stated, the following is the meaning of the term as follows.

Unless otherwise stated, the term "halo" or "halogen" as used herein includes fluorine (F), bromine (Br), chlorine (Cl), or iodine (I).

Unless otherwise stated, the term "alkyl" or "alkyl group" as used herein has a single bond of 1 to 60 carbon atoms, and means the saturated aliphatic functional radicals including a linear alkyl group, a branched chain alkyl group, a cycloalkyl group (alicyclic), a cycloalkyl group substituted with an alkyl group and an alkyl group substituted with a cycloalkyl.

Unless otherwise stated, the term "halo alkyl" or "halogen alkyl" as used herein includes an alkyl group substituted with a halogen.

Unless otherwise stated, the term "alkenyl" or "alkynyl" as used herein has, but not limited to, double or triple bonds of 2 to 60 carbon atoms, and includes a linear alkyl group, or a branched chain alkyl group.

Unless otherwise stated, the term "cycloalkyl" as used herein means, but not limited to, alkyl forming a ring having 3 to 60 carbon atoms.

Unless otherwise stated, the term "alkoxyl group", "alkoxy group" or "alkyloxy group" as used herein means oxygen radical attached to an alkyl group, but not limited to, and has 1 to 60 carbon atoms.

Unless otherwise stated, the term "aryloxyl group" or "aryloxy group" as used herein means oxygen radical attached to an aryl group, but not limited to, and has 6 to 60 carbon atoms.

Unless otherwise stated, the term "fluorenyl group" or "fluorenylene group" as used herein means univalent or bivalent functional group in which R, R' and R" are all hydrogen in the following structure, "substituted fluorenyl group" or "substituted fluorenylene group" means that at least any one of R, R' and R" is a substituent other than hydrogen, and it comprises the case where R and R' are bonded to each other to form the spiro compound together with the carbon to which they are bonded.

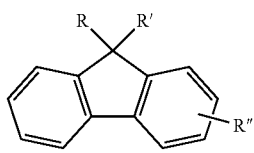

Unless otherwise stated, the term "aryl group" or "arylene group" as used herein has, but not limited to, 6 to 60 carbon atoms. The aryl group or arylene group include a monocyclic rings, ring assemblies, fused polycyclic system or spiro compounds.

Unless otherwise stated, the term "heterocyclic group" as used herein means, but not limited to, a non-aromatic ring as well as an aromatic ring like "heteroaryl group" or "heteroarylene group". The heterocyclic group as used herein means, but not limited to, a ring containing one or more heteroatoms, and having 2 to 60 carbon atoms. Unless otherwise stated, the term "heteroatom" as used herein represents N, O, S, P or Si. The heterocyclic group means a monocyclic, ring assemblies, fused polycyclic system or spiro compound containing one or more heteroatoms.

Also, the term "heterocyclic group" may comprise a ring including $SO_2$ instead of carbon consisting of a ring. For example, "heterocyclic group" includes the following compound.

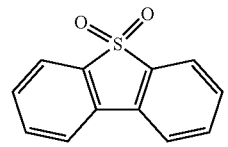

The term "ring" as used herein means, a monocyclic and polycyclic, an aliphatic ring and heterocyclic group containing at least one heteroatom, and an aromatic ring and a non-aromatic ring.

The term "polycyclic ring" as used herein may comprise ring assemblies such as biphenyl and terphenyl, fused polycyclic system and a spiro compound, an aromatic ring and a non-aromatic ring, and an aliphatic ring and heterocyclic group containing at least one heteroatom.

The term "ring assemblies" as used herein means, two or more cyclic systems (single rings or fused systems) which are directly joined to each other by double or single bonds are named ring assemblies when the number of such direct ring junctions is one less than the number of cyclic systems involved. The ring assemblies also mean, same or different ring systems are directly joined to each other by double or single bonds.

The term "fused polycyclic system" as used herein means, fused ring type which has at least two atoms as the common members, fused two or more aliphatic ring systems and a fused hetero ring system containing at least one heteroatom. Fused polycyclic system is an aromatic ring, a hetero aromatic ring, an aliphatic ring, or a combination thereof.

The term "spiro compound" as used herein has, a spiro union which means union having one atom as the only common member of two rings. The common atom is designated as 'spiro atom'. The compounds are defined as 'monospiro-', 'dispiro-' or 'trispiro-' depending on the number of spiro atoms in one compound.

Also, when prefixes are named subsequently, it means that substituents are listed in the order described first. For example, an arylalkoxy means an alkoxy substituted with an aryl, an alkoxylcarbonyl means a carbonyl substituted with an alkoxyl, and an arylcarbonylalkenyl also means an alkenyl substitutes with an arylcarbonyl, wherein the arylcarbonyl may be a carbonyl substituted with an aryl.

Unless otherwise stated, the term "substituted or unsubstituted" as used herein means that substitution is carried out by at least one substituent selected from the group consisting of, but not limited to, deuterium, halogen, an amino group, a nitrile group, a nitro group, a $C_1$-$C_{20}$ alkyl group, a $C_1$-$C_{20}$ alkoxy group, a $C_1$-$C_{20}$ alkylamine group, a $C_1$-$C_{20}$ alkylthiophene group, a $C_6$-$C_{20}$ arylthiophene group, a $C_2$-$C_{20}$ alkenyl group, a $C_2$-$C_{20}$ alkynyl group, a $C_3$-$C_{20}$ cycloalkyl group, a $C_6$-$C_{20}$ aryl group, a $C_6$-$C_{20}$ aryl group substituted by deuterium, a $C_8$-$C_{20}$ arylalkenyl group, a silane group, a boron group, a germanium group, and a $C_2$-$C_{20}$ heterocyclic group containing at least one heteroatom selected from the group consisting of O, N, S, Si, and P, but there is no limitation thereto.

A 'group name' comprised in an aryl group, an arylene group, a heterocyclic group and the like as example of each symbol and a substituent as used herein may be written in the name of functional group reflecting the valence, and may also be described as the name of a parent compound. For example, in the case of phenanthrene which is a kind of aryl group, it may be described by distinguishing valence such as 'phenanthryl' when it is 'monovalent group', and as 'phenanthrylene' when it is 'divalent group', and it may also be described as a parent compound name, 'phenanthrene', regardless of its valence. Similarly, in the case of pyrimidine, it may be described as 'pyrimidine' regardless of its valence, and it may also be described as the name of corresponding functional group such as pyrimidinyl group when it is monovalent group, and as pyrimidylene group when it is divalent group.

Otherwise specified, the formulas used in the present invention are as defined in the index definition of the substituent of the following formula.

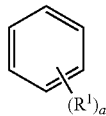

Wherein the substituent $R^1$ is absent where a is an integer of zero, the sole $R^1$ is linked to any one of the carbon atoms constituting the benzene ring where a is an integer of 1, the substituent $R^1$s may be the same and different and are linked to the benzene ring as follows when a is an integer of 2 or 3, the substituents $R^1$s may be linked to carbons of the benzene ring in a similar manner where a is an integer of 4 to 6, and hydrogen(s) bonded to carbon of the benzene ring may be omitted.

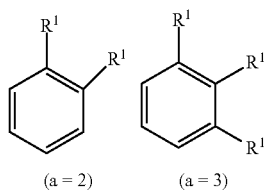

The FIGURE illustrates an organic electric element according to an embodiment of the present invention.

Referring to The FIGURE, an organic electric element 100 according to an embodiment of the present invention includes a first electrode 120 formed on a substrate 110, a second electrode 180, and an organic material layer formed between the first electrode 120 and the second electrode 180 and comprising the compound of the present invention. Here, the first electrode 120 may be an anode (positive electrode), and the second electrode 180 may be a cathode (negative electrode). In the case of an inverted organic electric element, the first electrode may be a cathode, and the second electrode may be an anode.

The organic material layer may include a hole injection layer 130, a hole transport layer 140, a light emitting layer 150, an electron transport layer 160, and an electron injection layer 170 formed in sequence on the first electrode 120. Here, at least one layer of the organic material layer may be omitted, or the organic material layer may further include a hole blocking layer, an electron blocking layer, an emission-auxiliary layer 151, the electron transport-auxiliary layer, a buffer layer 141, etc., the electron transport layer 160 or the like may serve as the hole blocking layer.

Although not shown, the organic electric element according to an embodiment of the present invention may further include a protective layer or a layer (Capping layer) for improving luminous efficiency formed on at least one side of sides of the first electrode and the second electrode, wherein at least one side is not facing the organic material layer.

The inventive compound employed in the organic material layer may be used as a material of a hole injection layer 130, a hole transport layer 140, an emission-auxiliary layer 151, an electron transport auxiliary layer, an electron transport layer 160, an electron injection layer 170, as host or dopant of a light emitting layer 150, or as a material of a layer for improving luminous efficiency. For example, the inventive compound may be used as material of the light emitting layer 150, the hole transport layer 140 and/or the emission-auxiliary layer 151.

On the other hand, even if the core is the same core, the band gap, the electrical characteristics, the interface characteristics and the like may be different depending on which substituent is bonded at which position. Therefore, it is necessary to study the selection of the core and the combination of the core and the sub-substituent bonded to the core. In particular, long life span and high efficiency can be simultaneously achieved when the optimal combination of energy levels and $T_1$ values, inherent material properties (mobility, interfacial properties, etc.), and the like among the respective layers of an organic material layer is achieved.

As already described above, generally, in order to solve the emission problem with a hole transport layer of an organic electric element, it is preferable that an emission-auxiliary layer is formed between the hole transport layer and a light emitting layer, and it is necessary to develop different emission-auxiliary layers according to respective light emitting layers (R, G, B). On the other hand, even if the core of an emission-auxiliary layer is similar, it is very difficult to infer the characteristics of an emission-auxiliary layer because it is necessary to grasp the correlation between the emission-auxiliary layer and a hole transport layer and a light emitting layer (host).

Therefore, according to the present invention, energy level and $T_1$ value between the respective layers of the organic material layer, inherent material properties (mobility, interfacial properties, etc.) and the like can be optimized by forming an emission-auxiliary layer with the compound represented by the Formula 1, and thus it is possible to simultaneously improve the life span and efficiency of the organic electric element.

The organic electric element according to an embodiment of the present invention may be manufactured using various deposition methods. The organic electric element according to an embodiment of the present invention may be manufactured using a PVD (physical vapor deposition) method or CVD (chemical vapor deposition) method. For example, the organic electric element may be manufactured by depositing a metal, a conductive metal oxide, or a mixture thereof on the substrate to form the anode 120, forming the organic material layer including the hole injection layer 130, the hole transport layer 140, the light emitting layer 150, the electron transport layer 160, and the electron injection layer 170 thereon, and then depositing a material, which can be used as the cathode 180, thereon. Also, an emitting auxiliary layer 151 may be formed between a hole transport layer 140 and a light emitting layer 150, and an electron transport auxiliary layer may be formed between a light emitting layer 150 and an electron transport layer 160.

Also, the organic material layer may be manufactured in such a manner that a smaller number of layers are formed using various polymer materials by a soluble process or solvent process, for example, spin coating, nozzle printing, inkjet printing, slot coating, dip coating, roll-to-roll, doctor blading, screen printing, or thermal transfer, instead of deposition. Since the organic material layer according to the present invention may be formed in various ways, the scope of protection of the present invention is not limited by a method of forming the organic material layer.

The organic electric element according to an embodiment of the present invention may be of a top emission type, a bottom emission type, or a dual emission type depending on the material used.

WOLED (White Organic Light Emitting Device) has advantages of high resolution realization, an excellent processability, and being produced by using conventional color filter technologies for LCDs. Various structures for WOLED which mainly used as back light units have been suggested and patented. WOLED may employ various arrangement methods, representatively, a parallel side-by-side arrangement method of R (Red), G (Green), B (Blue) light-emitting units, a vertical stack arrangement method of RGB light-emitting units, and a CCM (color conversion material) method in which electroluminescence from a blue (B) organic light emitting layer, and the present invention may be applied to such WOLED.

Also, the organic electric element according to an embodiment of the present invention may be any one of an organic light emitting diode, an organic solar cell, an organic photo conductor, an organic transistor, and an element for monochromatic or white illumination.

Another embodiment of the present invention provides an electronic device including a display device which includes the above described organic electric element, and a control unit for controlling the display device. Here, the electronic device may be a wired/wireless communication terminal which is currently used or will be used in the future, and covers all kinds of electronic devices including a mobile communication terminal such as a cellular phone, a personal digital assistant (PDA), an electronic dictionary, a point-to-multipoint (PMP), a remote controller, a navigation unit, a game player, various kinds of TVs, and various kinds of computers.

Hereinafter, the compound according to an aspect of the present invention will be described.

The compound according to an aspect of the present invention is represented by formula 1 below.

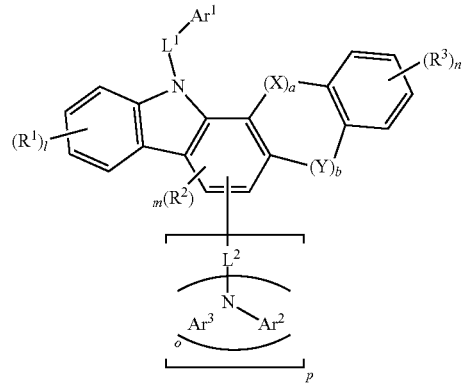

[Formula 1]

In the formula 1, each of symbols may be defined as follows.

X and Y are each independently O or S, a and b are each an integer of 0 or 1, and a+b is an integer of 1 or 2.

$R^1$, $R^2$ and $R^3$ are each independently selected from the group consisting of deuterium, halogen, a $C_6$-$C_{60}$ aryl group, a fluorenyl group, a $C_2$-$C_{60}$ heterocyclic group containing at least one heteroatom selected from the group consisting of O, N, S, Si, and P, a fused ring group formed by a $C_3$-$C_{60}$ aliphatic ring with a $C_6$-$C_{60}$ aromatic ring, a $C_1$-$C_{50}$ alkyl group, a $C_2$-$C_{20}$ alkenyl group, a $C_2$-$C_{20}$ alkynyl group, a $C_1$-$C_{30}$ alkoxyl group, a $C_6$-$C_{30}$ aryloxy group and -L'-N$(R_a)(R_b)$, l and n are each an integer of 0~4, m is an integer of 0~1, where l is an integer of 2 or more, adjacent $R^1$s may optionally be linked together to form a ring, where n is an integer of 2 or more, adjacent $R^3$s may optionally be linked together to form a ring.

Where $R^1$, $R^2$ and $R^3$ are each an aryl group, $R^1$, $R^2$ and $R^3$ may be preferably a $C_5$-$C_{30}$ aryl group, more preferably a $C_6$-$C_{18}$ aryl group, for example, phenyl, biphenyl, naphthyl, terphenyl or the like. The ring formed by adjacent $R^1$s and/or adjacent $R^3$s may be a $C_6$-$C_{60}$ aryl group, a fluorenyl group, a $C_2$-$C_{60}$ heterocyclic group containing at least one heteroatom selected from the group consisting of O, N, S, Si, and P, and a fused ring group formed by a $C_3$-$C_{60}$ aliphatic ring with a $C_6$-$C_{60}$ aromatic ring. Where adjacent $R^1$s and/or adjacent $R^3$s are linked together to each other to form an aryl group, the ring may be, for example, a benzene ring, as a result, naphthalene, phenanthrene or the like may be formed together with the benzene ring to which they are bonded.

p is an integer of 1~2, where p is an integer of 1, o is an integer of 2~5, and where p is an integer of 2, o is an integer of 1~5. Where o and p are each an integer of 2 or more, the plurality of $L^2$s, $Ar^2$s and $Ar^3$s may be each the same or different from each other.

$Ar^1$, $Ar^2$ and $Ar^3$ are each independently selected from the group consisting of a $C_6$-$C_{60}$ aryl group, a fluorenyl group, a $C_2$-$C_{60}$ heterocyclic group containing at least one heteroatom selected from the group consisting of O, N, S, Si, and P, a fused ring group formed by a $C_3$-$C_{60}$ aliphatic ring with a $C_6$-$C_{60}$ aromatic ring, a $C_1$-$C_{60}$ alkyl group, a $C_2$-$C_{20}$ alkenyl group, a $C_2$-$C_{20}$ alkynyl group, a $C_1$-$C_{30}$ alkoxyl group, a $C_6$-$C_{30}$ aryloxy group and -L'-N$(R_a)(R_b)$.

Where $Ar^1$, $Ar^2$ and $Ar^3$ are each an aryl group, $Ar^1$, $Ar^2$ and $Ar^3$ may be preferably a $C_6$-$C_{30}$ aryl group, more preferably a $C_6$-$C_{18}$ aryl group, for example, phenyl, biphenyl, naphthyl, terphenyl, phenanthrene, triphenylene or the like.

Where Ar$^1$, Ar$^2$ and Ar$^3$ are each a heterocyclic group, Ar$^1$, Ar$^2$ and Ar$^3$ may be preferably a C$_2$-C$_{30}$ heterocyclic group, more preferably a C$_2$-C$_{16}$ heterocyclic group, for example, pyridine, carbazole, dibenzothiophene, dibenzofuran, benzonaphthofuran, benzonaphthothiophene or the like.

Where Ar$^1$, Ar$^2$ and Ar$^3$ are each a fluorenyl group, Ar$^1$, Ar$^2$ and Ar$^3$ may be, for example, 9,9-dimethyl-9H-fluorene, 9,9-diphenyl-9H-fluorene, 9,9'-spirofluorene or the like.

L$^2$ is -(L$^a$-L$^b$), wherein L$^1$, L$^a$, L$^b$ and L' are each independently selected from the group consisting of a single bond, a C$_6$-C$_{60}$ arylene group, a fluorenylene group, a fused ring group formed by a C$_3$-C$_{60}$ aliphatic ring with a C$_6$-C$_{60}$ aromatic ring, and a C$_2$-C$_{60}$ heterocyclic group containing at least one heteroatom selected from the group consisting of O, N, S, Si, and P, Where L$^1$, L$^a$, L$^b$ and L' are each an arylene group, L$^1$, L$^a$, L$^b$ and L' may be each preferably a C$_6$-C$_{30}$ arylene group, more preferably a C$_6$-C$_{12}$ arylene group, for example, phenylene, biphenyl, naphthalene or the like. Where L$^1$, L$^a$, L$^b$ and L' are each a heterocyclic group, L$^1$, L$^a$, L$^b$ and L' may be each preferably a C$_2$-C$_{30}$ heterocyclic group, more preferably a C$_2$-C$_5$ heterocyclic group, for example, pyridine, pyrimidine, triazine or the like.

Preferably, L$^1$ and L$^2$ may be each independently selected from the following formulas (A-1)~(A-12)

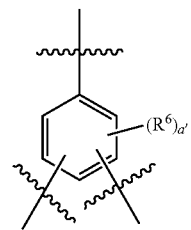
(A-1)

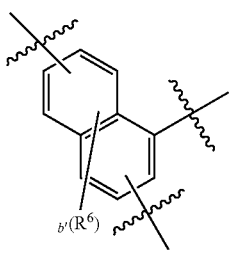
(A-2)

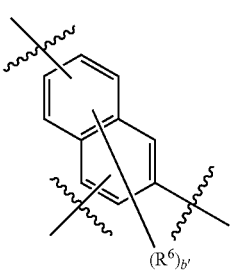
(A-3)

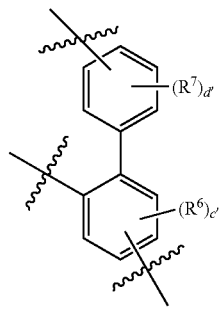
(A-4)

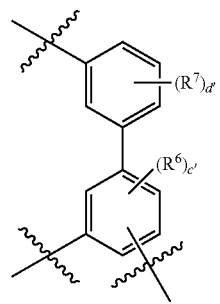
(A-5)

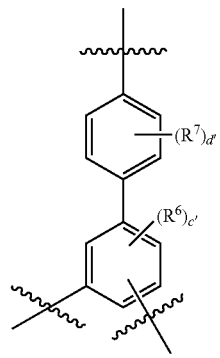
(A-6)

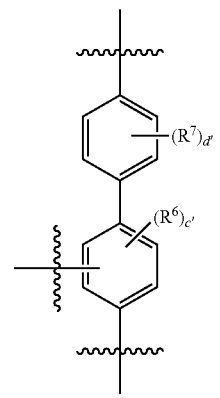
(A-7)

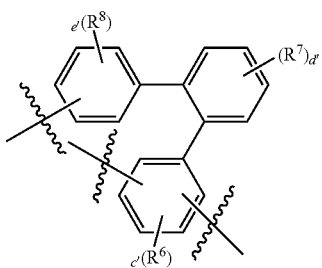
(A-8)

-continued

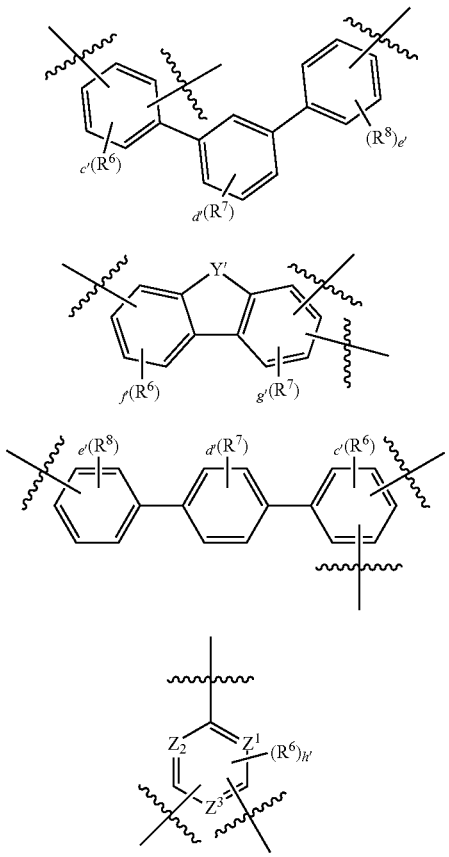

(A-8)

(A-10)

(A-11)

(A-12)

In the formulas (A-1)~(A-12), $R^6$-$R^8$ are defined the same as $R^1$-$R^3$ as defined in the Formula 1, a', c', d' and e' are each an integer of 0~4, b' is an integer of 0~6, f' and g' are each an integer of 0~3, h' is an integer of 0~1, and where a', c', d', e', f' and g' are each is an integer of 2 or more, adjacent $R^6$s, adjacent $R^7$s or adjacent $R^8$s may optionally be linked together to form a ring.

In the Formula (A-10), Y' is N($R^1$), O, S or C(R')(R"), wherein $R^1$ is defined the same as in the Formula 1 and R' and R" are each independently selected from the group consisting of a $C_6$-$C_{60}$ aryl group, a fluorenyl group, a $C_2$-$C_{60}$ heterocyclic group containing at least one heteroatom selected from the group consisting of O, N, S, Si, and P, a fused ring group formed by a $C_3$-$C_{60}$ aliphatic ring with a $C_6$-$C_{60}$ aromatic ring, and a $C_1$-$C_{50}$ alkyl group, and R' and R" may optionally be linked together with C to which they are bonded to form a spiro-compound.

In the Formula (A-12), $Z^1$-$Z^3$ are each C($R^1$) or N, and at least one of $Z^1$-$Z^3$ is N.

$R_a$ and $R_b$ are each independently selected from the group consisting of a $C_6$-$C_{60}$ aryl group, a fluorenyl group, a fused ring group formed by a $C_3$-$C_{60}$ aliphatic ring with a $C_6$-$C_{60}$ aromatic ring, and a $C_2$-$C_{60}$ heterocyclic group containing at least one heteroatom selected from the group consisting of O, N, S, Si, and P.

Where the above $R^1$-$R^3$, $Ar^1$-$Ar^3$, $R_a$, $R_b$, R', R", $L^1$, $L^a$, $L^b$ and L' are each the aryl group, fluorenyl group, heterocyclic group, fused ring group, alkyl group, alkenyl group, alkynyl group, alkoxyl group, aryloxyl group, arylene group, or fluorenylene group, they are each optionally further substituted with one or more substituents selected from the group consisting of deuterium, halogen, a silane group substituted or unsubstituted with $C_1$-$C_{20}$ alkyl group or $C_6$-$C_{20}$ aryl group, a siloxane group, a boron group, a germanium group, a cyano group, a nitro group, a $C_1$-$C_{20}$ alkylthio group, a $C_1$-$C_{20}$ alkoxyl group, a $C_1$-$C_{20}$ alkyl group, a $C_2$-$C_{20}$ alkenyl group, a $C_2$-$C_{20}$ alkynyl group, a $C_6$-$C_{20}$ aryl group, a $C_6$-$C_{20}$ aryl group substituted with deuterium, a fluorenyl group, a $C_2$-$C_{20}$ heterocyclic group containing at least one heteroatom selected from the group consisting of O, N, S, Si, and P, a $C_3$-$C_{20}$ cycloalkyl group, a $C_7$-$C_{20}$ arylalkyl group and a $C_8$-$C_{20}$ arylalkenyl group.

The Formula 1 may be represented by the following Formula 2 or 3 where p is an integer of 1, the Formula 1 may be represented by the following Formula 4 where p is an integer of 2 and o is an integer of 1, and the Formula 1 may be represented by the following Formula 5 where p is an integer of 1 and o is an integer of 2. In the following Formulas 2 to 5, each of symbols is the same as defined in the Formula 1.

<Formula 2>

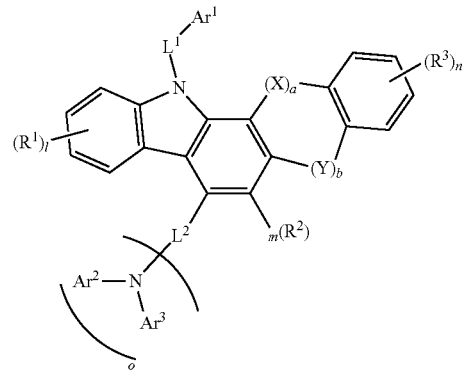

<Formula 3>

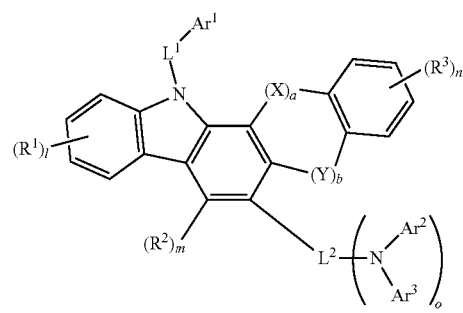

<Formula 4>

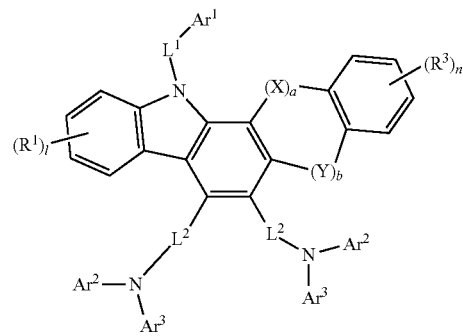

<Formula 5>

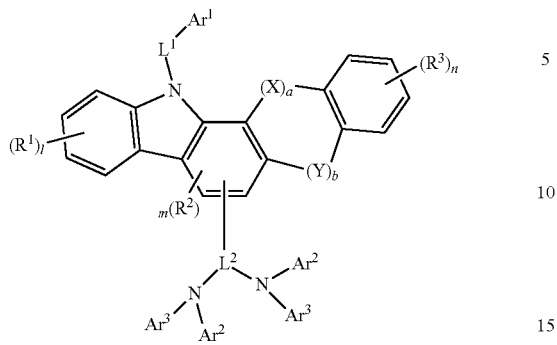

<Formula 8>

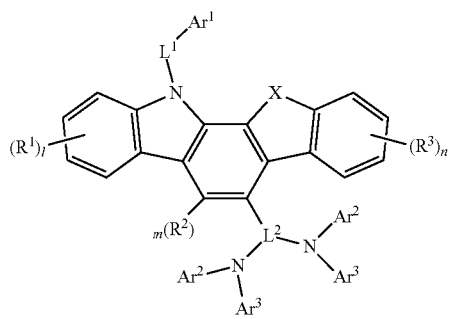

Further, the Formula 1 may be represented by the following Formula 6 where b is an integer of 0, the Formula 1 may be represented by the following Formula 7 where a is an integer of 0, and in the following Formulas 6 and 7, each of symbols is the same as defined in the Formula 1.

<Formula 9>

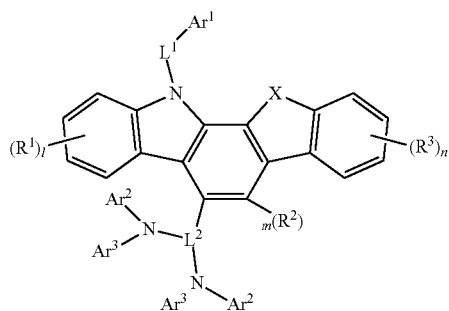

<Formula 6>

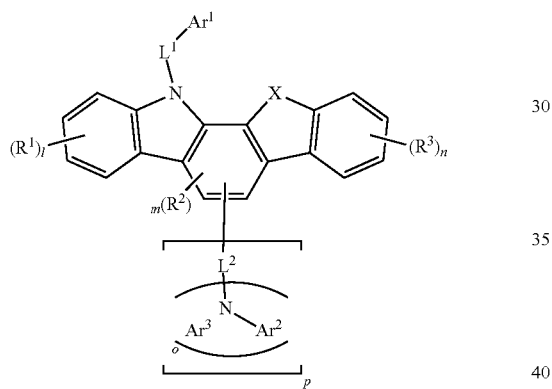

<Formula 10>

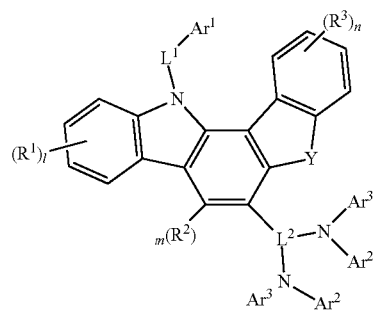

<Formula 7>

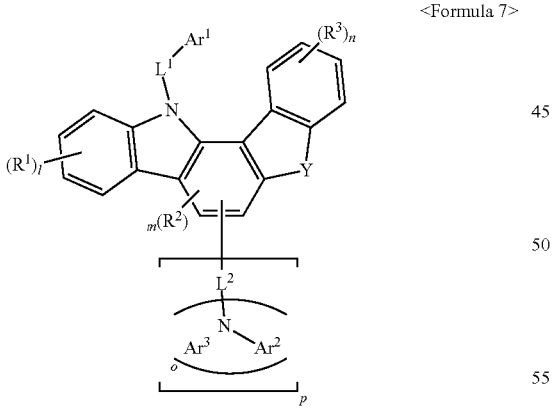

<Formula 11>

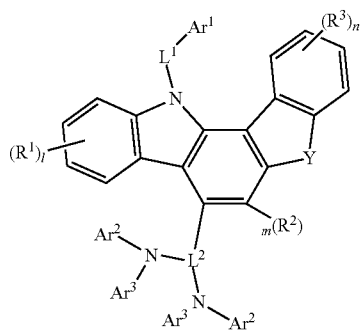

Further, the Formula 1 may be represented by the following Formulas 8 and 0 where b is an integer of 0, p is an integer of 1 and o is an integer of 2, the Formula 1 may be represented by the following Formulas 10 and 11 where a is an integer of 0, p is an integer of 1 and o is an integer of 2, and in the following Formulas 8 to 11, each of symbols is the same as defined in the Formula 1.

Specifically, the compound represented by formula 1 may be any one of the following compounds.

P-1
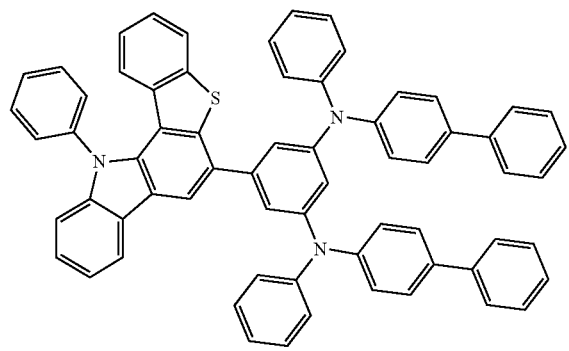
P-2
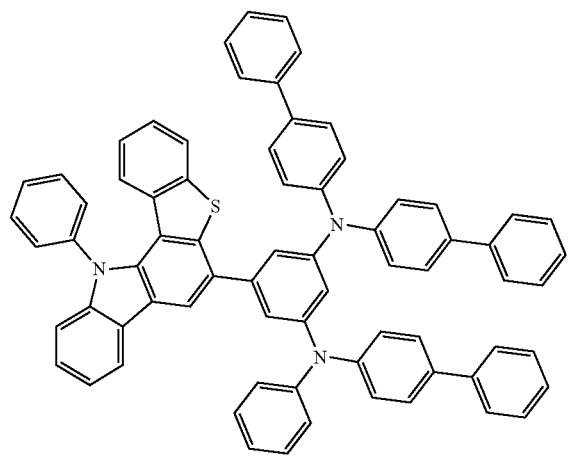
P-3
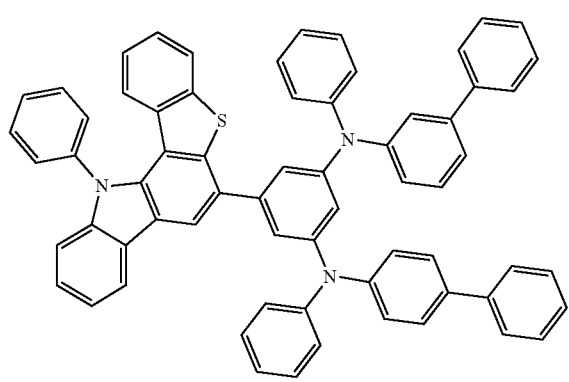
P-4
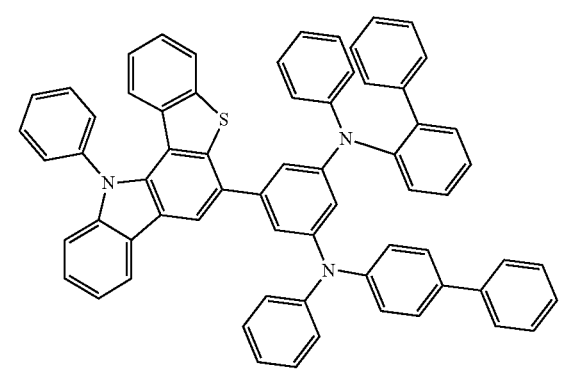
P-5
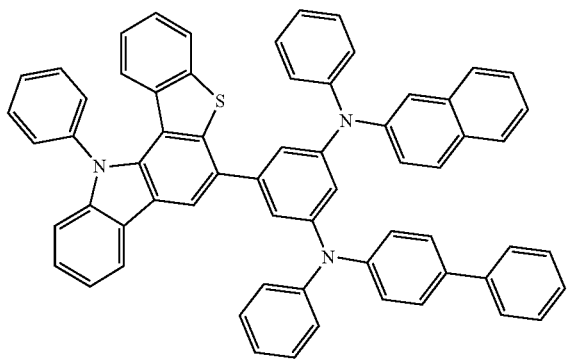
P-6
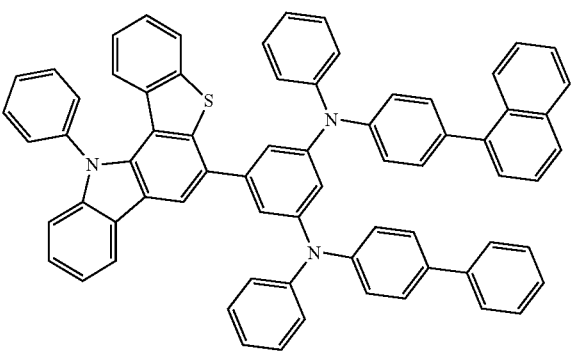
P-7
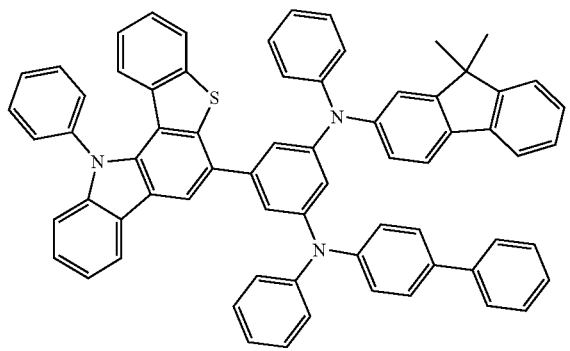
P-8
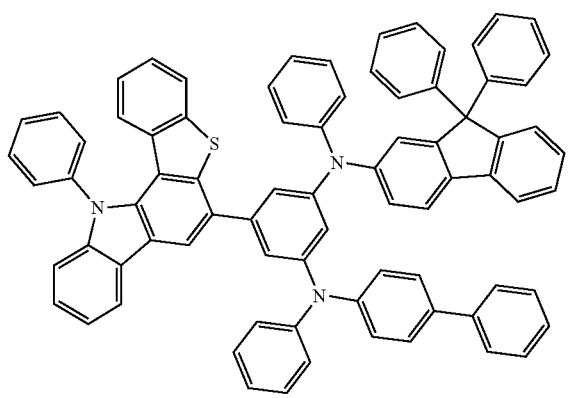

-continued
P-9
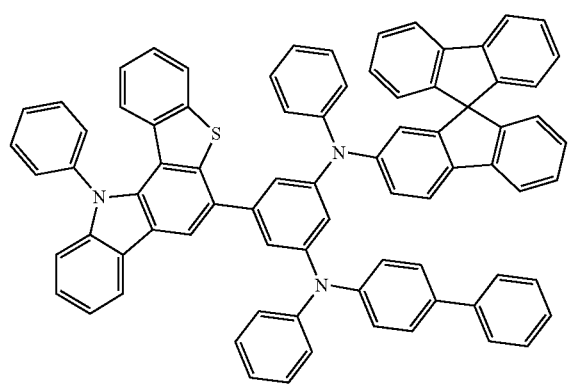
P-10
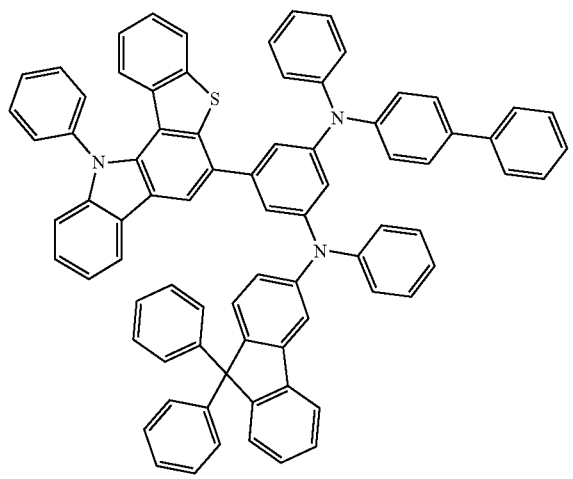
P-11
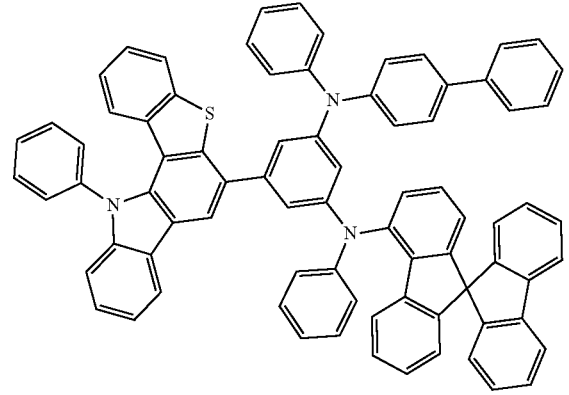
-continued
P-12
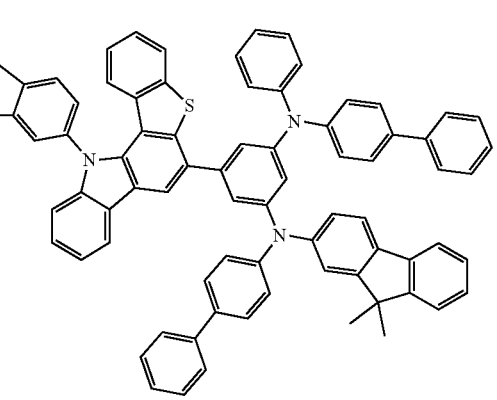
P-13
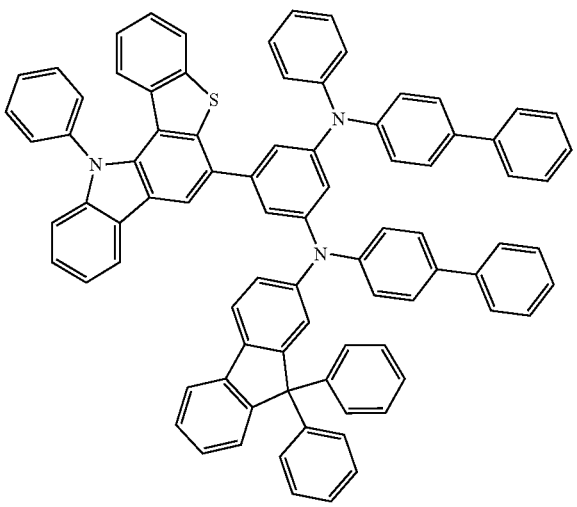
P-14
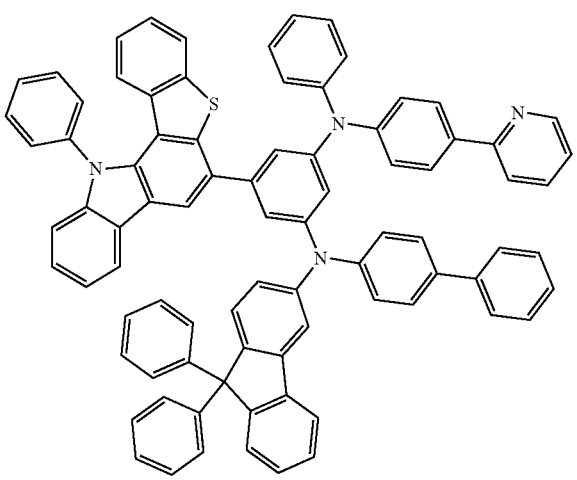

P-15
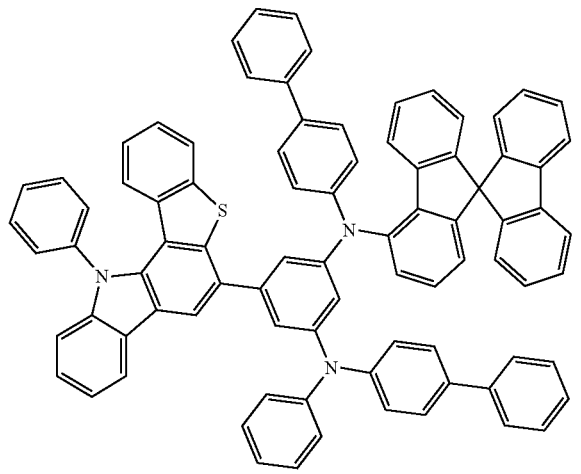
P-16
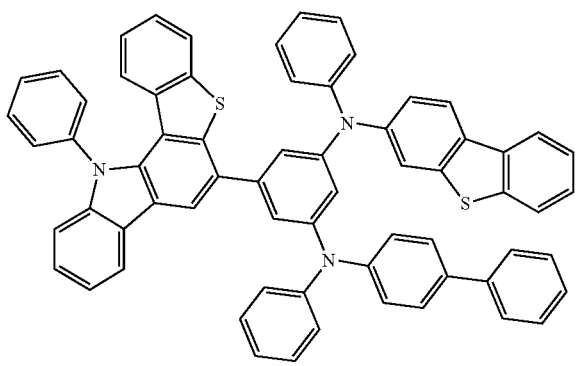
P-17
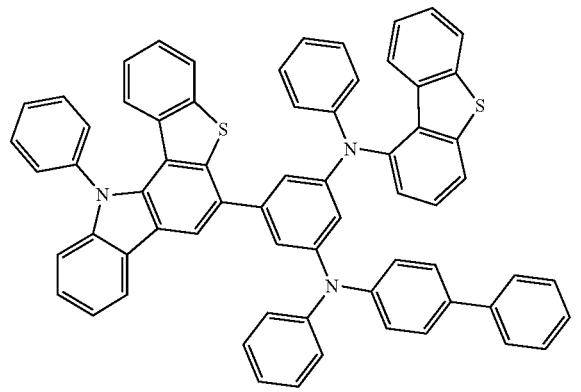
P-18
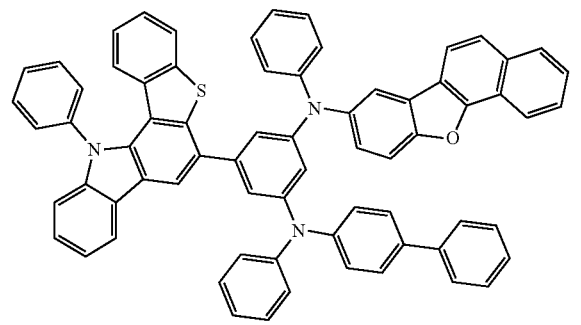
P-19
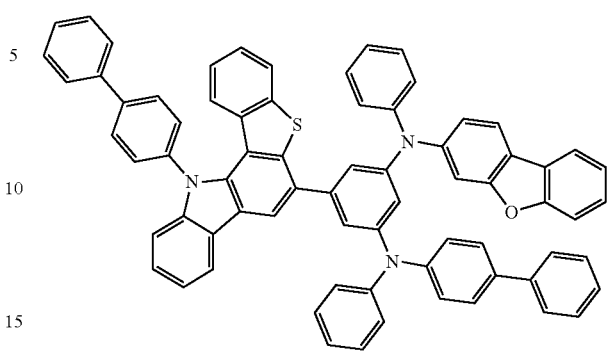
P-20
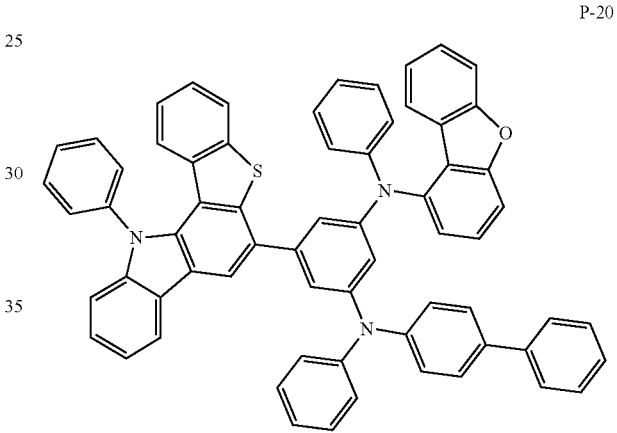
P-21
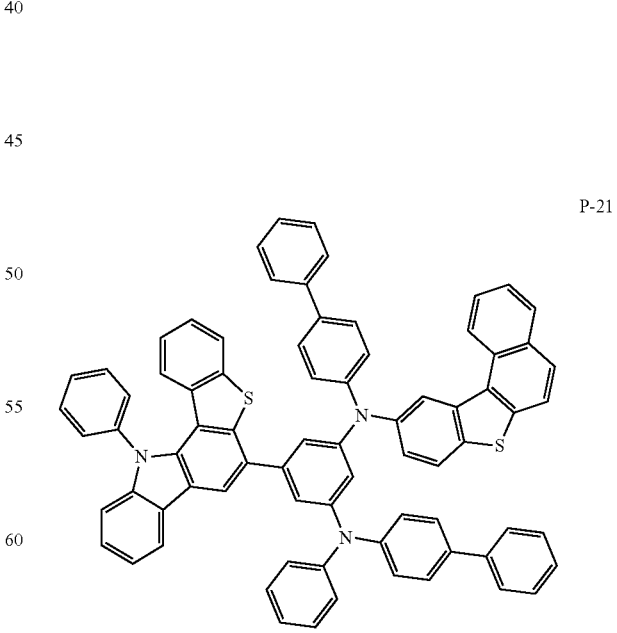

P-22
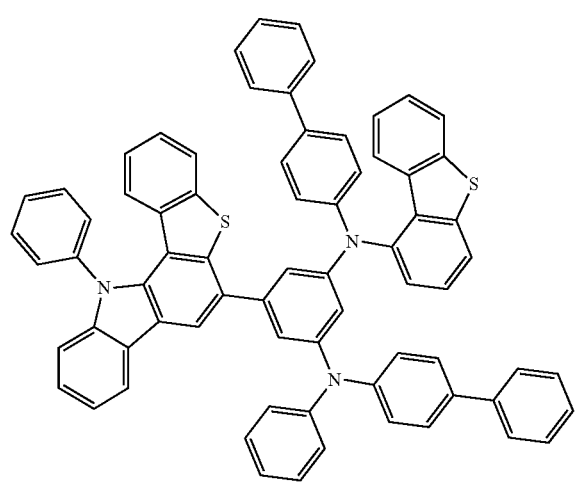
P-25
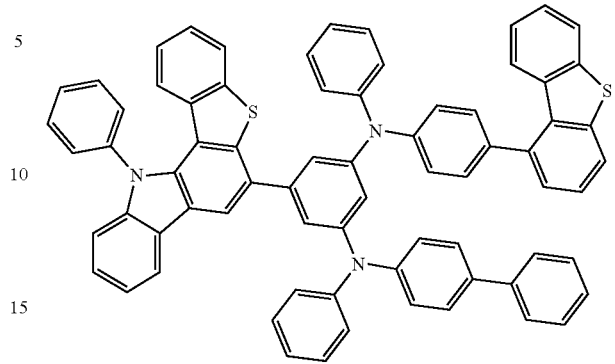
P-26
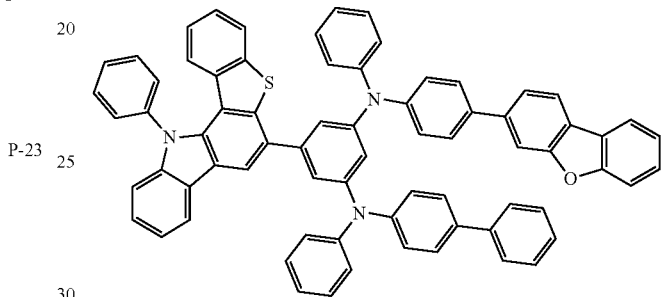
P-23
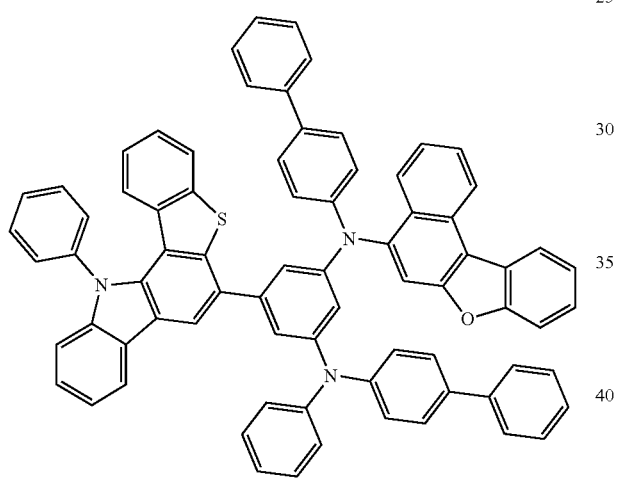
P-27
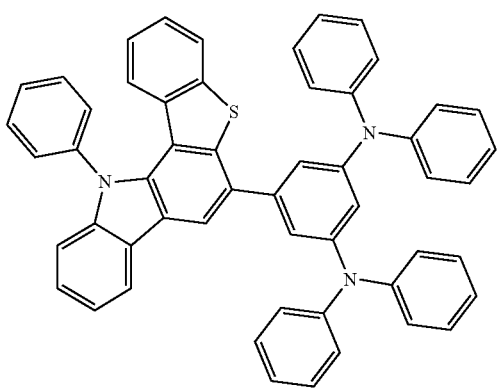
P-24
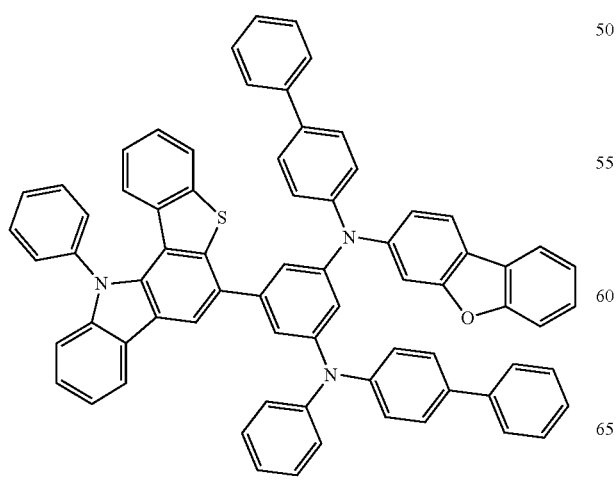
P-28
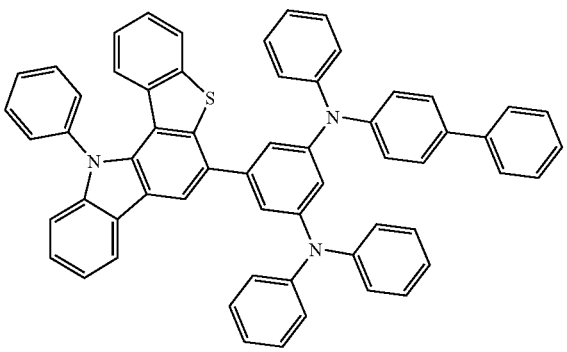

-continued
P-29
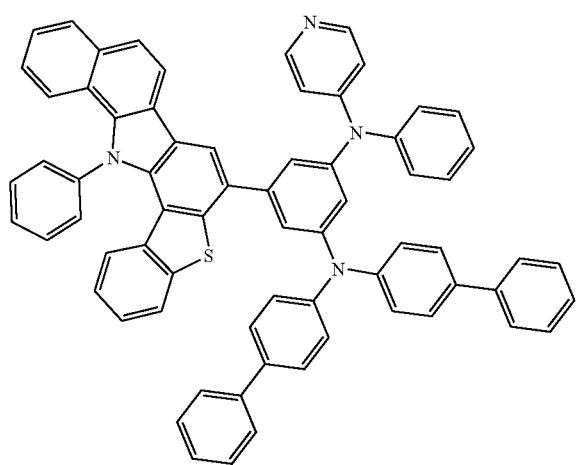
P-30
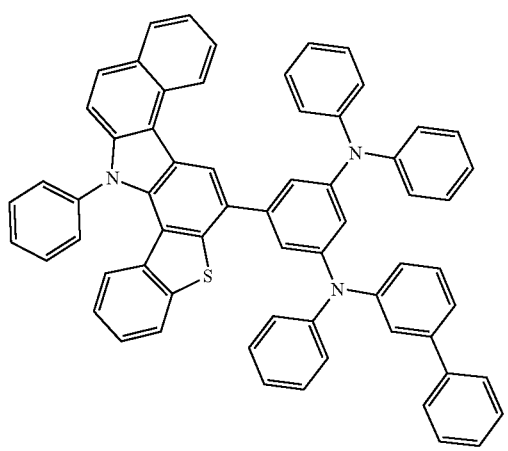
P-31
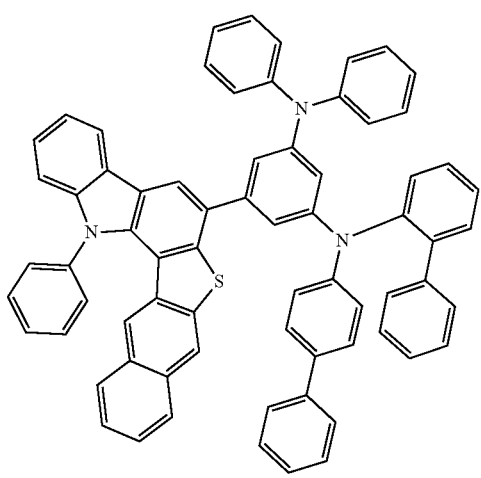
-continued
P-32
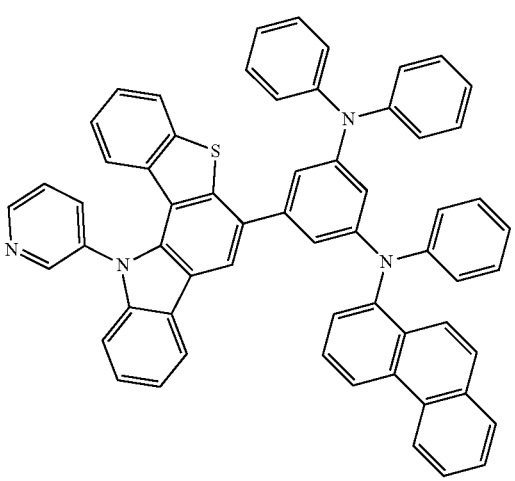
P-33
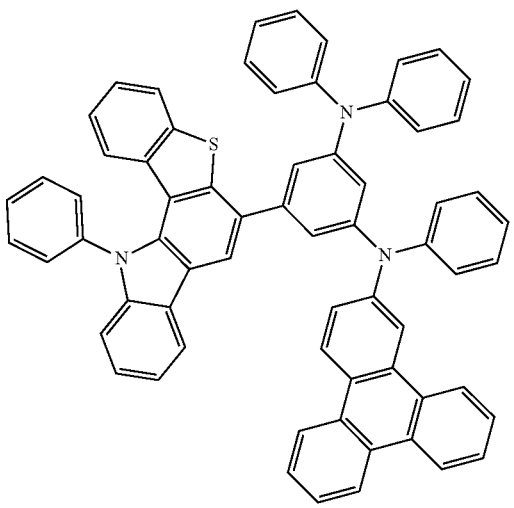
P-34
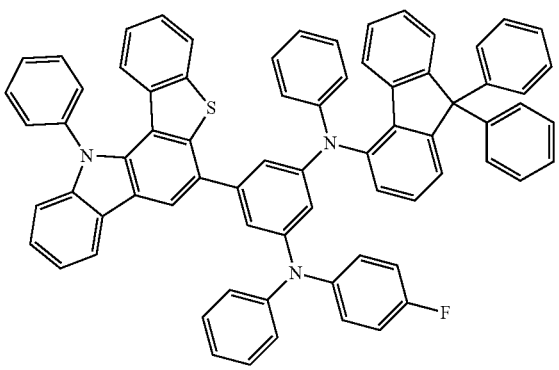

P-35
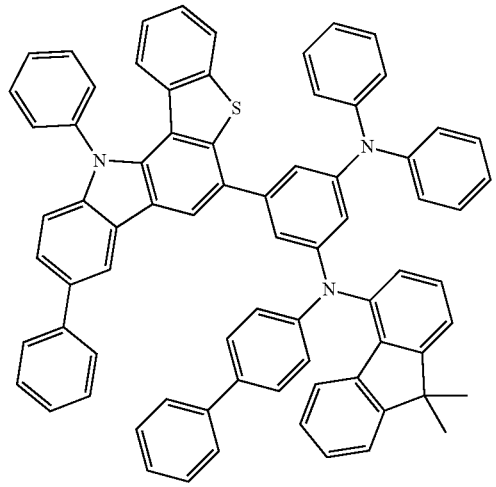
P-36
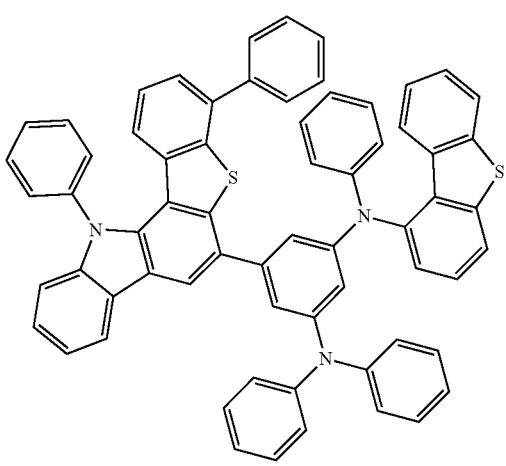
P-37
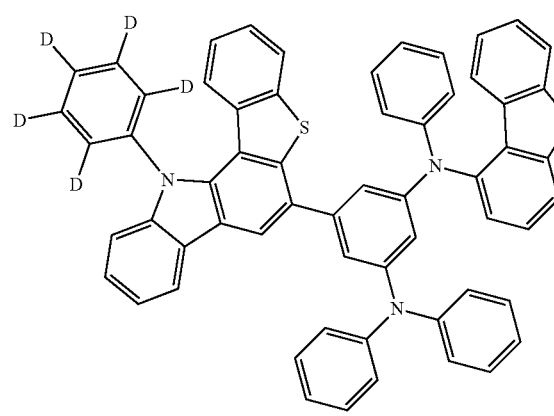
P-38
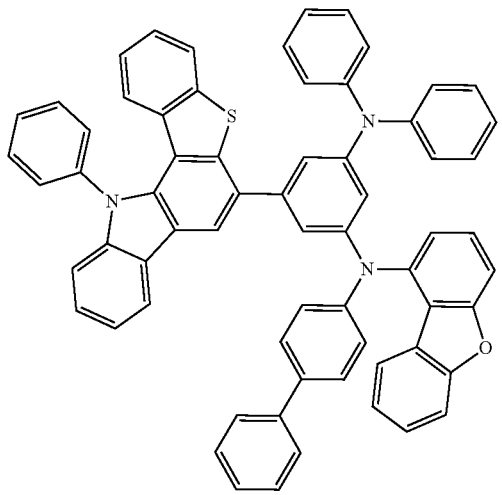
P-39
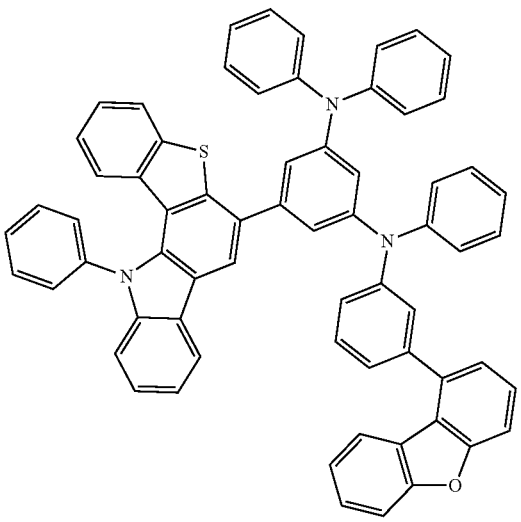
P-40
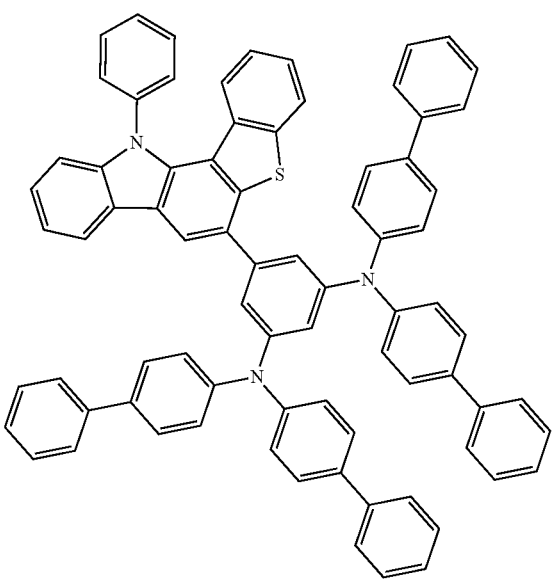

P-41
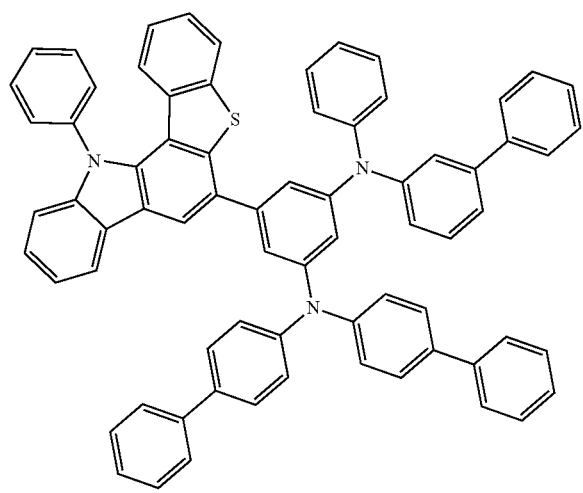
P-44
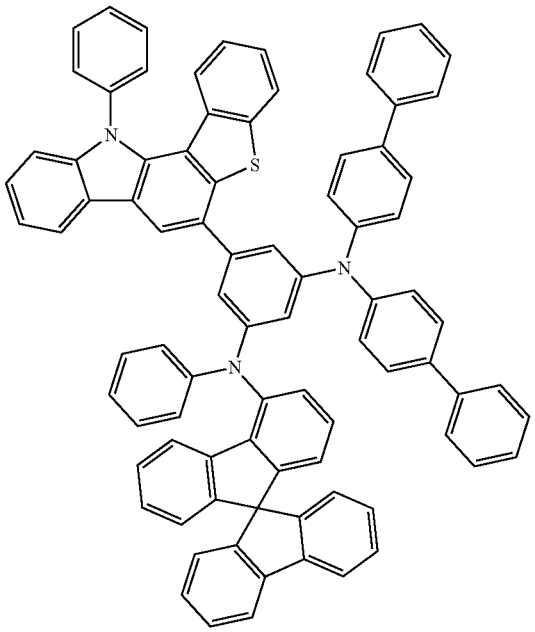
P-42
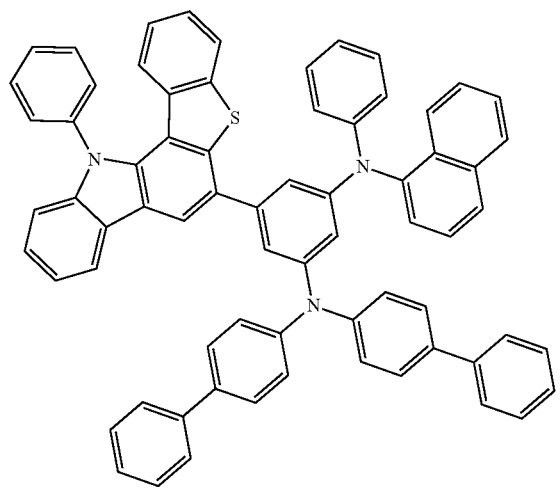
P-45
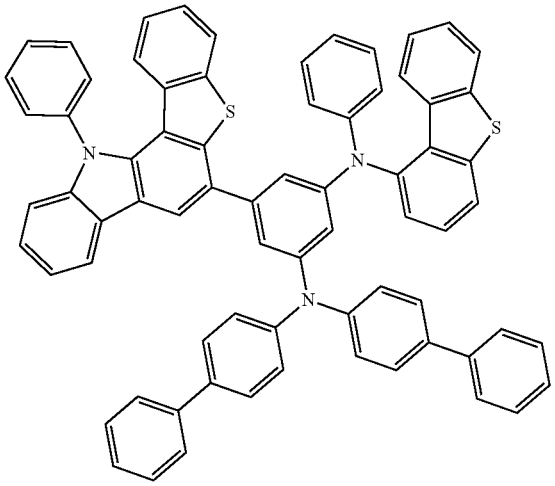
P-43
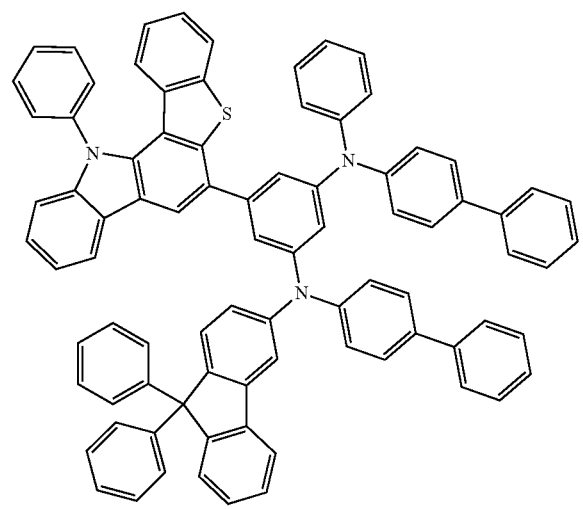
P-46
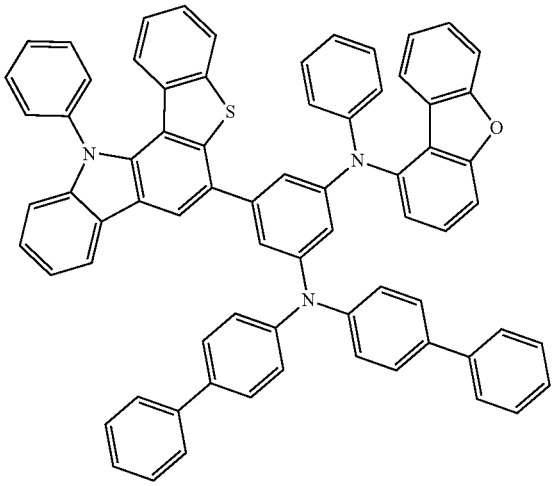

-continued
P-47
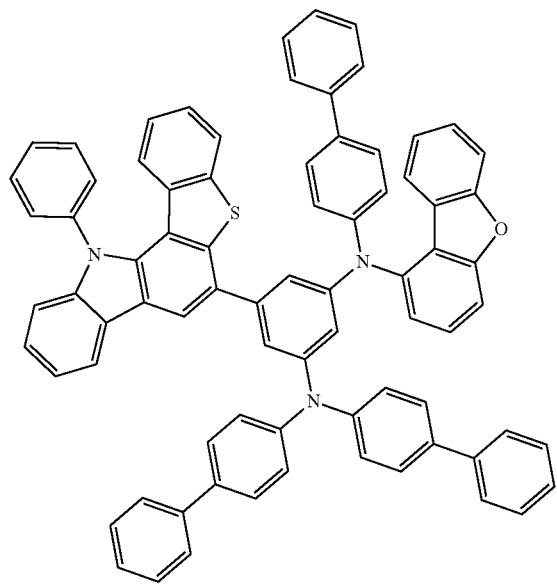
P-50
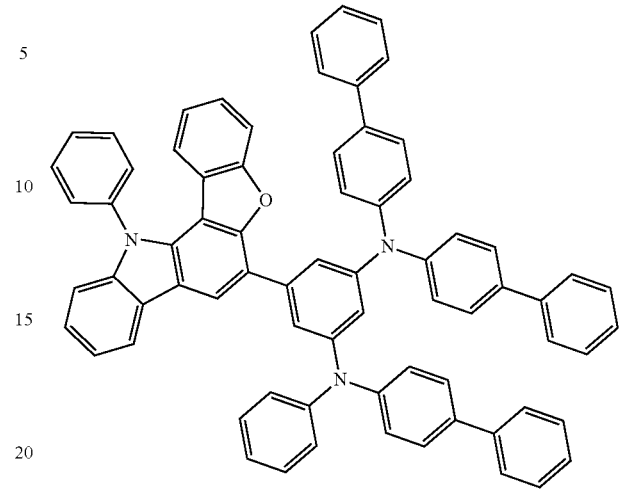
P-48
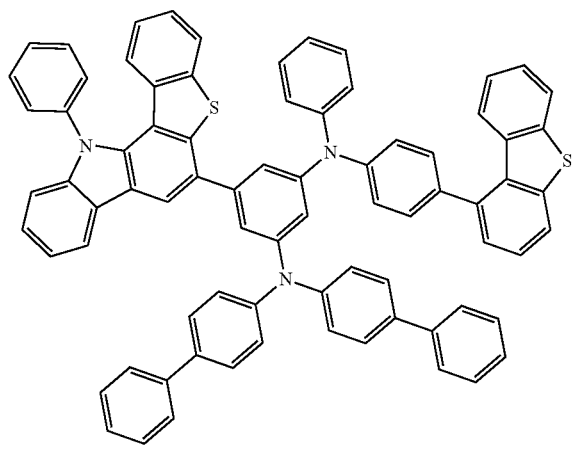
P-51
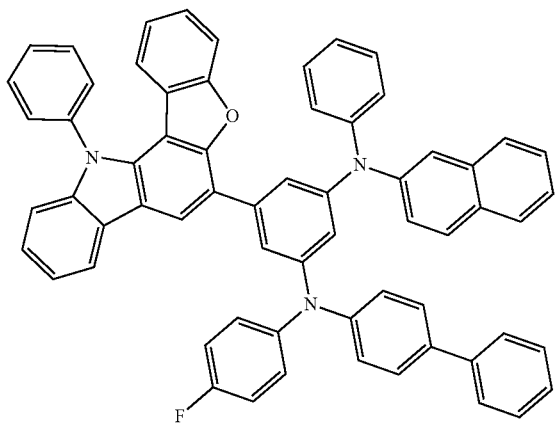
P-49
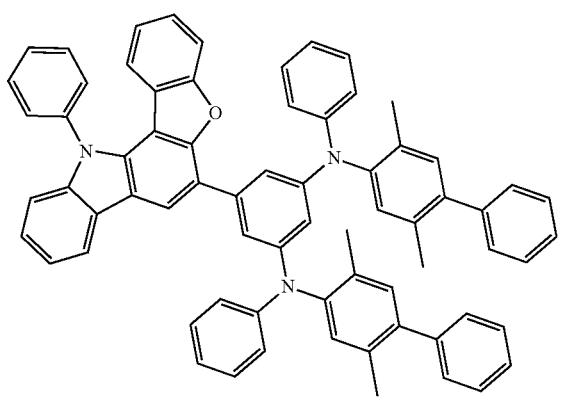
P-52
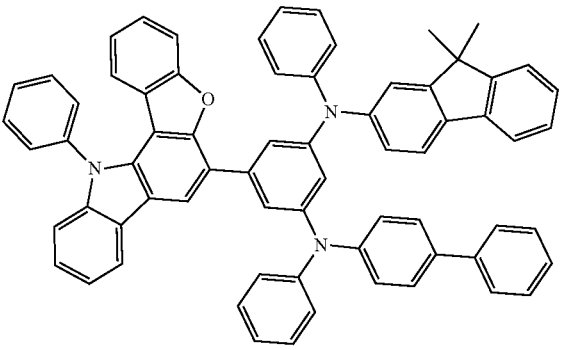

P-53
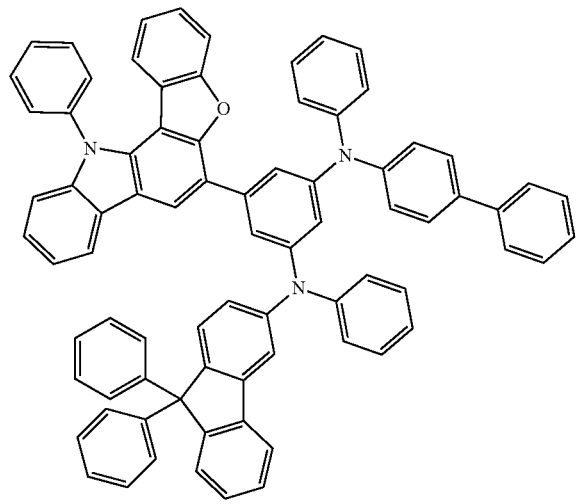
P-56
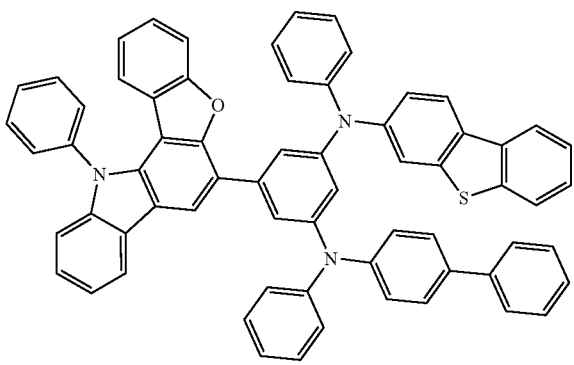
P-54
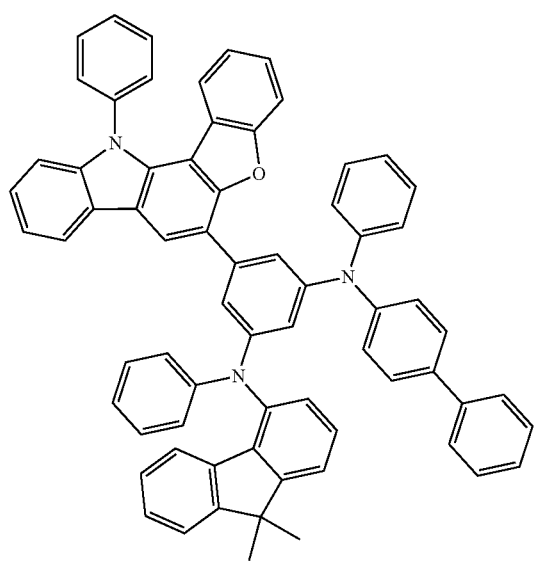
P-57
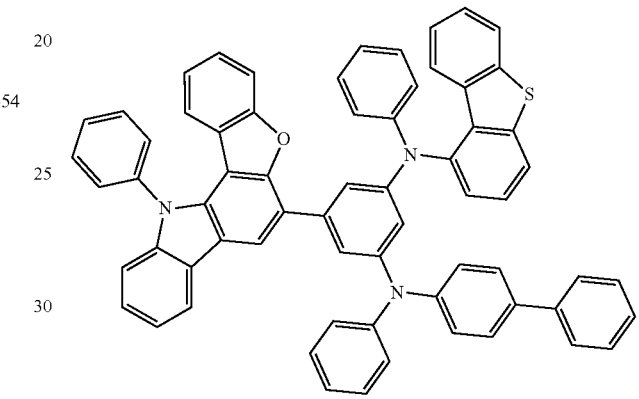
P-58
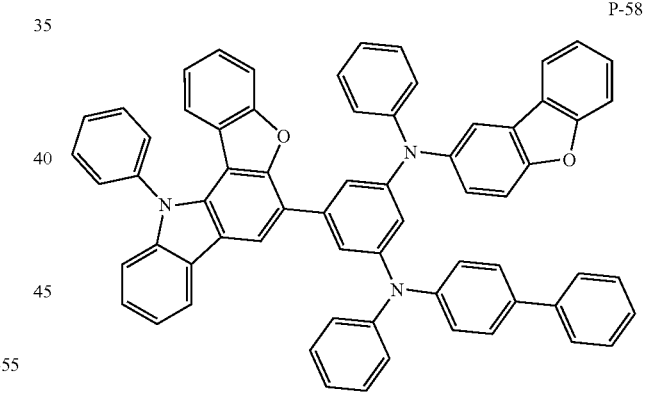
P-55
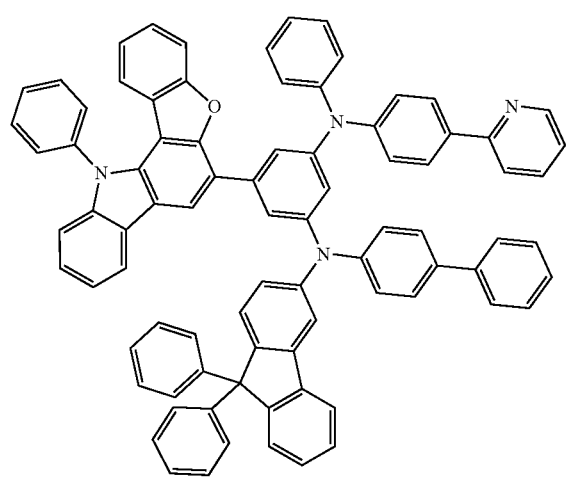
P-59
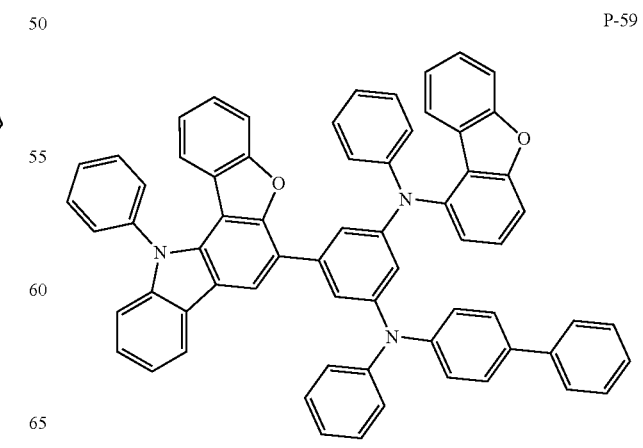

P-60
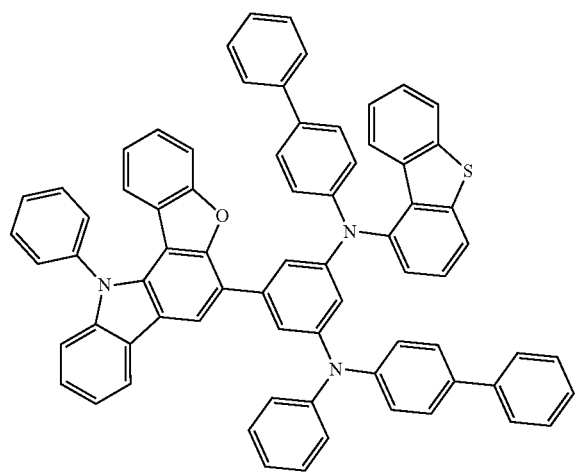
P-61
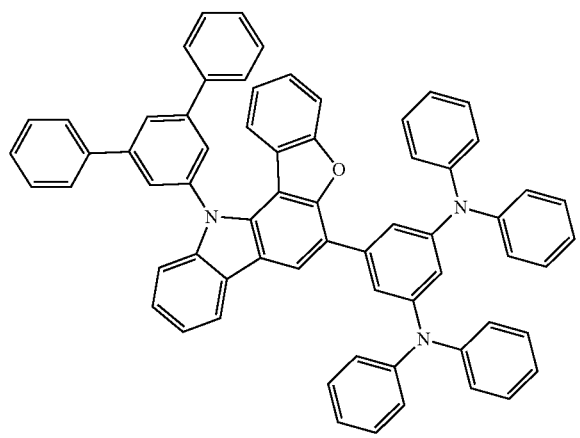
P-62
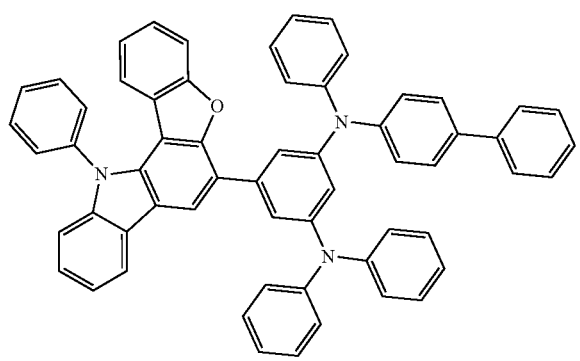
P-63
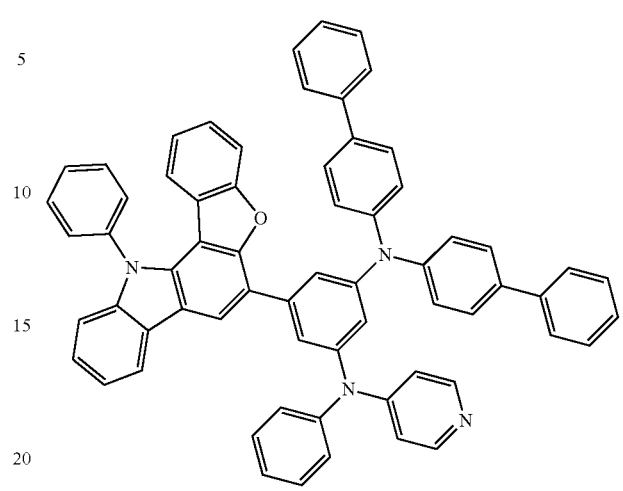
P-64
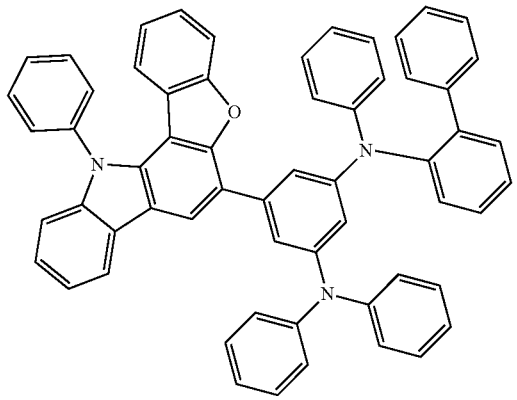
P-65
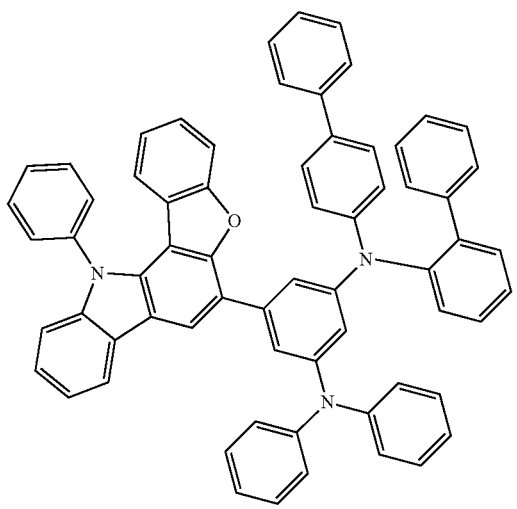

P-66
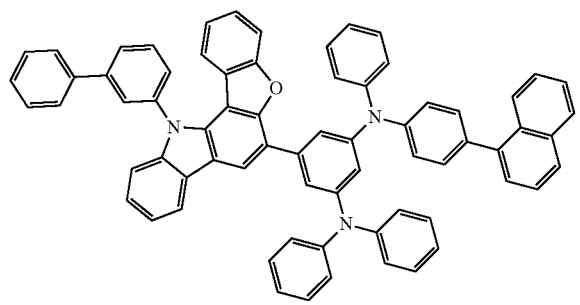
P-67
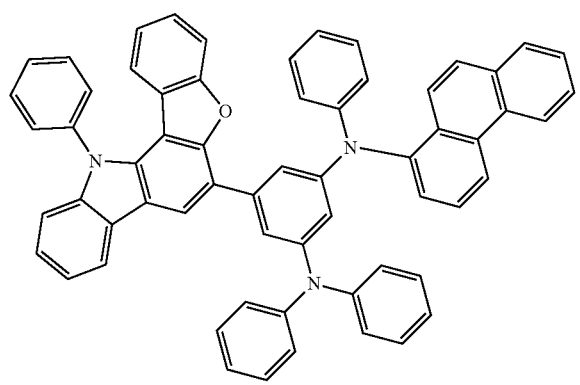
P-68
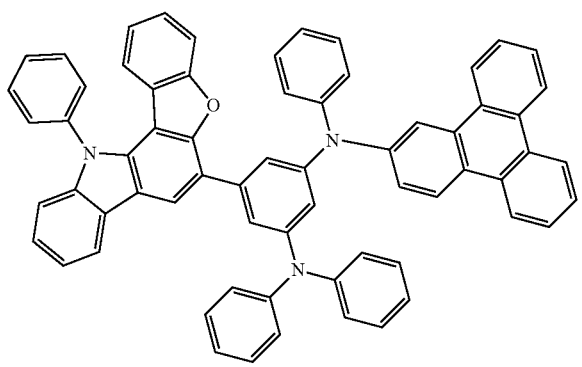
P-69
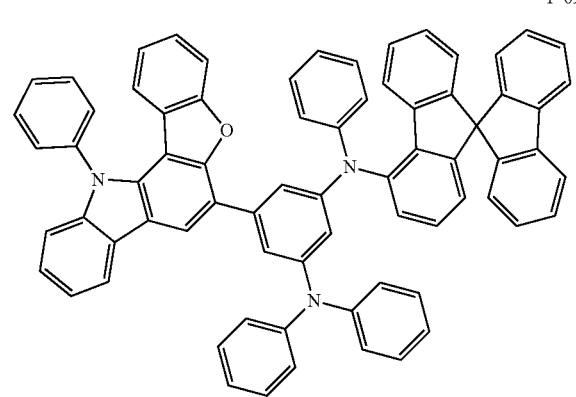
P-70
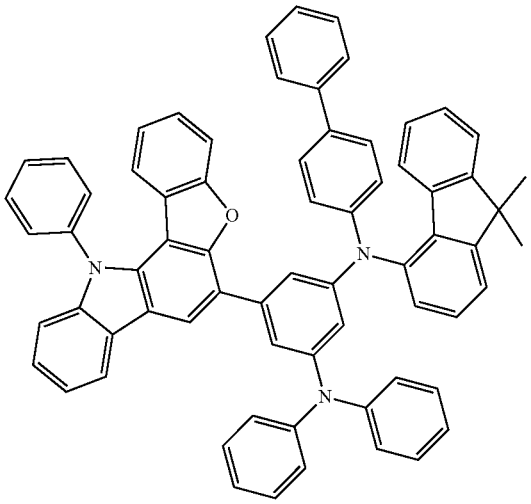
P-71
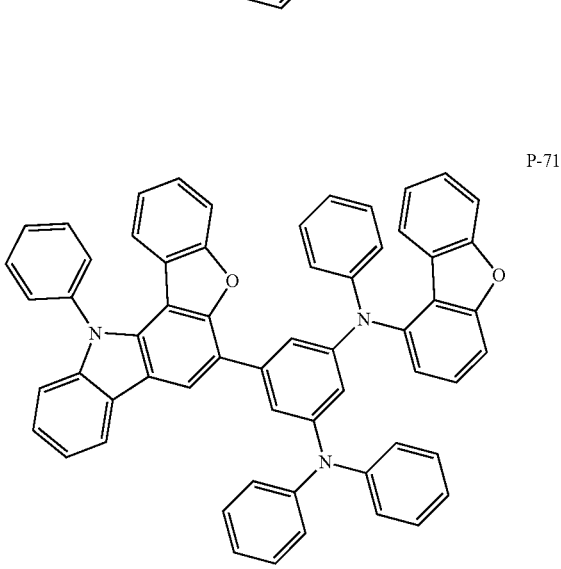
P-72
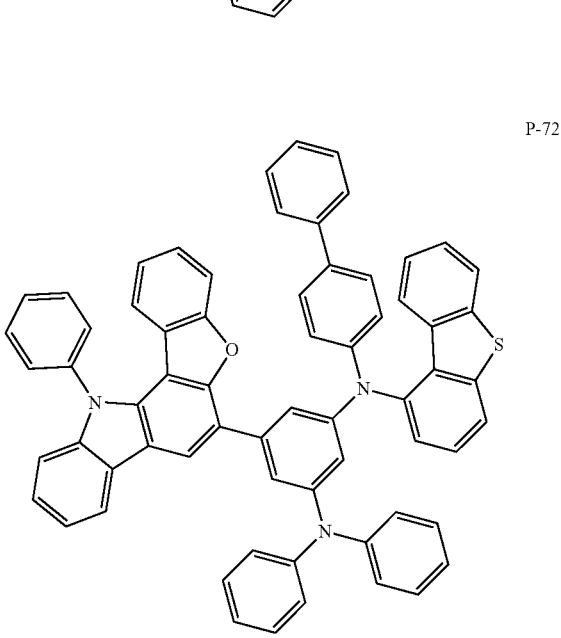

P-73
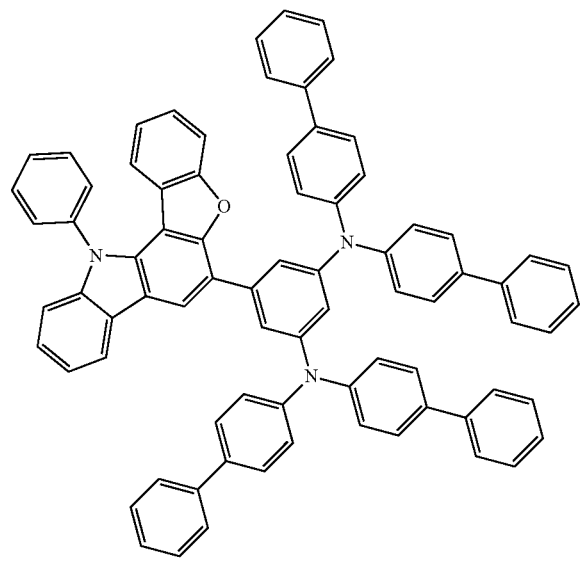
P-74
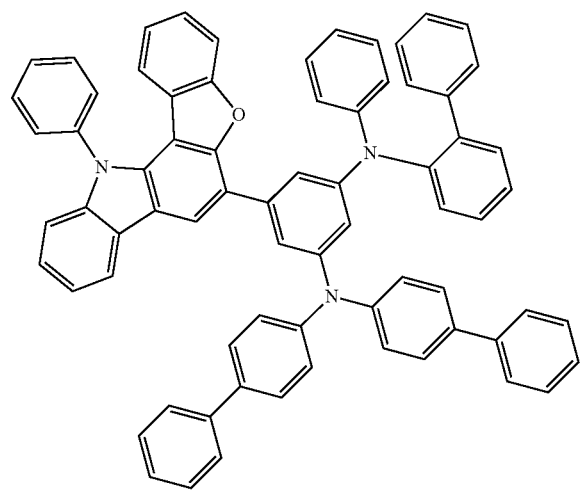
P-75
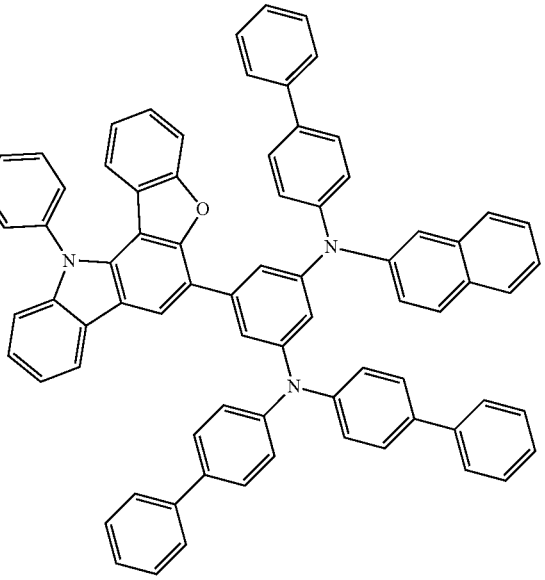
P-76
P-77
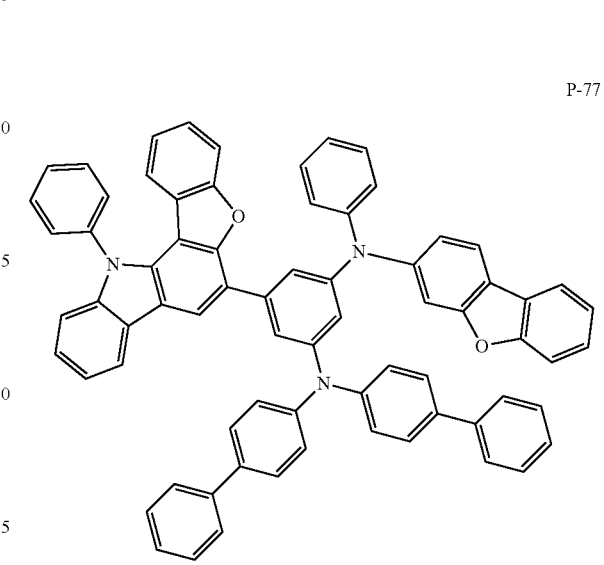

P-78
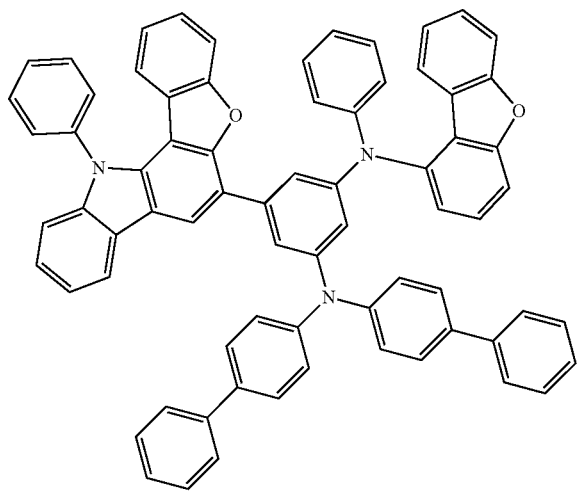
P-79
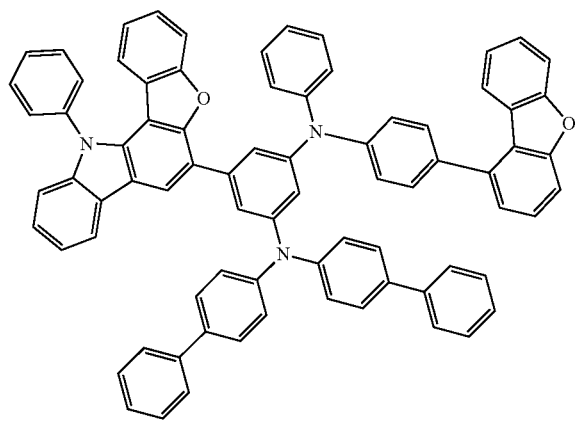
P-80
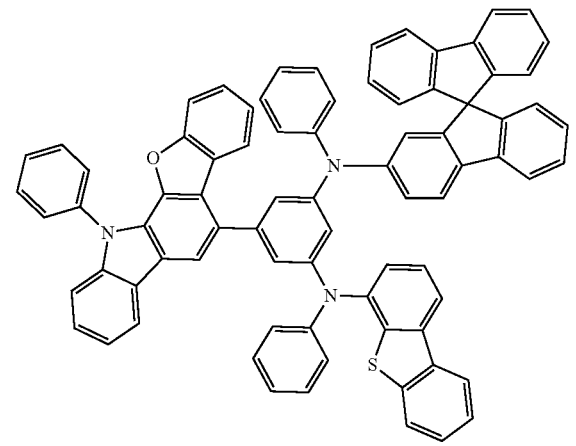
P-81
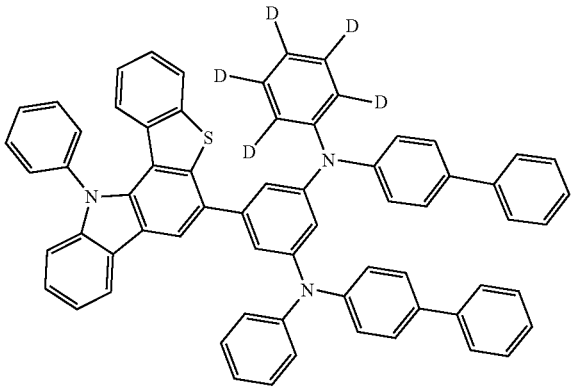
P-82
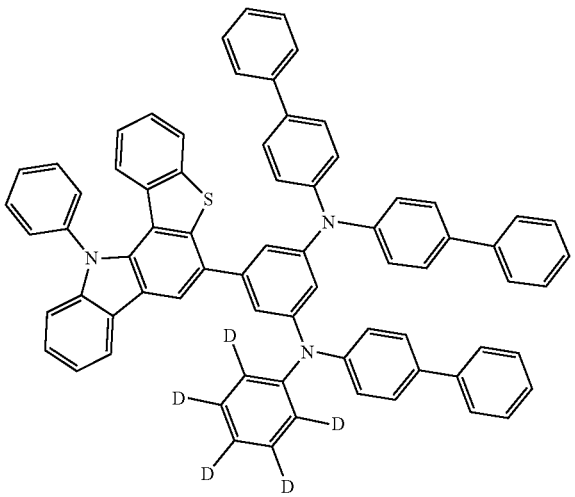
P-83
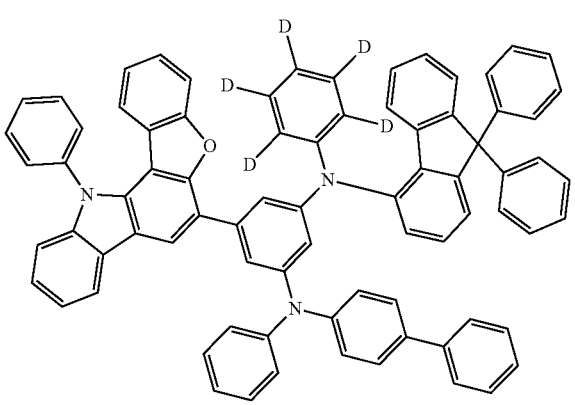

P-84

P-85

P-86

P-87

P-88

P-89

-continued
P-90
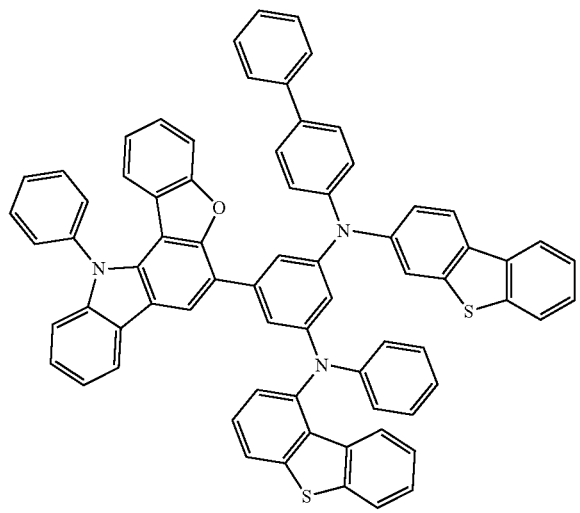
P-91
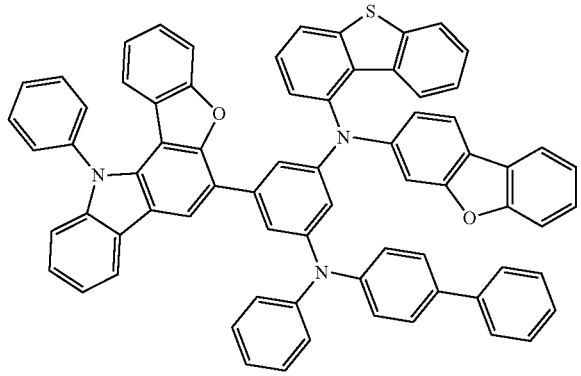
P-92
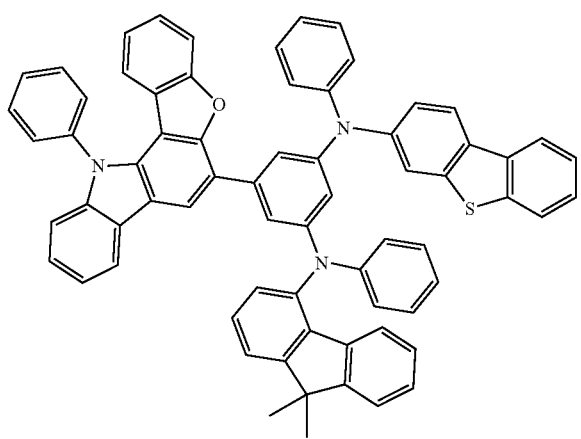
-continued
P-93
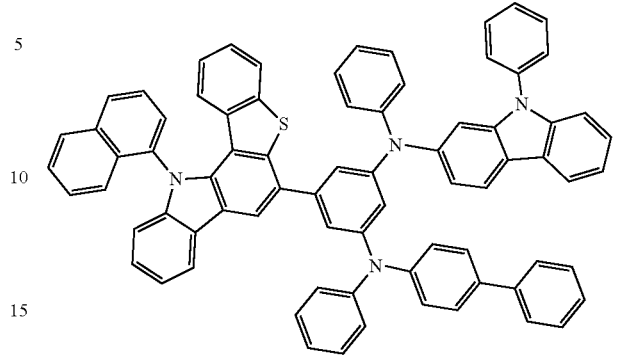
P-94
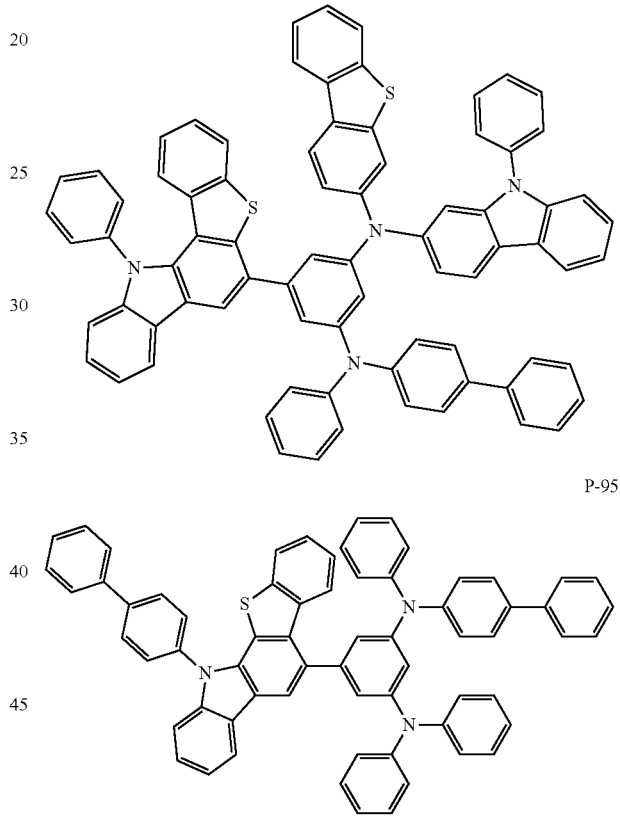
P-95
P-96
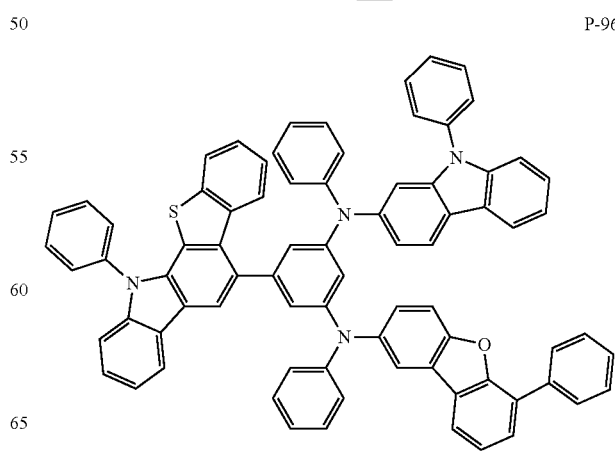

-continued
P-97
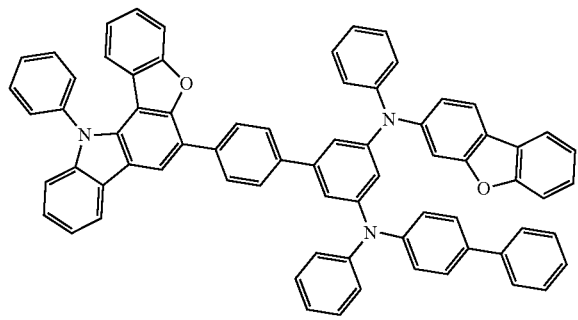
P-98
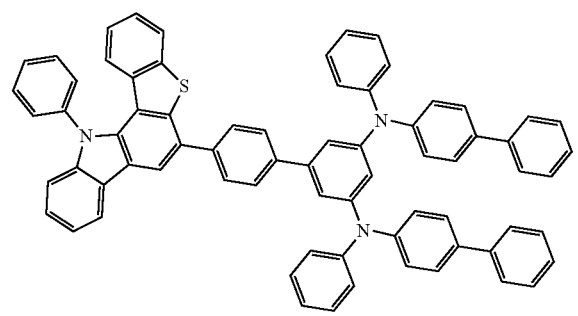
P-99
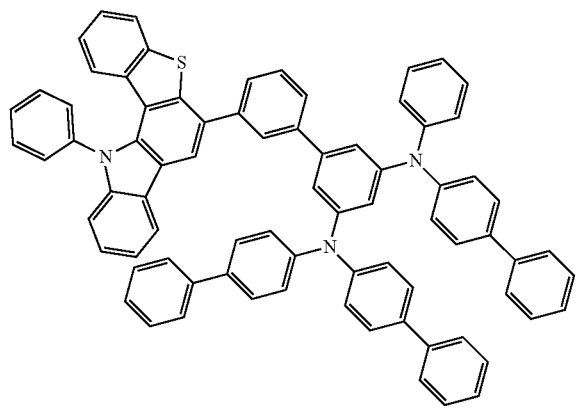
P-100
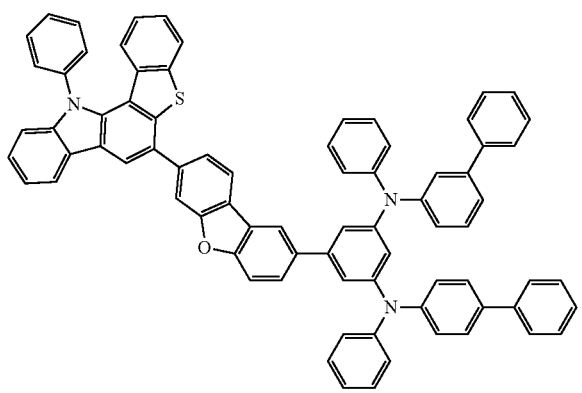
-continued
P-101
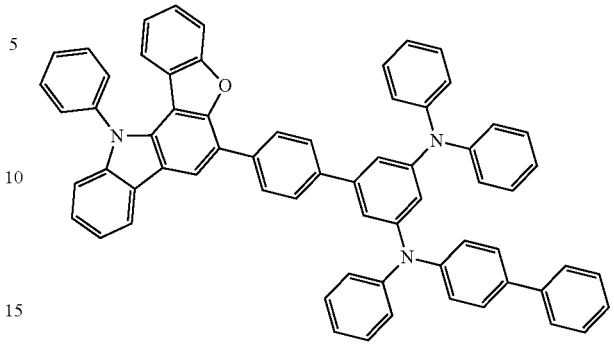
P-102
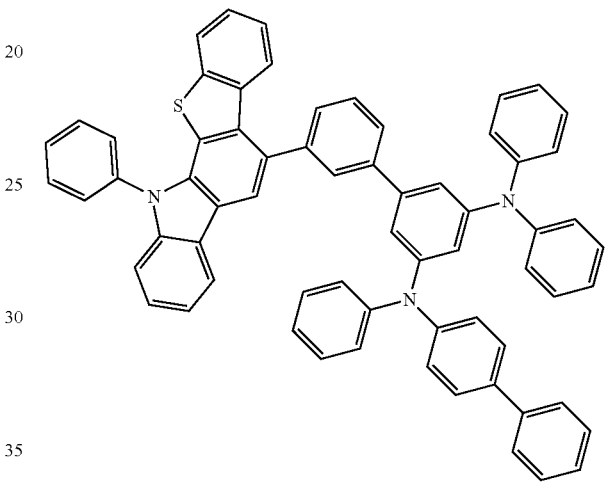
P-103
P-104
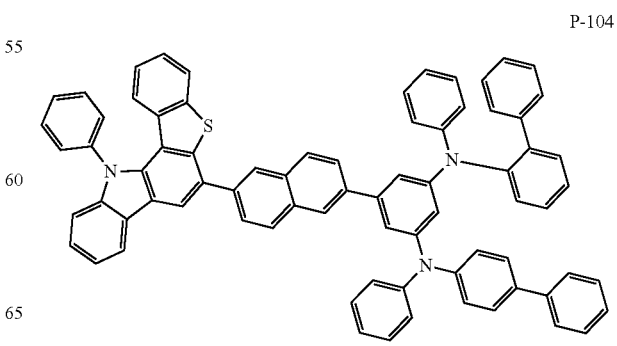

P-105
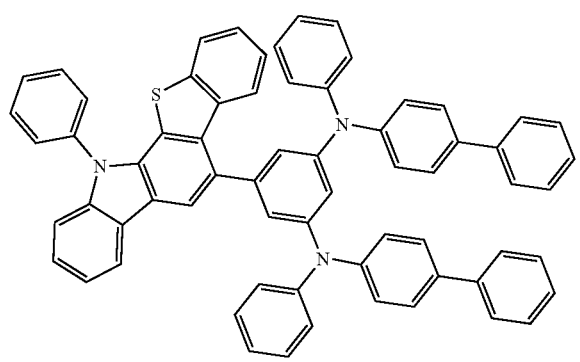
P-106
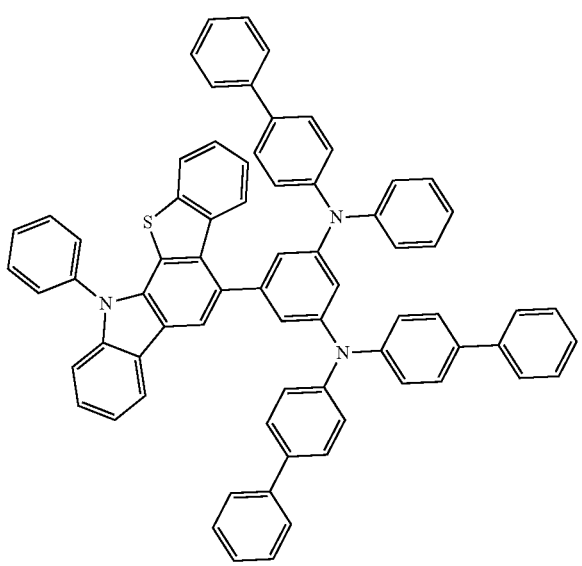
P-107
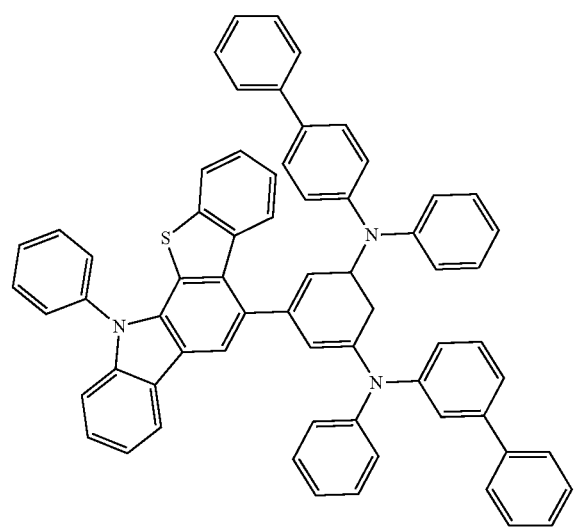
P-108
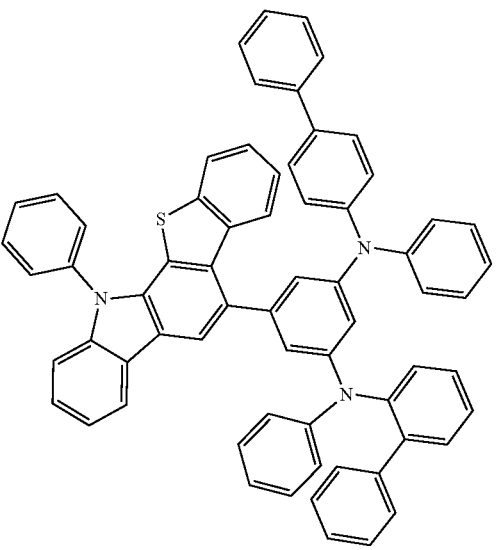
P-109
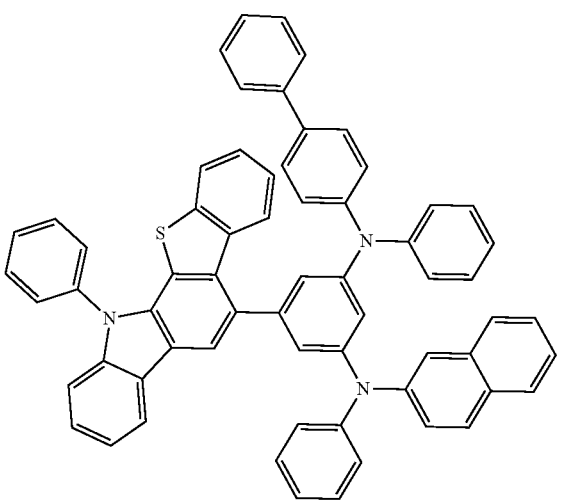
P-110
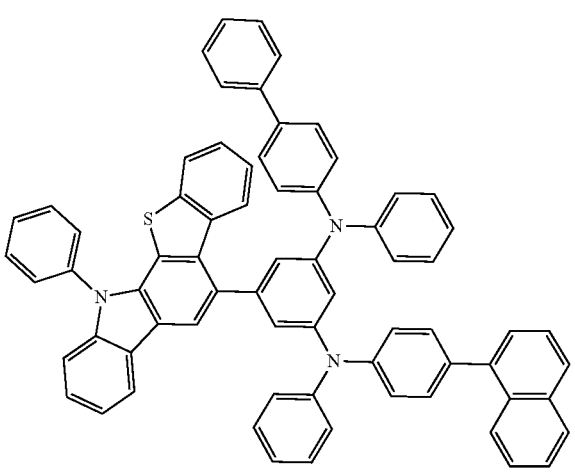

P-111
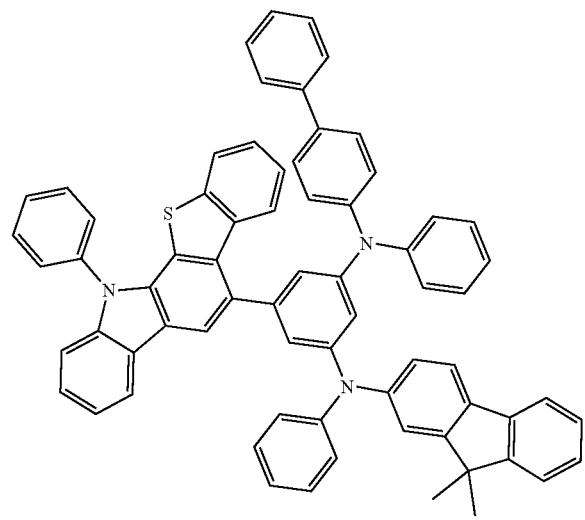
P-112
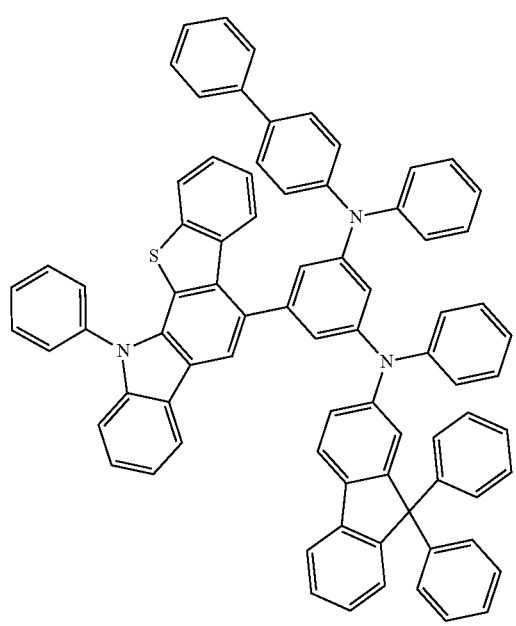
P-113
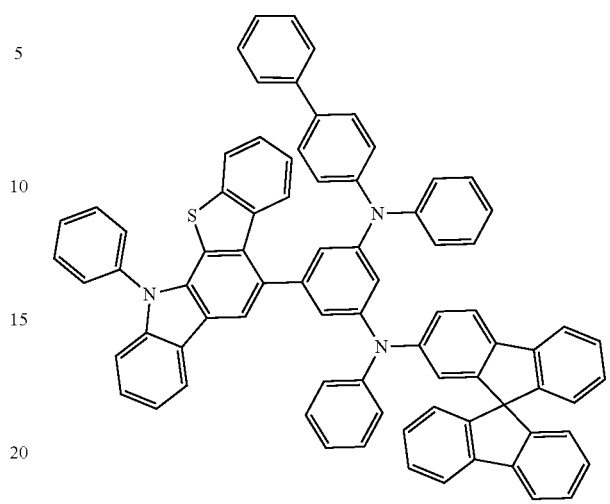
P-114
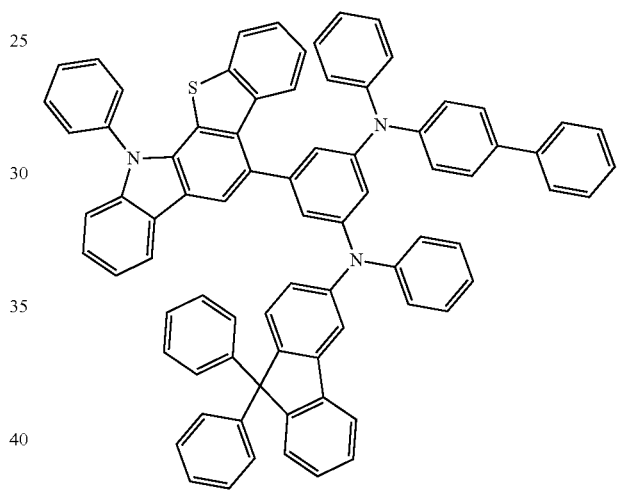
P-115
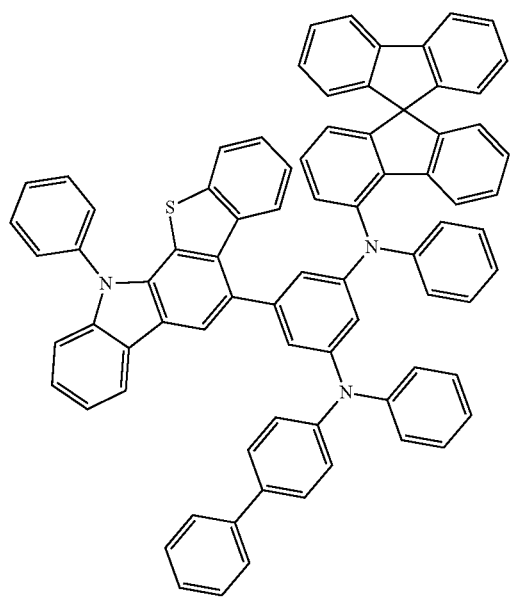

-continued
P-116
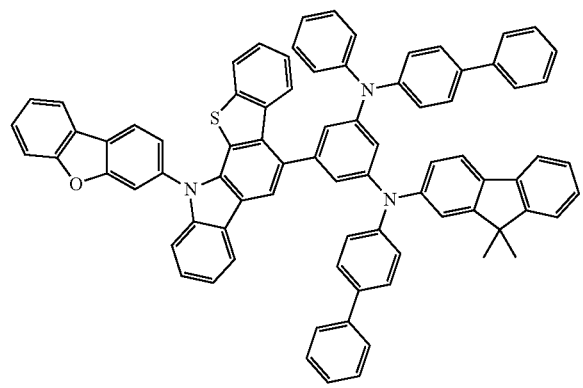
P-117
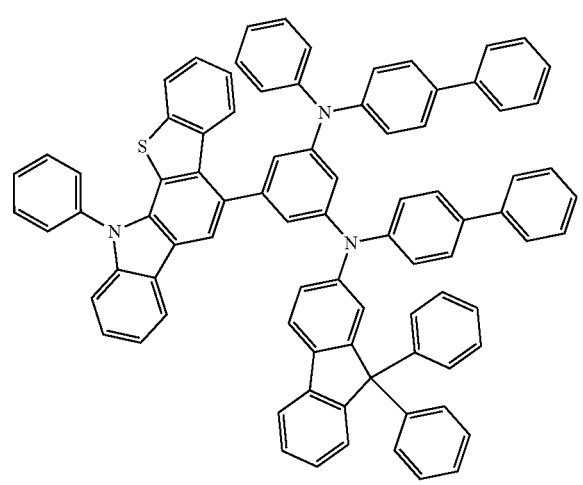
P-118
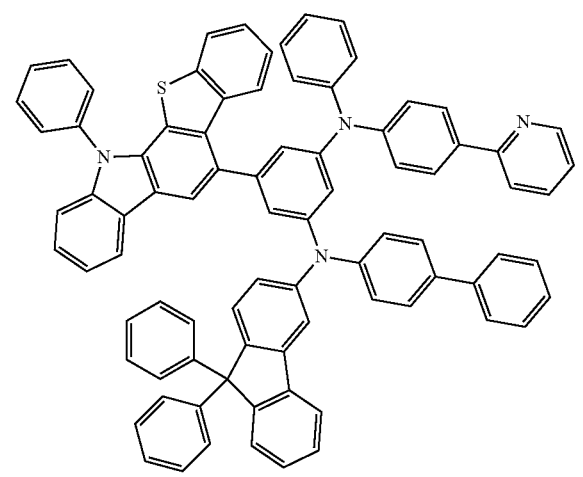
-continued
P-119
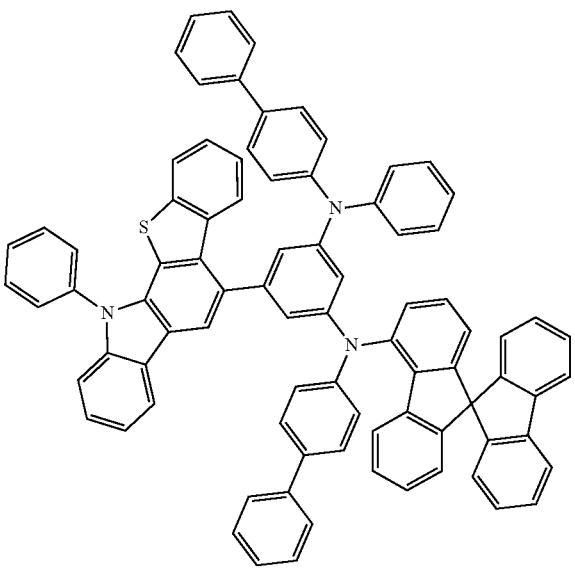
P-120
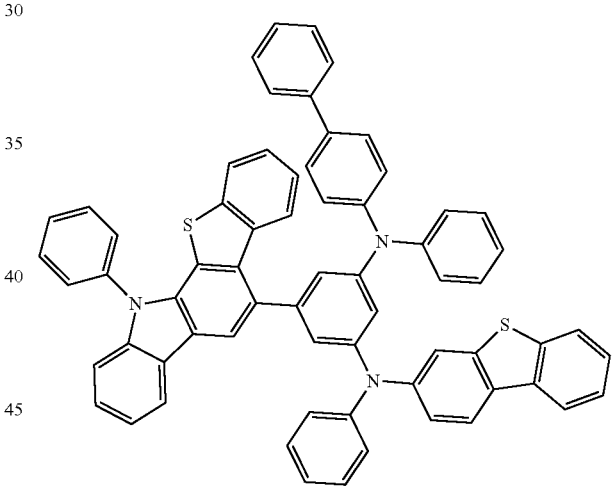
P-121
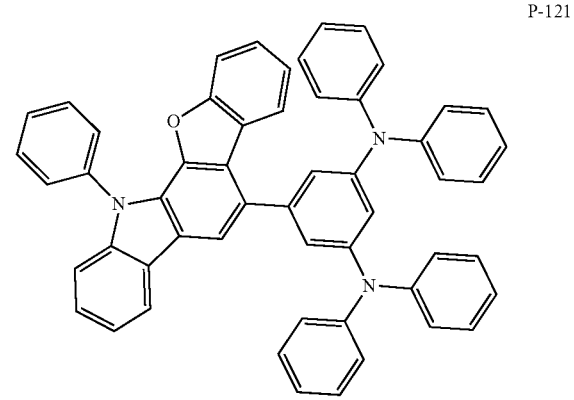

P-122
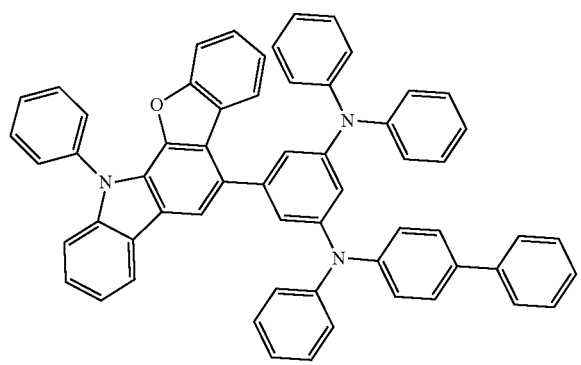
P-125
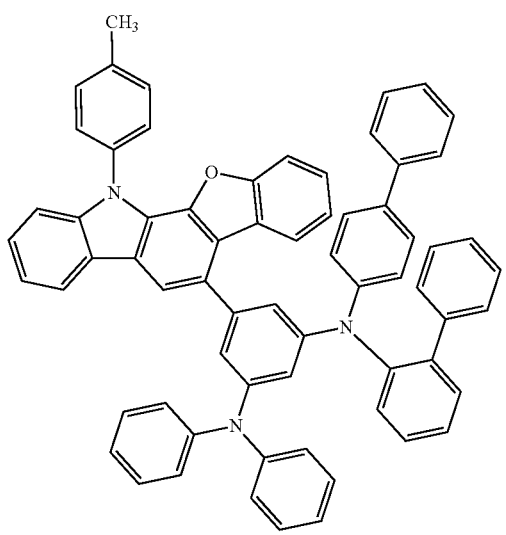
P-123
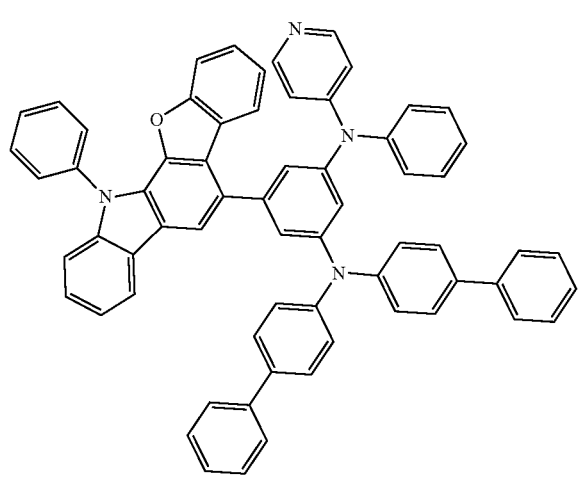
P-126
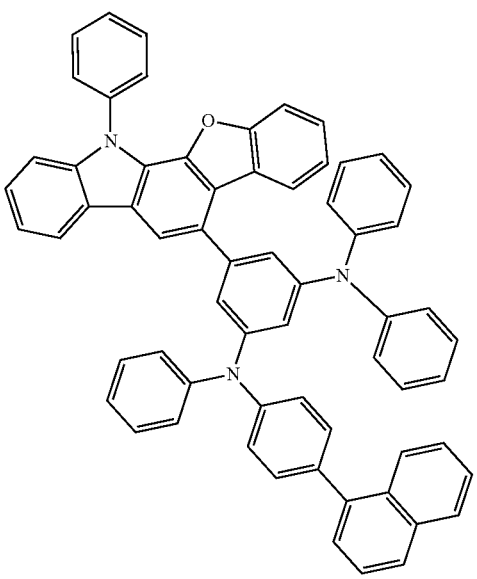
P-124
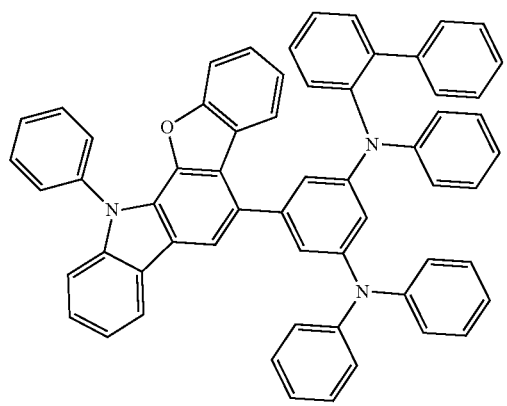
P-127
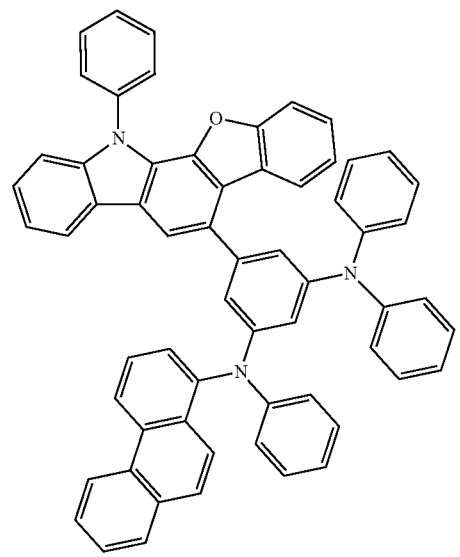

P-128
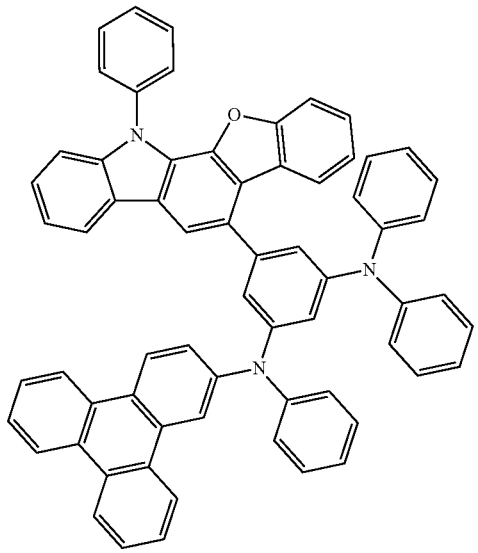
P-129
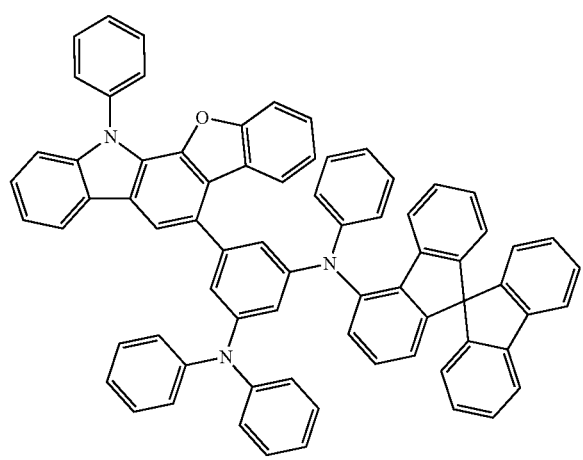
P-130
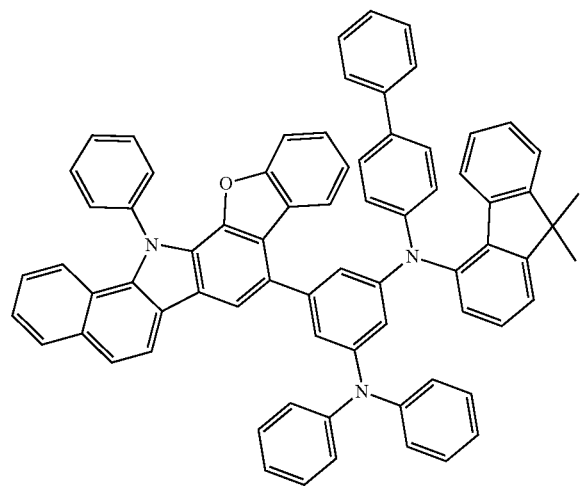
P-131
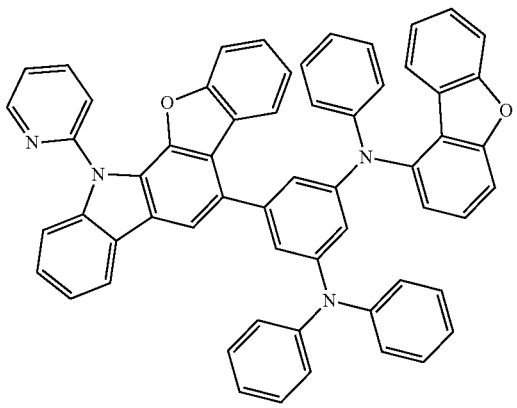
P-132
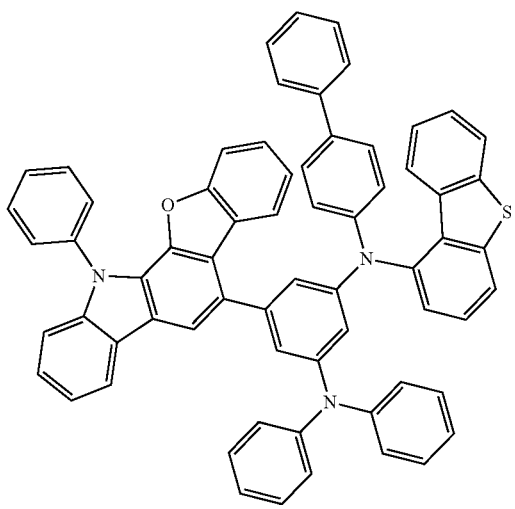
P-133
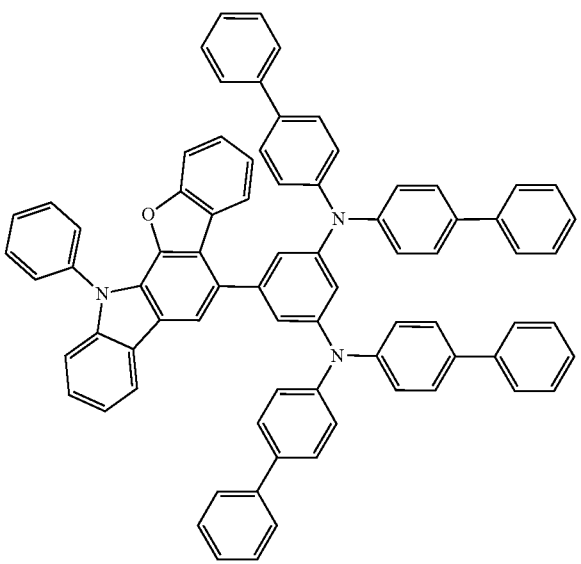

P-134
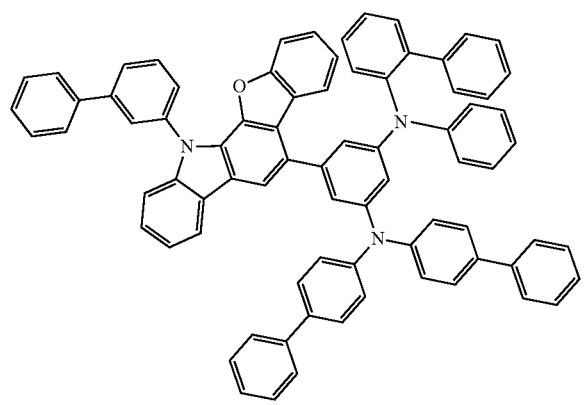
P-135
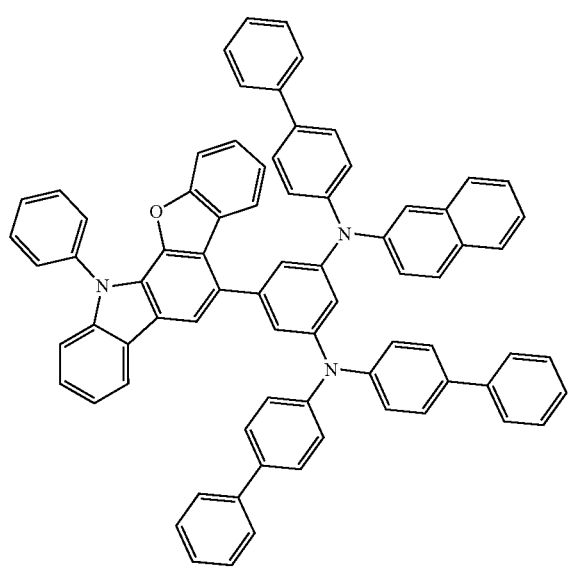
P-136
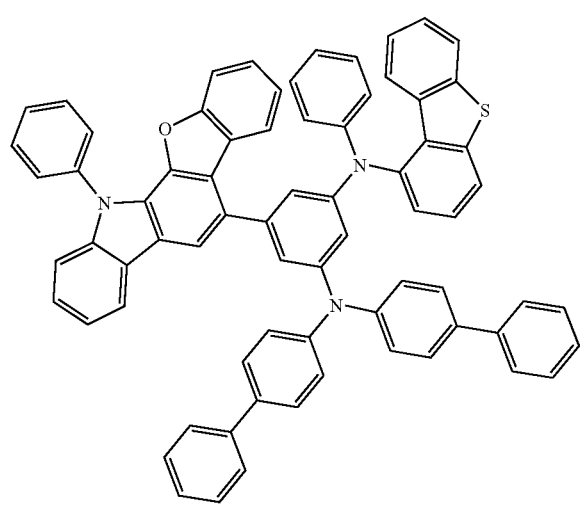
P-137
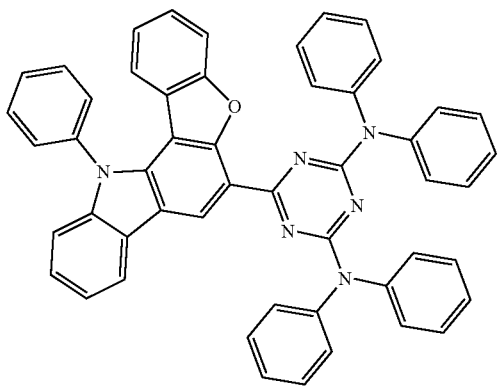
P-138
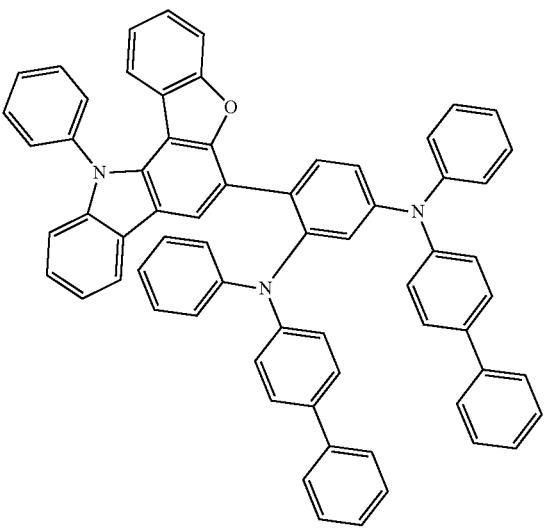
P-139
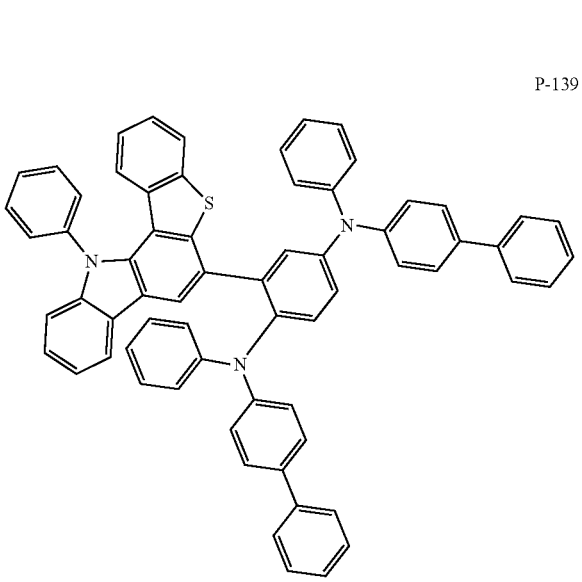

P-140
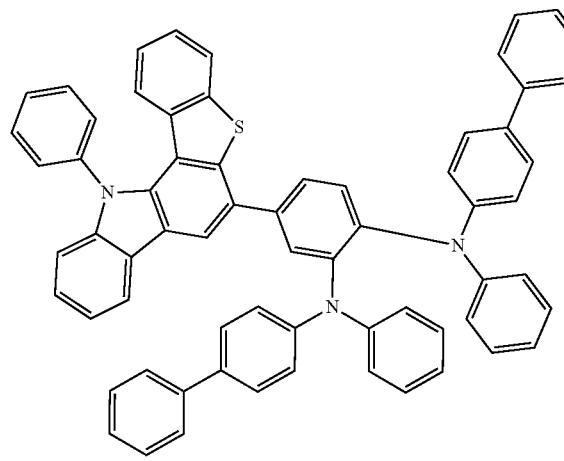
P-141
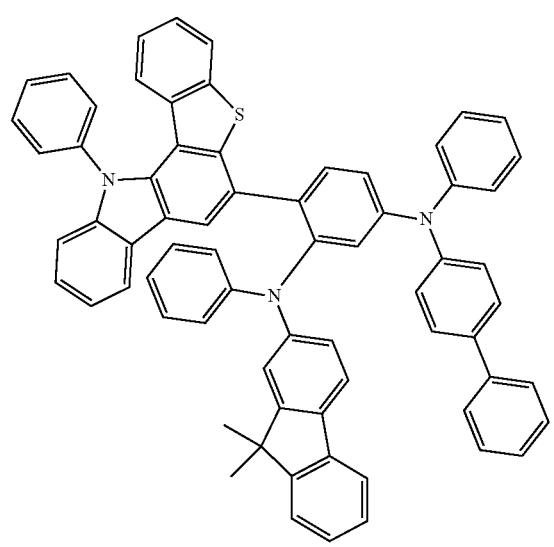
P-142
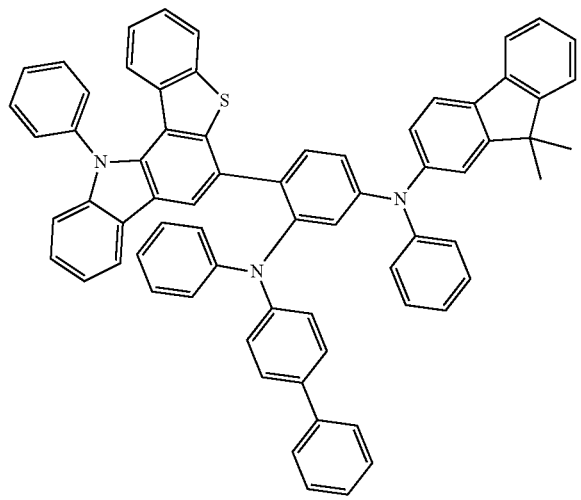
P-143
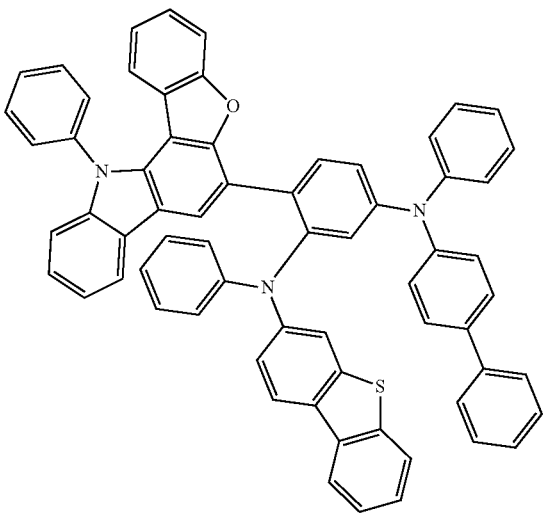
P-144
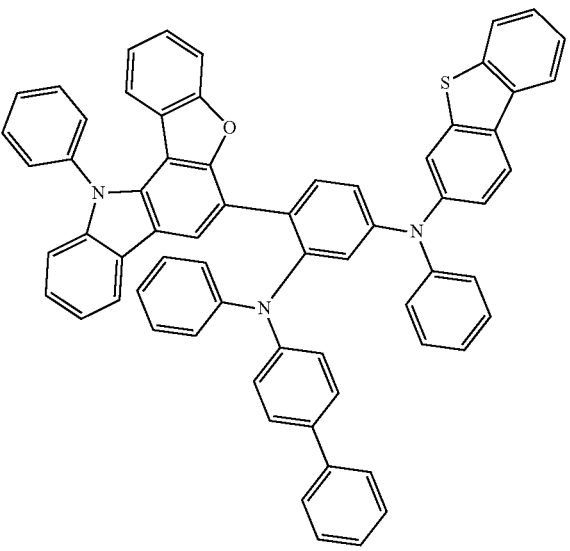

P-145
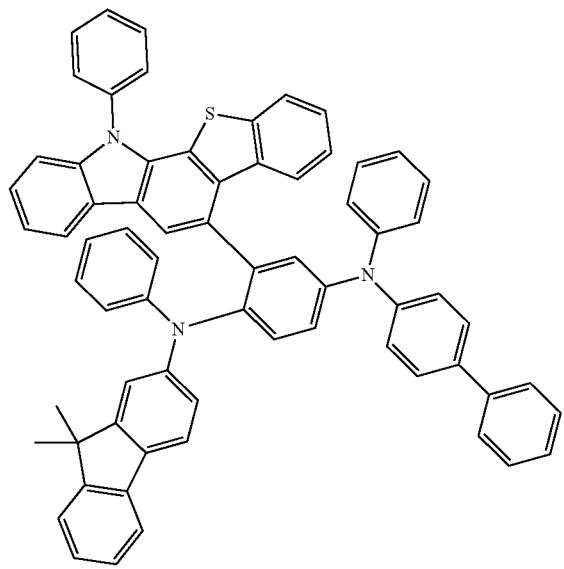
P-147
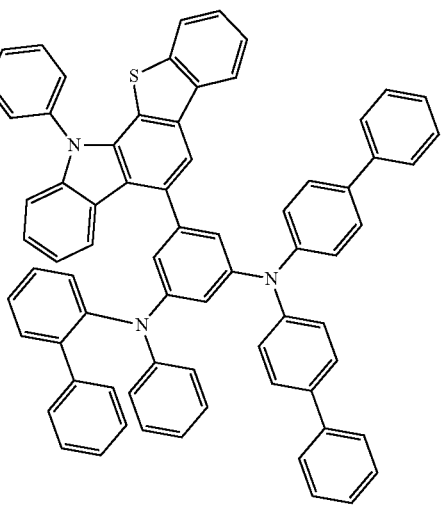
P-146
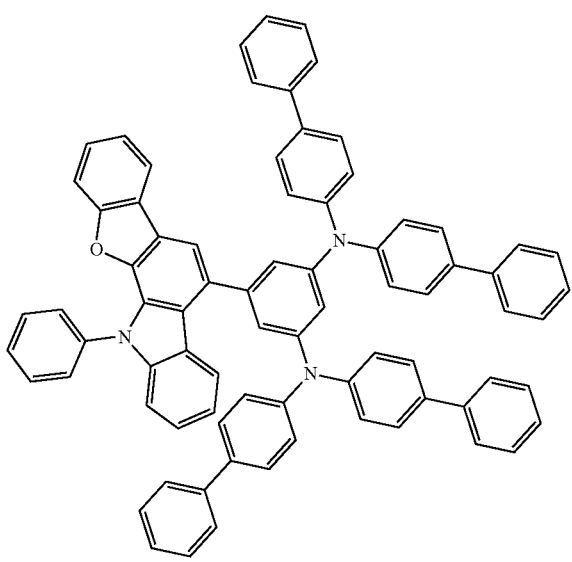
P-148
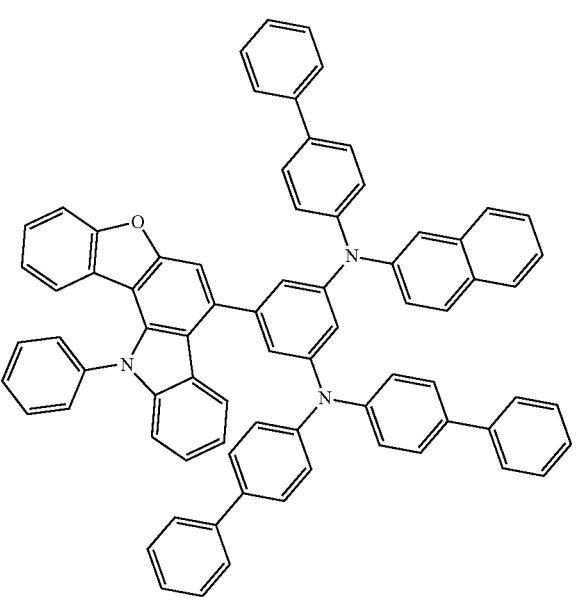

-continued
P-149
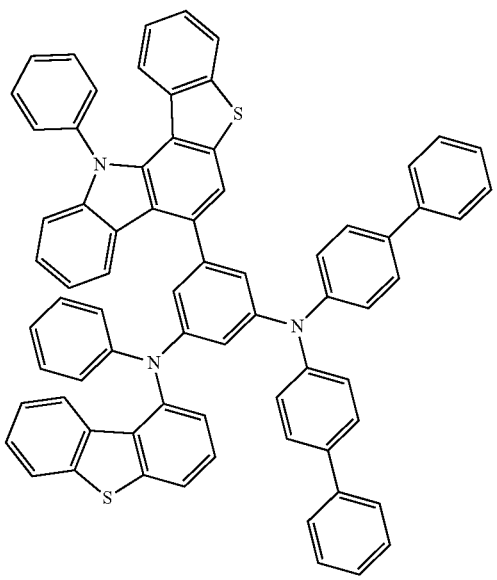
P-150
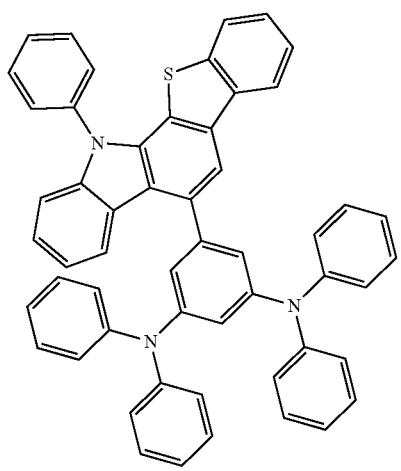
P-151
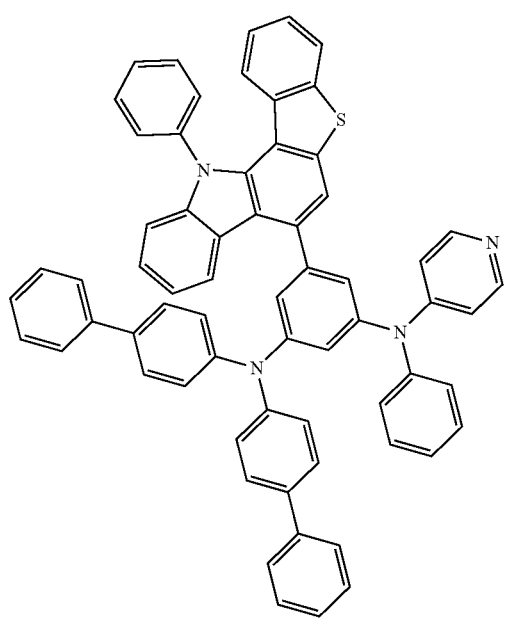
-continued
P-152
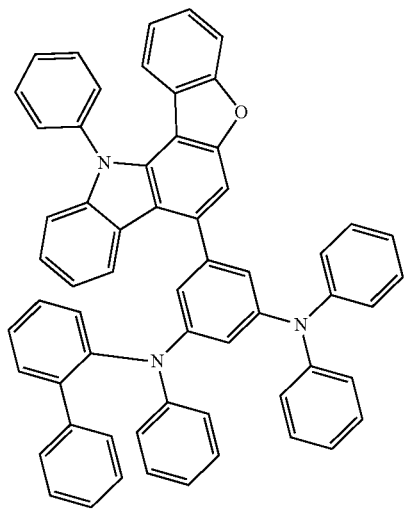
P-153
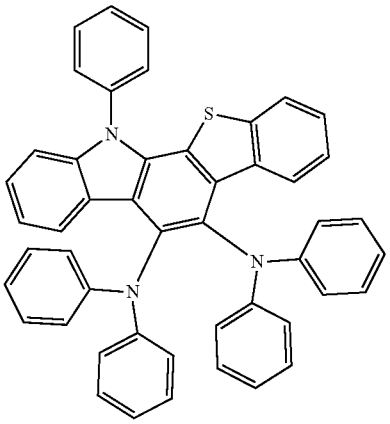
P-154
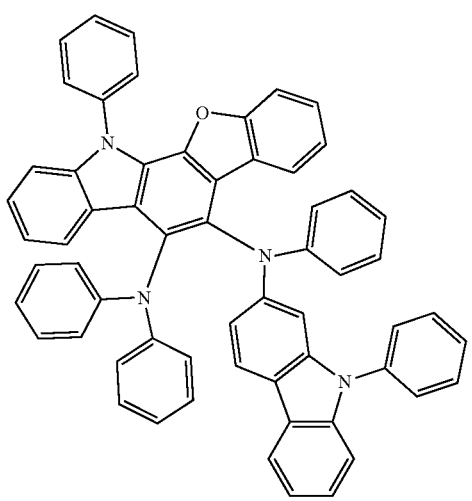

P-155

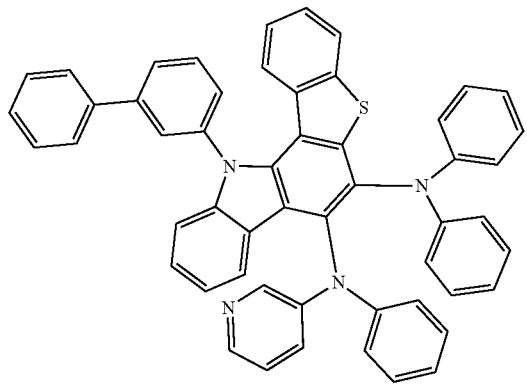

P-156

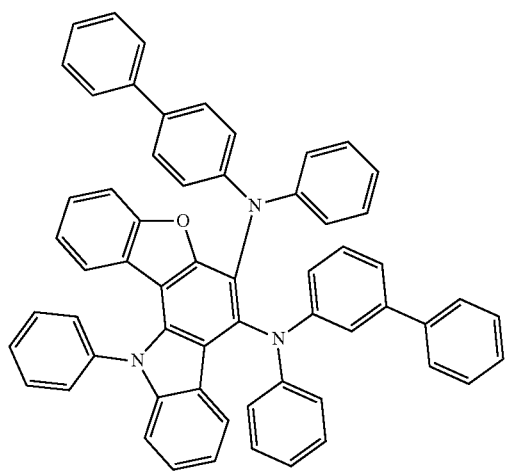

In another aspect of the present invention, the present invention provides an organic electric element comprising a first electrode, a second electrode, and an organic material layer formed between the first electrode and the second electrode, wherein the organic material layer comprises the compound represented by the formula 1 or is formed by the compound represented by the formula 1. Here, the compound represented by the formula 1 may be comprised in at least one of a hole injection layer, a hole transport layer, an emission-auxiliary layer, a light emitting layer, an electron transport auxiliary layer, an electron transport layers and an electron injection layer of the organic material layer as a single compound or as a component of the mixture of two or more kinds. That is, the compound represented by the formula 1 may be used as material of a hole injection layer, a hole transport layer, an emission-auxiliary layer, a light emitting layer, an electron transport auxiliary layer, an electron transport layers or an electron injection layer. Preferably, the compound represented by the formula 1 may be used as a phosphorescent host material of the light emitting layer, more preferably, a red phosphorescent host material.

In addition, the present invention, the present invention provides an organic electric element further comprising a layer for improving luminous efficiency formed on at least one side of sides of the first electrode and the second electrode, wherein at least one side is not facing the organic material layer.

Hereinafter, synthesis example of the compound represented by Formula 1 and preparation method of an organic electric element according to one embodiment of the present invention will be described in detail by way of examples. However, the present invention is not limited to the following examples.

Synthesis Example 1 (where p is 1)

For example, as shown in Reaction Scheme 1 below, the compounds (final products) represented by Formula 1 according to the present invention can be synthesized by reacting Sub 1 with Sub 2, but there is no limitation thereto.

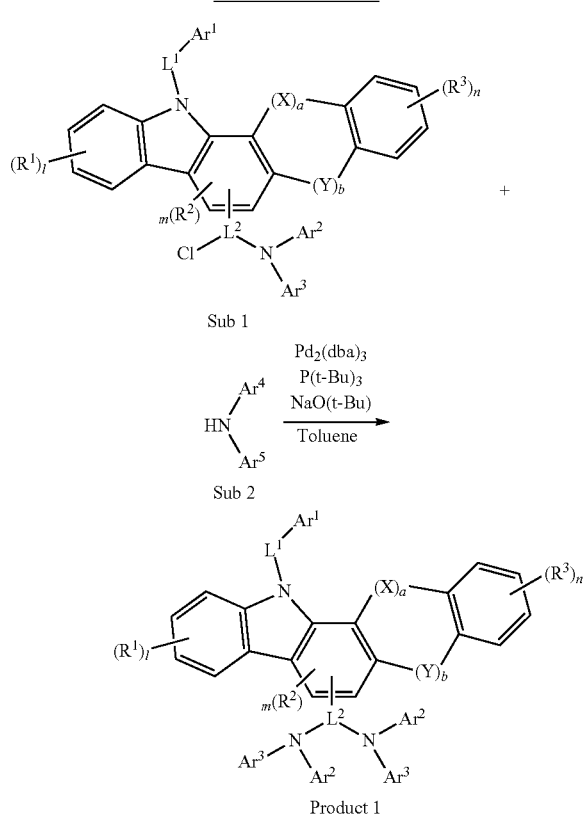

1. Synthesis Example of Sub 1

Sub 1 of the Reaction Scheme 1 can be synthesized according to the reaction route of the following Reaction Scheme 2, but there is no limitation thereto.

<Reaction Scheme 2>

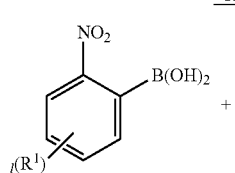

-continued
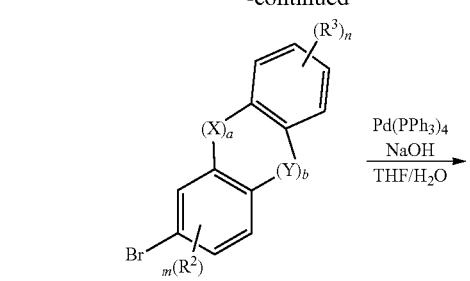
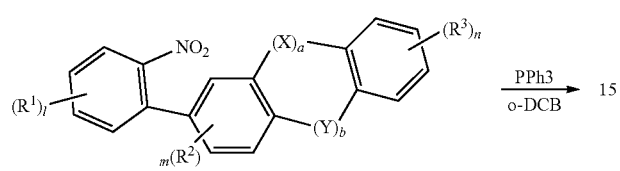
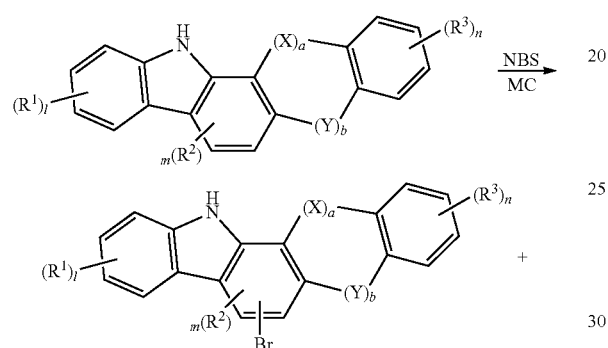
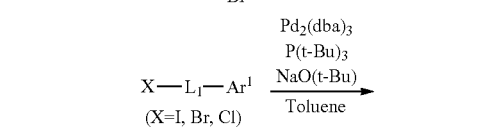
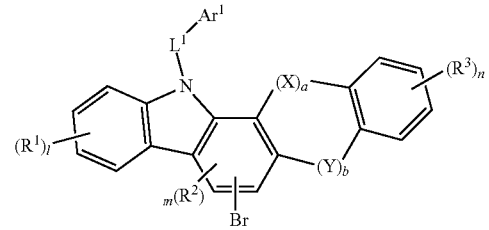
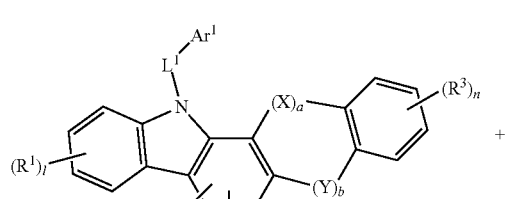
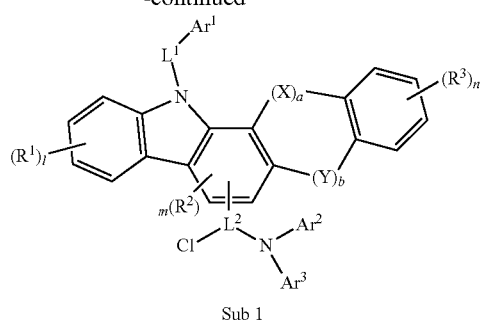
Sub 1
(1) Synthesis Example of Sub 1-2
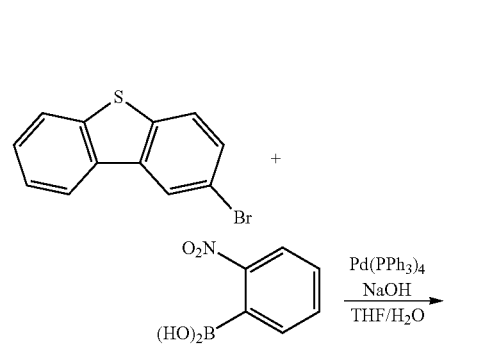
Sub 1-2-1
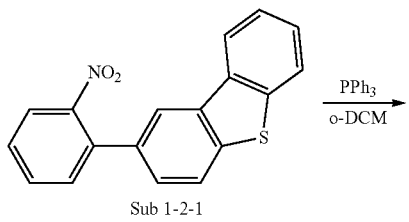
Sub 1-2-2
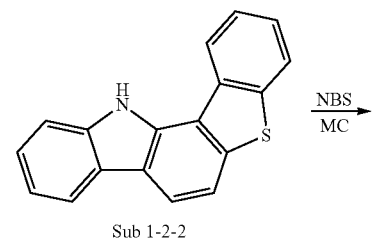
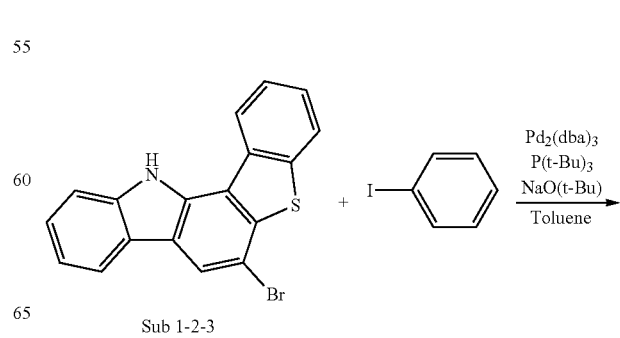
Sub 1-2-3

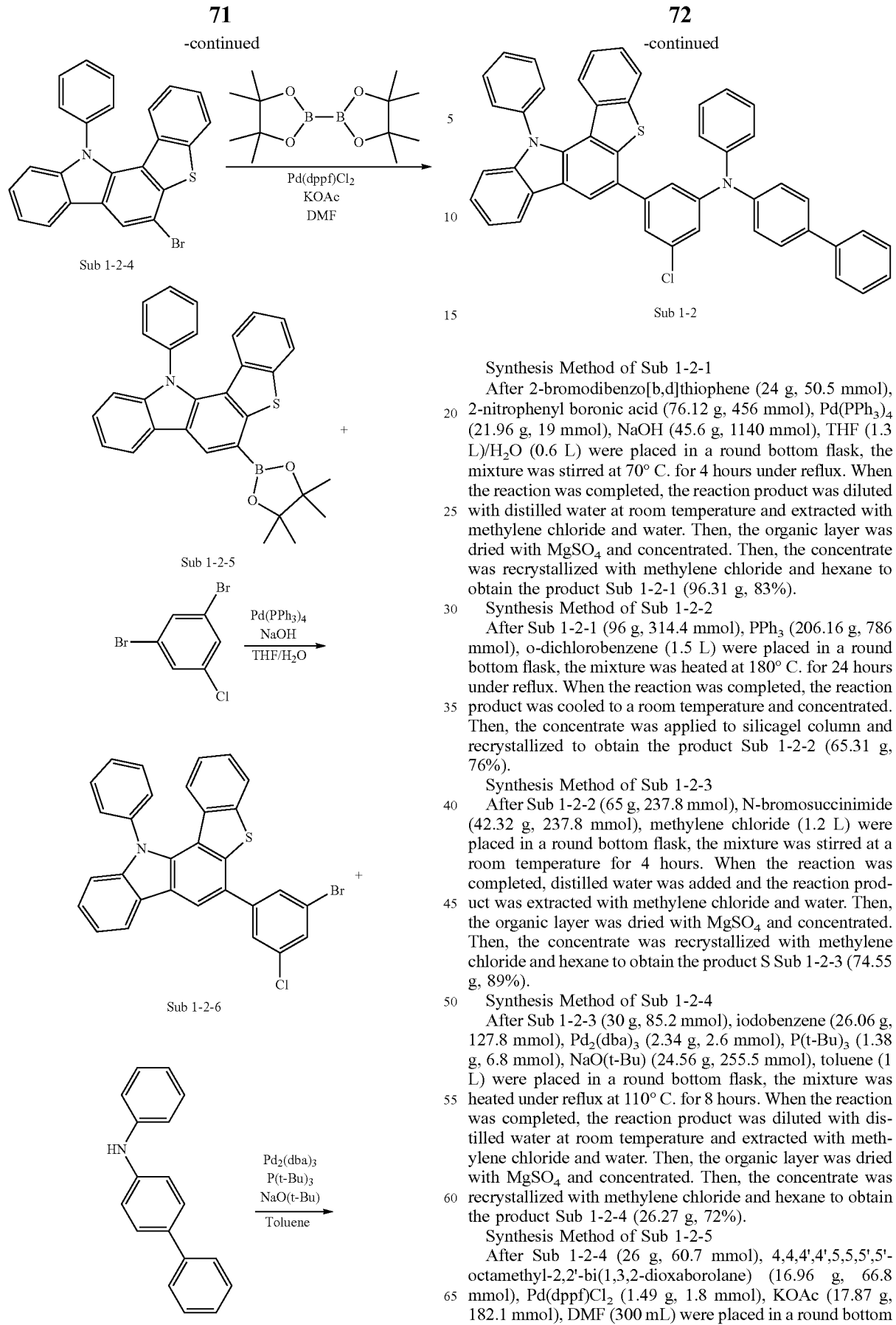

Synthesis Method of Sub 1-2-1

After 2-bromodibenzo[b,d]thiophene (24 g, 50.5 mmol), 2-nitrophenyl boronic acid (76.12 g, 456 mmol), Pd(PPh$_3$)$_4$ (21.96 g, 19 mmol), NaOH (45.6 g, 1140 mmol), THF (1.3 L)/H$_2$O (0.6 L) were placed in a round bottom flask, the mixture was stirred at 70° C. for 4 hours under reflux. When the reaction was completed, the reaction product was diluted with distilled water at room temperature and extracted with methylene chloride and water. Then, the organic layer was dried with MgSO$_4$ and concentrated. Then, the concentrate was recrystallized with methylene chloride and hexane to obtain the product Sub 1-2-1 (96.31 g, 83%).

Synthesis Method of Sub 1-2-2

After Sub 1-2-1 (96 g, 314.4 mmol), PPh$_3$ (206.16 g, 786 mmol), o-dichlorobenzene (1.5 L) were placed in a round bottom flask, the mixture was heated at 180° C. for 24 hours under reflux. When the reaction was completed, the reaction product was cooled to a room temperature and concentrated. Then, the concentrate was applied to silicagel column and recrystallized to obtain the product Sub 1-2-2 (65.31 g, 76%).

Synthesis Method of Sub 1-2-3

After Sub 1-2-2 (65 g, 237.8 mmol), N-bromosuccinimide (42.32 g, 237.8 mmol), methylene chloride (1.2 L) were placed in a round bottom flask, the mixture was stirred at a room temperature for 4 hours. When the reaction was completed, distilled water was added and the reaction product was extracted with methylene chloride and water. Then, the organic layer was dried with MgSO$_4$ and concentrated. Then, the concentrate was recrystallized with methylene chloride and hexane to obtain the product S Sub 1-2-3 (74.55 g, 89%).

Synthesis Method of Sub 1-2-4

After Sub 1-2-3 (30 g, 85.2 mmol), iodobenzene (26.06 g, 127.8 mmol), Pd$_2$(dba)$_3$ (2.34 g, 2.6 mmol), P(t-Bu)$_3$ (1.38 g, 6.8 mmol), NaO(t-Bu) (24.56 g, 255.5 mmol), toluene (1 L) were placed in a round bottom flask, the mixture was heated under reflux at 110° C. for 8 hours. When the reaction was completed, the reaction product was diluted with distilled water at room temperature and extracted with methylene chloride and water. Then, the organic layer was dried with MgSO$_4$ and concentrated. Then, the concentrate was recrystallized with methylene chloride and hexane to obtain the product Sub 1-2-4 (26.27 g, 72%).

Synthesis Method of Sub 1-2-5

After Sub 1-2-4 (26 g, 60.7 mmol), 4,4,4',4',5,5,5',5'-octamethyl-2,2'-bi(1,3,2-dioxaborolane) (16.96 g, 66.8 mmol), Pd(dppf)Cl$_2$ (1.49 g, 1.8 mmol), KOAc (17.87 g, 182.1 mmol), DMF (300 mL) were placed in a round bottom flask, the mixture was heated under reflux at 110° C. for 8 hours. When the reaction was completed, the reaction product was diluted with distilled water at room temperature and extracted with methylene chloride and water. Then, the organic layer was dried with MgSO$_4$ and concentrated. Then, the concentrate was dissolved in methylene chloride and then was applied to silica filter. Then, the resultant was concentrated and recrystallized with methylene chloride and hexane to obtain the product Sub 1-2-5 (24.82 g, 86%).

Synthesis Method of Sub 1-2-6

After Sub 1-2-5 (24 g, 50.5 mmol), 1,3-dibromo-5-chlorobenzene (16.38 g, 60.6 mmol), Pd(PPh$_3$)$_4$ (2.92 g, 2.5 mmol), NaOH (6.06 g, 151.4 mmol), THF (180 mL)/H$_2$O (90 mL) were placed in a round bottom flask, the mixture was heated under reflux at 70° C. for 4 hours. When the reaction was completed, the reaction product was diluted with distilled water at room temperature and extracted with methylene chloride and water. Then, the organic layer was dried with MgSO$_4$ and concentrated. Then, the concentrate was recrystallized with methylene chloride and hexane to obtain the product Sub 1-2-6 (20.4 g, 75%).

Synthesis Method of Sub 1-2

After Sub 1-2-6 (10 g, 18.6 mmol), N-phenyl-[1,1'-biphenyl]-4-amine (4.55 g, 18.6 mmol), Pd$_2$(dba)$_3$ (0.51 g, 0.6 mmol), P(t-Bu)$_3$ (0.30 g, 1.5 mmol), NaO(t-Bu) (5.35 g, 55.7 mmol), toluene (200 mL) were placed in a round bottom flask, the mixture was heated under reflux at 110° C. for 8 hours. When the reaction was completed, the reaction product was diluted with distilled water at room temperature and extracted with methylene chloride and water. Then, the organic layer was dried with MgSO$_4$ and concentrated. Then, the concentrate was recrystallized with methylene chloride and hexane to obtain the product Sub 1-2 (10.18 g, 78%).

(2) Synthesis Example of Sub 1-5

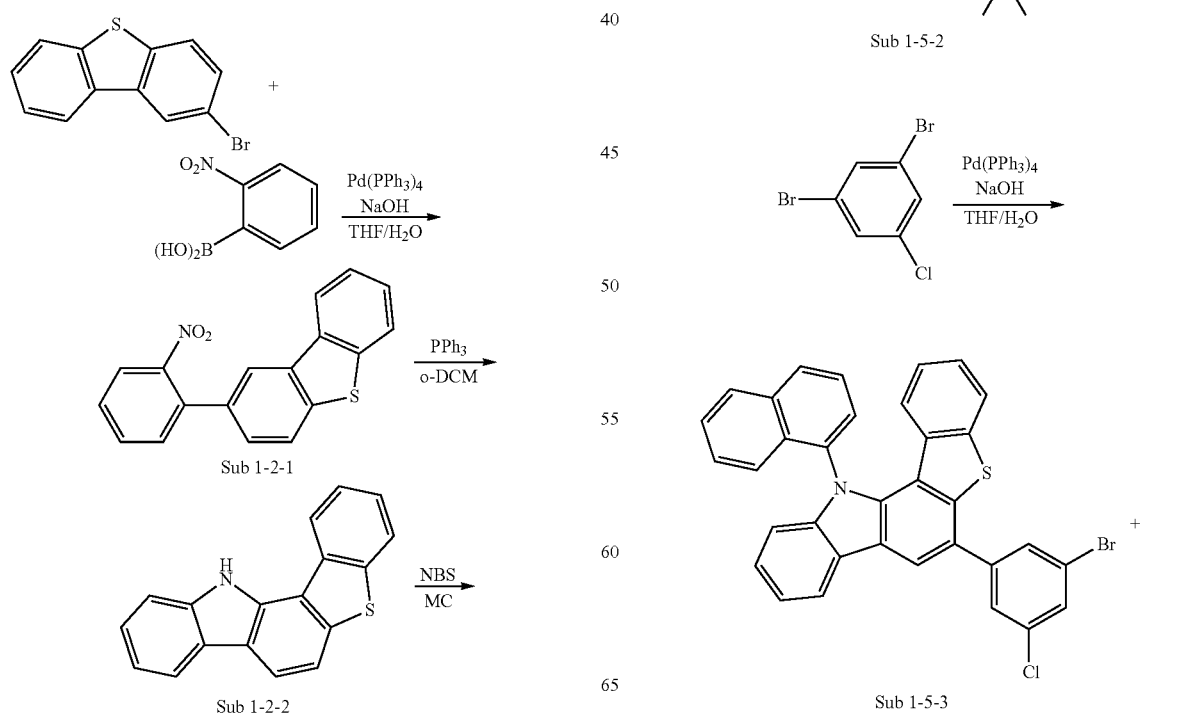

-continued

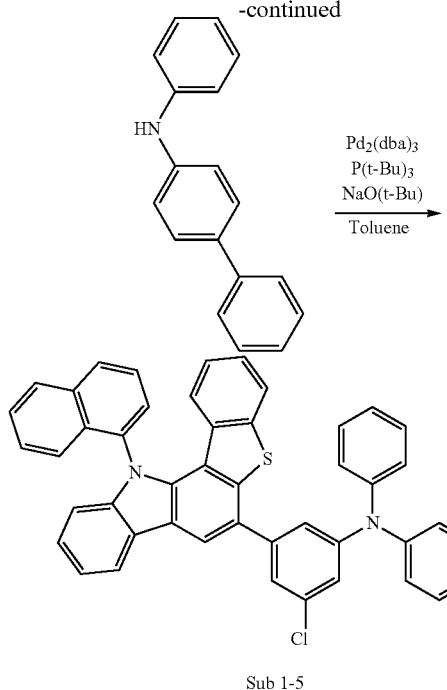

Sub 1-5

Synthesis Method of Sub 1-5-1

After Sub 1-2-3 (30 g, 85.2 mmol), 1-iodonaphthalene (32.46 g, 127.8 mmol), Pd$_2$(dba)$_3$ (2.34 g, 2.6 mmol), P(t-Bu)$_3$ (1.38 g, 6.8 mmol), NaO(t-Bu) (24.56 g, 255.5 mmol), toluene (1 L) were placed in a round bottom flask, the mixture was heated under reflux at 110° C. for 8 hours. When the reaction was completed, the reaction product was diluted with distilled water at room temperature and extracted with methylene chloride and water. Then, the organic layer was dried with MgSO$_4$ and concentrated. Then, the concentrate was recrystallized with methylene chloride and hexane to obtain the product Sub 1-5-1 (23.22 g, 57%).

Synthesis Method of Sub 1-5-2

After Sub 1-5-1 (23 g, 48.1 mmol), 4,4,4',4',5,5,5',5'-octamethyl-2,2'-bi(1,3,2-dioxaborolane) (13.43 g, 52.9 mmol), Pd(dppf)Cl$_2$ (1.18 g, 1.4 mmol), KOAc (14.15 g, 144.2 mmol), DMF (240 mL) were placed in a round bottom flask, the mixture was heated under reflux at 110° C. for 8 hours. When the reaction was completed, the reaction product was diluted with distilled water at room temperature and extracted with methylene chloride and water. Then, the organic layer was dried with MgSO$_4$ and concentrated. Then, the concentrate was dissolved in methylene chloride and then was applied to silica filter. Then, the resultant was concentrated and recrystallized with methylene chloride and hexane to obtain the product Sub 1-5-2 (20.46 g, 81%).

Synthesis Method of Sub 1-5-3

After Sub 1-5-2 (20 g, 38.1 mmol), 1,3-dibromo-5-chlorobenzene (12.35 g, 45.7 mmol), Pd(PPh$_3$)$_4$ (2.2 g, 1.9 mmol), NaOH (4.57 g, 114.2 mmol), THF (140 mL)/H$_2$O (70 mL) were placed in a round bottom flask, the mixture was heated under reflux at 70° C. for 4 hours. When the reaction was completed, the reaction product was diluted with distilled water at room temperature and extracted with methylene chloride and water. Then, the organic layer was dried with MgSO$_4$ and concentrated. Then, the concentrate was recrystallized with methylene chloride and hexane to obtain the product Sub 1-5-3 (17.48 g, 78%).

Synthesis Method of Sub 1-5

After Sub 1-5-3 (17 g, 28.9 mmol), N-phenyl-[1,1'-biphenyl]-4-amine (7.08 g, 28.9 mmol), Pd$_2$(dba)$_3$ (0.79 g, 0.9 mmol), P(t-Bu)$_3$ (0.47 g, 2.3 mmol), NaO(t-Bu) (8.32 g, 86.6 mmol), toluene (290 mL) were placed in a round bottom flask, the mixture was heated under reflux at 110° C. for 8 hours. When the reaction was completed, the reaction product was diluted with distilled water at room temperature and extracted with methylene chloride and water. Then, the organic layer was dried with MgSO$_4$ and concentrated. Then, the concentrate was recrystallized with methylene chloride and hexane to obtain the product Sub 1-5 (16.09 g, 74%).

(3) Synthesis Example of Sub 1-8

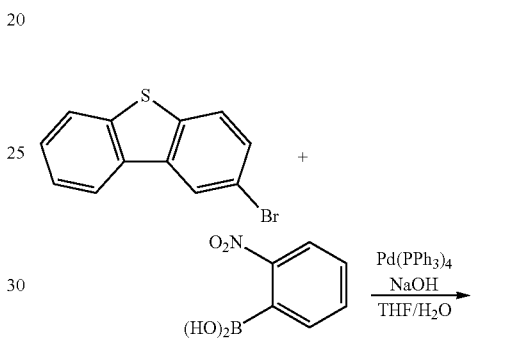

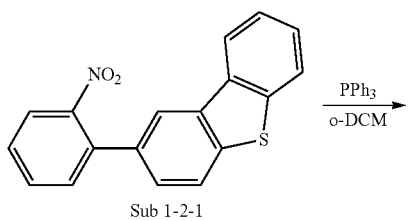

Sub 1-2-1

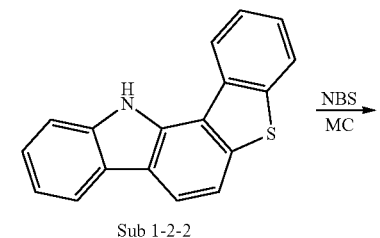

Sub 1-2-2

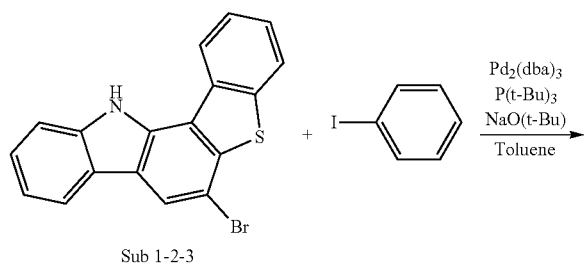

Sub 1-2-3

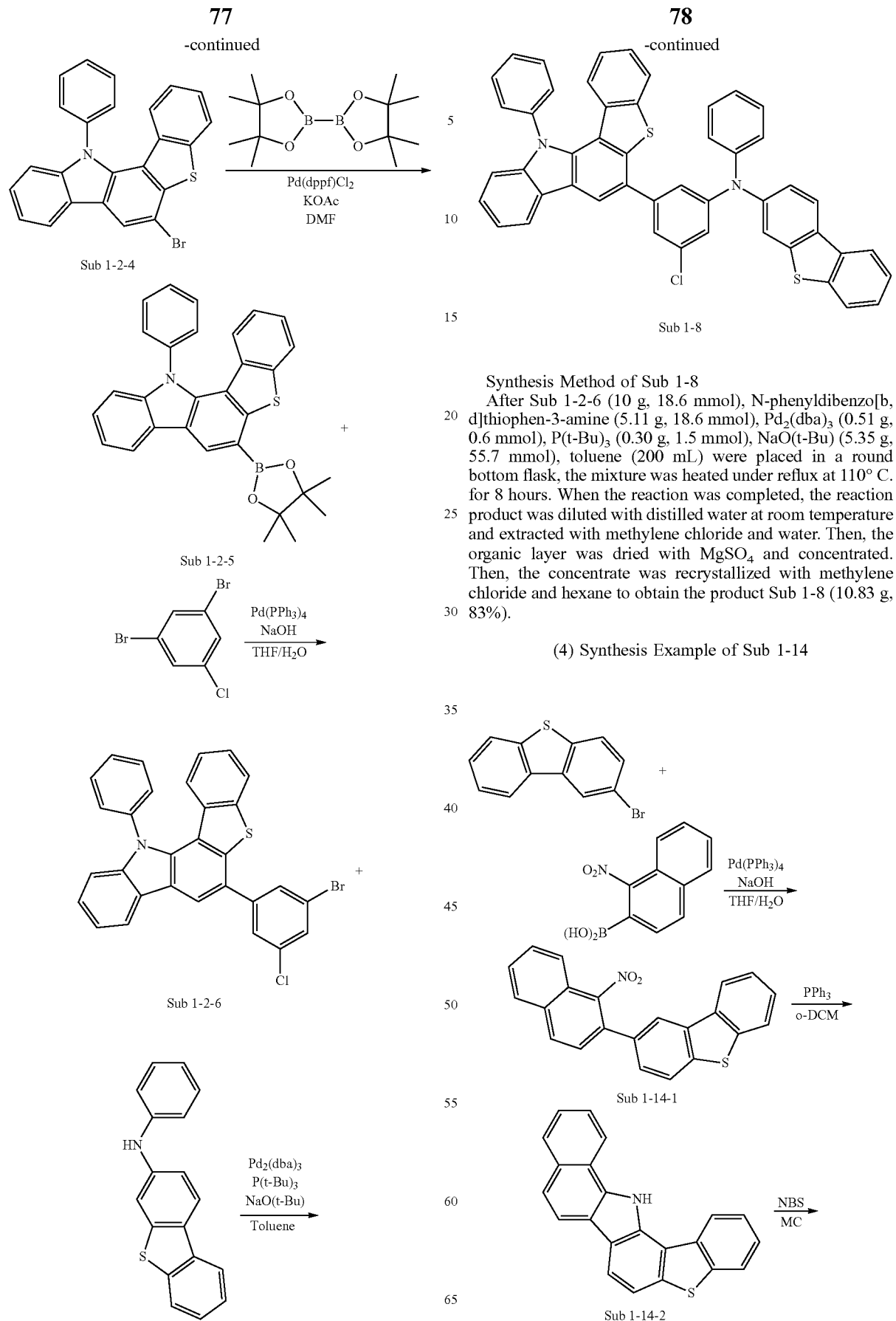

Synthesis Method of Sub 1-8

After Sub 1-2-6 (10 g, 18.6 mmol), N-phenyldibenzo[b,d]thiophen-3-amine (5.11 g, 18.6 mmol), Pd$_2$(dba)$_3$ (0.51 g, 0.6 mmol), P(t-Bu)$_3$ (0.30 g, 1.5 mmol), NaO(t-Bu) (5.35 g, 55.7 mmol), toluene (200 mL) were placed in a round bottom flask, the mixture was heated under reflux at 110° C. for 8 hours. When the reaction was completed, the reaction product was diluted with distilled water at room temperature and extracted with methylene chloride and water. Then, the organic layer was dried with MgSO$_4$ and concentrated. Then, the concentrate was recrystallized with methylene chloride and hexane to obtain the product Sub 1-8 (10.83 g, 83%).

(4) Synthesis Example of Sub 1-14

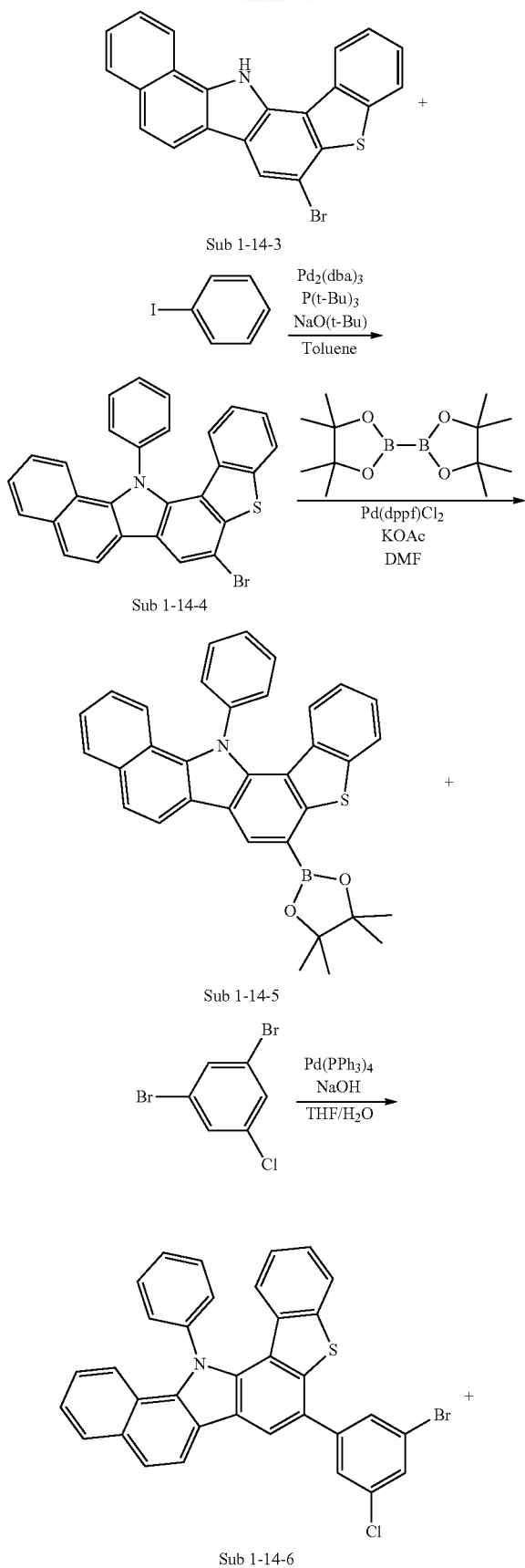

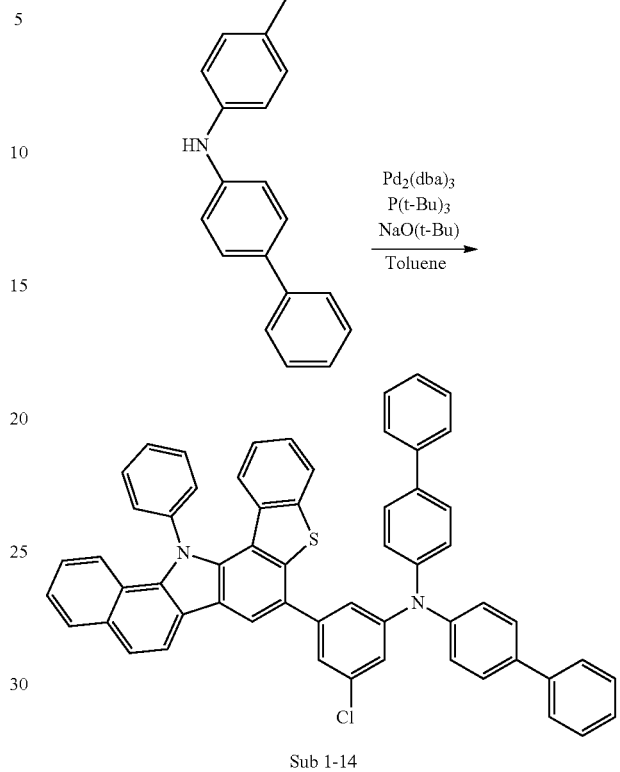

Synthesis Method of Sub 1-14-1

After 2-bromodibenzo[b,d]thiophene (30 g, 114 mmol), (1-nitronaphthalen-2-yl)boronic acid (29.69 g, 136.8 mmol), Pd(PPh$_3$)$_4$ (6.59 g, 5.7 mmol), NaOH (13.68 g, 342 mmol), THF (420 mL)/H$_2$O (210 L) were placed in a round bottom flask, the mixture was heated under reflux at 70° C. for 4 hours. When the reaction was completed, the reaction product was diluted with distilled water at room temperature and extracted with methylene chloride and water. Then, the organic layer was dried with MgSO$_4$ and concentrated. Then, the concentrate was recrystallized with methylene chloride and hexane to obtain the product Sub 1-14-1 (32.01 g, 79%).

Synthesis Method of Sub 1-14-2

After Sub 1-14-1 (27 g, 76.0 mmol), PPh$_3$ (49.81 g, 189.9 mmol), o-dichlorobenzene (380 mL) were placed in a round bottom flask, the mixture was heated at 180° C. for 24 hours under reflux. When the reaction was completed, the reaction product was cooled to a room temperature and concentrated. Then, the concentrate was applied to silicagel column and recrystallized to obtain the product Sub 1-14-2 (17.44 g, 71%).

Synthesis Method of Sub 1-14-3

After Sub 1-4-2 (17 g, 52.6 mmol), N-bromosuccinimide (9.36 g, 52.6 mmol), methylene chloride (260 mL) were placed in a round bottom flask, the mixture was stirred at a room temperature for 4 hours. When the reaction was completed, distilled water was added and the reaction product was extracted with methylene chloride and water. Then, the organic layer was dried with MgSO$_4$ and concentrated. Then, the concentrate was recrystallized with methylene chloride and hexane to obtain the product Sub 1-14-3 (17.76 g, 84%).

Synthesis Method of Sub 1-14-4

After Sub 1-14-3 (18 g, 44.7 mmol), iodobenzene (13.69 g, 67.1 mmol), Pd$_2$(dba)$_3$ (1.23 g, 1.3 mmol), P(t-Bu)$_3$ (0.72 g, 3.6 mmol), NaO(t-Bu) (12.9 g, 134.2 mmol), toluene (550 mL) were placed in a round bottom flask, the mixture was heated under reflux at 110° C. for 8 hours. When the reaction was completed, the reaction product was diluted with distilled water at room temperature and extracted with methylene chloride and water. Then, the organic layer was dried with MgSO$_4$ and concentrated. Then, the concentrate was recrystallized with methylene chloride and hexane to obtain the product Sub 1-14-4 (16.05 g, 75%).

Synthesis Method of Sub 1-14-5

After Sub 1-14-4 (16 g, 33.4 mmol), 4,4,4',4',5,5,5',5'-octamethyl-2,2'-bi(1,3,2-dioxaborolane) (9.34 g, 36.8 mmol), Pd(dppf)Cl$_2$ (0.82 g, 1.0 mmol), KOAc (9.85 g, 100.3 mmol), DMF (170 mL) were placed in a round bottom flask, the mixture was heated under reflux at 110° C. for 8 hours. When the reaction was completed, the reaction product was diluted with distilled water at room temperature and extracted with methylene chloride and water. Then, the organic layer was dried with MgSO$_4$ and concentrated. Then, the concentrate was dissolved in methylene chloride and then was applied to silica filter. Then, the resultant was concentrated and recrystallized with methylene chloride and hexane to obtain the product Sub 1-14-5 (14.94 g, 85%).

Synthesis Method of Sub 1-14-6

After Sub 1-14-6 (15 g, mmol), 1,3-dibromo-5-chlorobenzene (9.26 g, 34.3 mmol), Pd(PPh$_3$)$_4$ (1.65 g, 1.4 mmol), NaOH (3.43 g, 85.6 mmol), THF (100 mL)/H$_2$O (50 mL) were placed in a round bottom flask, the mixture was heated under reflux at 70° C. for 4 hours. When the reaction was completed, the reaction product was diluted with distilled water at room temperature and extracted with methylene chloride and water. Then, the organic layer was dried with MgSO$_4$ and concentrated. Then, the concentrate was recrystallized with methylene chloride and hexane to obtain the product Sub 1-14-6 (13.11 g, 78%).

Synthesis Method of Sub 1-14

After Sub 1-14-6 (13 g, 22.1 mmol), di([1,1'-biphenyl]-4-yl)amine (7.1 g, 22.1 mmol), Pd$_2$(dba)$_3$ (0.61 g, 0.7 mmol), P(t-Bu)$_3$ (0.36 g, 1.8 mmol), NaO(t-Bu) (6.36 g, 66.2 mmol), toluene (220 mL) were placed in a round bottom flask, the mixture was heated under reflux at 110° C. for 8 hours. When the reaction was completed, the reaction product was diluted with distilled water at room temperature and extracted with methylene chloride and water. Then, the organic layer was dried with MgSO$_4$ and concentrated. Then, the concentrate was recrystallized with methylene chloride and hexane to obtain the product Sub 1-14 (14.8 g, 81%).

(5) Synthesis Example of Sub 1-23

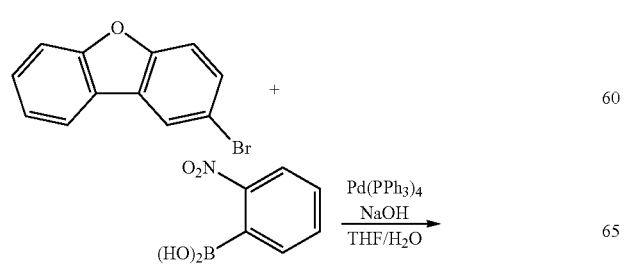

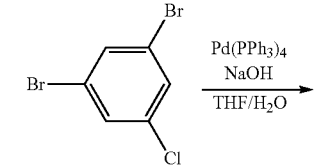

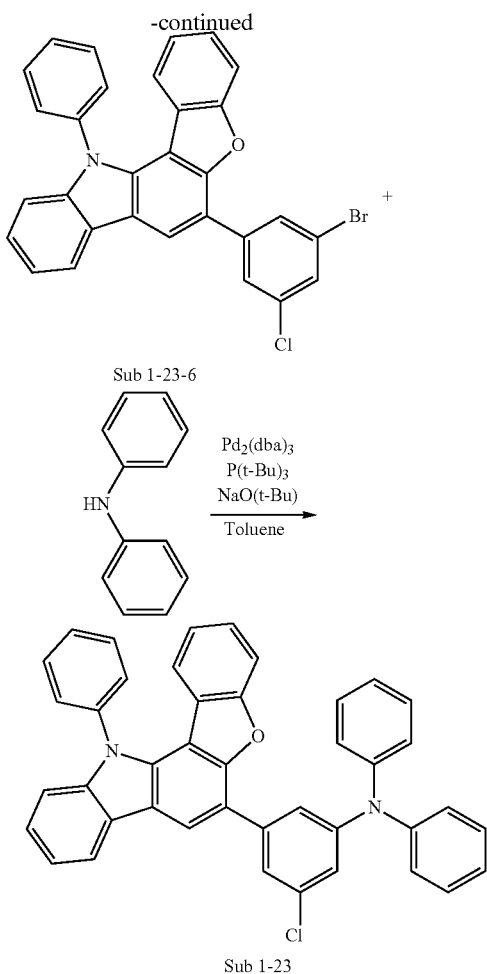

Sub 1-23

Synthesis Method of Sub 1-23-1

After 2-bromodibenzo[b,d]furan (250 g, 1011.8 mmol), 2-nitrophenyl boronic acid (202.68 g, 1214.1 mmol), Pd(PPh$_3$)$_4$ (58.46 g, 50.6 mmol), NaOH (121.41 g, 3035.3 mmol), THF (3.7 L)/H$_2$O (1.9 L) were placed in a round bottom flask, the mixture was heated under reflux at 70° C. for 4 hours. When the reaction was completed, the reaction product was diluted with distilled water at room temperature and extracted with methylene chloride and water. Then, the organic layer was dried with MgSO$_4$ and concentrated. Then, the concentrate was recrystallized with methylene chloride and hexane to obtain the product Sub 1-23-1 (225.38 g, 77%).

Synthesis Method of Sub 1-23-2

After Sub 1-23-1 (223 g, 770.9 mmol), PPh$_3$ (505.47 g, 1927.1 mmol), o-dichlorobenzene (3.8 L) were placed in a round bottom flask, the mixture was heated at 180° C. for 24 hours under reflux. When the reaction was completed, the reaction product was cooled to a room temperature and concentrated. Then, the concentrate was applied to silicagel column and recrystallized to obtain the product Sub 1-23-2 (144.78 g, 73%).

Synthesis Method of Sub 1-23-3

After Sub 1-23-2 (145 g, 563.6 mmol), N-bromosuccinimide (100.31 g, 563.6 mmol), m chloride (2.8 L) were placed in a round bottom flask, the mixture was stirred at a room temperature for 4 hours. When the reaction was completed, distilled water was added and the reaction product was extracted with methylene chloride and water. Then, the organic layer was dried with MgSO$_4$ and concentrated. Then, the concentrate was recrystallized with methylene chloride and hexane to obtain the product Sub 1-23-3 (164.83 g, 87%).

Synthesis Method of Sub 1-23-4

After Sub 1-2-3 (120 g, 356.9 mmol), iodobenzene (109.23 g, 535.4 mmol), Pd$_2$(dba)$_3$ (9.81 g, 10.7 mmol), P(t-Bu)$_3$ (2.78 g, 28.6 mmol), NaO(t-Bu) (102.92 g, 1070.8 mmol), toluene (4.4 L) were placed in a round bottom flask, the mixture was heated under reflux at 110° C. for 8 hours. When the reaction was completed, distilled water was added and the reaction product was extracted with methylene chloride and water. Then, the organic layer was dried with MgSO$_4$ and concentrated. Then, the concentrate was recrystallized with methylene chloride and hexane to obtain the product Sub 1-23-4 (108.9 g, 89%).

Synthesis Method of Sub 1-23-5

After Sub 1-23-4 (70 g, 169.8 mmol), 4,4,4',4',5,5,5',5'-octamethyl-2,2'-bi(1,3,2-dioxaborolane) (47.43 g, 186.8 mmol), Pd(dppf)Cl$_2$ (4.16 g, 5.1 mmol), KOAc (49.99 g, 509.4 mmol), DMF (850 mL) were placed in a round bottom flask, the mixture was heated under reflux at 110° C. for 8 hours. When the reaction was completed, the reaction product was diluted with distilled water at room temperature and extracted with methylene chloride and water. Then, the organic layer was dried with MgSO$_4$ and concentrated. Then, the concentrate was dissolved in methylene chloride and then was applied to silica filter. Then, the resultant was concentrated and recrystallized with methylene chloride and hexane to obtain the product Sub 1-23-5 (69.41 g, 89%).

Synthesis Method of Sub 1-23-6

After Sub 1-23-5 (69 g, 150.2 mmol), 1,3-dibromo-5-chlorobenzene (48.73 g, 180.3 mmol), Pd(PPh$_3$)$_4$ (8.68 g, 7.5 mmol), NaOH (18.03 g, 450.6 mmol), THF (550 mL)/H$_2$O (270 mL) were placed in a round bottom flask, the mixture was heated under reflux at 70° C. for 4 hours. When the reaction was completed, the reaction product was diluted with distilled water at room temperature and extracted with methylene chloride and water. Then, the organic layer was dried with MgSO$_4$ and concentrated. Then, the concentrate was recrystallized with methylene chloride and hexane to obtain the product Sub 1-23-6 (62.83 g, 80%).

Synthesis Method of Sub 1-23

After Sub 1-23-6 (10 g, 19.1 mmol), diphenylamine (3.24 g, 19.1 mmol), Pd$_2$(dba)$_3$ (0.53 g, 0.6 mmol), P(t-Bu)$_3$ (0.31 g, 1.5 mmol), NaO(t-Bu) (5.51 g, 57.4 mmol), toluene (190 mL) were placed in a round bottom flask, the mixture was heated under reflux at 110° C. for 8 hours. When the reaction was completed, the reaction product was diluted with distilled water and extracted with methylene chloride and water. Then, the organic layer was dried with MgSO$_4$ and concentrated. Then, the concentrate was recrystallized with methylene chloride and hexane to obtain the product Sub 1-23 (10.09 g, 89%).

(6) Synthesis Example of Sub 1-24

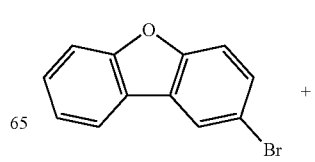

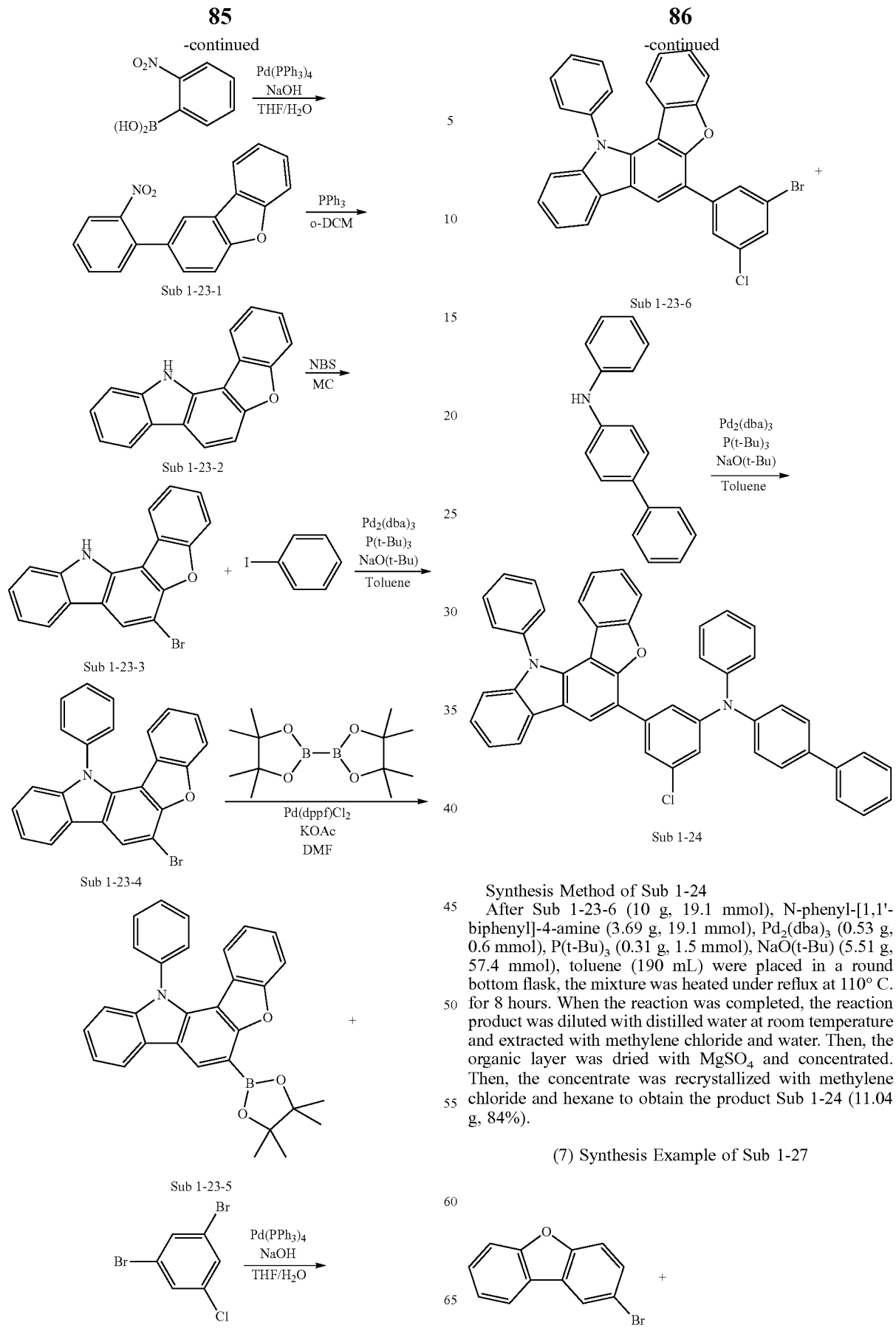

Synthesis Method of Sub 1-24

After Sub 1-23-6 (10 g, 19.1 mmol), N-phenyl-[1,1'-biphenyl]-4-amine (3.69 g, 19.1 mmol), Pd$_2$(dba)$_3$ (0.53 g, 0.6 mmol), P(t-Bu)$_3$ (0.31 g, 1.5 mmol), NaO(t-Bu) (5.51 g, 57.4 mmol), toluene (190 mL) were placed in a round bottom flask, the mixture was heated under reflux at 110° C. for 8 hours. When the reaction was completed, the reaction product was diluted with distilled water at room temperature and extracted with methylene chloride and water. Then, the organic layer was dried with MgSO$_4$ and concentrated. Then, the concentrate was recrystallized with methylene chloride and hexane to obtain the product Sub 1-24 (11.04 g, 84%).

(7) Synthesis Example of Sub 1-27

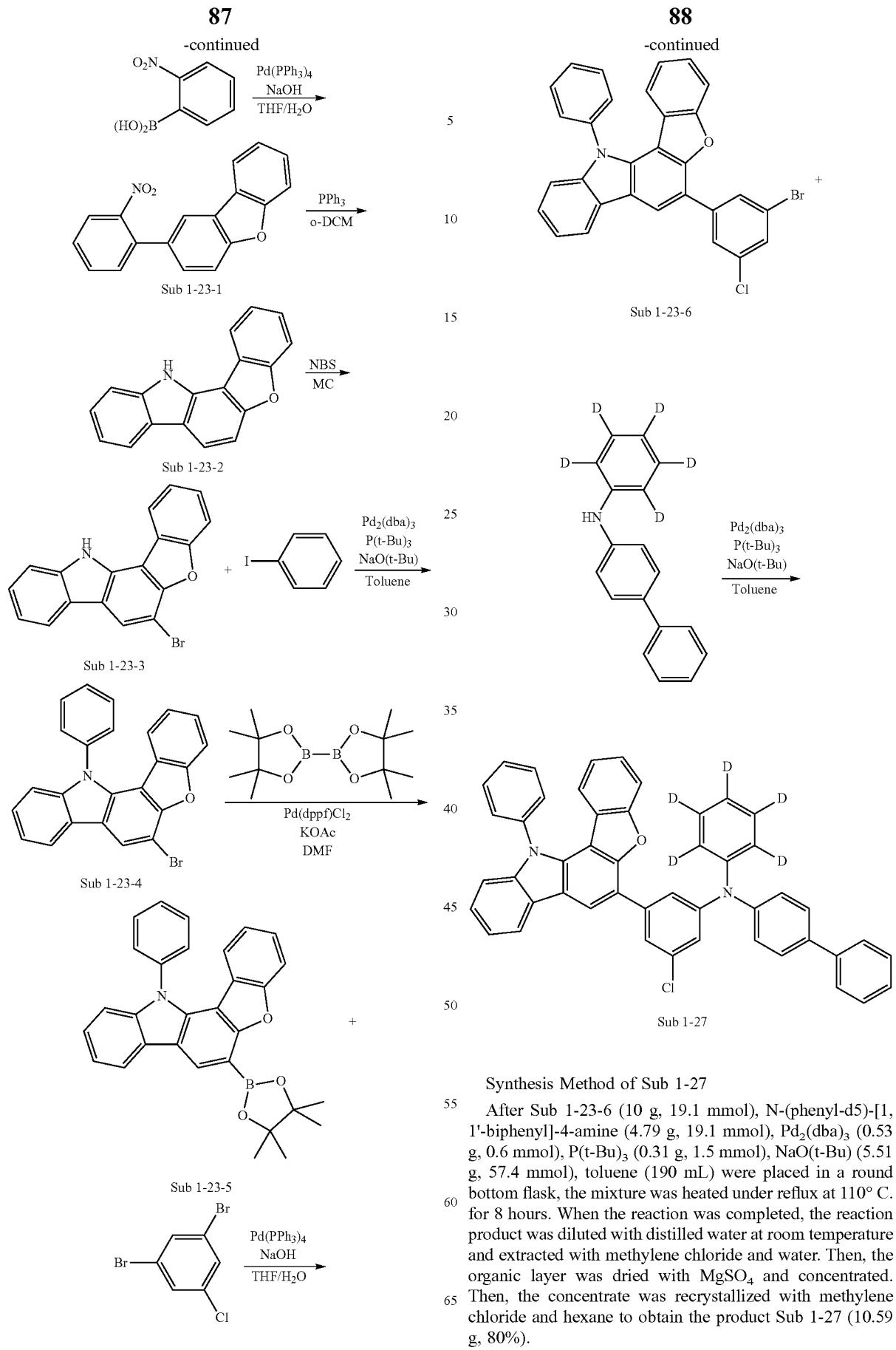

Synthesis Method of Sub 1-27

After Sub 1-23-6 (10 g, 19.1 mmol), N-(phenyl-d5)-[1,1'-biphenyl]-4-amine (4.79 g, 19.1 mmol), Pd$_2$(dba)$_3$ (0.53 g, 0.6 mmol), P(t-Bu)$_3$ (0.31 g, 1.5 mmol), NaO(t-Bu) (5.51 g, 57.4 mmol), toluene (190 mL) were placed in a round bottom flask, the mixture was heated under reflux at 110° C. for 8 hours. When the reaction was completed, the reaction product was diluted with distilled water at room temperature and extracted with methylene chloride and water. Then, the organic layer was dried with MgSO$_4$ and concentrated. Then, the concentrate was recrystallized with methylene chloride and hexane to obtain the product Sub 1-27 (10.59 g, 80%).

(8) Synthesis Example of Sub 1-32
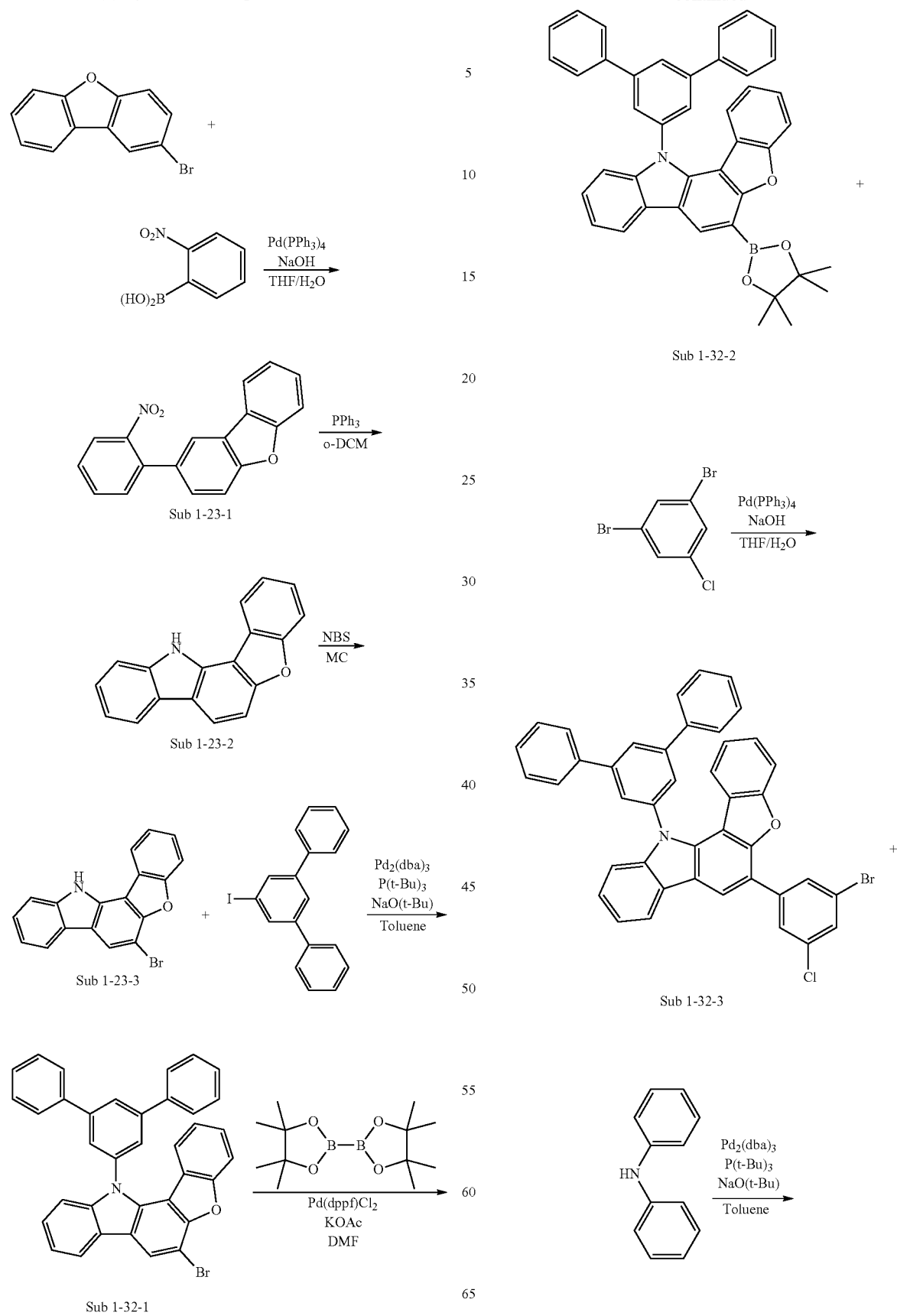

-continued

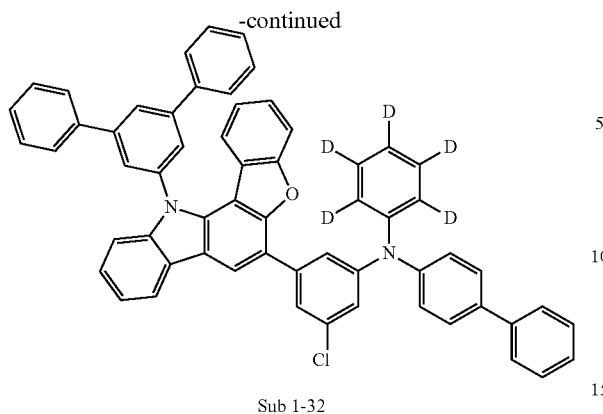

Sub 1-32

Synthesis Method of Sub 1-32-1

After Sub 1-23-3 (120 g, 356.9 mmol), 5'-iodo-1,1':3',1"-terphenyl (190.72 g, 535.4 mmol), Pd$_2$(dba)$_3$ (9.81 g, 10.7 mmol), P(t-Bu)$_3$ (5.78 g, 28.6 mmol), NaO(t-Bu) (102.92 g, 1070.8 mmol), toluene (4.5 L) were placed in a round bottom flask, the mixture was heated under reflux at 110° C. for 8 hours. When the reaction was completed, the reaction product was diluted with distilled water at room temperature and extracted with methylene chloride and water. Then, the organic layer was dried with MgSO$_4$ and concentrated. Then, the concentrate was recrystallized with methylene chloride and hexane to obtain the product Sub 1-32-1 (149.1 g, 74%).

Synthesis Method of Sub 1-32-2

After Sub 1-32-1 (70 g, 124 mmol), 4,4,4',4',5,5,5',5'-octamethyl-2,2'-bi(1,3,2-dioxaborolane) (34.64 g, 136.4 mmol), Pd(dppf)Cl$_2$ (3.04 g, 3.7 mmol), KOAc (36.51 g, 372 mmol), DMF (620 mL) were placed in a round bottom flask, the mixture was heated under reflux at 110° C. for 8 hours. When the reaction was completed, the reaction product was diluted with distilled water at room temperature and extracted with methylene chloride and water. Then, the organic layer was dried with MgSO$_4$ and concentrated. Then, the concentrate was dissolved in methylene chloride and then was applied to silica filter. Then, the resultant was concentrated and recrystallized with methylene chloride and hexane to obtain the product Sub 1-32-3 (67.49 g, 89%).

Synthesis Method of Sub 1-32-3

After Sub 1-32-2 (69 g, 112.8 mmol), 1,3-dibromo-5-chlorobenzene (36.6 g, 135.4 mmol), Pd(PPh$_3$)$_4$ (6.52 g, 5.6 mmol), NaOH (13.54 g, 338.5 mmol), THF (410 mL)/H$_2$O (200 mL) were placed in a round bottom flask, the mixture was heated under reflux at 70° C. for 4 hours. When the reaction was completed, the reaction product was diluted with distilled water at room temperature and extracted with methylene chloride and water. Then, the organic layer was dried with MgSO$_4$ and concentrated. Then, the concentrate was recrystallized with methylene chloride and hexane to obtain the product Sub 1-32-3 (60.93 g, 80%).

Synthesis Method of Sub 1-32

After Sub 1-32-3 (10 g, 14.8 mmol), diphenylamine (2.51 g, 14.8 mmol), Pd$_2$(dba)$_3$ (0.41 g, 0.4 mmol), P(t-Bu)$_3$ (0.24 g, 1.2 mmol), NaO(t-Bu) (4.27 g, 44.4 mmol), toluene (150 mL) were placed in a round bottom flask, the mixture was heated under reflux at 110° C. for 8 hours. When the reaction was completed, the reaction product was diluted with distilled water at room temperature and extracted with methylene chloride and water. Then, the organic layer was dried with MgSO$_4$ and concentrated. Then, the concentrate was recrystallized with methylene chloride and hexane to obtain the product Sub 1-32 (9.05 g, 80%).

(9) Synthesis Example of Sub 1-37

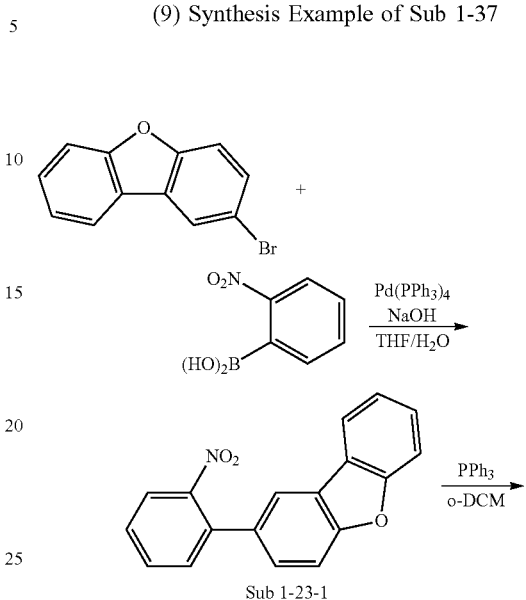

Sub 1-23-1

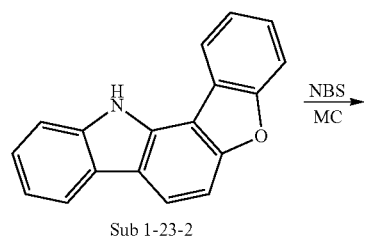

Sub 1-23-2

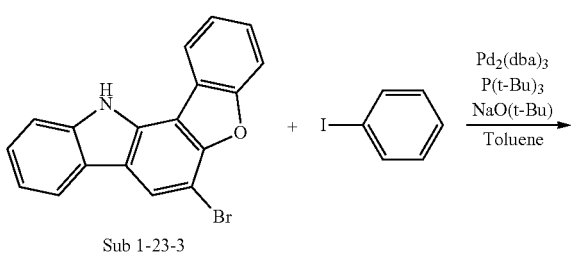

Sub 1-23-3

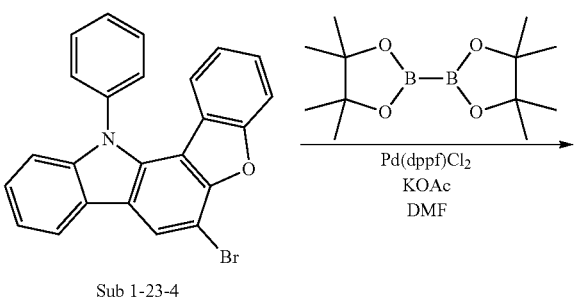

Sub 1-23-4

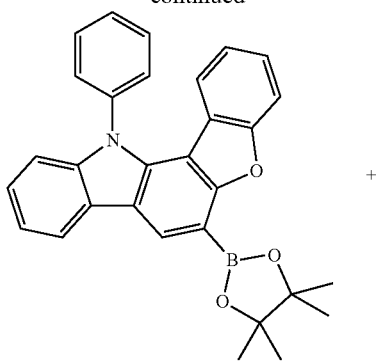

Sub 1-23-5

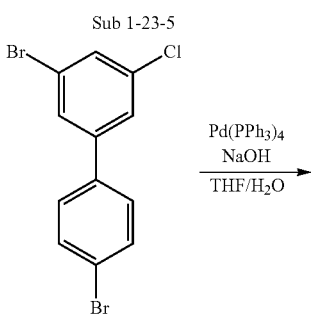

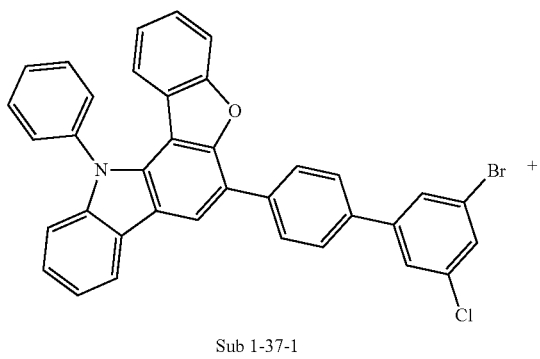

Sub 1-37-1

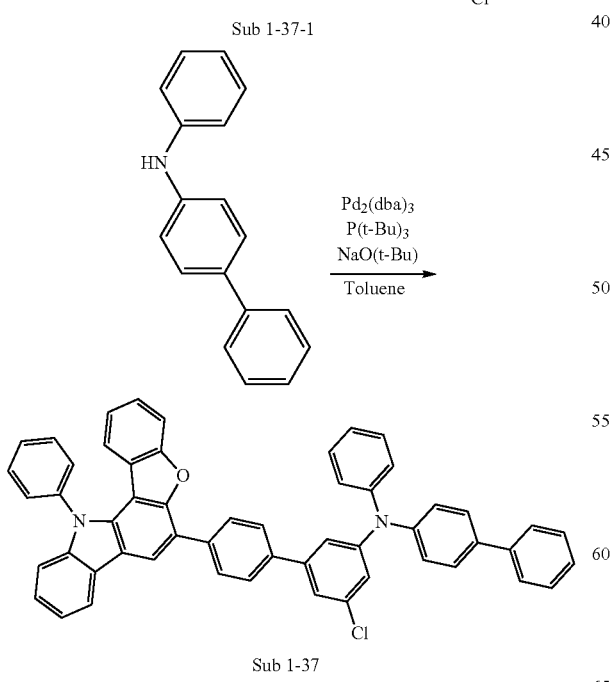

Sub 1-37

Synthesis Method of Sub 1-37-1

After Sub 1-23-5 (20 g, 43.5 mmol), 3,4'-dibromo-5-chloro-1,1'-biphenyl (18.1 g, 52.2 mmol), Pd(PPh$_3$)$_4$ (2.52 g, 2.2 mmol), NaOH (5.22 g, 130.6 mmol), THF (160 mL)/H$_2$O (80 mL) were placed in a round bottom flask, the mixture was heated under reflux at 70° C. for 4 hours. When the reaction was completed, the reaction product was diluted with distilled water at room temperature and extracted with methylene chloride and water. Then, the organic layer was dried with MgSO$_4$ and concentrated. Then, the concentrate was recrystallized with methylene chloride and hexane to obtain the product Sub 1-37-1 (23.21 g, 89%).

Synthesis Method of Sub 1-37

After Sub 1-37-1 (10 g, 19.1 mmol), diphenylamine (3.24 g, 19.1 mmol), Pd$_2$(dba)$_3$ (0.53 g, 0.6 mmol), P(t-Bu)$_3$ (0.31 g, 1.5 mmol), NaO(t-Bu) (5.51 g, 57.4 mmol), toluene (190 mL) were placed in a round bottom flask, the mixture was heated under reflux at 110° C. for 8 hours. When the reaction was completed, the reaction product was diluted with distilled water at room temperature and extracted with methylene chloride and water. Then, the organic layer was dried with MgSO$_4$ and concentrated. Then, the concentrate was recrystallized with methylene chloride and hexane to obtain the product Sub 1-23 (10.09 g, 89%).

(10) Synthesis Example of Sub 1-41

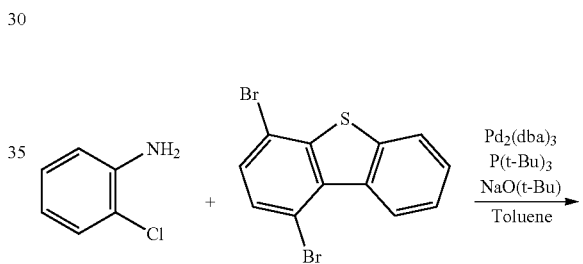

Sub 1-41-1

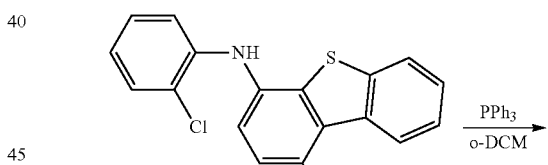

Sub 1-41-2

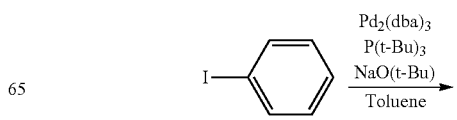

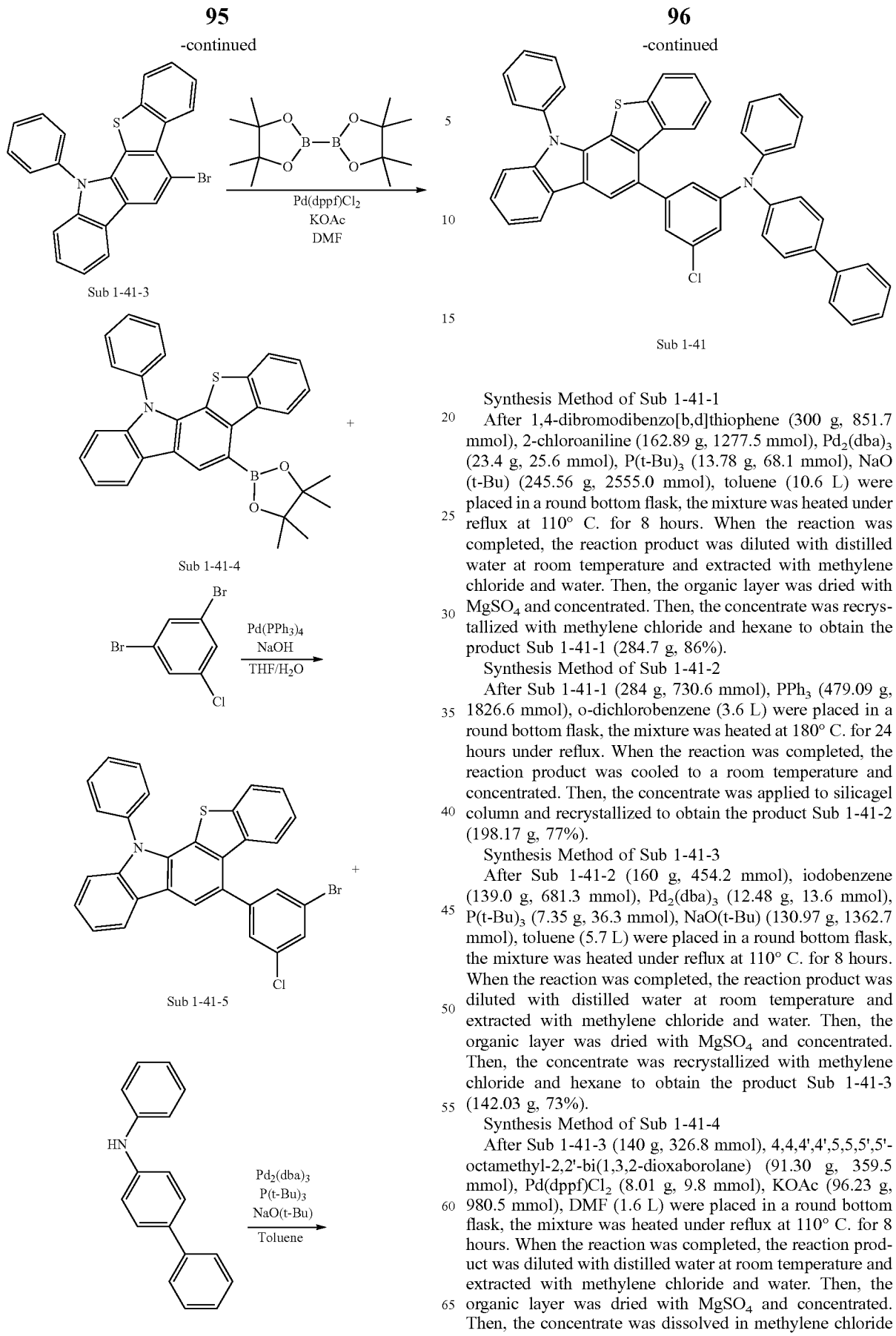

Synthesis Method of Sub 1-41-1

After 1,4-dibromodibenzo[b,d]thiophene (300 g, 851.7 mmol), 2-chloroaniline (162.89 g, 1277.5 mmol), Pd$_2$(dba)$_3$ (23.4 g, 25.6 mmol), P(t-Bu)$_3$ (13.78 g, 68.1 mmol), NaO(t-Bu) (245.56 g, 2555.0 mmol), toluene (10.6 L) were placed in a round bottom flask, the mixture was heated under reflux at 110° C. for 8 hours. When the reaction was completed, the reaction product was diluted with distilled water at room temperature and extracted with methylene chloride and water. Then, the organic layer was dried with MgSO$_4$ and concentrated. Then, the concentrate was recrystallized with methylene chloride and hexane to obtain the product Sub 1-41-1 (284.7 g, 86%).

Synthesis Method of Sub 1-41-2

After Sub 1-41-1 (284 g, 730.6 mmol), PPh$_3$ (479.09 g, 1826.6 mmol), o-dichlorobenzene (3.6 L) were placed in a round bottom flask, the mixture was heated at 180° C. for 24 hours under reflux. When the reaction was completed, the reaction product was cooled to a room temperature and concentrated. Then, the concentrate was applied to silicagel column and recrystallized to obtain the product Sub 1-41-2 (198.17 g, 77%).

Synthesis Method of Sub 1-41-3

After Sub 1-41-2 (160 g, 454.2 mmol), iodobenzene (139.0 g, 681.3 mmol), Pd$_2$(dba)$_3$ (12.48 g, 13.6 mmol), P(t-Bu)$_3$ (7.35 g, 36.3 mmol), NaO(t-Bu) (130.97 g, 1362.7 mmol), toluene (5.7 L) were placed in a round bottom flask, the mixture was heated under reflux at 110° C. for 8 hours. When the reaction was completed, the reaction product was diluted with distilled water at room temperature and extracted with methylene chloride and water. Then, the organic layer was dried with MgSO$_4$ and concentrated. Then, the concentrate was recrystallized with methylene chloride and hexane to obtain the product Sub 1-41-3 (142.03 g, 73%).

Synthesis Method of Sub 1-41-4

After Sub 1-41-3 (140 g, 326.8 mmol), 4,4,4',4',5,5,5',5'-octamethyl-2,2'-bi(1,3,2-dioxaborolane) (91.30 g, 359.5 mmol), Pd(dppf)Cl$_2$ (8.01 g, 9.8 mmol), KOAc (96.23 g, 980.5 mmol), DMF (1.6 L) were placed in a round bottom flask, the mixture was heated under reflux at 110° C. for 8 hours. When the reaction was completed, the reaction product was diluted with distilled water at room temperature and extracted with methylene chloride and water. Then, the organic layer was dried with MgSO$_4$ and concentrated. Then, the concentrate was dissolved in methylene chloride and then was applied to silica filter. Then, the resultant was concentrated and recrystallized with methylene chloride and hexane to obtain the product Sub 1-41-4 (130.52 g, 84%).

Synthesis Method of Sub 1-41-5

After Sub 1-41-4 (100 g, 210.3 mmol), 1,3-dibromo-5-chlorobenzene (68.24 g, 252.4 mmol), Pd(PPh$_3$)$_4$ (12.15 g, 10.5 mmol), NaOH (25.24 g, 631.0 mmol), THF (770 mL)/H$_2$O (380 mL) were placed in a round bottom flask, the mixture was heated under reflux at 70° C. for 4 hours. When the reaction was completed, the reaction product was diluted with distilled water at room temperature and extracted with methylene chloride and water. Then, the organic layer was dried with MgSO$_4$ and concentrated. Then, the concentrate was recrystallized with methylene chloride and hexane to obtain the product Sub 1-41-5 (89.55 g, 79%).

Synthesis Method of Sub 1-41

After Sub 1-41-5 (20 g, 37.1 mmol), N-phenyl-[1,1'-biphenyl]-4-amine (9.11 g, 37.1 mmol), Pd$_2$(dba)$_3$ (1.02 g, 1.1 mmol), P(t-Bu)$_3$ (0.60 g, 3.0 mmol), NaO(t-Bu) (10.70 g, 111.3 mmol), toluene (370 mL) were placed in a round bottom flask, the mixture was heated under reflux at 110° C. for 8 hours. When the reaction was completed, the reaction product was diluted with distilled water at room temperature and extracted with methylene chloride and water. Then, the organic layer was dried with MgSO$_4$ and concentrated. Then, the concentrate was recrystallized with methylene chloride and hexane to obtain the product Sub 1-41 (21.66 g, 83%).

(11) Synthesis Example of Sub 1-42

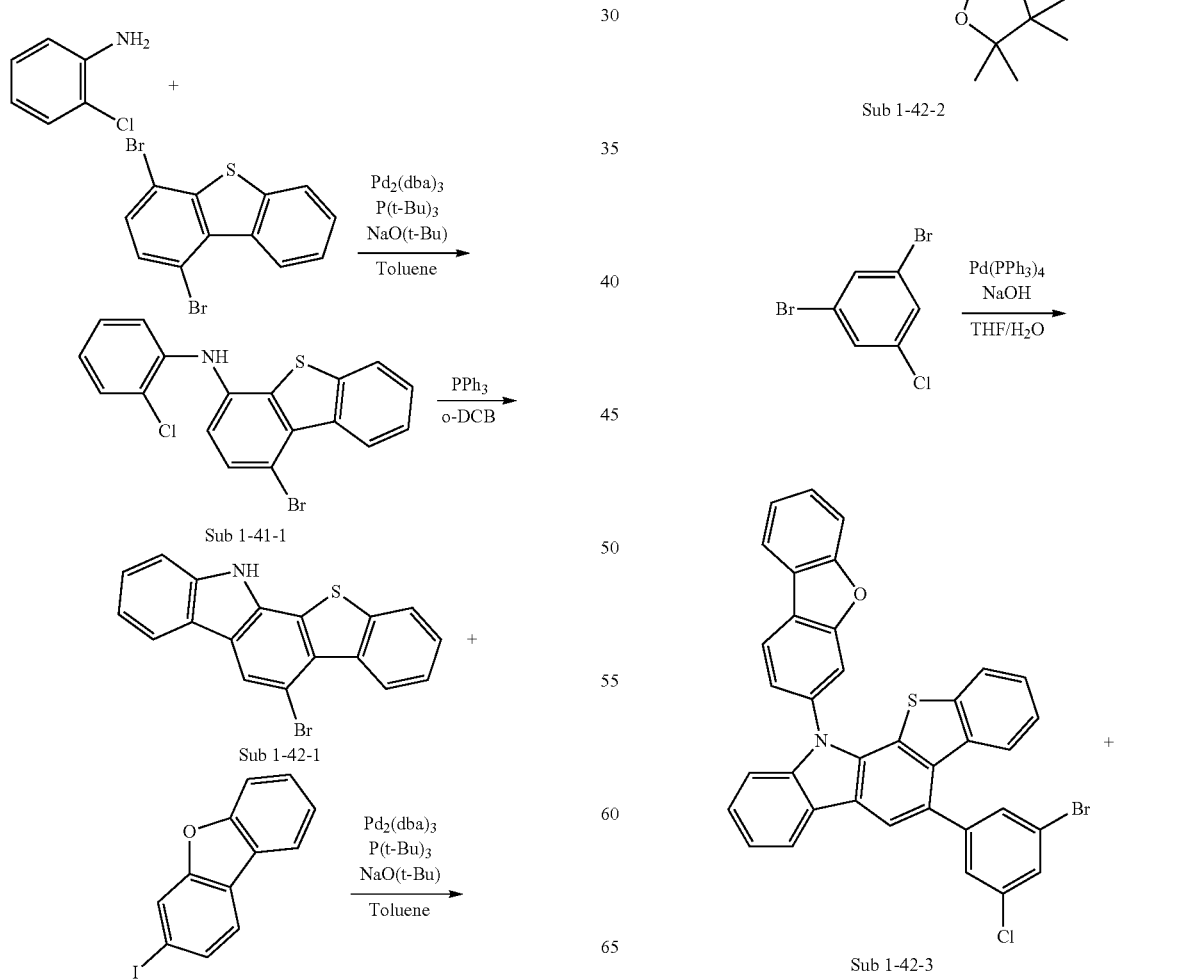

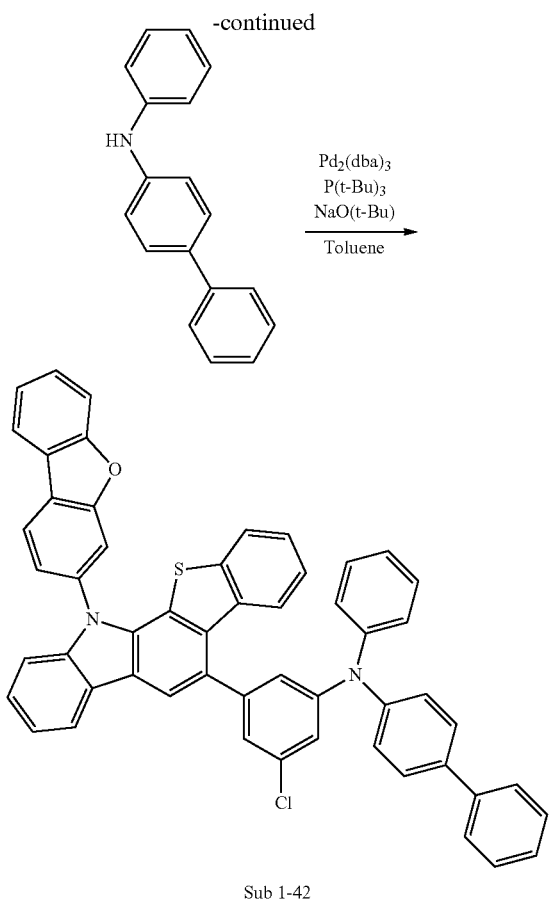

Sub 1-42

Synthesis Method of Sub 1-42-1

After Sub 1-41-2 (160 g, 454.2 mmol), 3-iododibenzofuran (139.0 g, 681.3 mmol), Pd₂(dba)₃ (12.48 g, 13.6 mmol), P(t-Bu)₃ (7.35 g, 36.3 mmol), NaO(t-Bu) (130.97 g, 1362.7 mmol), toluene (5.7 L) were placed in a round bottom flask, the mixture was heated under reflux at 110° C. for 8 hours. When the reaction was completed, the reaction product was diluted with distilled water at room temperature and extracted with methylene chloride and water. Then, the organic layer was dried with MgSO₄ and concentrated. Then, the concentrate was recrystallized with methylene chloride and hexane to obtain the product Sub 1-42-1 (142.03 g, 73%).

Synthesis Method of Sub 1-42-2

After Sub 1-42-1 (140 g, 326.8 mmol), 4,4,4',4',5,5,5',5'-octamethyl-2,2'-bi(1,3,2-dioxaborolane) (91.30 g, 359.5 mmol), Pd(dppf)Cl₂ (8.01 g, 9.8 mmol), KOAc (96.23 g, 980.5 mmol), DMF (1.6 L) were placed in a round bottom flask, the mixture was heated under reflux at 110° C. for 8 hours. When the reaction was completed, the reaction product was diluted with distilled water at room temperature and extracted with methylene chloride and water. Then, the organic layer was dried with MgSO₄ and concentrated. Then, the concentrate was dissolved in methylene chloride and then was applied to silica filter. Then, the resultant was concentrated and recrystallized with methylene chloride and hexane to obtain the product Sub 1-42-2 (g, 89%).

Synthesis Method of Sub 1-42-3

After Sub 1-42-2 (100 g, 210.3 mmol), 1,3-dibromo-5-chlorobenzene (68.24 g, 252.4 mmol), Pd(PPh₃)₄ (12.15 g, 10.5 mmol), NaOH (25.24 g, 631.0 mmol), THF (770 mL)/H₂O (380 mL) were placed in a round bottom flask, the mixture was heated under reflux at 70° C. for 4 hours. When the reaction was completed, the reaction product was diluted with distilled water at room temperature and extracted with methylene chloride and water. Then, the organic layer was dried with MgSO₄ and concentrated. Then, the concentrate was recrystallized with methylene chloride and hexane to obtain the product Sub 1-42-3 (89.55 g, 79%).

Synthesis Method of Sub 1-42

After Sub 1-42-3 (20 g, 37.1 mmol), N-phenyl-[1,1'-biphenyl]-4-amine (9.11 g, 37.1 mmol), Pd₂(dba)₃ (1.02 g, 1.1 mmol), P(t-Bu)₃ (0.60 g, 3.0 mmol), NaO(t-Bu) (10.70 g, 111.3 mmol), toluene (370 mL) were placed in a round bottom flask, the mixture was heated under reflux at 110° C. for 8 hours. When the reaction was completed, the reaction product was diluted with distilled water at room temperature and extracted with methylene chloride and water. Then, the organic layer was dried with MgSO₄ and concentrated. Then, the concentrate was recrystallized with methylene chloride and hexane to obtain the product Sub 1-42 (21.66 g, 83%).

(12) Synthesis Example of Sub 1-43

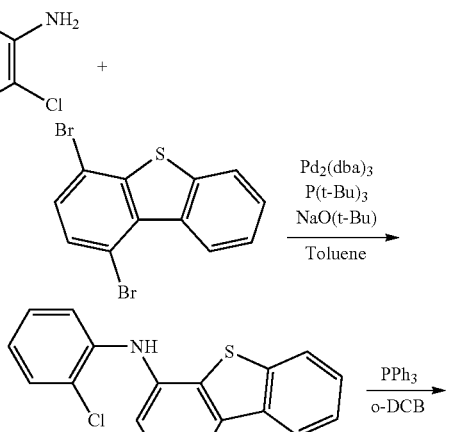

Sub 1-41-1

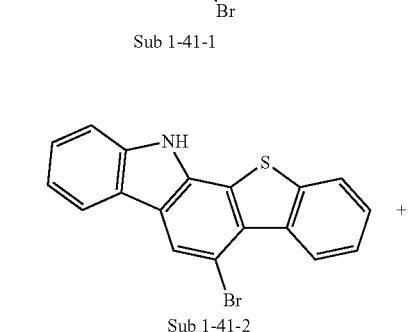

Sub 1-41-2

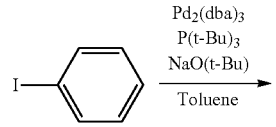

-continued

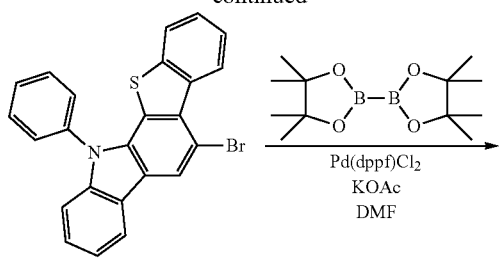

Sub 1-41-3

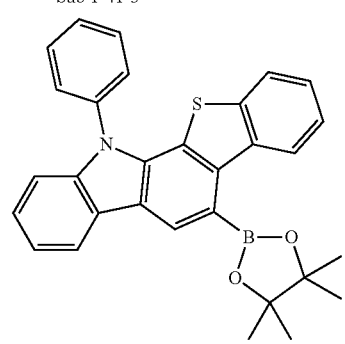

Sub 1-41-4

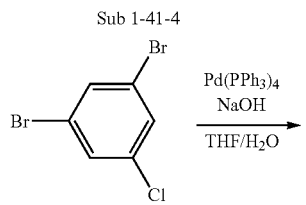

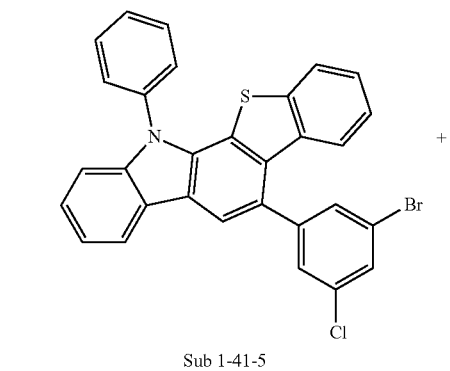

Sub 1-41-5

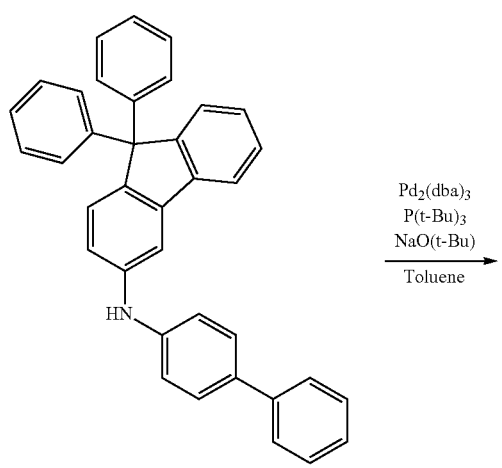

-continued

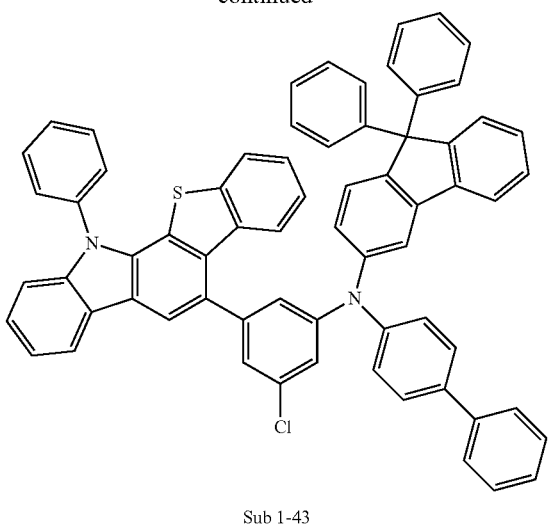

Sub 1-43

Synthesis Method of Sub 1-43

After Sub 1-41-5 (20 g, 37.1 mmol), N-([1,1'-biphenyl]-4-yl)-9,9-diphenyl-9H-fluoren-3-amine (18.02 g, 37.1 mmol), $Pd_2(dba)_3$ (1.02 g, 1.1 mmol), $P(t-Bu)_3$ (0.60 g, 3.0 mmol), NaO(t-Bu) (10.70 g, 111.3 mmol), toluene (370 mL) were placed in a round bottom flask, the mixture was heated under reflux at 110° C. for 8 hours. When the reaction was completed, the reaction product was diluted with distilled water at room temperature and extracted with methylene chloride and water. Then, the organic layer was dried with $MgSO_4$ and concentrated. Then, the concentrate was recrystallized with methylene chloride and hexane to obtain the product Sub 1-42 (28.37 g, 81%).

(13) Synthesis Example of Sub 1-44

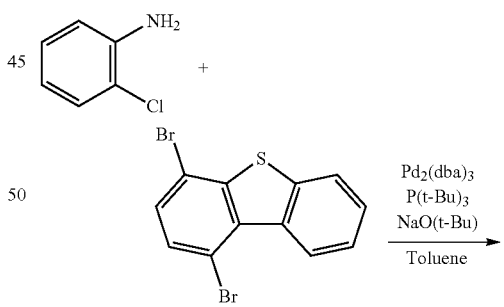

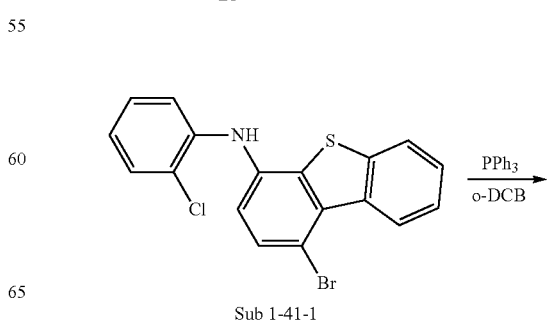

Sub 1-41-1

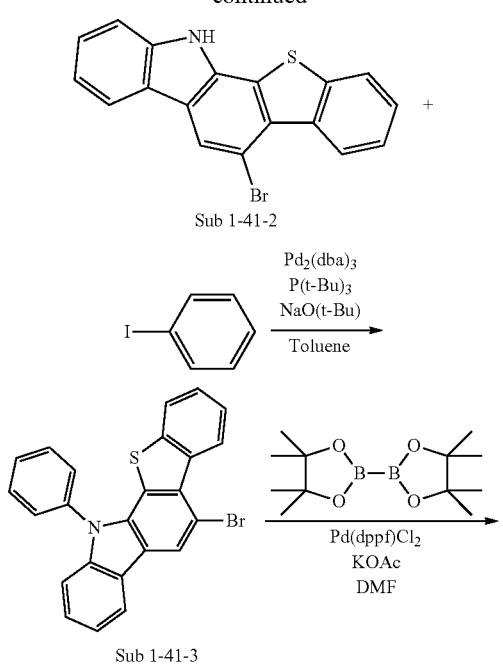

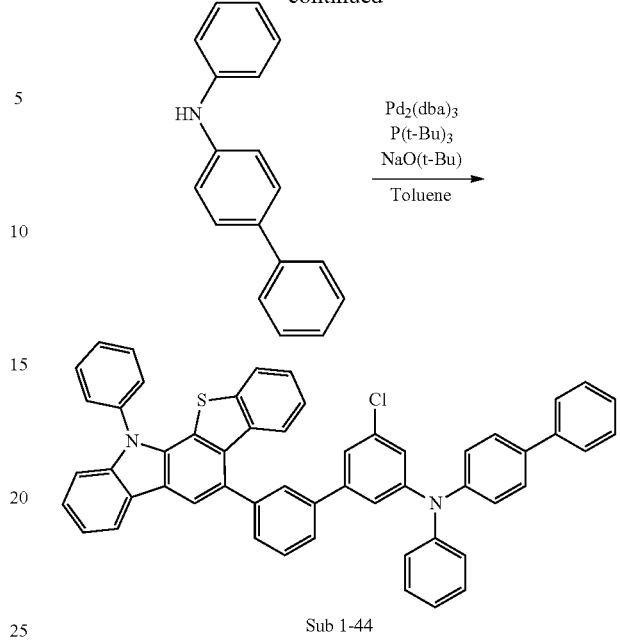

Synthesis Method of Sub 1-44-1

After Sub 1-41-4 (20 g, 42.1 mmol), 3,3'-dibromo-5-chloro-1,1'-biphenyl (17.49 g, 50.5 mmol), Pd(PPh$_3$)$_4$ (2.43 g, 2.1 mmol), NaOH (5.05 g, 126.2 mmol), THF (150 mL)/H$_2$O (70 mL) were placed in a round bottom flask, the mixture was heated under reflux at 70° C. for 4 hours. When the reaction was completed, the reaction product was diluted with distilled water at room temperature and extracted with methylene chloride and water. Then, the organic layer was dried with MgSO$_4$ and concentrated. Then, the concentrate was recrystallized with methylene chloride and hexane to obtain the product Sub 1-44-1 (89.55 g, 79%).

Synthesis Method of Sub 1-44

After Sub 1-44-1 (20 g, 32.5 mmol), N-phenyl-[1,1'-biphenyl]-4-amine (7.98 g, 32.5 mmol), Pd$_2$(dba)$_3$ (0.89 g, 1.0 mmol), P(t-Bu)$_3$ (0.53 g, 2.6 mmol), NaO(t-Bu) (9.38 g, 97.6 mmol), toluene (370 mL) were placed in a round bottom flask, the mixture was heated under reflux at 110° C. for 8 hours. When the reaction was completed, the reaction product was diluted with distilled water at room temperature and extracted with methylene chloride and water. Then, the organic layer was dried with MgSO$_4$ and concentrated. Then, the concentrate was recrystallized with methylene chloride and hexane to obtain the product Sub 1-44 (22.31 g, 88%).

(14) Synthesis Example of Sub 1-45

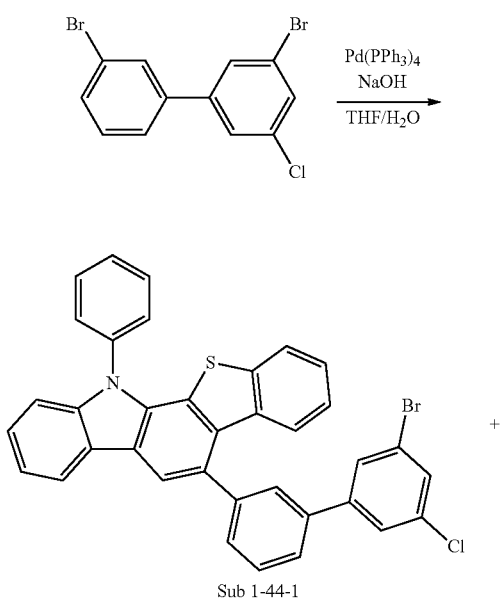

105
-continued

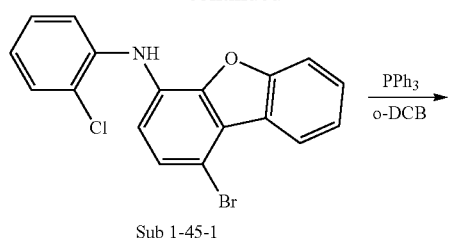
Sub 1-45-1

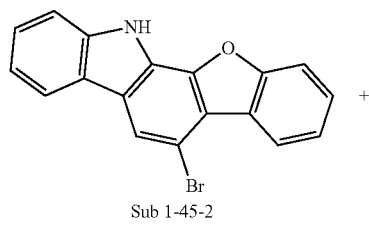
Sub 1-45-2

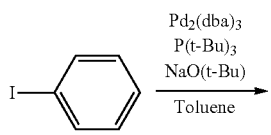

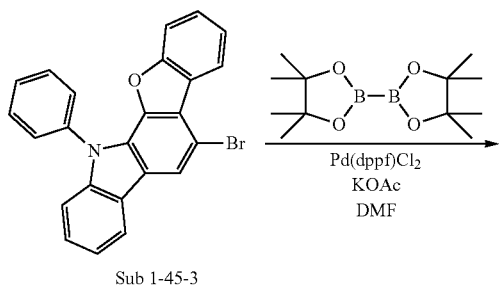
Sub 1-45-3

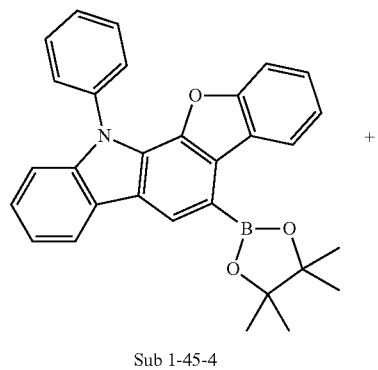
Sub 1-45-4

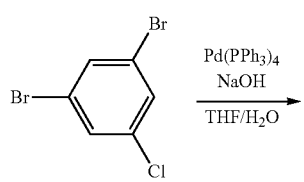

106
-continued

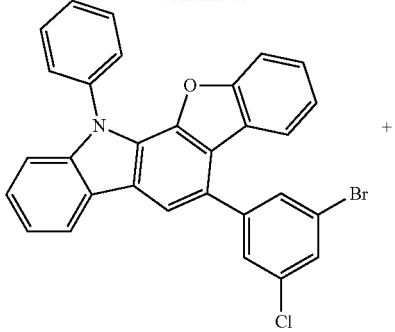
Sub 1-45-5

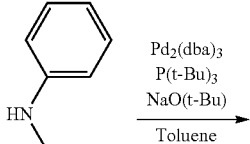

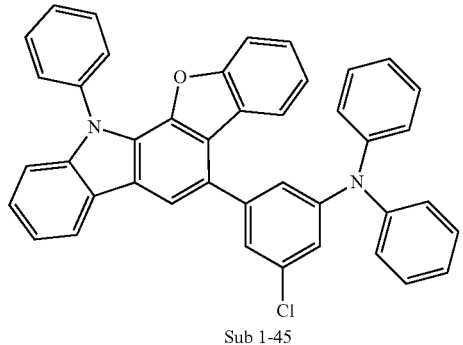
Sub 1-45

Synthesis Method of Sub 1-45-1

After 1,4-dibromodibenzo[b,d]furan (50 g, 153.4 mmol), 2-chloroaniline (29.35 g, 230.1 mmol), Pd₂(dba)₃ (4.21 g, 4.6 mmol), P(t-Bu)₃ (2.48 g, 12.3 mmol), NaO(t-Bu) (44.22 g, 460.1 mmol), toluene (1.9 L) were placed in a round bottom flask, the mixture was heated under reflux at 110° C. for 8 hours. When the reaction was completed, the reaction product was diluted with distilled water at room temperature and extracted with methylene chloride and water. Then, the organic layer was dried with MgSO₄ and concentrated. Then, the concentrate was recrystallized with methylene chloride and hexane to obtain the product Sub 1-41-1 (45.15 g, 79%).

Synthesis Method of Sub 1-45-2

After Sub 1-45-1 (45 g, 120.8 mmol), PPh₃ (79.18 g, 301.9 mmol), o-dichlorobenzene (600 mL) were placed in a round bottom flask, the mixture was heated under reflux at 180° C. for 24 hours. When the reaction was completed, the reaction product was cooled to a room temperature and concentrated. Then, the concentrate was applied to silicagel column and recrystallized to obtain the product Sub 1-45-2 (32.48 g, 80%).

Synthesis Method of Sub 1-45-3

After Sub 1-45-2 (32 g, 95.2 mmol), iodobenzene (29.13 g, 142.8 mmol), Pd₂(dba)₃ (2.61 g, 2.9 mmol), P(t-Bu)₃ (1.54 g, 7.6 mmol), NaO(t-Bu) (27.44 g, 285.6 mmol), toluene (1.1 L) were placed in a round bottom flask, the mixture was heated under reflux at 110° C. for 8 hours.

When the reaction was completed, the reaction product was diluted with distilled water at room temperature and extracted with methylene chloride and water. Then, the organic layer was dried with MgSO₄ and concentrated. Then, the concentrate was recrystallized with methylene chloride and hexane to obtain the product Sub 1-45-3 (29.04 g, 74%).

Synthesis Method of Sub 1-45-4

After Sub 1-45-3 (29 g, 70.3 mmol), 4,4,4',4',5,5,5',5'-octamethyl-2,2'-bi(1,3,2-dioxaborolane) (19.65 g, 77.4 mmol), Pd(dppf)Cl₂ (1.72 g, 2.1 mmol), KOAc (20.71 g, 211.0 mmol), DMF (352 mL) were placed in a round bottom flask, the mixture was heated under reflux at 110° C. for 8 hours. When the reaction was completed, the reaction product was diluted with distilled water at room temperature and extracted with methylene chloride and water. Then, the organic layer was dried with MgSO₄ and concentrated. Then, the concentrate was dissolved in methylene chloride and then was applied to silica filter. Then, the resultant was concentrated and recrystallized with methylene chloride and hexane to obtain the product Sub 1-45-4 (25.53 g, 79%).

Synthesis Method of Sub 1-45-5

After Sub 1-45-4 (25 g, 54.4 mmol), 1,3-dibromo-5-chlorobenzene (17.66 g, 65.3 mmol), Pd(PPh₃)₄ (3.14 g, 2.7 mmol), NaOH (6.53 g, 163.3 mmol), THF (200 mL)/H₂O (100 mL) were placed in a round bottom flask, the mixture was heated under reflux at 70° C. for 4 hours. When the reaction was completed, the reaction product was diluted with distilled water at room temperature and extracted with methylene chloride and water. Then, the organic layer was dried with MgSO₄ and concentrated. Then, the concentrate was recrystallized with methylene chloride and hexane to obtain the product Sub 1-45-5 (20.77 g, 73%).

Synthesis Method of Sub 1-45

After Sub 1-45-5 (20 g, 38.3 mmol), diphenylamine (6.47 g, 38.3 mmol), Pd₂(dba)₃ (1.05 g, 1.1 mmol), P(t-Bu)₃ (0.62 g, 3.1 mmol), NaO(t-Bu) (11.03 g, 114.8 mmol), toluene (380 mL) were placed in a round bottom flask, the mixture was heated under reflux at 110° C. for 8 hours. When the reaction was completed, the reaction product was diluted with distilled water at room temperature and extracted with methylene chloride and water. Then, the organic layer was dried with MgSO₄ and concentrated. Then, the concentrate was recrystallized with methylene chloride and hexane to obtain the product Sub 1-45 (18.23 g, 78%).

(17) Synthesis Example of Sub 1-49

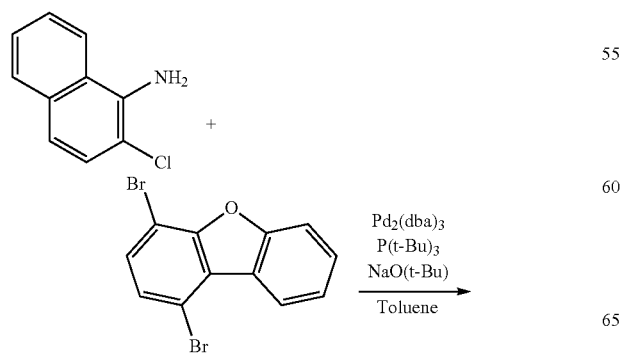

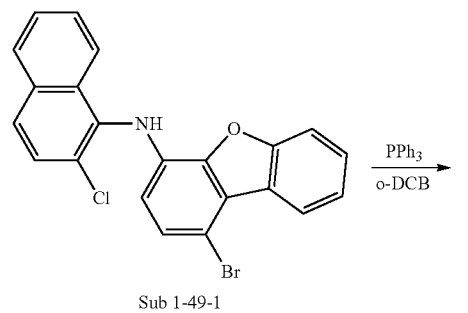

Sub 1-49-1

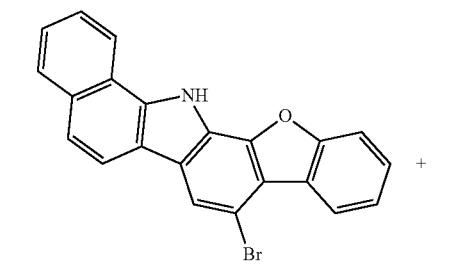

Sub 1-49-2

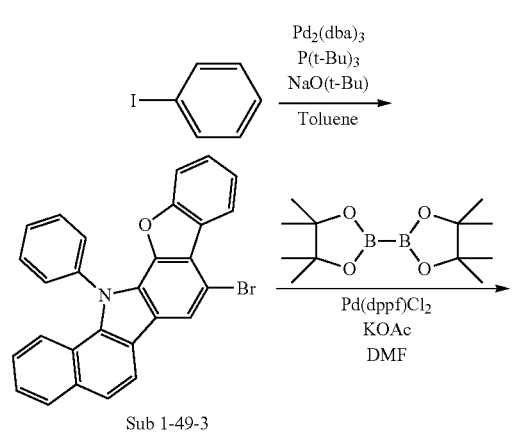

Sub 1-49-3

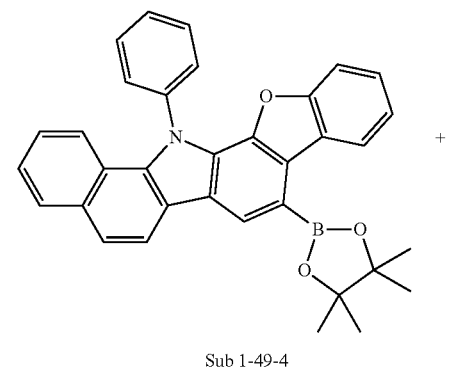

Sub 1-49-4

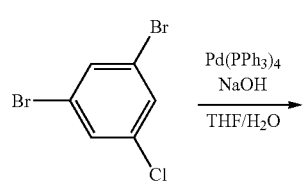

-continued

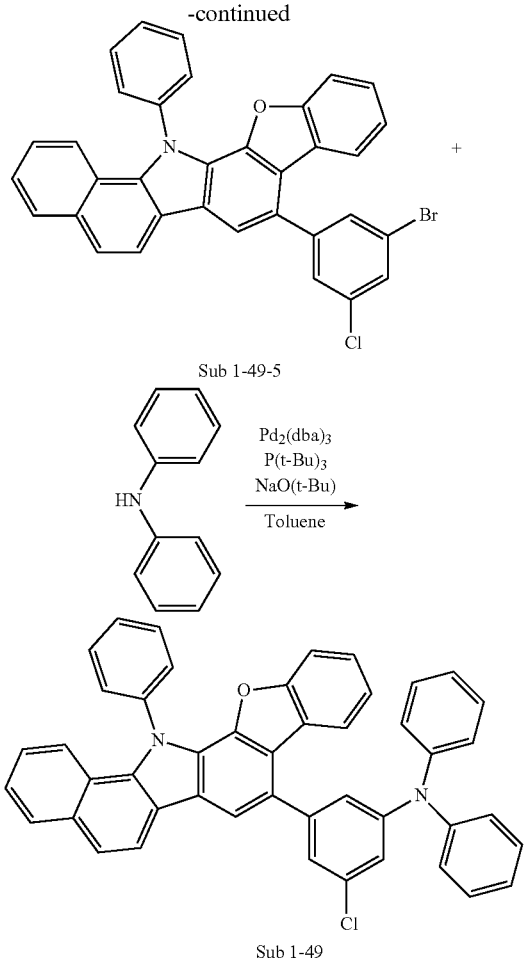

Sub 1-49-5

Sub 1-49

Synthesis Method of Sub 1-49-1

After 1,4-dibromodibenzo[b,d]furan (30 g, 92.0 mmol), 2-chloronaphthalen-1-amine (24.52 g, 138.0 mmol), Pd$_2$(dba)$_3$ (2.53 g, 2.8 mmol), P(t-Bu)$_3$ (1.49 g, 7.4 mmol), NaO(t-Bu) (26.53 g, 276.1 mmol), toluene (1.1 L) were placed in a round bottom flask, the mixture was heated under reflux at 110° C. for 8 hours. When the reaction was completed, the reaction product was diluted with distilled water at room temperature and extracted with methylene chloride and water. Then, the organic layer was dried with MgSO$_4$ and concentrated. Then, the concentrate was recrystallized with methylene chloride and hexane to obtain the product Sub 1-49-1 (29.18 g, 75%).

Synthesis Method of Sub 1-49-2

After Sub 1-49-1 (29 g, 68.6 mmol), PPh$_3$ (44.99 g, 171.5 mmol), o-dichlorobenzene (340 mL) were placed in a round bottom flask, the mixture was heated at 180° C. for 24 hours under reflux. When the reaction was completed, the reaction product was cooled to a room temperature and concentrated. Then, the concentrate was applied to silicagel column and recrystallized to obtain the product Sub 1-49-2 (19.34 g, 73%).

Synthesis Method of Sub 1-49-3

After Sub 1-49-2 (19 g, 49.2 mmol), iodobenzene (15.05 g, 73.8 mmol), Pd$_2$(dba)$_3$ (1.35 g, 1.5 mmol), P(t-Bu)$_3$ (0.80 g, 3.9 mmol), NaO(t-Bu) (14.18 g, 147.6 mmol), toluene (610 mL) were placed in a round bottom flask, the mixture was heated under reflux at 110° C. for 8 hours. When the reaction was completed, the reaction product was diluted with distilled water at room temperature and extracted with methylene chloride and water. Then, the organic layer was dried with MgSO$_4$ and concentrated. Then, the concentrate was recrystallized with methylene chloride and hexane to obtain the product Sub 1-49-3 (18.88 g, 83%).

Synthesis Method of Sub 1-49-4

After Sub 1-49-3 (18 g, 33.4 mmol), 4,4,4',4',5,5,5',5'-octamethyl-2,2'-bi(1,3,2-dioxaborolane) (10.83 g, 40.0 mmol), Pd(dppf)Cl$_2$ (0.95 g, 1.2 mmol), KOAc (11.46 g, 116.8 mmol), DMF (200 mL) were placed in a round bottom flask, the mixture was heated under reflux at 110° C. for 8 hours. When the reaction was completed, the reaction product was diluted with distilled water at room temperature and extracted with methylene chloride and water. Then, the organic layer was dried with MgSO$_4$ and concentrated. Then, the concentrate was dissolved in methylene chloride and then was applied to silica filter. Then, the resultant was concentrated and recrystallized with methylene chloride and hexane to obtain the product Sub 1-49-4 (17.65 g, 89%).

Synthesis Method of Sub 1-49-5

After Sub 1-49-4 (17 g, 33.4 mmol), 1,3-dibromo-5-chlorobenzene (10.83 g, 40.0 mmol), Pd(PPh$_3$)$_4$ (1.93 g, 1.7 mmol), NaOH (4.00 g, 100.1 mmol), THF (60 mL)/H$_2$O (120 mL) were placed in a round bottom flask, the mixture was heated under reflux at 70° C. for 4 hours. When the reaction was completed, the reaction product was diluted with distilled water at room temperature and extracted with methylene chloride and water. Then, the organic layer was dried with MgSO$_4$ and concentrated. Then, the concentrate was recrystallized with methylene chloride and hexane to obtain the product Sub 1-49-5 (13.57 g, 71%).

Synthesis Method of Sub 1-49

After Sub 1-49-5 (13 g, 22.7 mmol), diphenylamine (3.8 g, 22.7 mmol), Pd$_2$(dba)$_3$ (0.62 g, 0.7 mmol), P(t-Bu)$_3$ (0.37 g, 1.8 mmol), NaO(t-Bu) (6.54 g, 68.1 mmol), toluene (380 mL) were placed in a round bottom flask, the mixture was heated under reflux at 110° C. for 8 hours. When the reaction was completed, the reaction product was diluted with distilled water at room temperature and extracted with methylene chloride and water. Then, the organic layer was dried with MgSO$_4$ and concentrated. Then, the concentrate was recrystallized with methylene chloride and hexane to obtain the product Sub 1-49 (12.8 g, 85%).

The compounds belonging to Sub 1 may be, but not limited to, the following compounds, and Table 1 shows MASS DATA (FD-MS) of them.

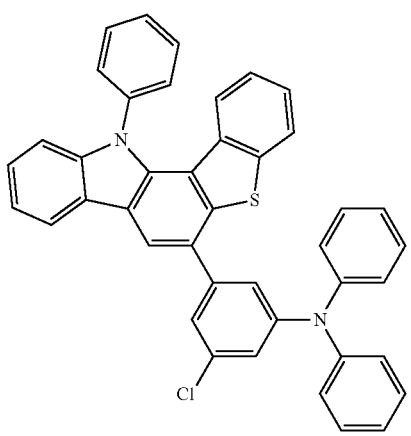

Sub 1-1

-continued
Sub 1-2
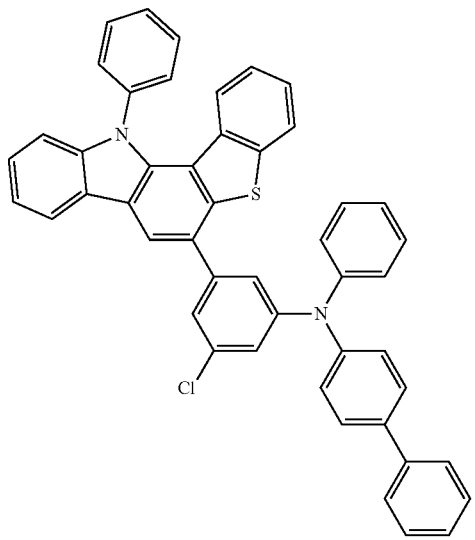
Sub 1-3
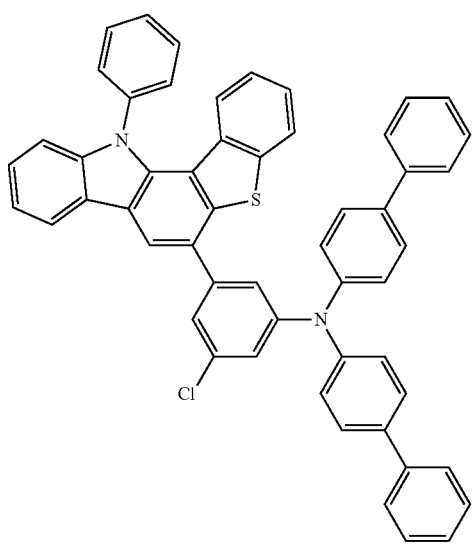
Sub 1-4
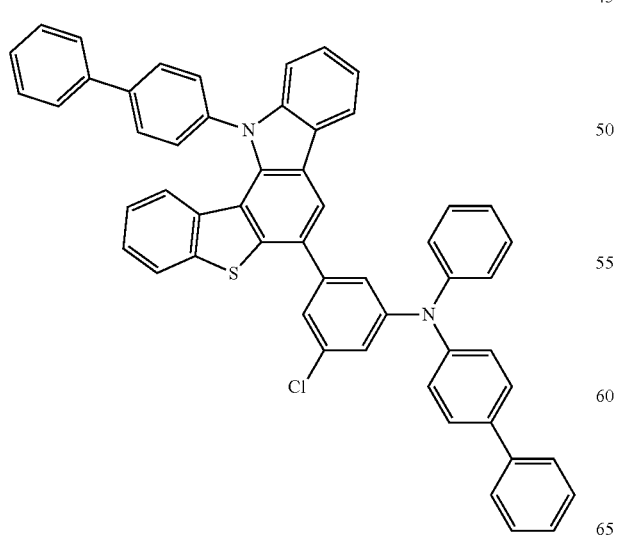
-continued
Sub 1-5
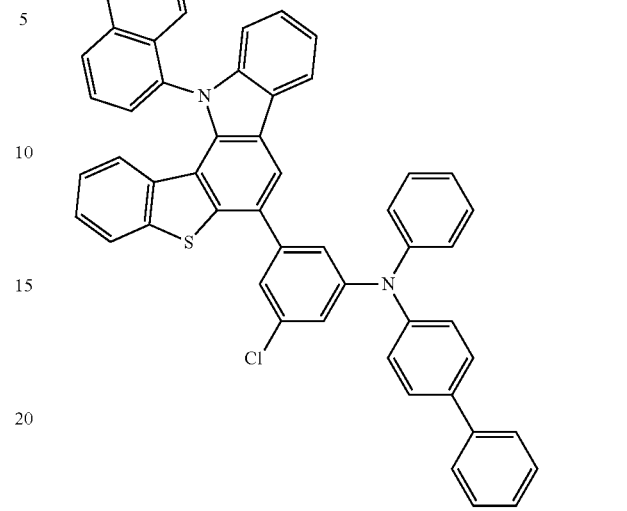
Sub 1-6
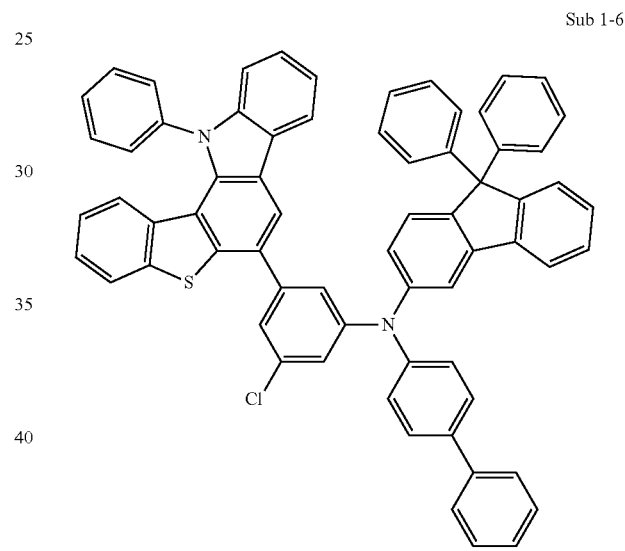
Sub 1-7
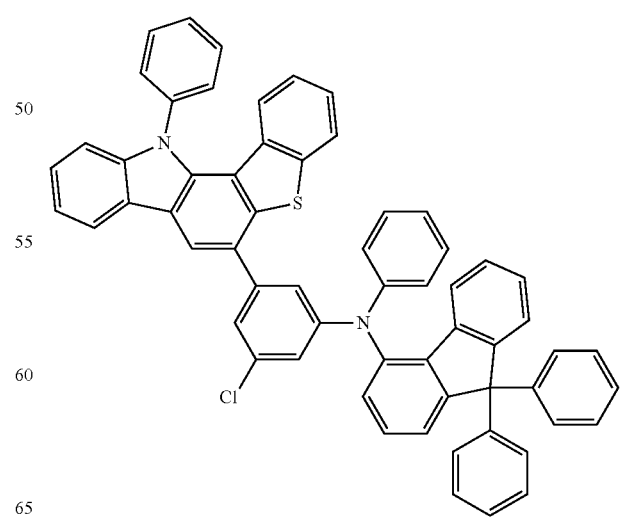

Sub 1-8
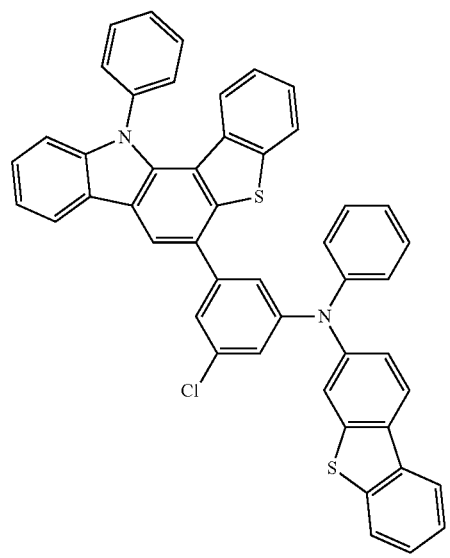
Sub 1-9
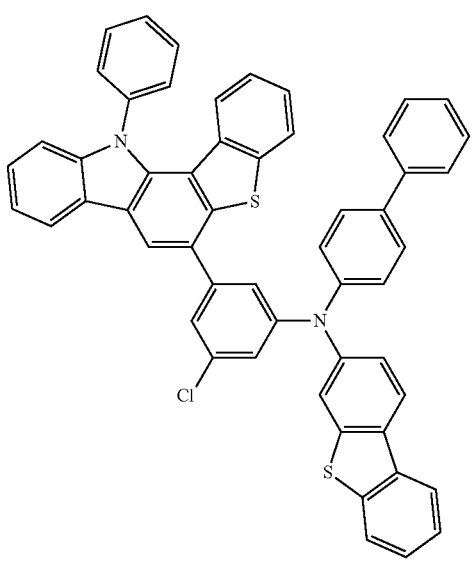
Sub 1-10
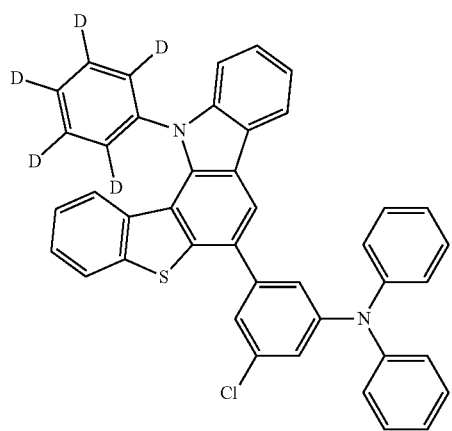
Sub 1-11
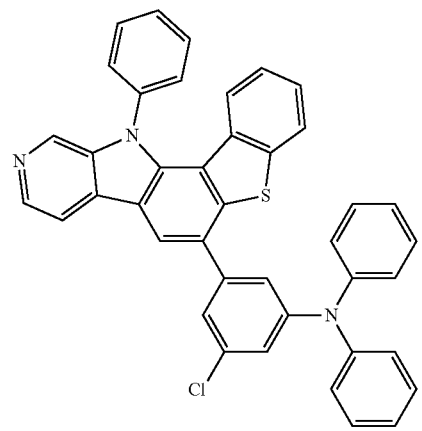
Sub 1-12
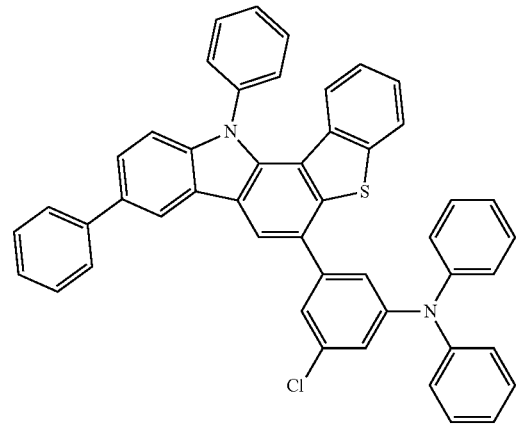
Sub 1-13
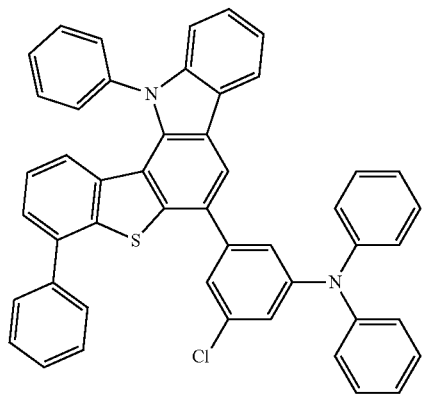

Sub 1-14
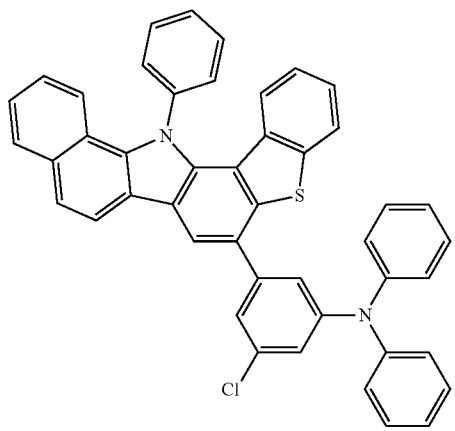
Sub 1-15
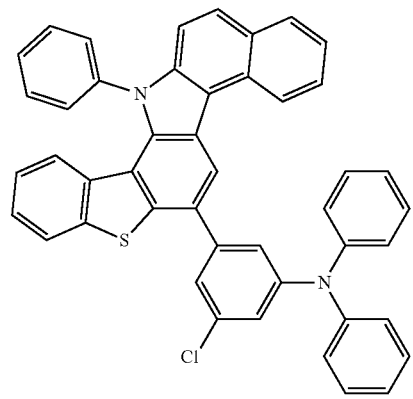
Sub 1-16
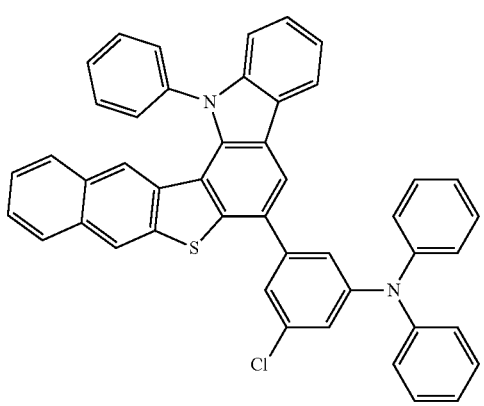
Sub 1-17
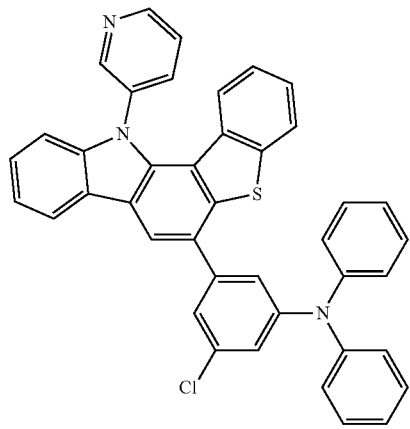
Sub 1-18
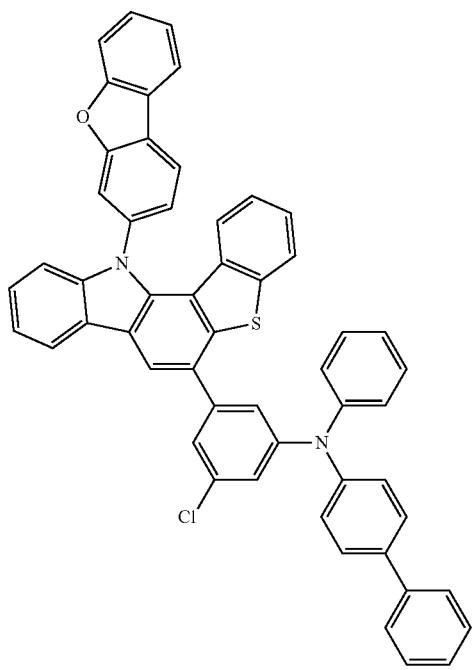

Sub 1-19
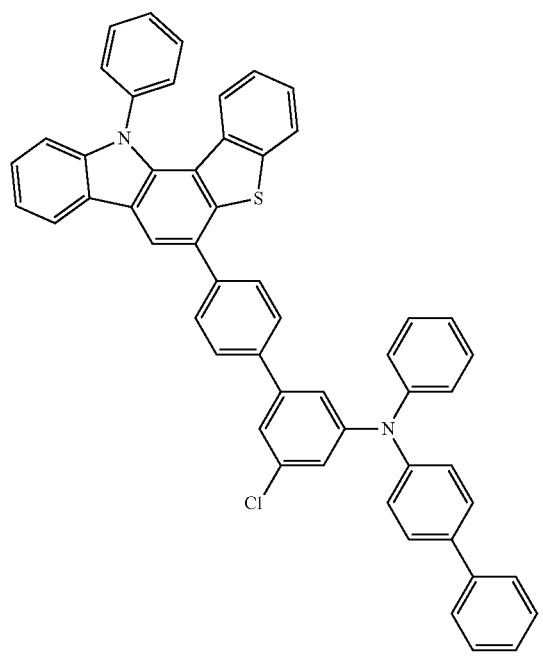
Sub 1-20
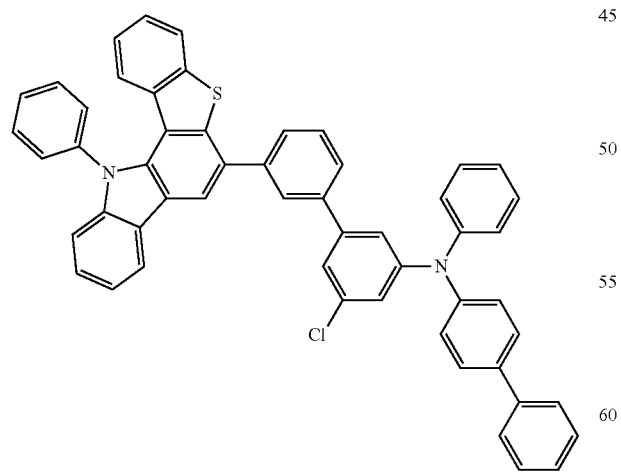
Sub 1-21
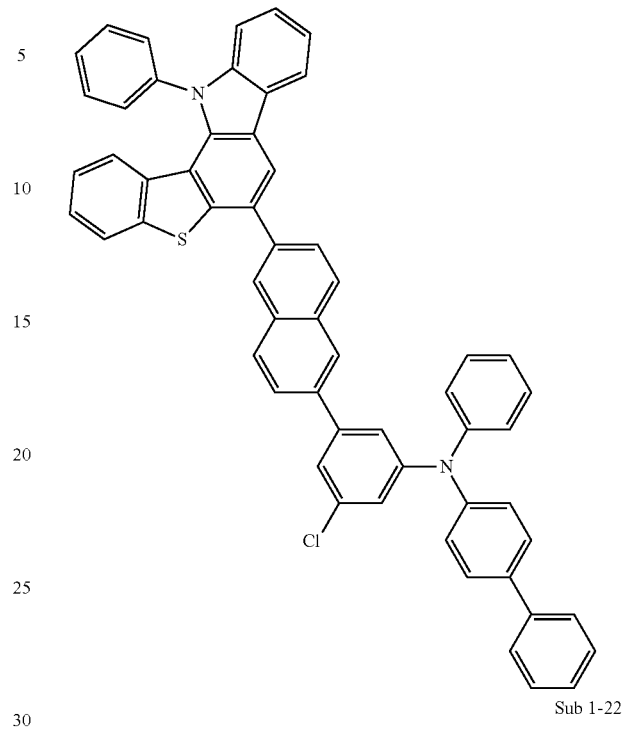
Sub 1-22
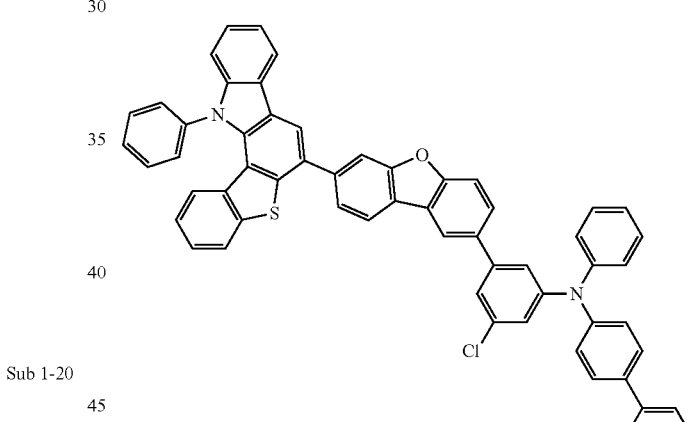
Sub 1-23
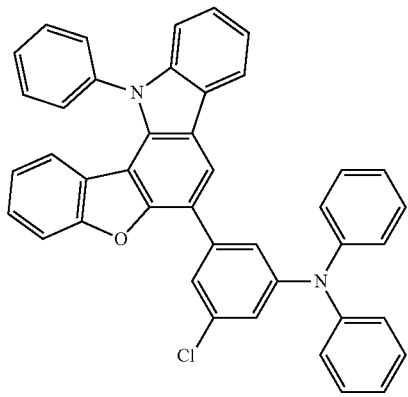

Sub 1-24
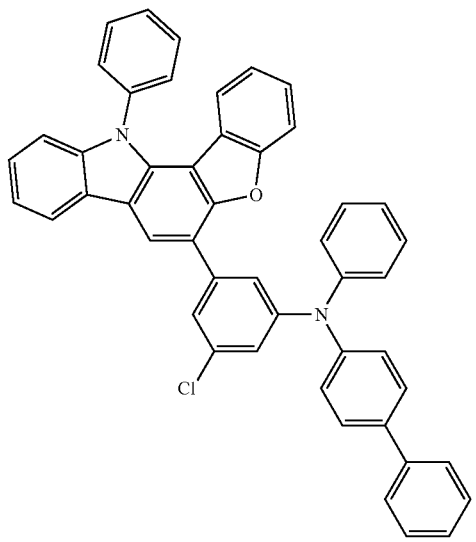
Sub 1-25
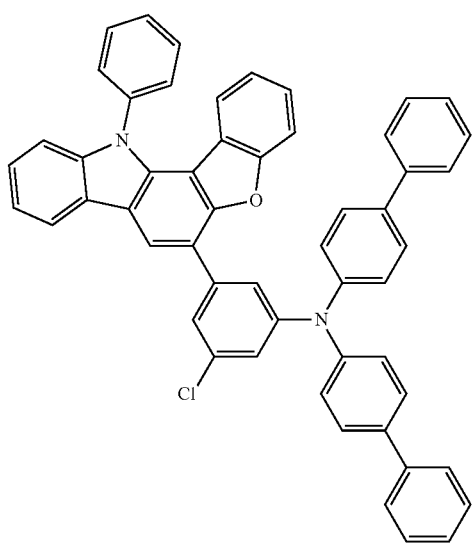
Sub 1-26
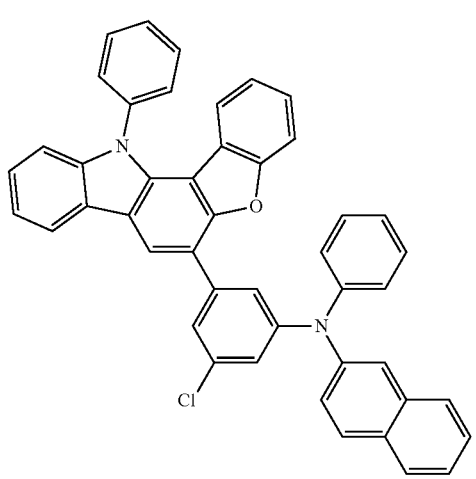
Sub 1-27
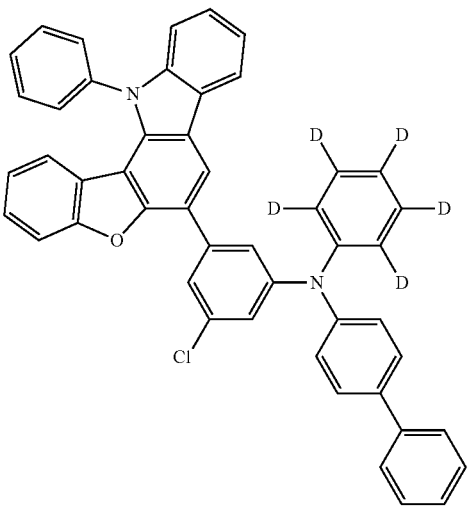
Sub 1-28
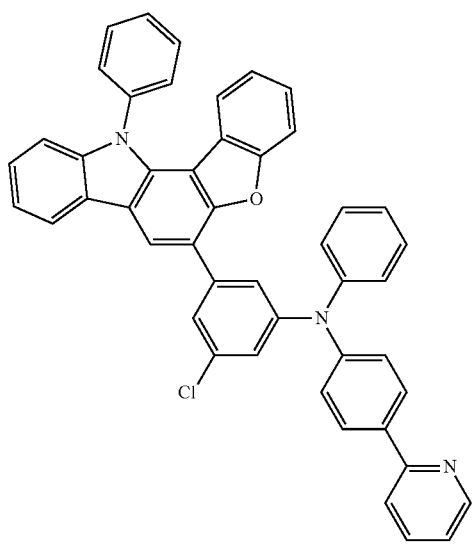
Sub 1-29
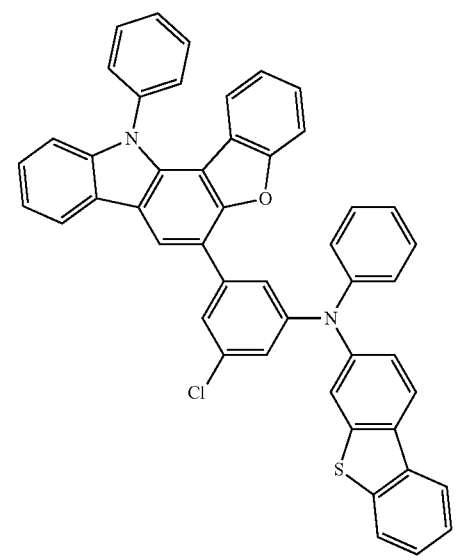

-continued
Sub 1-30
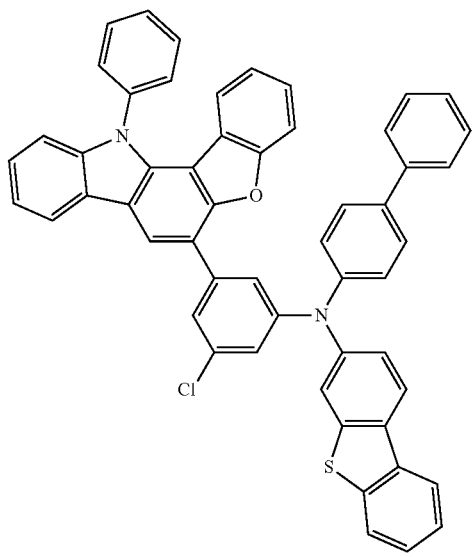
Sub 1-31
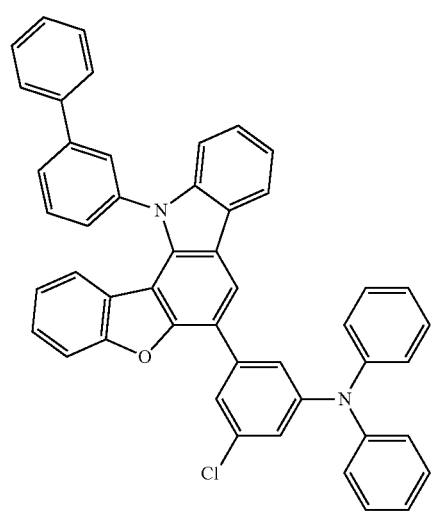
Sub 1-32
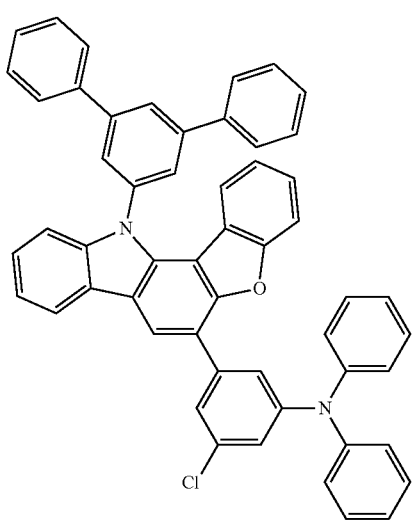
-continued
Sub 1-33
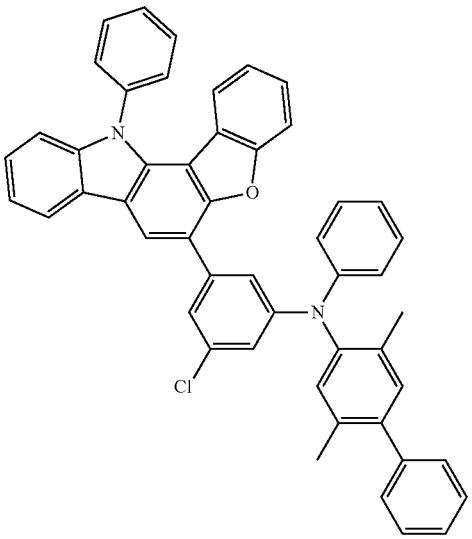
Sub 1-34
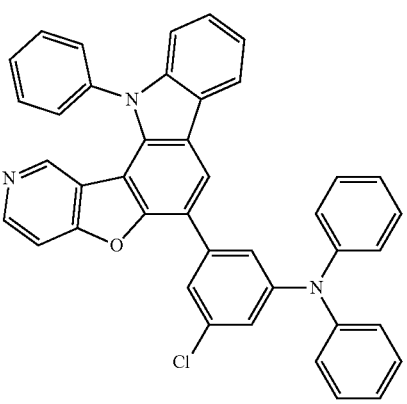
Sub 1-35
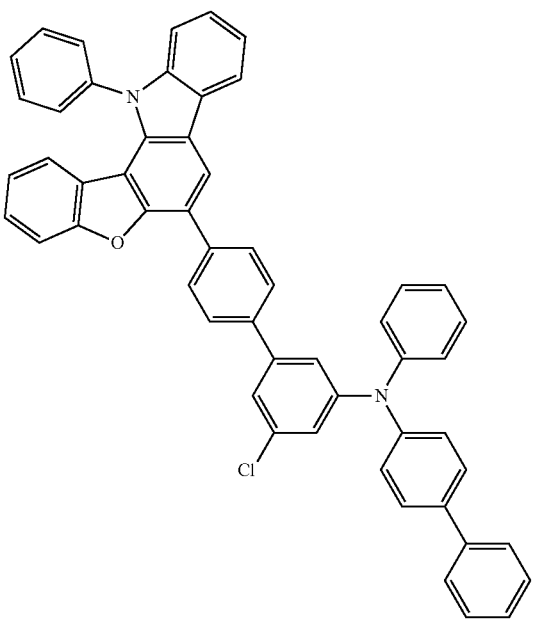

Sub 1-36
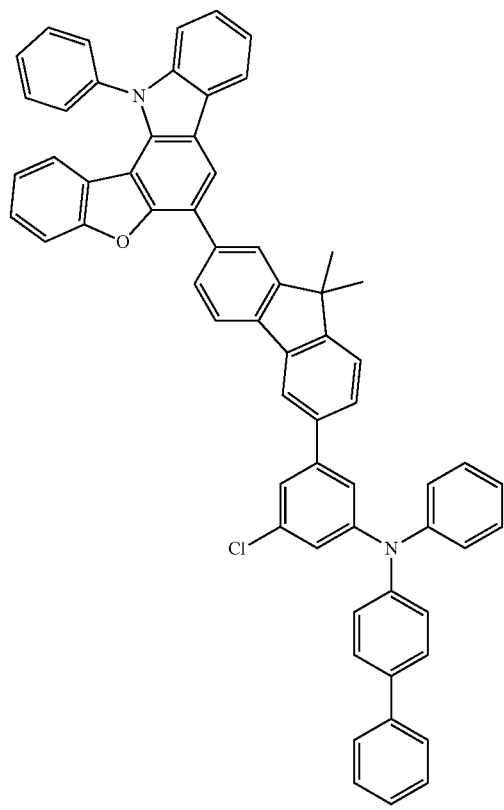
Sub 1-37
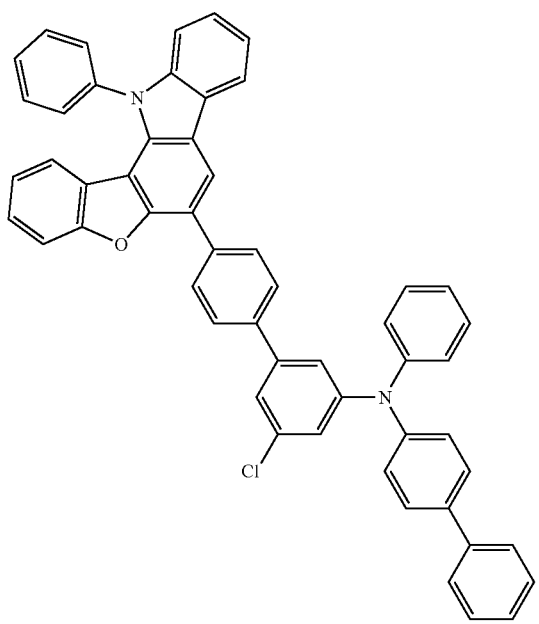
Sub 1-38
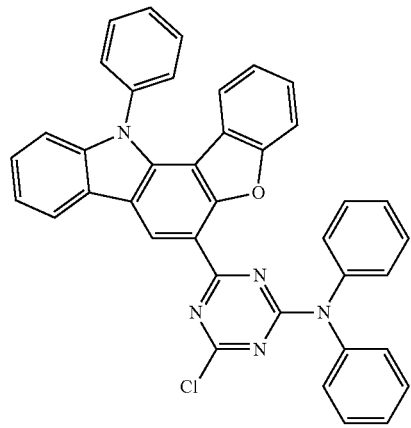
Sub 1-39
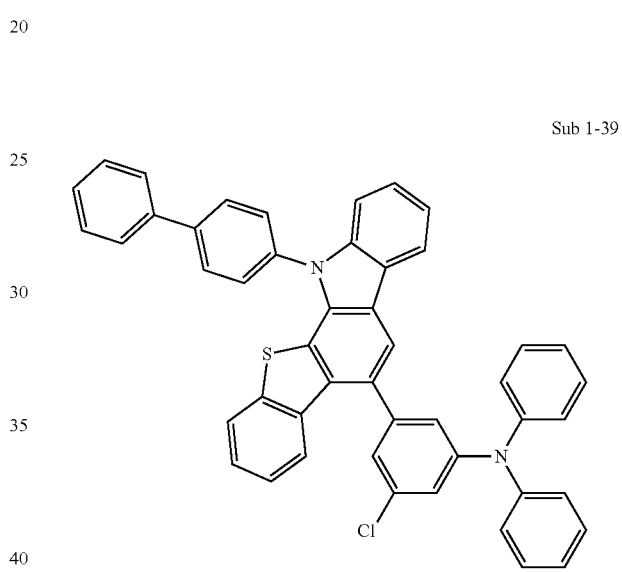
Sub 1-40
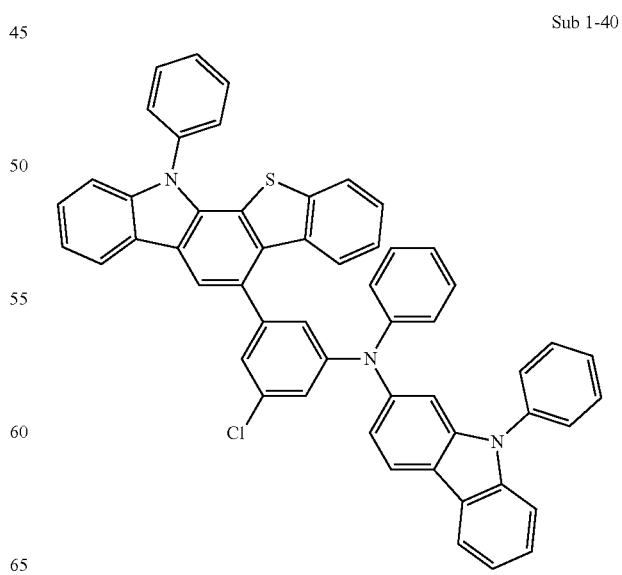

Sub 1-41
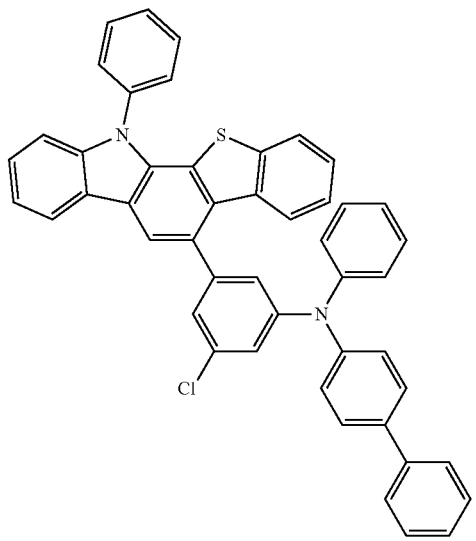
Sub 1-42
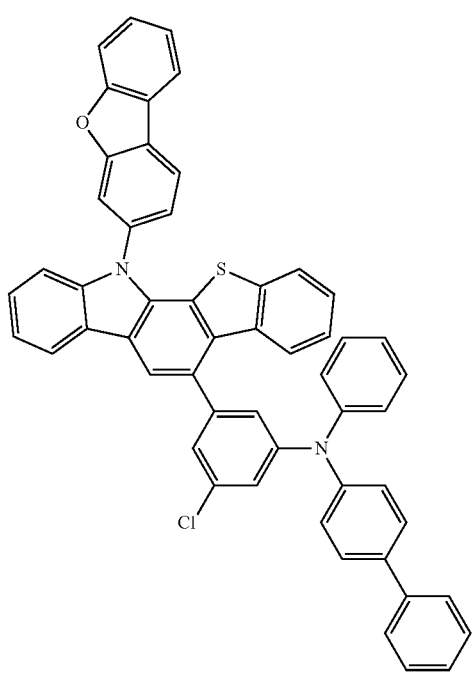
Sub 1-43
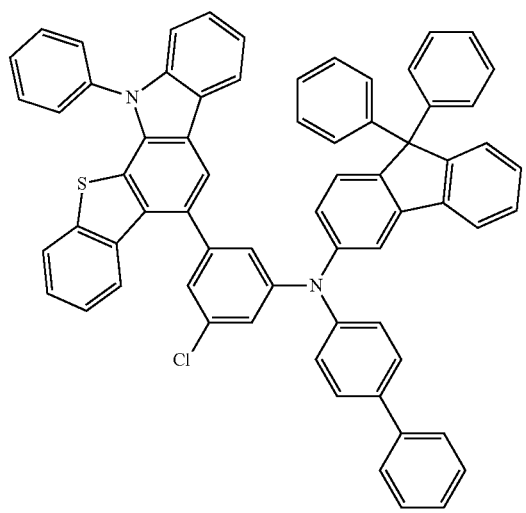
Sub 1-44
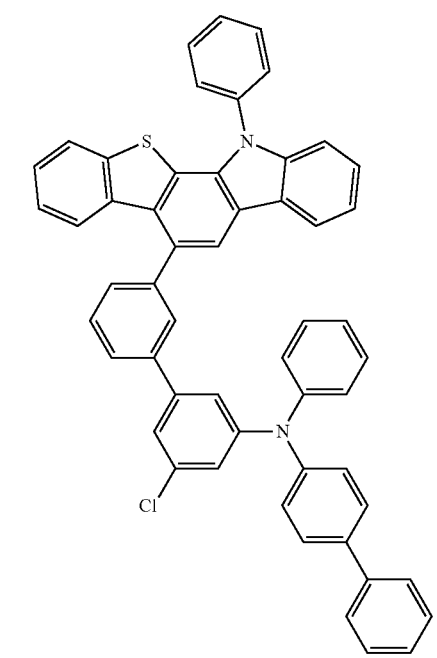
Sub 1-45
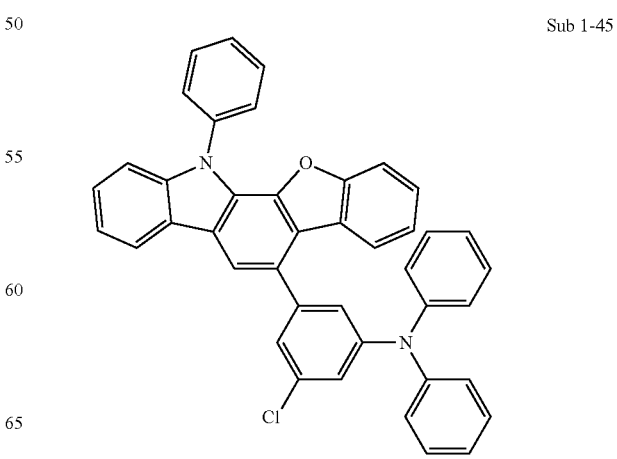

Sub 1-46
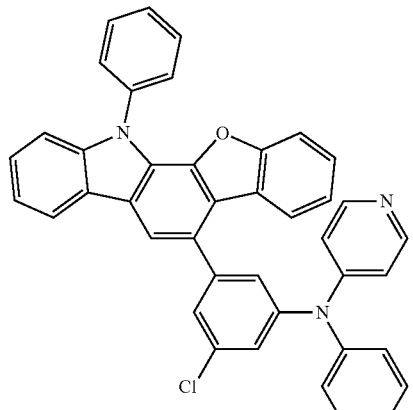
Sub 1-49
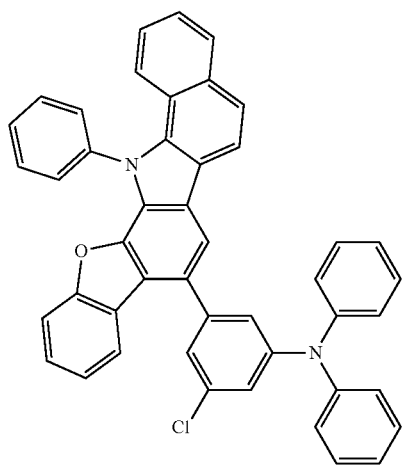
Sub 1-47
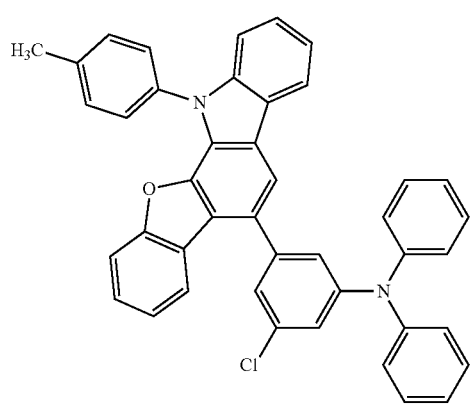
Sub 1-50
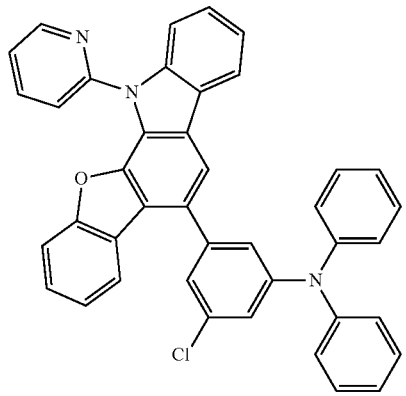
Sub 1-48
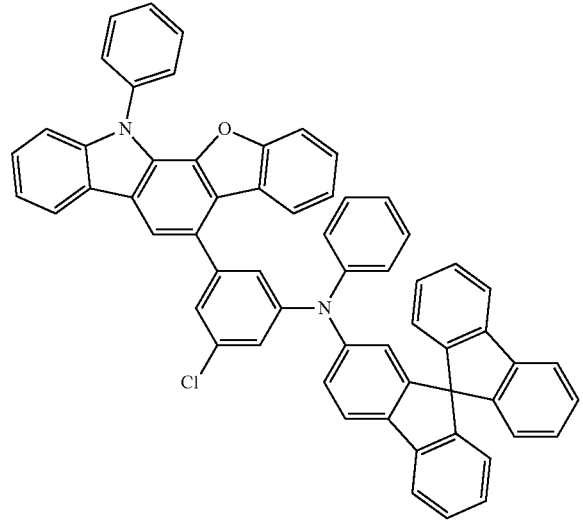
Sub 1-51
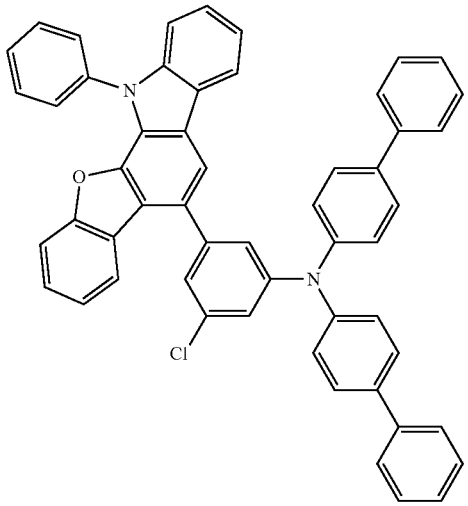

-continued

Sub 1-52

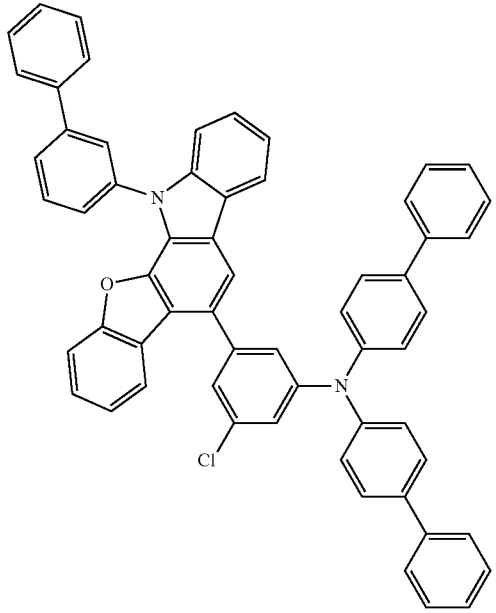

<Reaction Scheme 3>

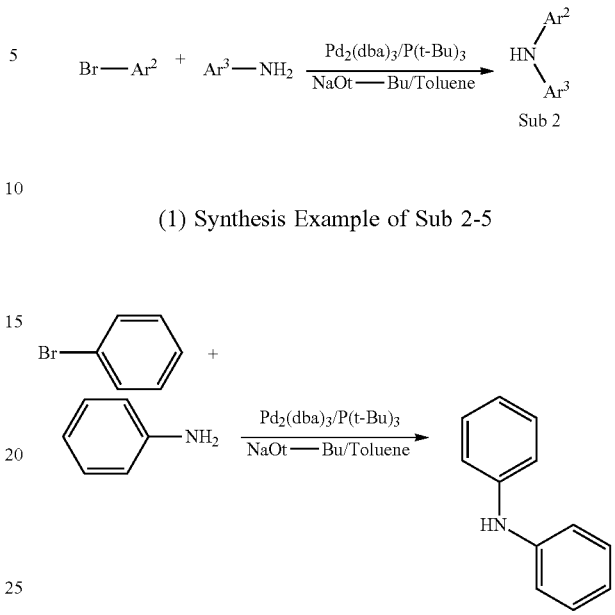

(1) Synthesis Example of Sub 2-5

TABLE 1

| Compound | FD-MS | Compound | FD-MS |
| --- | --- | --- | --- |
| Sub 1-1 | m/z = 626.16 ($C_{42}H_{27}ClN_2S$ = 627.20) | Sub 1-2 | m/z = 702.19 ($C_{48}H_{31}ClN_2S$ = 703.30) |
| Sub 1-3 | m/z = 778.22 ($C_{54}H_{35}ClN_2S$ = 779.40) | Sub 1-4 | m/z = 778.22 ($C_{54}H_{35}ClN_2S$ = 779.40) |
| Sub 1-5 | m/z = 752.21 ($C_{52}H_{33}ClN_2S$ = 753.36) | Sub 1-6 | m/z = 942.28 ($C_{67}H_{43}ClN_2S$ = 943.61) |
| Sub 1-7 | m/z = 866.25 ($C_{61}H_{39}ClN_2S$ = 867.51) | Sub 1-8 | m/z = 732.15 ($C_{48}H_{29}ClN_2S_2$ = 733.34) |
| Sub 1-9 | m/z = 808.18 ($C_{54}H_{33}ClN_2S_2$ = 809.4) | Sub 1-10 | m/z = 631.19 ($C_{42}H_{22}D_5ClN_2S$ = 632.23) |
| Sub 1-11 | m/z = 627.15 ($C_{41}H_{26}ClN_3S$ = 628.19) | Sub 1-12 | m/z = 702.19 ($C_{48}H_{31}ClN_2S$ = 703.30) |
| Sub 1-13 | m/z = 702.19 ($C_{48}H_{31}ClN_2S$ = 703.30) | Sub 1-14 | m/z = 828.24 ($C_{58}H_{37}ClN_2S$ = 829.46) |
| Sub 1-15 | m/z = 676.17 ($C_{46}H_{29}ClN_2S$ = 677.26) | Sub 1-16 | m/z = 676.17 ($C_{46}H_{29}ClN_2S$ = 677.26) |
| Sub 1-17 | m/z = 627.15 ($C_{41}H_{26}ClN_3S$ = 627.15) | Sub 1-18 | m/z = 792.20 ($C_{54}H_{33}ClN_2OS$ = 793.38) |
| Sub 1-19 | m/z = 778.22 ($C_{54}H_{35}ClN_2S$ = 779.40) | Sub 1-20 | m/z = 778.22 ($C_{54}H_{35}ClN_2S$ = 779.40) |
| Sub 1-21 | m/z = 828.24 ($C_{58}H_{37}ClN_2S$ = 829.46) | Sub 1-22 | m/z = 868.23 ($C_{60}H_{37}ClN_2OS$ = 869.48) |
| Sub 1-23 | m/z = 610.18 ($C_{42}H_{27}ClN_2O$ = 611.14) | Sub 1-24 | m/z = 686.21 ($C_{48}H_{31}ClN_2O$ = 687.24) |
| Sub 1-25 | m/z = 762.24 ($C_{54}H_{35}ClN_2O$ = 763.34) | Sub 1-26 | m/z = 660.20 ($C_{46}H_{29}ClN_2O$ = 661.20) |
| Sub 1-27 | m/z = 661.20 ($C_{48}H_{26}D_5ClN_2O$ = 692.27) | Sub 1-28 | m/z = 687.21 ($C_{47}H_{30}ClN_3O$ = 688.23) |
| Sub 1-29 | m/z = 716.17 ($C_{48}H_{29}ClN_2OS$ = 717.28) | Sub 1-30 | m/z = 792.20 ($C_{54}H_{33}ClN_2OS$ = 793.38) |
| Sub 1-31 | m/z = 686.21 ($C_{48}H_{31}ClN_2O$ = 687.24) | Sub 1-32 | m/z = 762.24 ($C_{54}H_{35}ClN_2O$ = 763.34) |
| Sub 1-33 | m/z = 714.24 ($C_{50}H_{35}ClN_2O$ = 715.29) | Sub 1-34 | m/z = 611.18 ($C_{41}H_{26}ClN_3O$ = 612.13) |
| Sub 1-35 | m/z = 762.24 ($C_{54}H_{35}ClN_2O$ = 763.34) | Sub 1-36 | m/z = 878.31 ($C_{63}H_{43}ClN_2O$ = 879.50) |
| Sub 1-37 | m/z = 762.24 ($C_{54}H_{35}ClN_2O$ = 763.34) | Sub 1-38 | m/z = 613.17 ($C_{39}H_{24}ClN_5O$ = 614.11) |
| Sub 1-39 | m/z = 702.19 ($C_{48}H_{31}ClN_2S$ = 703.3) | Sub 1-40 | m/z = 791.22 ($C_{54}H_{34}ClN_3S$ = 792.40) |
| Sub 1-41 | m/z = 702.19 ($C_{48}H_{31}ClN_2S$ = 703.30) | Sub 1-42 | m/z = 792.20 ($C_{54}H_{33}ClN_2OS$ = 793.38) |
| Sub 1-43 | m/z = 942.28 ($C_{67}H_{43}ClN_2S$ = 943.61) | Sub 1-44 | m/z = 778.22 ($C_{54}H_{35}ClN_2S$ = 779.40) |
| Sub 1-45 | m/z = 610.18 ($C_{42}H_{27}ClN_2O$ = 611.14) | Sub 1-46 | m/z = 611.18 ($C_{41}H_{26}ClN_3O$ = 612.13) |
| Sub 1-47 | m/z = 624.20 ($C_{43}H_{29}ClN_2O$ = 625.17) | Sub 1-48 | m/z = 848.26 ($C_{61}H_{37}ClN_2O$ = 849.43) |
| Sub 1-49 | m/z = 660.20 ($C_{46}H_{29}ClN=O$ = 661.2) | Sub 1-50 | m/z = 611.18 ($C_{41}H_{26}ClN_3O$ = 612.13) |
| Sub 1-51 | m/z = 762.24 ($C_{54}H_{35}ClN_2O$ = 763.34) | Sub 1-52 | m/z = 838.28 ($C_{60}H_{39}ClN_2O$ = 839.44) |

2. Synthesis Example of Sub 2

Sub 2 of the Reaction Scheme 1 can be synthesized according to the reaction route of the following Reaction Scheme 3, but there is no limitation thereto.

After bromobenzene (37.1 g, 236.2 mmol) was placed in a round bottom flask and it was dissolved in toluene (2200 mL), aniline (20 g, 214.8 mmol), Pd$_2$(dba)$_3$ (9.83 g, 10.7 mmol), P(t-Bu)$_3$ (4.34 g, 21.5 mmol), NaOt-Bu (62 g, 644.3 mmol) were added thereto in sequence and the mixture was stirred at 100° C. When the reaction was completed, the reaction product was extracted with ether and water. Then, the organic layer was dried with MgSO$_4$ and concentrated. Then, the concentrate was recrystallized to obtain 28 g (yield: 77%) of the product.

(2) Synthesis Example of Sub 2-6

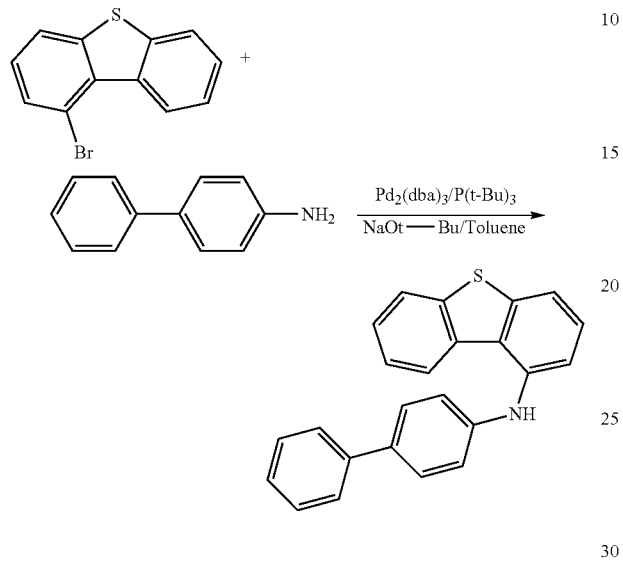

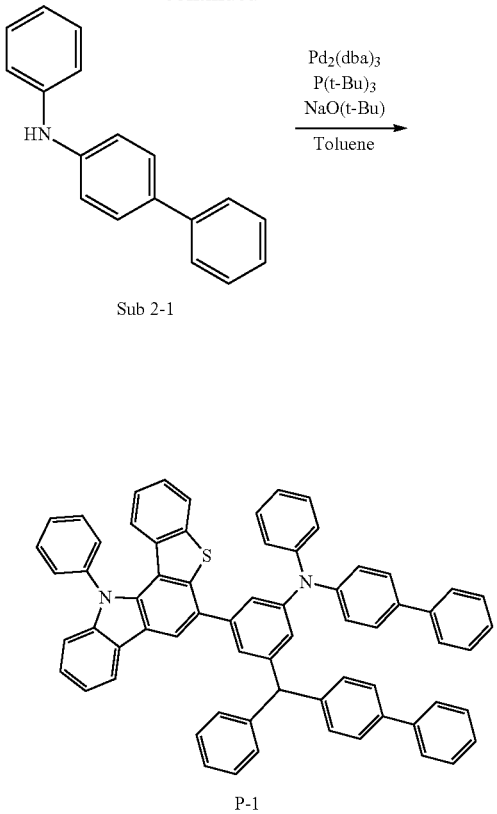

Sub 2-1

P-1

1-Bromodibenzo[b,d]thiophene (42.8 g, 162.5 mmol), toluene (1550 mL), [1,1'-biphenyl]-4-amine (25 g, 147.7 mmol), Pd$_2$(dba)$_3$ (6.76 g, 162.5 mmol), P(t-Bu)$_3$ (3 g, 14.8 mmol), NaOt-Bu (42.6 g, 443.2 mmol) were treated in the same manner as in the above synthesis method of Sub 2-1 to obtain 37.9 g (yield: 73%) of the product.

3. Synthesis Method of Product

After Compound Sub 1 (1 eq.) was placed in a round bottom flask and Compound Sub 2 (1 eq.), Pd$_2$(dba)$_3$ (0.03-0.05 eq.), P(t-Bu)$_3$ (0.08 eq.), NaO(t-Bu) (3 eq.), toluene (3 mmol) were added thereto, the mixture was heated under reflux at 100° C. When the reaction was completed, the reaction product was diluted with distilled water at room temperature and extracted with methylene chloride and water. Then, the organic layer was dried with MgSO$_4$ and concentrated. Then, the concentrate was recrystallized with toluene and acetone to obtain the product.

Synthesis of Compound P-1

After Sub 1-2 (5 g, 7.1 mmol), Sub 2-1 (1.74 g, 7.1 mmol), Pd$_2$(dba)$_3$ (0.20 g, 0.2 mmol), P(t-Bu)$_3$ (0.12 g, 0.8 mmol), NaO(t-Bu) (2.05 g, 21.3 mmol), toluene (71 mL) were placed in a round bottom flask, the mixture was heated under reflux at 110° C. for 3 hours. When the reaction was completed, the reaction product was diluted with distilled water at room temperature and extracted with methylene chloride and water. Then, the organic layer was dried with MgSO$_4$ and concentrated. After the concentrate was dissolved in toluene and was applied to silica filter. Then, the resultant was concentrated and recrystallized with toluene and acetone to obtain the product P-1 (5.25 g, 81%).

Synthesis of Compound P-12

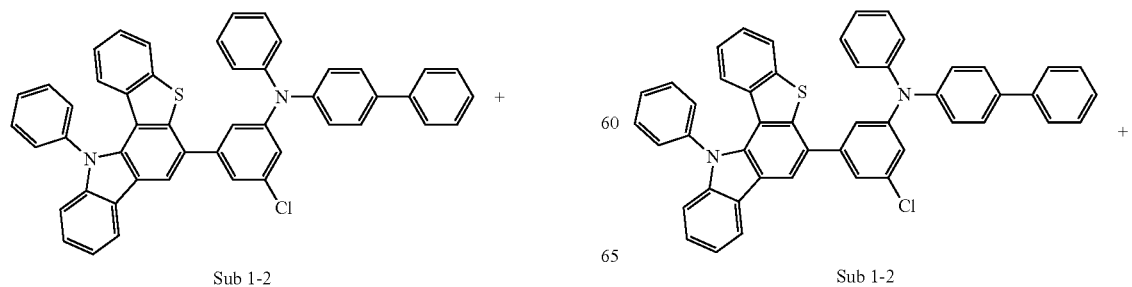

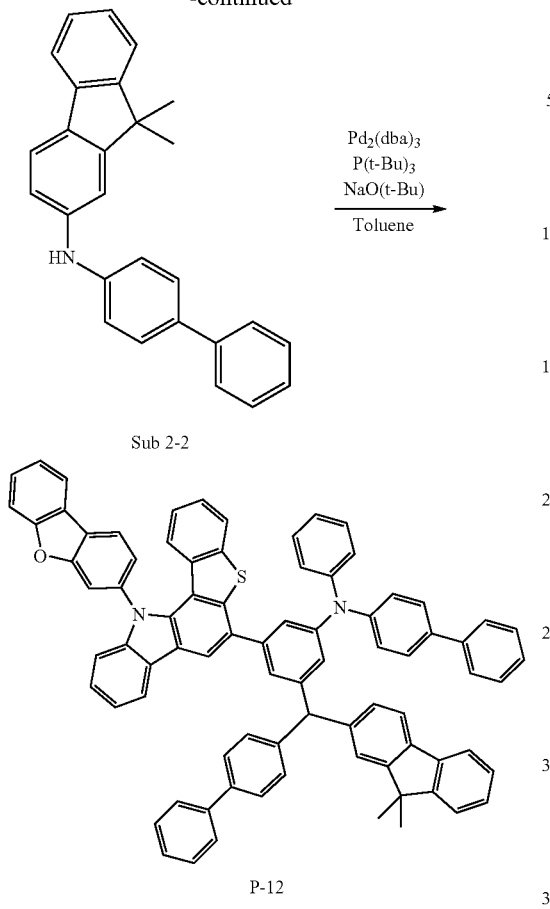

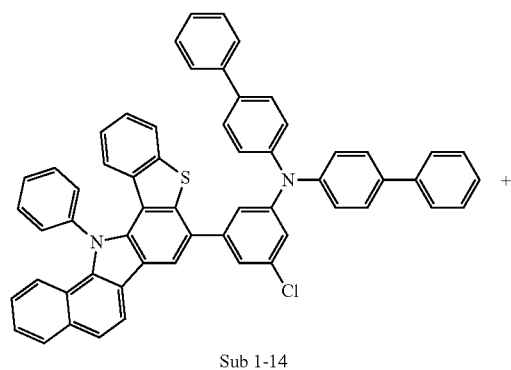

After Sub 1-2 (5 g, 7.1 mmol), Sub 2-2 (2.57 g, 7.1 mmol), Pd$_2$(dba)$_3$ (0.2 g, 0.2 mmol), P(t-Bu)$_3$ (0.12 g, 0.6 mmol), NaO(t-Bu) (2.05 g, 21.3 mmol), toluene (71 mL) were placed in a round bottom flask, the mixture was heated under reflux at 110° C. for 3 hours. When the reaction was completed, the reaction product was diluted with distilled water at room temperature and extracted with methylene chloride and water. Then, the organic layer was dried with MgSO$_4$ and concentrated. After the concentrate was dissolved in toluene and was applied to silica filter. Then, the resultant was concentrated and recrystallized with toluene and acetone to obtain the product P-12 (6.2 g, 78%).

Synthesis of Compound P-29

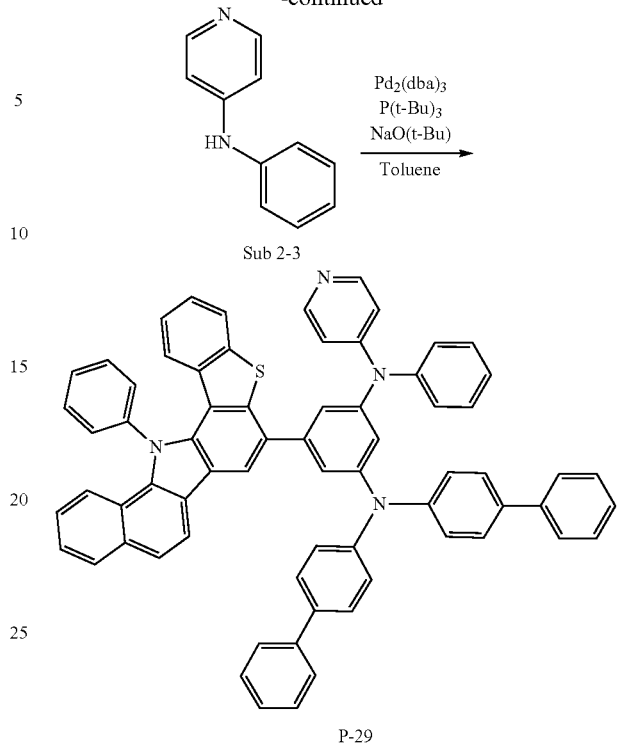

After Sub 1-14 (5 g, 6.0 mmol), Sub 2-3 (1.03 g, 6.0 mmol), Pd$_2$(dba)$_3$ (0.17 g, 0.2 mmol), P(t-Bu)$_3$ (0.1 g, 0.5 mmol), NaO(t-Bu) (1.74 g, 18.1 mmol), toluene (mL) were placed in a round bottom flask, the mixture was heated under reflux at 110° C. for 3 hours. When the reaction was completed, the reaction product was diluted with distilled water at room temperature and extracted with methylene chloride and water. Then, the organic layer was dried with MgSO$_4$ and concentrated. After the concentrate was dissolved in toluene and was applied to silica filter. Then, the resultant was concentrated and recrystallized with toluene and acetone to obtain the product P-29 (4.47 g, 77%).

Synthesis of Compound P-57

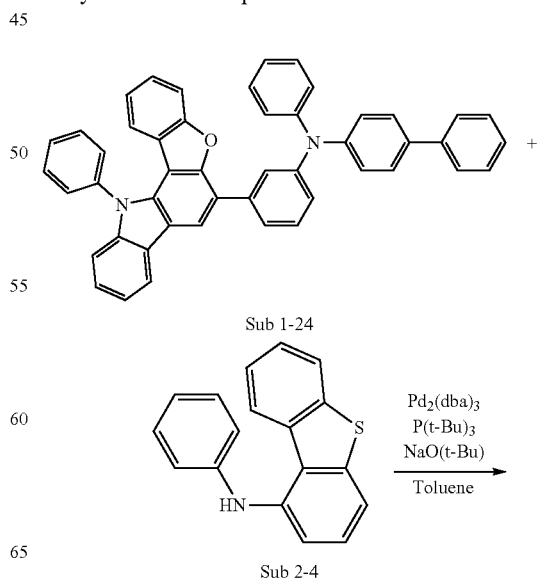

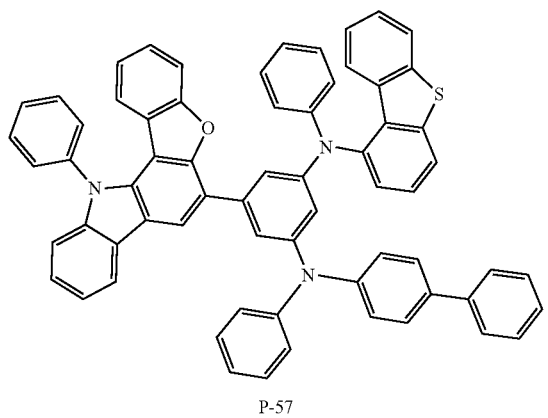

P-57

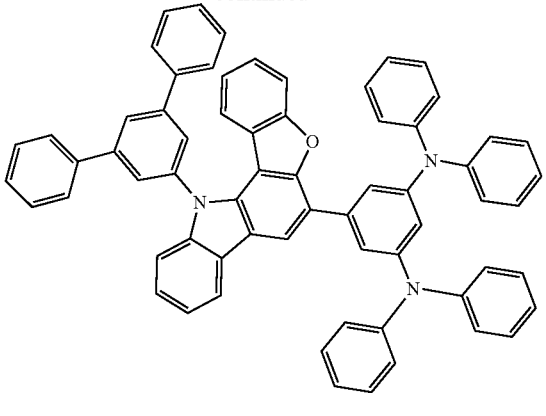

P-61

After Sub 1-24 (5 g, 7.7 mmol), Sub 2-4 (2.11 g, 7.7 mmol), Pd$_2$(dba)$_3$ (0.21 g, 0.2 mmol), P(t-Bu)$_3$ (0.12 g, 0.6 mmol), NaO(t-Bu) (2.21 g, 23.0 mmol), toluene (77 mL) were placed in a round bottom flask, the mixture was heated under reflux at 110° C. for 3 hours. When the reaction was completed, the reaction product was diluted with distilled water at room temperature and extracted with methylene chloride and water. Then, the organic layer was dried with MgSO$_4$ and concentrated. After the concentrate was dissolved in toluene and was applied to silica filter. Then, the resultant was concentrated and recrystallized with toluene and acetone to obtain the product P-57 (5.25 g, 74%).

Synthesis of Compound P-61

After Sub 1-32 (5 g, 6.6 mmol), Sub 2-5 (1.11 g, 6.6 mmol), Pd$_2$(dba)$_3$ (0.18 g, 0.2 mmol), P(t-Bu)$_3$ (0.11 g, 0.5 mmol), NaO(t-Bu) (1.89 g, 19.7 mmol), toluene (66 mL) were placed in a round bottom flask, the mixture was heated under reflux at 110° C. for 3 hours. When the reaction was completed, the reaction product was diluted with distilled water at room temperature and extracted with methylene chloride and water. Then, the organic layer was dried with MgSO$_4$ and concentrated. After the concentrate was dissolved in toluene and was applied to silica filter. Then, the resultant was concentrated and recrystallized with toluene and acetone to obtain the product P-61 (4.75 g, 81%).

Synthesis of Compound P-72

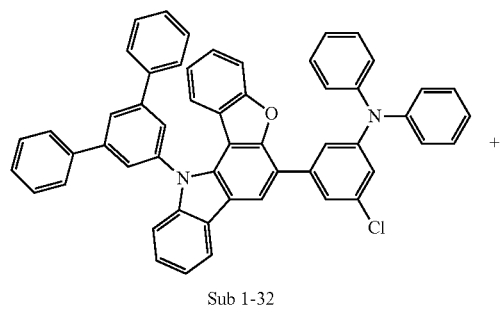

Sub 1-32

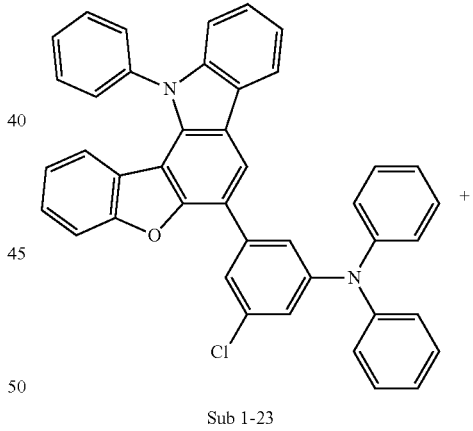

Sub 1-23

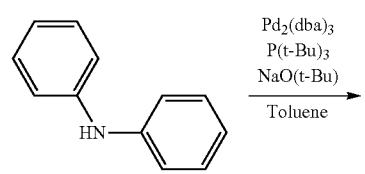

Sub 2-5

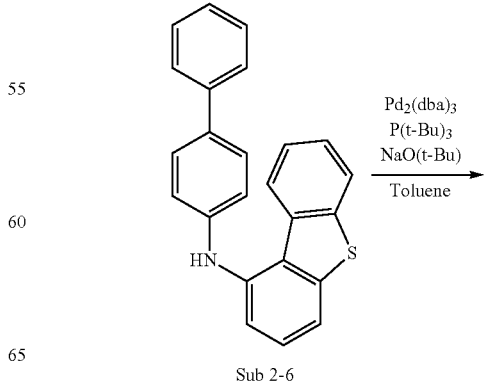

Sub 2-6

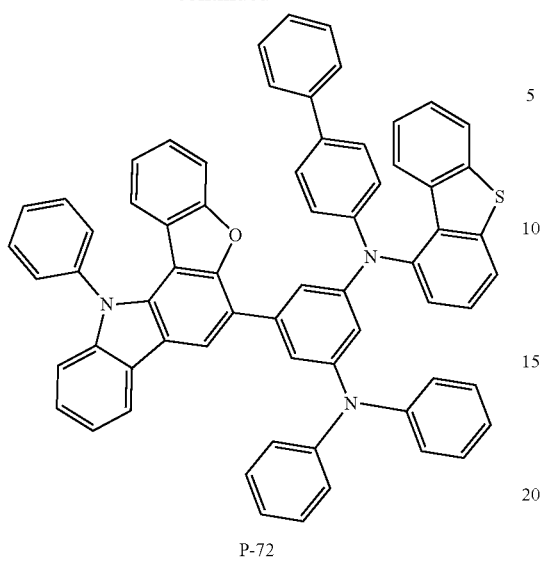

P-72

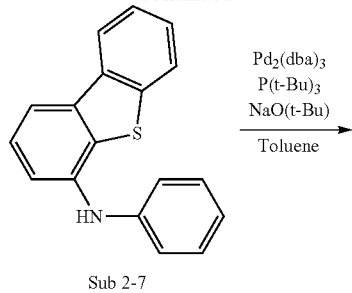

Sub 2-7

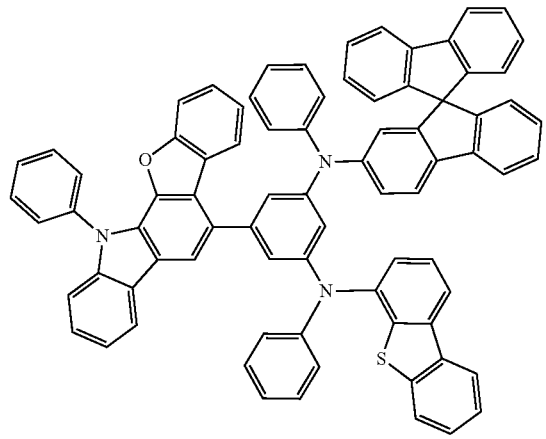

P-80

After Sub 1-23 (5 g, 8.2 mmol), Sub 2-6 (2.88 g, 8.2 mmol), $Pd_2(dba)_3$ (0.22 g, 0.2 mmol), $P(t-Bu)_3$ (0.13 g, 0.7 mmol), NaO(t-Bu) (2.36 g, 24.5 mmol), toluene (82 mL) were placed in a round bottom flask, the mixture was heated under reflux at 110° C. for 3 hours. When the reaction was completed, the reaction product was diluted with distilled water at room temperature and extracted with methylene chloride and water. Then, the organic layer was dried with $MgSO_4$ and concentrated. After the concentrate was dissolved in toluene and was applied to silica filter. Then, the resultant was concentrated and recrystallized with toluene and acetone to obtain the product P-72 (5.53 g, 73%).

Synthesis of Compound P-80

After Sub 1-48 (5 g, 5.9 mmol), Sub 2-7 (1.62 g, 5.9 mmol), $Pd_2(dba)_3$ (0.16 g, 0.2 mmol), $P(t-Bu)_3$ (0.1 g, 0.5 mmol), NaO(t-Bu) (1.7 g, 17.7 mmol), toluene (59 mL) were placed in a round bottom flask, the mixture was heated under reflux at 110° C. for 3 hours. When the reaction was completed, the reaction product was diluted with distilled water at room temperature and extracted with methylene chloride and water. Then, the organic layer was dried with $MgSO_4$ and concentrated. After the concentrate was dissolved in toluene and was applied to silica filter. Then, the resultant was concentrated and recrystallized with toluene and acetone to obtain the product P-80 (4.42 g, 69%).

Synthesis of Compound P-84

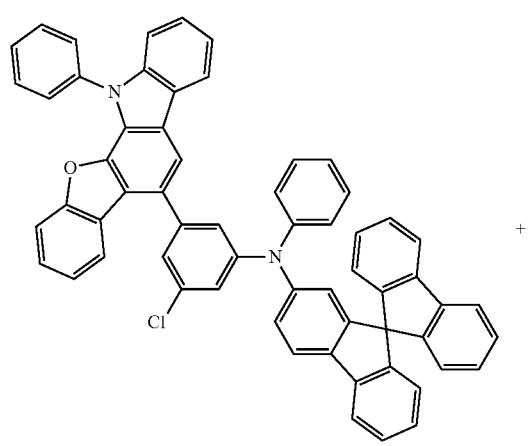

Sub 1-48

+

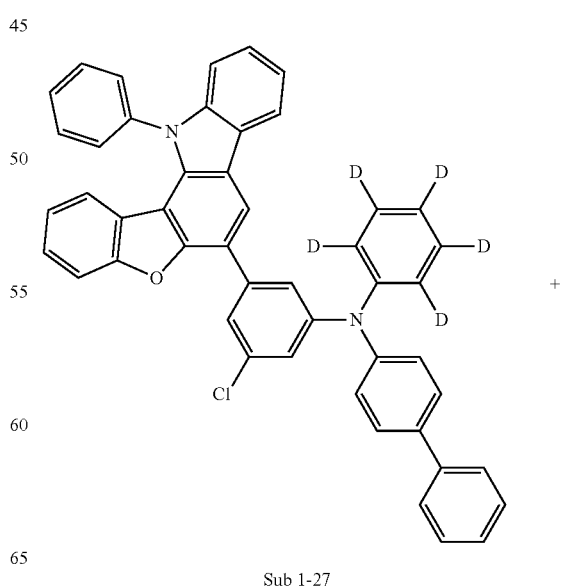

Sub 1-27

+

139

-continued

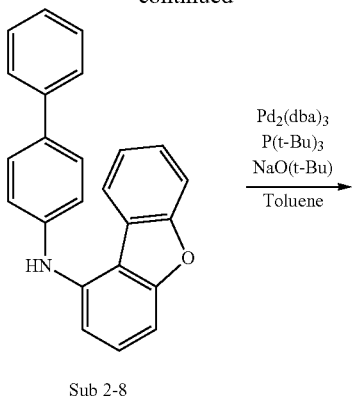

Sub 2-8

140

Synthesis of Compound P-89

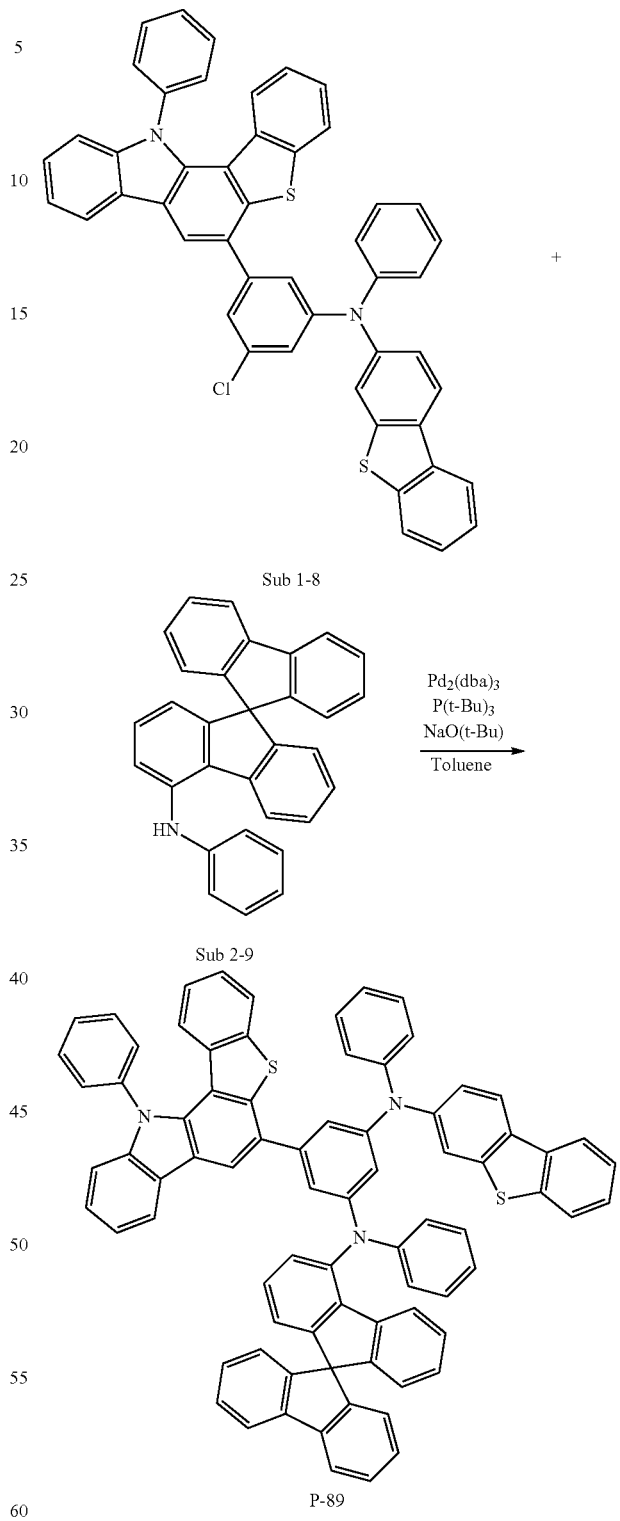

After Sub 1-27 (5 g, 7.2 mmol), Sub 2-8 (2.42 g, 7.2 mmol), Pd₂(dba)₃ (0.2 g, 0.2 mmol), P(t-Bu)₃ (0.12 g, 0.6 mmol), NaO(t-Bu) (2.08 g, 21.7 mmol), toluene (72 mL) were placed in a round bottom flask, the mixture was heated under reflux at 110° C. for 3 hours. When the reaction was completed, the reaction product was diluted with distilled water at room temperature and extracted with methylene chloride and water. Then, the organic layer was dried with MgSO₄ and concentrated. After the concentrate was dissolved in toluene and was applied to silica filter. Then, the resultant was concentrated and recrystallized with toluene and acetone to obtain the product P-84 (5.23 g, 73%).

After Sub 1-8 (5 g, 6.8 mmol), Sub 2-9 (2.78 g, 6.8 mmol), Pd₂(dba)₃ (0.19 g, 0.2 mmol), P(t-Bu)₃ (0.11 g, 0.5 mmol), NaO(t-Bu) (1.97 g, 20.5 mmol), toluene (68 mL) were placed in a round bottom flask, the mixture was heated under reflux at 110° C. for 3 hours. When the reaction was completed, the reaction product was diluted with distilled Synthesis of Compound P-93

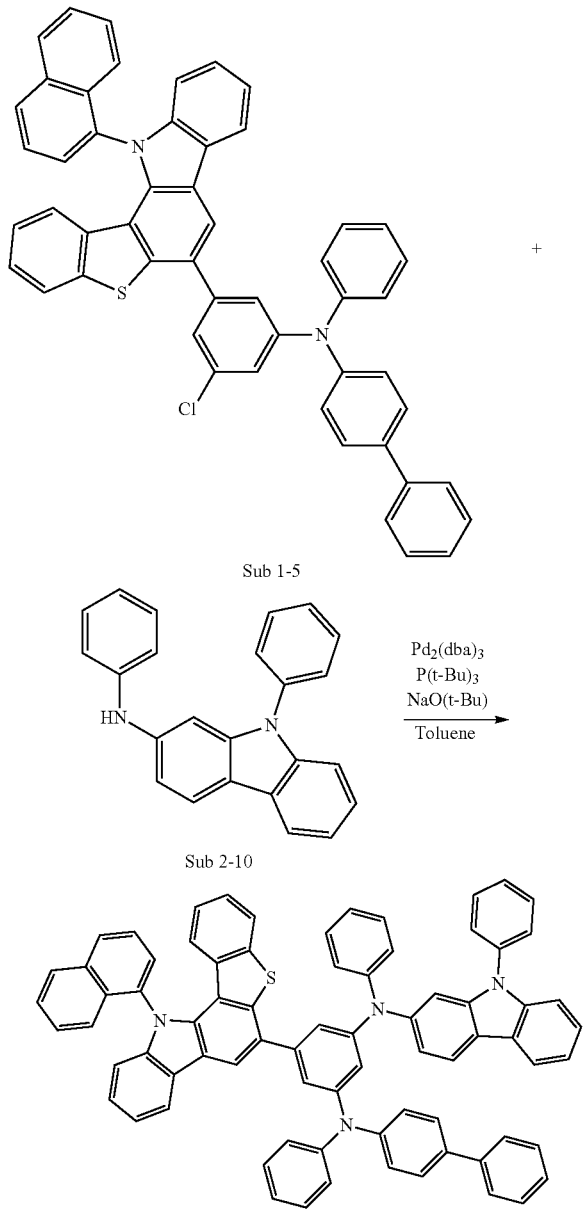

Synthesis of Compound P-101

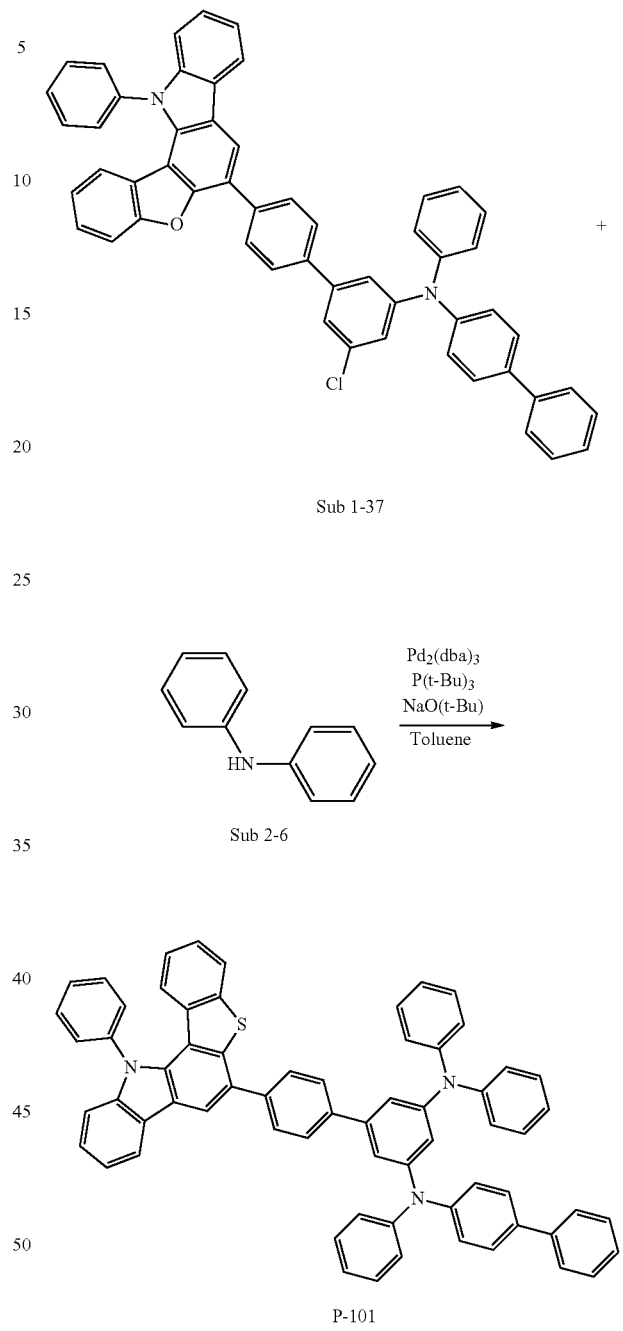

After Sub 1-5 (5 g, 6.6 mmol), Sub 2-10 (2.22 g, 6.6 mmol), Pd₂(dba)₃ (0.18 g, 0.2 mmol), P(t-Bu)₃ (0.11 g, 0.5 mmol), NaO(t-Bu) (1.91 g, 19.9 mmol), toluene (66 mL) were placed in a round bottom flask, the mixture was heated under reflux at 110° C. for 3 hours. When the reaction was completed, the reaction product was diluted with distilled water at room temperature and extracted with methylene chloride and water. Then, the organic layer was dried with MgSO₄ and concentrated. After the concentrate was dissolved in toluene and was applied to silica filter. Then, the resultant was concentrated and recrystallized with toluene and acetone to obtain the product P-93 (5.37 g, 77%).

After Sub 1-37 (5 g, 6.6 mmol), Sub 2-5 (1.11 g, 6.6 mmol), Pd₂(dba)₃ (0.18 g, 0.2 mmol), P(t-Bu)₃ (0.11 g, 0.5 mmol), NaO(t-Bu) (1.89 g, 19.7 mmol), toluene (66 mL) were placed in a round bottom flask, the mixture was heated under reflux at 110° C. for 3 hours. When the reaction was completed, the reaction product was diluted with distilled water at room temperature and extracted with methylene chloride and water. Then, the organic layer was dried with MgSO₄ and concentrated. After the concentrate was dissolved in toluene and was applied to silica filter. Then, the resultant was concentrated and recrystallized with toluene and acetone to obtain the product P-101 (4.4 g, 75%).

Synthesis of Compound P-102

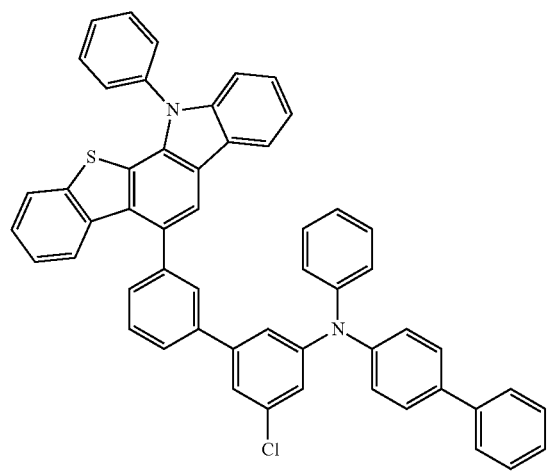

Sub 1-44

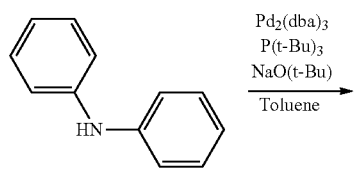

Sub 2-5

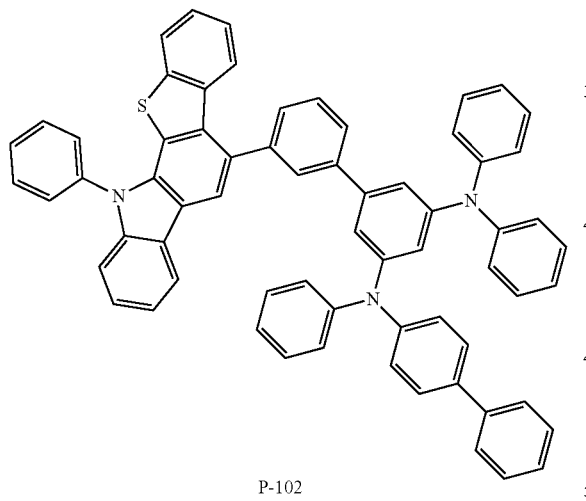

P-102

After Sub 1-44 (5 g, 6.4 mmol), Sub 2-5 (1.09 g, 6.4 mmol), Pd$_2$(dba)$_3$ (0.18 g, 0.2 mmol), P(t-Bu)$_3$ (0.10 g, 0.5 mmol), NaO(t-Bu) (1.85 g, 19.2 mmol), toluene (64 mL) were placed in a round bottom flask, the mixture was heated under reflux at 110° C. for 3 hours. When the reaction was completed, the reaction product was diluted with distilled water at room temperature and extracted with methylene chloride and water. Then, the organic layer was dried with MgSO$_4$ and concentrated. After the concentrate was dissolved in toluene and was applied to silica filter. Then, the resultant was concentrated and recrystallized with toluene and acetone to obtain the product P-102 (4.56 g, 78%).

Synthesis of Compound P-109

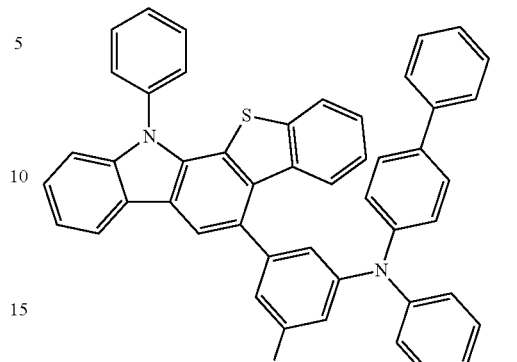

Sub 1-41

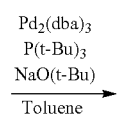

Sub 2-11

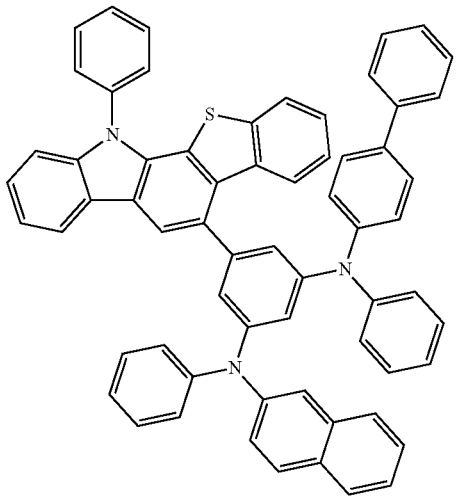

P-109

After Sub 1-41 (5 g, 7.1 mmol), Sub 2-11 (1.56 g, 7.1 mmol), Pd$_2$(dba)$_3$ (0.2 g, 0.2 mmol), P(t-Bu)$_3$ (0.12 g, 0.6 mmol), NaO(t-Bu) (2.05 g, 21.3 mmol), toluene (71 mL) were placed in a round bottom flask, the mixture was heated under reflux at 110° C. for 3 hours. When the reaction was completed, the reaction product was diluted with distilled water at room temperature and extracted with methylene chloride and water. Then, the organic layer was dried with MgSO$_4$ and concentrated. After the concentrate was dissolved in toluene and was applied to silica filter. Then, the resultant was concentrated and recrystallized with toluene and acetone to obtain the product P-109 (4.03 g, 64%).

Synthesis of Compound P-116

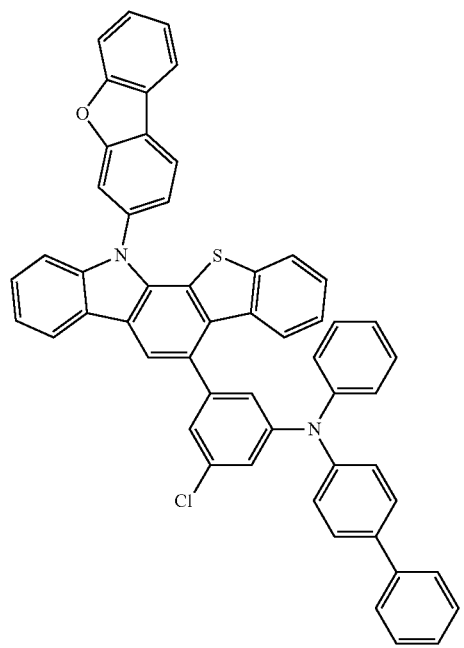

Sub 1-42

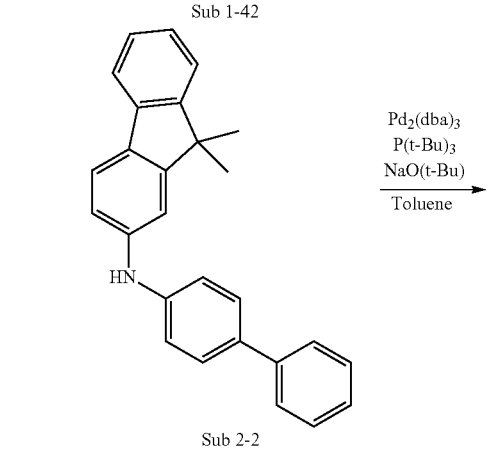

Sub 2-2

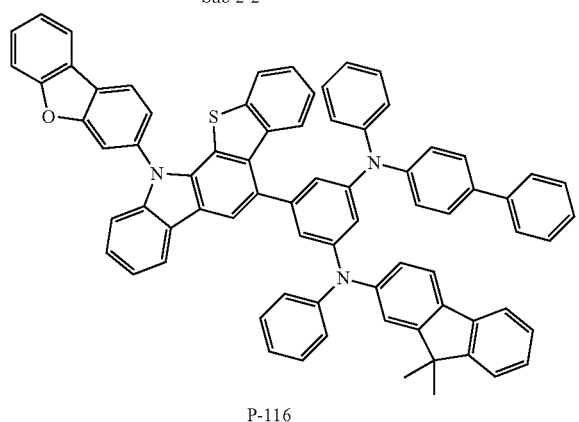

P-116

After Sub 1-42 (5 g, 6.3 mmol), Sub 2-2 (2.28 g, 6.3 mmol), Pd$_2$(dba)$_3$ (0.17 g, 0.2 mmol), P(t-Bu)$_3$ (0.1 g, 0.2 mmol), NaO(t-Bu) (0.1 g, 0.5 mmol), toluene (63 mL) were placed in a round bottom flask, the mixture was heated under reflux at 110° C. for 3 hours. When the reaction was completed, the reaction product was diluted with distilled water at room temperature and extracted with methylene chloride and water. Then, the organic layer was dried with MgSO$_4$ and concentrated. After the concentrate was dissolved in toluene and was applied to silica filter. Then, the resultant was concentrated and recrystallized with toluene and acetone to obtain the product P-116 (5.0 g, 71%).

Synthesis of Compound P-118

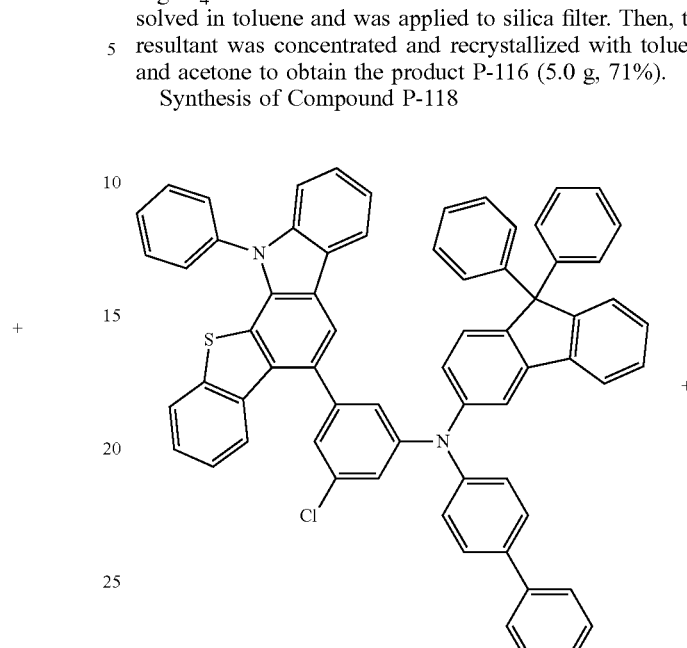

Sub 1-43

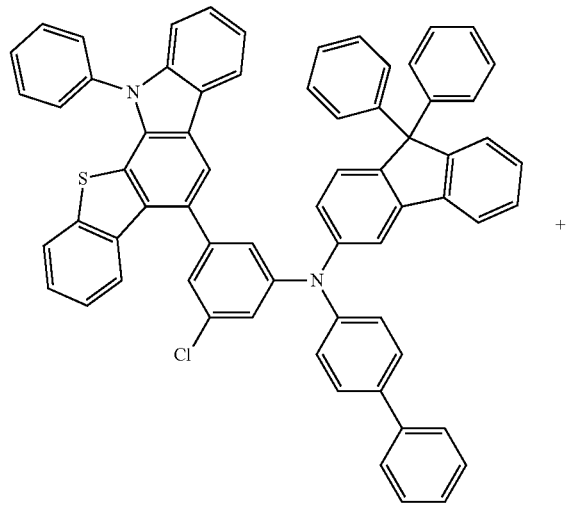

Sub 2-12

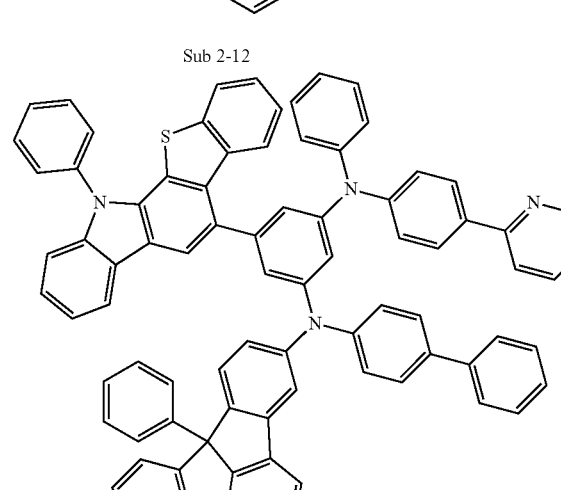

P-118

After Sub 1-43 (5 g, 5.3 mmol), Sub 2-12 (1.31 g, 5.3 mmol), Pd$_2$(dba)$_3$ (0.15 g, 0.2 mmol), P(t-Bu)$_3$ (0.09 g, 0.4 mmol), NaO(t-Bu) (1.53 g, 15.9 mmol), toluene (53 mL) were placed in a round bottom flask, the mixture was heated under reflux at 110° C. for 3 hours. When the reaction was completed, the reaction product was diluted with distilled water at room temperature and extracted with methylene chloride and water. Then, the organic layer was dried with MgSO$_4$ and concentrated. After the concentrate was dissolved in toluene and was applied to silica filter. Then, the resultant was concentrated and recrystallized with toluene and acetone to obtain the product P-118 (4.28 g, 70%).

Synthesis of Compound P-127

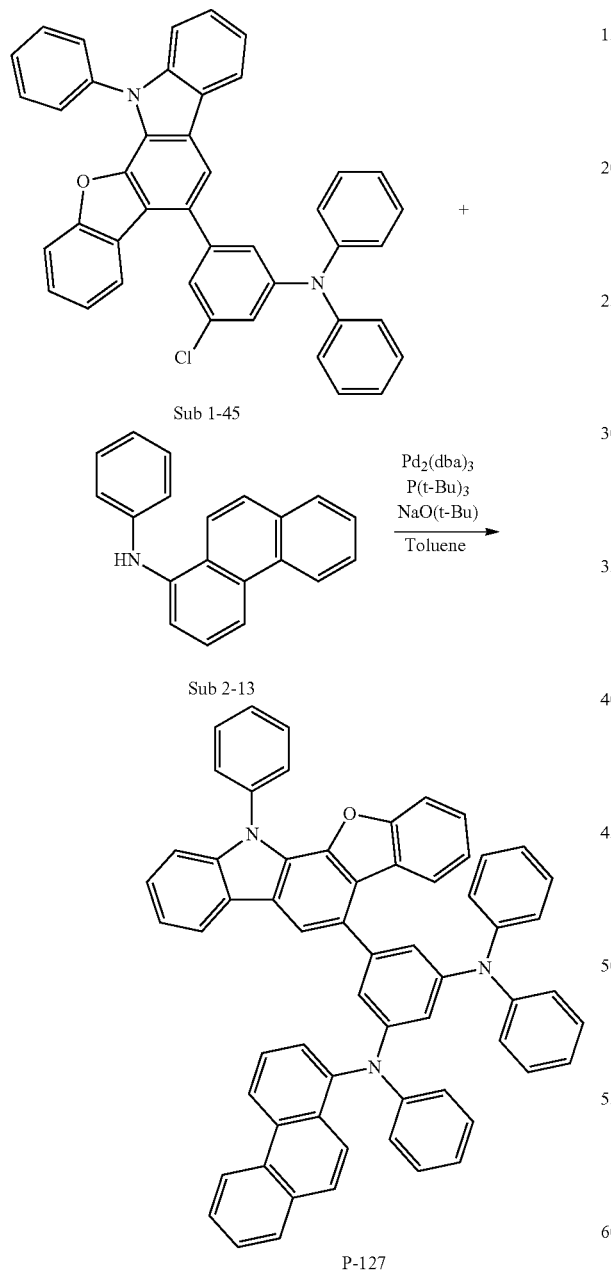

P-127 under reflux at 110° C. for 3 hours. When the reaction was completed, the reaction product was diluted with distilled water at room temperature and extracted with methylene chloride and water. Then, the organic layer was dried with MgSO$_4$ and concentrated. After the concentrate was dissolved in toluene and was applied to silica filter. Then, the resultant was concentrated and recrystallized with toluene and acetone to obtain the product P-127 (5.32 g, 77%).

Synthesis of Compound P-130

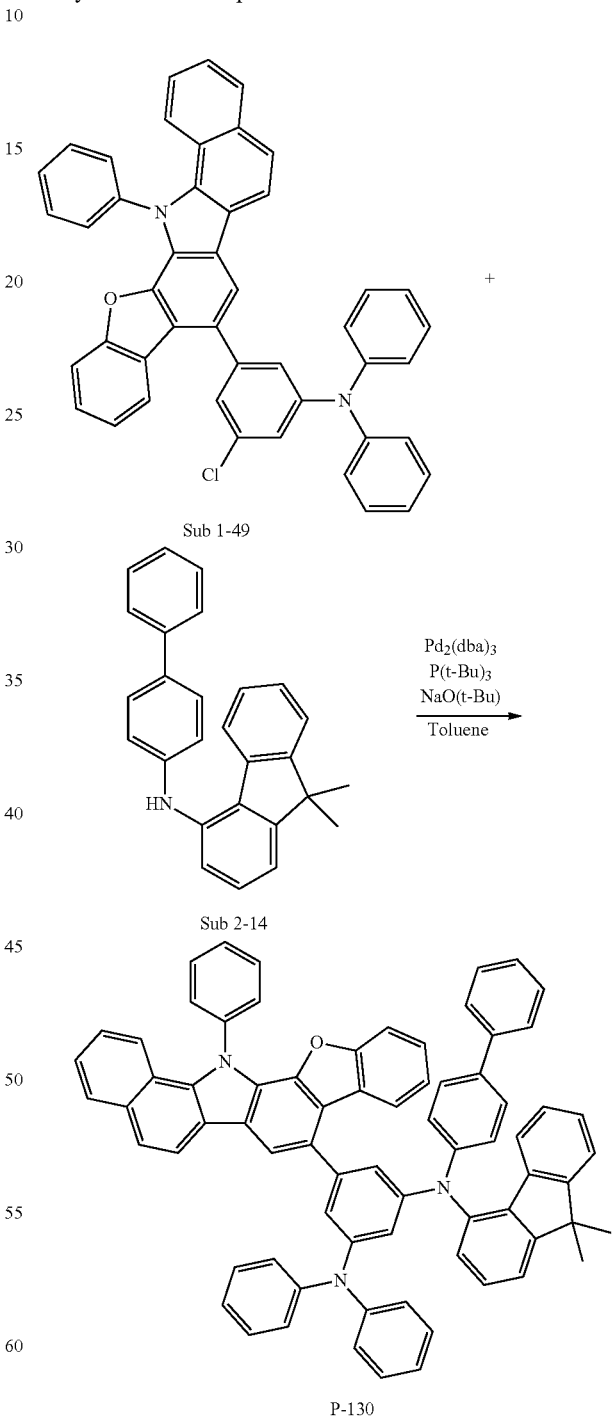

P-130

After Sub 1-45 (5 g, 8.2 mmol), Sub 2-13 (2.2 g, 8.2 mmol), Pd$_2$(dba)$_3$ (0.22 g, 0.2 mmol), P(t-Bu)$_3$ (0.13 g, 0.7 mmol), NaO(t-Bu) (2.36 g, 24.5 mmol), toluene (82 mL) were placed in a round bottom flask, the mixture was heated After Sub 1-49 (5 g, 7.6 mmol), Sub 2-14 (2.73 g, 7.6 mmol), Pd$_2$(dba)$_3$ (0.21 g, 0.2 mmol), P(t-Bu)$_3$ (0.12 g, 0.6 mmol), NaO(t-Bu) (2.18 g, 22.7 mmol), toluene (76 mL)

were placed in a round bottom flask, the mixture was heated under reflux at 110° C. for 3 hours. When the reaction was completed, the reaction product was diluted with distilled water at room temperature and extracted with methylene chloride and water. Then, the organic layer was dried with $MgSO_4$ and concentrated. After the concentrate was dissolved in toluene and was applied to silica filter. Then, the resultant was concentrated and recrystallized with toluene and acetone to obtain the product P-130 (6.04 g, 81%).

Synthesis Example 2 (where p is 2)

As shown in Reaction Scheme 4 below, the compounds (final products) represented by Formula 1 according to the present invention can be synthesized by reacting Sub 3 with Sub 2, but there is no limitation thereto.

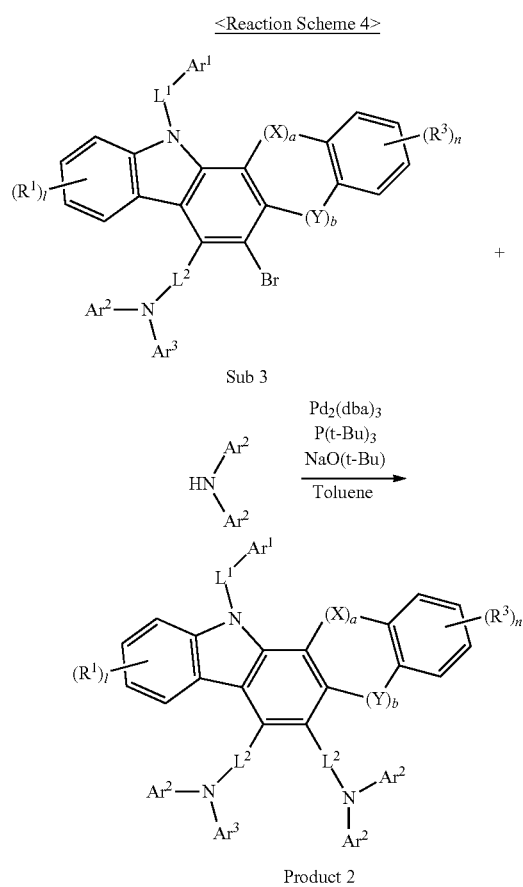

Synthesis Example of Sub 3

Sub 3 of the Reaction Scheme 4 can be synthesized according to the reaction routes of the following Reaction Scheme 5, but it is not limited thereto.

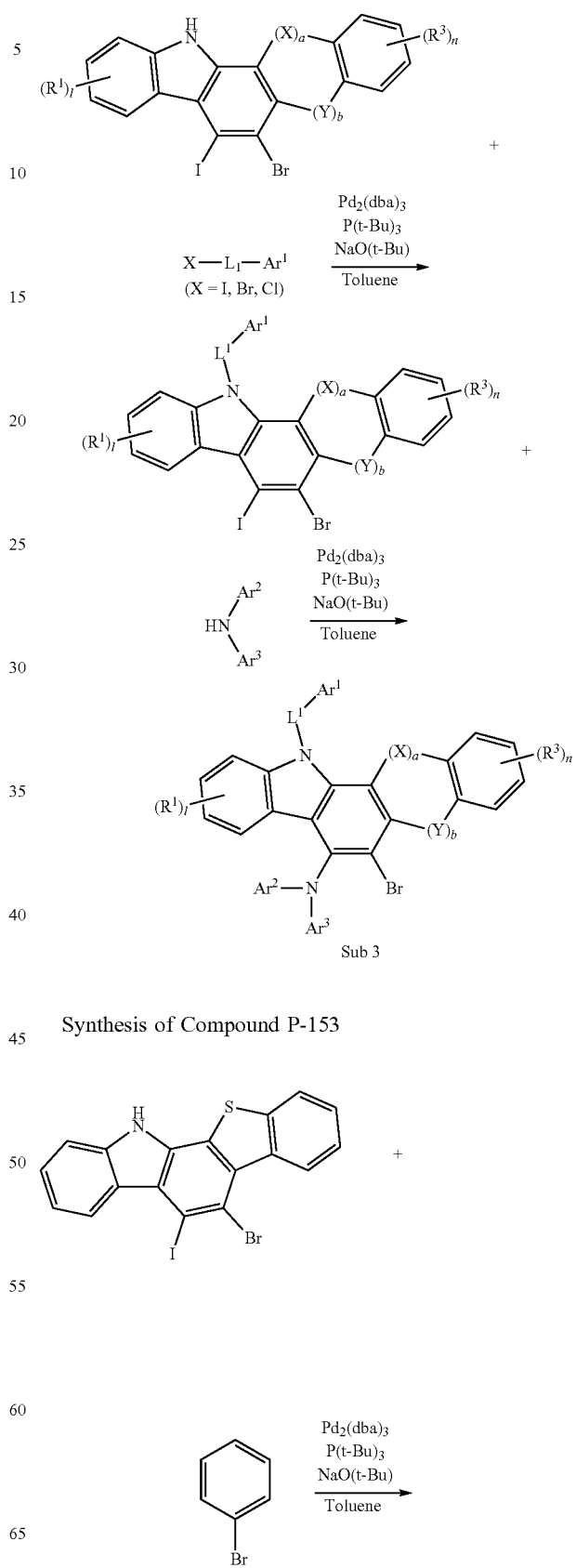

Synthesis of Compound P-153

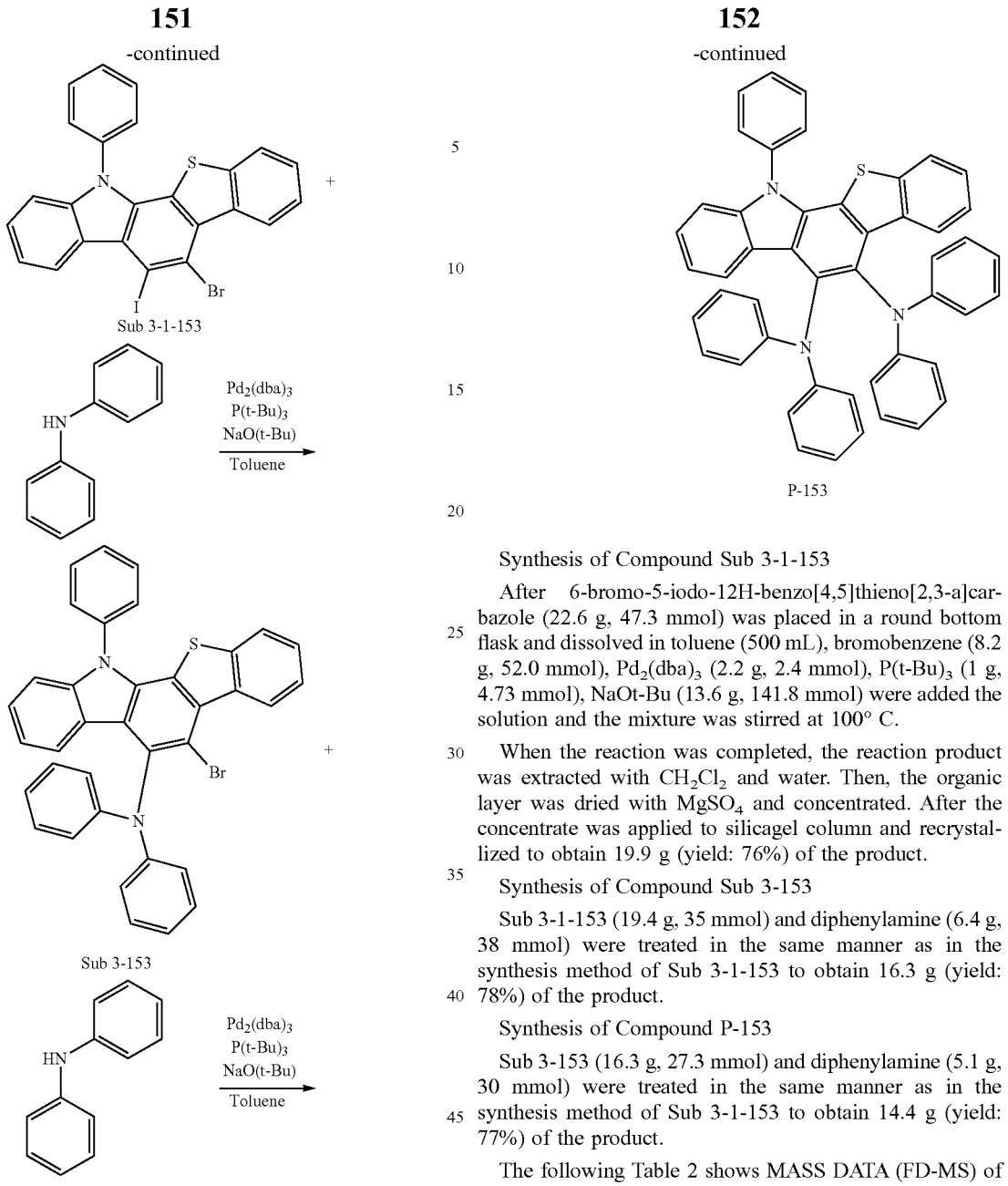

Synthesis of Compound Sub 3-1-153

After 6-bromo-5-iodo-12H-benzo[4,5]thieno[2,3-a]carbazole (22.6 g, 47.3 mmol) was placed in a round bottom flask and dissolved in toluene (500 mL), bromobenzene (8.2 g, 52.0 mmol), Pd$_2$(dba)$_3$ (2.2 g, 2.4 mmol), P(t-Bu)$_3$ (1 g, 4.73 mmol), NaOt-Bu (13.6 g, 141.8 mmol) were added the solution and the mixture was stirred at 100° C.

When the reaction was completed, the reaction product was extracted with CH$_2$Cl$_2$ and water. Then, the organic layer was dried with MgSO$_4$ and concentrated. After the concentrate was applied to silicagel column and recrystallized to obtain 19.9 g (yield: 76%) of the product.

Synthesis of Compound Sub 3-153

Sub 3-1-153 (19.4 g, 35 mmol) and diphenylamine (6.4 g, 38 mmol) were treated in the same manner as in the synthesis method of Sub 3-1-153 to obtain 16.3 g (yield: 78%) of the product.

Synthesis of Compound P-153

Sub 3-153 (16.3 g, 27.3 mmol) and diphenylamine (5.1 g, 30 mmol) were treated in the same manner as in the synthesis method of Sub 3-1-153 to obtain 14.4 g (yield: 77%) of the product.

The following Table 2 shows MASS DATA (FD-MS) of the compounds P-1 to P-156 belonging to the Formula 1.

TABLE 2

| Compound | FD-MS | Compound | FD-MS |
|---|---|---|---|
| P-1 | m/z = 911.33 (C$_{66}$H$_{45}$N$_3$S = 912.17) | P-2 | m/z = 987.36 (C$_{72}$H$_{49}$N$_3$S = 988.27) |
| P-3 | m/z = 911.33 (C$_{66}$H$_{45}$N$_3$S = 912.17) | P-4 | m/z = 911.33 (C$_{66}$H$_{45}$N$_3$S = 912.17) |
| P-5 | m/z = 885.32 (C$_{64}$H$_{43}$N$_3$S = 886.13) | P-6 | m/z = 961.35 (C$_{70}$H$_{47}$N$_3$S = 962.23) |
| P-7 | m/z = 951.36 (C$_{69}$H$_{49}$N$_3$S = 952.23) | P-8 | m/z = 1075.40 (C$_{79}$H$_{53}$N$_3$S = 1076.37) |
| P-9 | m/z = 1073.38 (C$_{79}$H$_{51}$N$_3$S = 1074.36) | P-10 | m/z = 1075.40 (C$_{79}$H$_{53}$N$_3$S = 1076.37) |
| P-11 | m/z = 1073.38 (C$_{79}$H$_{51}$N$_3$S = 1074.36) | P-12 | m/z = 1117.41(C$_{81}$H$_{55}$N$_3$OS = 1118.41) |
| P-13 | m/z = 1151.43 (C$_{85}$H$_{57}$N$_3$S = 1152.47) | P-14 | m/z = 1152.42 (C$_{84}$H$_{56}$N$_4$S = 1153.46) |
| P-15 | m/z = 1149.41 (C$_{85}$H$_{55}$N$_3$S = 1150.46) | P-16 | m/z = 941.29 (C$_{66}$H$_{43}$N$_3$S$_2$ = 942.21) |
| P-17 | m/z = 941.29 (C$_{66}$H$_{43}$N$_3$S$_2$ = 942.21) | P-18 | m/z = 975.33 (C$_{70}$H$_{45}$N$_3$OS = 976.21) |
| P-19 | m/z = 1001.34(C$_{72}$H$_{47}$N$_3$OS = 1002.25) | P-20 | m/z = 925.31 (C$_{66}$H$_{43}$N$_3$OS = 926.15) |
| P-21 | m/z = 1067.34 (C$_{76}$H$_{49}$N$_3$S$_2$ = 1068.37) | P-22 | m/z = 1017.32 (C$_{72}$H$_{47}$N$_3$S$_2$ = 1018.31) |
| P-23 | m/z = 1051.36(C$_{76}$H$_{49}$N$_3$OS = 1052.31) | P-24 | m/z = 1001.34(C$_{72}$H$_{47}$N$_3$OS = 1002.25) |
| P-25 | m/z = 1017.32 (C$_{72}$H$_{47}$N$_3$S$_2$ = 1018.31) | P-26 | m/z = 1001.34(C$_{72}$H$_{47}$N$_3$OS = 1002.25) |
| P-27 | m/z = 759.27 (C$_{54}$H$_{37}$N$_3$S = 759.97) | P-28 | m/z = 835.30 (C$_{60}$H$_{41}$N$_3$S = 836.07) |
| P-29 | m/z = 962.34 (C$_{69}$H$_{46}$N$_4$S = 963.22) | P-30 | m/z = 885.32 (C$_{64}$H$_{43}$N$_3$S = 886.13) |
| P-31 | m/z = 961.35 (C$_{70}$H$_{47}$N$_3$S = 962.23) | P-32 | m/z = 860.30 (C$_{61}$H$_{40}$N$_4$S = 861.08) |
| P-33 | m/z = 909.32 (C$_{66}$H$_{43}$N$_3$S = 910.15) | P-34 | m/z = 1017.36 (C$_{73}$H$_{48}$FN$_3$S = 1018.3) |

TABLE 2-continued

| Compound | FD-MS | Compound | FD-MS |
|---|---|---|---|
| P-35 | m/z = 1027.40 ($C_{75}H_{53}N_3S$ = 1028.33) | P-36 | m/z = 941.29 ($C_{66}H_{43}N_3S_2$ = 942.21) |
| P-37 | m/z = 854.31($C_{60}H_{34}D_5N_3OS$ = 855.08) | P-38 | m/z = 925.31 ($C_{66}H_{43}N_3OS$ = 926.15) |
| P-39 | m/z = 925.31 ($C_{66}H_{43}N_3OS$ = 926.15) | P-40 | m/z = 1063.40 ($C_{78}H_{53}N_3S$ = 1064.36) |
| P-41 | m/z = 987.36 ($C_{72}H_{49}N_3S$ = 988.27) | P-42 | m/z = 961.35 ($C_{70}H_{47}N_3S$ = 962.23) |
| P-43 | m/z = 1151.43 ($C_{85}H_{57}N_3S$ = 1152.47) | P-44 | m/z = 1149.41 ($C_{85}H_{55}N_3S$ = 1150.46) |
| P-45 | m/z = 1017.32 ($C_{72}H_{47}N_3S_2$ = 1018.31) | P-46 | m/z = 1001.34($C_{72}H_{47}N_3OS$ = 1002.25) |
| P-47 | m/z = 1077.38($C_{78}H_{51}N_3OS$ = 1078.35) | P-48 | m/z = 1093.35($C_{78}H_{51}N_3S_2$ = 1094.41) |
| P-49 | m/z = 951.42 ($C_{70}H_{53}N_3O$ = 952.21) | P-50 | m/z = 971.39 ($C_{72}H_{49}N_3O$ = 972.20) |
| P-51 | m/z = 887.33 ($C_{64}H_{42}FN_3O$ = 888.06) | P-52 | m/z = 935.39 ($C_{69}H_{49}N_3O$ = 936.17) |
| P-53 | m/z = 1059.42 ($C_{79}H_{53}N_3O$ = 1060.31) | P-54 | m/z = 935.39 ($C_{69}H_{49}N_3O$ = 936.17) |
| P-55 | m/z = 1136.45 ($C_{84}H_{56}N_4O$ = 1137.40) | P-56 | m/z = 925.31 ($C_{66}H_{43}N_3OS$ = 926.15) |
| P-57 | m/z = 925.31 ($C_{66}H_{43}N_3OS$ = 926.15) | P-58 | m/z = 909.34 ($C_{66}H_{43}N_3O_2$ = 910.09) |
| P-59 | m/z = 909.34 ($C_{66}H_{43}N_3O_2$ = 910.09) | P-60 | m/z = 1001.34($C_{72}H_{47}N_3OS$ = 1002.25) |
| P-61 | m/z = 895.36($C_{66}H_{45}N_3O$ = 896.11000) | P-62 | m/z = 819.32 ($C_{60}H_{41}N_3O$ = 820.01) |
| P-63 | m/z = 896.35 ($C_{65}H_{44}N_4O$ = 897.09) | P-64 | m/z = 819.32 ($C_{60}H_{41}N_3O$ = 820.01) |
| P-65 | m/z = 895.36 ($C_{66}H_{45}N_3O$ = 896.11) | P-66 | m/z = 945.37 ($C_{70}H_{47}N_3O$ = 946.17) |
| P-67 | m/z = 843.32 ($C_{62}H_{41}N_3O$ = 844.03) | P-68 | m/z = 893.34 ($C_{66}H_{43}N_3O$ = 894.09) |
| P-69 | m/z = 981.37 ($C_{73}H_{47}N_3O$ = 982.20) | P-70 | m/z = 935.39 ($C_{69}H_{49}N_3O$ = 936.17) |
| P-71 | m/z = 833.30 ($C_{60}H_{39}N_3O_2$ = 833.99) | P-72 | m/z = 925.31 ($C_{66}H_{43}N_3OS$ = 926.15) |
| P-73 | m/z = 1047.42 ($C_{78}H_{53}N_3O$ = 1048.30) | P-74 | m/z = 971.39 ($C_{72}H_{49}N_3O$ = 972.20) |
| P-75 | m/z = 1021.40 ($C_{76}H_{51}N_3O$ = 1022.26) | P-76 | m/z = 1001.34($C_{72}H_{47}N_3OS$ = 1002.25) |
| P-77 | m/z = 985.37 ($C_{72}H_{47}N_3O_2$ = 986.19) | P-78 | m/z = 985.37 ($C_{72}H_{47}N_3O_2$ = 986.19) |
| P-79 | m/z = 1061.40($C_{78}H_{51}N_3O_2$ = 1062.29) | P-80 | m/z = 1087.36($C_{79}H_{49}N_3OS$ = 1088.34) |
| P-81 | m/z = 916.36 ($C_{66}H_{40}D_5N_3S$ = 917.20) | P-82 | m/z = 992.40 ($C_{72}H_{44}D_5N_3S$ = 993.30) |
| P-83 | m/z = 1064.45 ($C_{79}H_{48}D_5N_3O$ = 1065.34) | P-84 | m/z = 990.40 ($C_{72}H_{42}D_5N_3O_2$ = 991.2) |
| P-85 | m/z = 1047.28 ($C_{72}H_{43}N_3S_3$ = 1048.35) | P-86 | m/z = 1015.32 ($C_{72}H_{45}N_3O_2S$ = 1016.23) |
| P-87 | m/z = 1031.30 ($C_{72}H_{45}N_3OS_2$ = 1032.29) | P-88 | m/z = 1015.32($C_{72}H_{45}N_3O_2S$ = 1016.23) |
| P-89 | m/z = 1103.34 ($C_{79}H_{49}N_3S_2$ = 1104.40) | P-90 | m/z = 1031.30 ($C_{72}H_{45}N_3OS_2$ = 1032.29) |
| P-91 | m/z = 1015.32 ($C_{72}H_{45}N_3O_2S$ = 1016.23) | P-92 | m/z = 965.34 ($C_{69}H_{47}N_3OS$ = 966.22) |
| P-93 | m/z = 1050.38 ($C_{76}H_{50}N_4S$ = 1051.32) | P-94 | m/z = 1106.35 ($C_{78}H_{50}N_4S_2$ = 1107.41) |
| P-95 | m/z = 911.33 ($C_{66}H_{45}N_3S$ = 912.17) | P-96 | m/z = 1090.37($C_{78}H_{50}N_4OS$ = 1091.35) |
| P-97 | m/z = 985.37 ($C_{72}H_{47}N_3O_2$ = 986.19) | P-98 | m/z = 987.36 ($C_{72}H_{49}N_3S$ = 988.27) |
| P-99 | m/z = 1063.40 ($C_{78}H_{53}N_3S$ = 1064.36) | P-100 | m/z = 1077.38($C_{78}H_{51}N_3OS$ = 1078.35) |
| P-101 | m/z = 895.36 ($C_{66}H_{45}N_3O$ = 896.11) | P-102 | m/z = 911.33 ($C_{66}H_{45}N_3S$ = 912.17) |
| P-103 | m/z = 1087.45 ($C_{81}H_{57}N_3O$ = 1088.37) | P-104 | m/z = 1037.38 ($C_{76}H_{51}N_3S$ = 1038.33) |
| P-105 | m/z = 911.33 ($C_{66}H_{45}N_3S$ = 912.17) | P-106 | m/z = 987.36 ($C_{72}H_{49}N_3S$ = 988.27) |
| P-107 | m/z = 913.35 ($C_{66}H_{47}N_3S$ = 914.18) | P-108 | m/z = 911.33 ($C_{66}H_{45}N_3S$ = 912.17) |
| P-109 | m/z = 885.32 ($C_{64}H_{43}N_3S$ = 886.13) | P-110 | m/z = 961.35 ($C_{70}H_{47}N_3S$ = 962.23) |
| P-111 | m/z = 951.36 ($C_{69}H_{49}N_3S$ = 952.23) | P-112 | m/z = 1075.40 ($C_{79}H_{53}N_3S$ = 1076.37) |
| P-113 | m/z = 1073.38 ($C_{79}H_{51}N_3S$ = 1074.36) | P-114 | m/z = 1075.40 ($C_{79}H_{53}N_3S$ = 1076.37) |
| P-115 | m/z = 1073.38 ($C_{79}H_{51}N_3S$ = 1074.36) | P-116 | m/z1117.41 ($C_{81}H_{55}N_3OS$ = 1118.41) |
| P-117 | m/z = 1151.43 ($C_{85}H_{57}N_3S$ = 1152.47) | P-118 | m/z = 1152.42 ($C_{84}H_{56}N_4S$ = 1153.46) |
| P-119 | m/z = 1149.41($C_{85}H_{55}N_3S$ = 1150.46) | P-120 | m/z = 941.29 ($C_{66}H_{43}N_3S_2$ = 942.21) |
| P-121 | m/z = 743.29 ($C_{54}H_{37}N_3O$ = 743.91) | P-122 | m/z = 819.32 ($C_{60}H_{41}N_3O$ = 820.01) |
| P-123 | m/z = 896.35 ($C_{65}H_{44}N_4O$ = 897.09) | P-124 | m/z = 819.32 ($C_{60}H_{41}N_3O$ = 820.01) |
| P-125 | m/z = 909.37 ($C_{67}H_{47}N_3O$ = 910.13) | P-126 | m/z = 869.34 ($C_{64}H_{43}N_3O$ = 870.07) |
| P-127 | m/z = 843.32 ($C_{62}H_{41}N_3O$ = 844.03) | P-128 | m/z = 893.34 ($C_{66}H_{43}N_3O$ = 894.09) |
| P-129 | m/z = 981.37 ($C_{73}H_{47}N_3O$ = 982.20) | P-130 | m/z = 985.40 ($C_{73}H_{51}N_3O$ = 986.23) |
| P-131 | m/z = 834.30 ($C_{59}H_{38}N_4O_2$ = 834.98) | P-132 | m/z = 925.31 ($C_{66}H_{43}N_3OS$ = 926.15) |
| P-133 | m/z = 1047.42($C_{78}H_{53}N_3O$ = 1048.30) | P-134 | m/z = 1047.42 ($C_{78}H_{53}N_3O$ = 1048.30) |
| P-135 | m/z = 1021.40 ($C_{76}H_{51}N_3O$ = 1022.3) | P-136 | m/z = 1001.34 ($C_{72}H_{47}NOS$ = 1002.25) |
| P-137 | m/z = 746.28 ($C_{51}H_{34}N_6O$ = 746.87) | P-138 | m/z = 911.33 ($C_{66}H_{45}N_3S$ = 912.17) |
| P-139 | m/z = 911.33 ($C_{66}H_{45}N_3S$ = 912.17) | P-140 | m/z = 911.33 ($C_{66}H_{45}N_3S$ = 912.17) |
| P-141 | m/z = 951.36 ($C_{69}H_{49}N_3S$ = 952.23) | P-142 | m/z = 951.36 ($C_{69}H_3S$ = 952.23) |
| P-143 | m/z = 925.31 ($C_{66}H_{43}N_3OS$ = 926.15) | P-144 | m/z = 925.31 ($C_{66}H_{43}N_3OS$ = 926.15) |
| P-145 | m/z = 951.36 ($C_{69}H_{49}N_3S$ = 952.23) | P-146 | m/z = 1047.42 ($C_{78}H_{53}N_3O$ = 926.15) |
| P-147 | m/z = 1063.40 ($C_{78}H_{53}N_3S$ = 1064.36) | P-148 | m/z = 1021.40 ($C_{76}H_{51}N_3O$ = 1022.3) |
| P-149 | m/z = 1017.32($C_{72}H_{47}N_3S_2$ = 1018.31) | P-150 | m/z = 759.27 ($C_{54}H_{37}N_3S$ = 759.97) |
| P-151 | m/z = 912.33($C_{65}H_{44}N_4S$ = 913.16) | P-152 | m/z = 819.32 ($C_{60}H_{41}N_3O$ = 820.01) |
| P-153 | m/z = 683.24 ($C_{48}H_{33}N_3S$ = 683.87) | P-154 | m/z = 832.32 ($C_{60}H_{40}N_4O$ = 833.01) |
| P-155 | m/z = 760.27 ($C_{53}H_{36}N_4S$ = 760.96) | P-156 | m/z = 819.32 ($C_{60}H_{41}N_3O$ = 820.01) |

Fabrication and Evaluation of Organic Electronic Element

[Example 1] Green OLED (an Emission-Auxiliary Layer)

First, an ITO layer (anode) was formed on a glass substrate, and then $N^1$-(naphthalen-2-yl)-$N^4$,$N^4$-bis(4-(naphthalen-2-yl)phenyl)amino)phenyl)-$N^1$-phenylbenzene-1,4-diamine (hereinafter, "2-TNATA") was vacuum-deposited on the ITO layer to form a hole injection layer with a thickness of 60 nm.

Subsequently, 4,4'-bis[N-(1-napthyl)-N-phenyl-amino]biphenyl (hereinafter, "NPD") was vacuum-deposited with a thickness of 60 nm on the hole injection layer to form a hole transport layer. Subsequently, a film of the compound P-1 of the present invention was vacuum-deposited on the hole transport layer to form an emission-auxiliary layer with a thickness of 20 nm.

4,4'-N,N'-dicarbazole-biphenyl (hereinafter, "CBP") as a host material and tris(2-phenylpyridine)-iridium (hereinafter, "Ir(ppy)$_3$") as a dopant material in a weight ratio of 95:5 were deposited on the emission-auxiliary layer to form a light emitting layer with a thickness of 30 nm.

Next, a film of (1,1'-bisphenyl-4-olato)bis(2-methyl-8-quinolinolato)aluminum (hereinafter, "BAlq") was vacuum-deposited with a thickness of 10 nm on the light emitting layer to form a hole blocking layer, and a film of tris(8-quinolinolato)aluminum (hereinafter, "Alq$_3$") was formed with a thickness of 40 nm to form an electron transport layer. Next, LiF was deposited with a thickness of 0.2 nm to form an electron injection layer, and then Al was deposited with a thickness of 150 to form a cathode. In this way, the OLED was completed.

[Example 2] to [Example 30]

The OLEDs were fabricated in the same manner as described in Example 1 except that the compounds of the present invention described in the following Table 3, instead of the compound P-1 of the present invention, were used as an emission-auxiliary layer material.

[Comparative Example 1] to [Comparative Example 5]

In case of Comparative Example 1, the OLED was fabricated in the same manner as described in Example 1 except that an emission-auxiliary layer was not formed and in cases of Comparative Examples 2 to 5, the OLEDs were fabricated in the same manner as described in Example 1 except that one of the following Comparative compounds A to D, instead of the compound P-1 of the present invention, was used as an emission-auxiliary layer material.

<Comp. compd A>

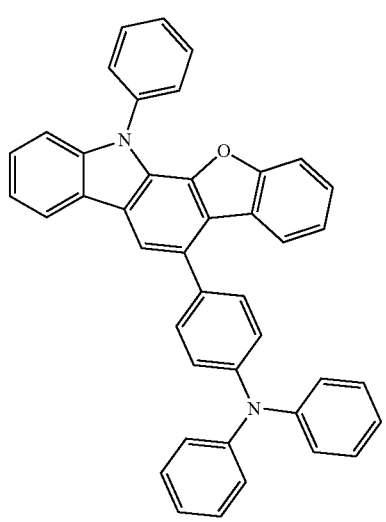

<Comp. compd B>

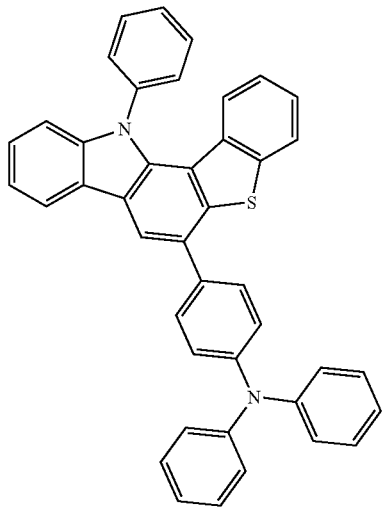

<Comp. compd C>

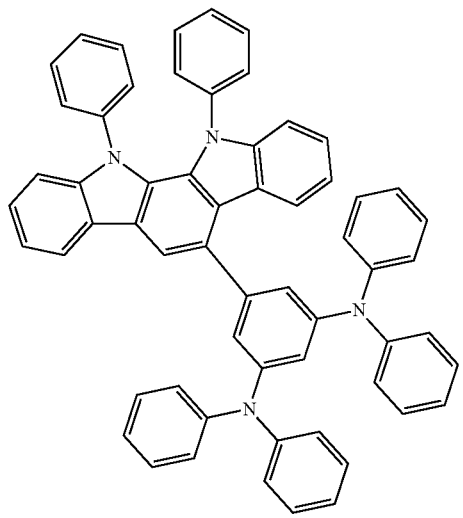

<Comp. compd D>

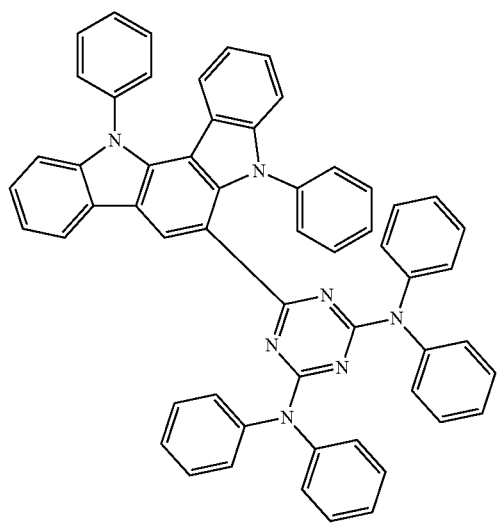

Electroluminescence (EL) characteristics were measured with a PR-650 (Photoresearch) by applying a forward bias DC voltage to the OLEDs prepared in Examples 1 to 30 of the present invention and Comparative Examples 1 to 5. And, the T95 life time was measured using a life time measuring apparatus manufactured by Macscience Inc. at reference brightness of 5000 cd/m². The measurement results are shown in Tables 3 below.

TABLE 3

| | Compound | Voltage (V) | Current Density (mA/cm²) | Brightness (cd/m²) | Efficiency (cd/A) | Lifetime T(95) | CIE x | CIE y |
|---|---|---|---|---|---|---|---|---|
| Comp. Ex(1) | — | 5.9 | 13.6 | 5000.0 | 36.8 | 116.9 | 0.33 | 0.61 |
| Comp. Ex(2) | Comp. compd A | 6.1 | 12.1 | 5000.0 | 41.3 | 118.7 | 0.33 | 0.61 |
| Comp. Ex(3) | Comp. compd B | 6..0 | 11.8 | 5000.0 | 42.3 | 124.5 | 0.33 | 0.61 |
| Comp. Ex(4) | Comp. compd C | 5.9 | 10.8 | 5000.0 | 46.5 | 133.1 | 0.33 | 0.62 |
| Comp. Ex (5) | Comp. compd D | 5.8 | 11.1 | 5000.0 | 45.1 | 130.5 | 0.33 | 0.62 |
| Ex. (1) | P-1 | 5.5 | 8.7 | 5000.0 | 57.6 | 146.7 | 0.33 | 0.62 |
| Ex. (2) | P-5 | 5.4 | 8.3 | 5000.0 | 60.0 | 145.3 | 0.33 | 0.61 |
| Ex. (3) | P-7 | 5.4 | 8.6 | 5000.0 | 58.3 | 146.1 | 0.33 | 0.61 |
| Ex. (4) | P-16 | 5.5 | 8.5 | 5000.0 | 58.9 | 145.8 | 0.33 | 0.62 |
| Ex. (5) | P-19 | 5.4 | 8.4 | 5000.0 | 59.6 | 145.8 | 0.33 | 0.61 |
| Ex. (6) | P-21 | 5.5 | 8.5 | 5000.0 | 59.0 | 146.9 | 0.33 | 0.62 |
| Ex. (7) | P-26 | 5.4 | 8.4 | 5000.0 | 59.7 | 145.7 | 0.33 | 0.62 |
| Ex. (8) | P-30 | 5.5 | 8.8 | 5000.0 | 57.0 | 147.0 | 0.33 | 0.62 |
| Ex. (9) | P-33 | 5.5 | 8.3 | 5000.0 | 59.9 | 146.6 | 0.33 | 0.61 |
| Ex. (10) | P-37 | 5.4 | 8.5 | 5000.0 | 59.0 | 145.2 | 0.33 | 0.62 |
| Ex. (11) | P-50 | 5.3 | 8.8 | 5000.0 | 57.0 | 149.7 | 0.33 | 0.61 |
| Ex. (12) | P-52 | 5.4 | 8.8 | 5000.0 | 56.6 | 149.4 | 0.33 | 0.62 |
| Ex. (13) | P-56 | 5.4 | 9.1 | 5000.0 | 55.1 | 149.7 | 0.33 | 0.61 |
| Ex. (14) | P-58 | 5.5 | 9.0 | 5000.0 | 55.5 | 148.3 | 0.33 | 0.61 |
| Ex. (15) | P-61 | 5.3 | 8.9 | 5000.0 | 56.2 | 149.7 | 0.33 | 0.62 |
| Ex. (16) | P-67 | 5.5 | 9.0 | 5000.0 | 55.6 | 149.1 | 0.33 | 0.61 |
| Ex. (17) | P-75 | 5.4 | 9.1 | 5000.0 | 55.0 | 148.9 | 0.33 | 0.61 |
| Ex. (18) | P-78 | 5.5 | 9.1 | 5000.0 | 55.2 | 148.4 | 0.33 | 0.62 |
| Ex. (19) | P-89 | 5.4 | 8.5 | 5000.0 | 58.8 | 145.1 | 0.33 | 0.61 |
| Ex. (20) | P-95 | 5.6 | 9.1 | 5000.0 | 54.8 | 141.1 | 0.33 | 0.61 |
| Ex. (21) | P-99 | 5.3 | 8.7 | 5000.0 | 57.8 | 145.4 | 0.33 | 0.62 |
| Ex. (22) | P-106 | 5.5 | 9.1 | 5000.0 | 54.8 | 141.5 | 0.33 | 0.61 |
| Ex. (23) | P-114 | 5.4 | 9.2 | 5000.0 | 54.3 | 140.5 | 0.33 | 0.62 |
| Ex. (24) | P-120 | 5.4 | 9.2 | 5000.0 | 54.6 | 141.8 | 0.33 | 0.62 |
| Ex. (25) | P-122 | 5.6 | 9.9 | 5000.0 | 50.4 | 143.2 | 0.33 | 0.61 |
| Ex. (26) | P-129 | 5.5 | 9.7 | 5000.0 | 51.5 | 144.7 | 0.33 | 0.61 |
| Ex. (27) | P-136 | 5.4 | 10.0 | 5000.0 | 50.2 | 145.0 | 0.33 | 0.61 |
| Ex. (28) | P-137 | 5.5 | 9.9 | 5000.0 | 50.4 | 143.0 | 0.33 | 0.62 |
| Ex. (29) | P-149 | 5.3 | 8.5 | 5000.0 | 58.6 | 145.8 | 0.33 | 0.62 |
| Ex. (30) | P-150 | 5.4 | 9.1 | 5000.0 | 54.9 | 141.5 | 0.33 | 0.61 |

From the results of Table 3, it can be seen that the driving force of the organic electroluminescent element can be lowered and the luminous efficiency and lifetime of the organic electroluminescent device are remarkably improved when compounds of the present invention for the organic electroluminescent element were used as an emission-auxiliary layer material, compared to the case of not forming an emission-auxiliary layer or Comparative Examples using Comparative compounds A to D.

The device characteristics of Comparative Examples 2 and 3 using Comparative Compounds A and B, respectively, in which amine group is substituted in the 5-ring heterocycle as the central core were superior to Comparative Example 1 not forming an emission-auxiliary layer. In addition, the device characteristics of Comparative Examples 4 and 5 using Comparative Compounds C and D, respectively, as material of an emission-auxiliary layer were superior to Comparative Examples 2 and 3, wherein Compounds C and D having the 5-ring heterocyclic ring of N—N type substituted with homologous heteroatoms were substituted with two amine groups.

In addition, in the cases of the present invention using the 5-ring heterocyclic ring of N—O type or N—S type as material of an emission-auxiliary layer, the device characteristics such as the driving voltage, the efficiency, and the lifetime were much better than those of the comparative examples 4 and 5, wherein the compounds of the present invention are similar to the Comparative compounds C and D in that three of amine groups in heterocyle are substituted, but it differs in that the Comparative compounds C and D are each the N—N type including the same heteroatoms and the present invention is the N—O or N—S type comprising different heteroatoms.

Therefore, it can be seen that an organic electroluminescent element employing the Comparative compounds C, D or the compound of the present invention, in which two amine groups are substituted, as an emission-auxiliary layer material was superior to the organic electroluminescent element employing Comparative compounds A or B, in which one amine group is substituted. This is because the addition of amine groups improves the hole characteristics and improves the hole injection and mobility, which is considered to be a major factor in improving the performance of the device.

Comparing Comparative Examples 4 and 5 with Examples of the present invention, there is a difference in the kind of the hetero atom comprised in the five-ring heterocycle used as an emission-auxiliary layer material. When the molecules of a five-ring cyclic compound are stacked at the time of forming an emission-auxiliary layer of the organic electroluminescent device, they have a strong electrical interaction as the number of adjacent π-electrons increases. This is closely related to the charge carrier mobility.

Particularly, as described above, when a homogeneous five-ring cyclic compounds being N—N type of are stacked, they are arranged in an edge-to-face. On the other hand, the a heterogeneous five-ring cyclic compound comprising different heteroatoms is packed in antiparallelcofacial π-stacking structure in which the molecules face each other in the opposite direction, so that the arrangement order of the molecules becomes face-to-face form. As a result, carrier mobility and oxidation stability are relatively increased due to the steric effect of the substituent bonding to heteroatom N arranged asymmetrically, which is the cause of this stacking structure. Therefore, even if the compound has a similar core, the physical properties of the compound vary depending on the kind of the heteroatom and the type of the secondary substituent, and this may act as a major factor for improving the device performance, as a result, the characteristics of the device can be remarkably varied.

Although exemplary embodiments of the present invention have been described for illustrative purposes, those skilled in the art will appreciate that various modifications, additions and substitutions are possible, without departing from the scope and spirit of the invention as disclosed in the accompanying claims. Therefore, the embodiment disclosed in the present invention is intended to illustrate the scope of the technical idea of the present invention, and the scope of the present invention is not limited by the embodiment. The scope of the present invention shall be construed on the basis of the accompanying claims, and it shall be construed that all of the technical ideas included within the scope equivalent to the claims belong to the present invention.

The invention claimed is:

1. A compound of Formula 1:

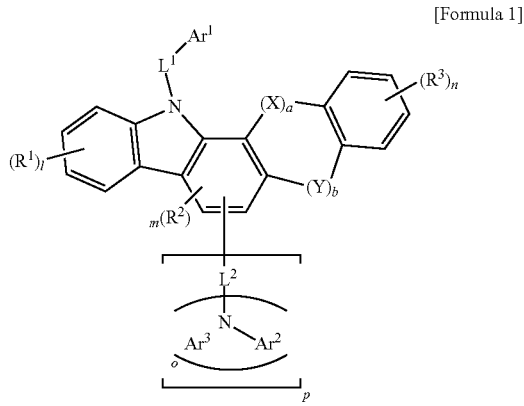

[Formula 1]

wherein:

X and Y are each independently O or S, a and b are each an integer of 0 or 1, and a+b is an integer of 1 or 2, $R^1$, $R^2$ and $R^3$ are each independently selected from the group consisting of deuterium, halogen, a $C_6$-$C_{60}$ aryl group, a fluorenyl group, a $C_2$-$C_{60}$ heterocyclic group containing at least one heteroatom selected from the group consisting of O, N, S, Si, and P, a fused ring group formed by a $C_3$-$C_{60}$ aliphatic ring with a $C_6$-$C_{60}$ aromatic ring, a $C_1$-$C_{60}$ alkyl group, a $C_2$-$C_{20}$ alkenyl group, a $C_2$-$C_{20}$ alkynyl group, a $C_1$-$C_{30}$ alkoxyl group, a $C_6$-$C_{30}$ aryloxy group and -L'-N($R_a$)($R_b$), l and n are each an integer of 0 to 4, m is 0 or 1, adjacent $R^1$s may optionally be linked together to form a ring when l is an integer of 2 or more, and adjacent $R^3$s may optionally be linked together to form a ring when n is an integer of 2 or more, p is 1, o is an integer of 2 to 5, $Ar^1$, $Ar^2$ and $Ar^3$ are each independently selected from the group consisting of a $C_6$-$C_{60}$ aryl group, a fluorenyl group, a $C_2$-$C_{60}$ heterocyclic group containing at least one heteroatom selected from the group consisting of O, N, S, Si, and P, a fused ring group formed by a $C_3$-$C_{60}$ aliphatic ring with a $C_6$-$C_{60}$ aromatic ring, a $C_1$-$C_{60}$ alkyl group, a $C_2$-$C_{20}$ alkenyl group, a $C_2$-$C_{20}$ alkynyl group, a $C_1$-$C_{30}$ alkoxyl group, a $C_6$-$C_{30}$ aryloxy group and -L'-N($R_a$)($R_b$), $L^2$ is -($L^a$-$L^b$), wherein $L^1$, $L^a$, $L^b$ and L' are each independently selected from the group consisting of a single bond, a $C_6$-$C_{60}$ arylene group, a fluorenylene group, a fused ring group formed by a $C_3$-$C_{60}$ aliphatic ring with a $C_6$-$C_{60}$ aromatic ring, and a $C_2$-$C_{60}$ heterocyclic group containing at least one heteroatom selected from the group consisting of O, N, S, Si, and P, with a proviso that at least one of $L^a$ and $L^b$ is other than a single bond, $R_a$ and $R_b$ are each independently selected from the group consisting of a $C_6$-$C_{60}$ aryl group, a fluorenyl group, a fused ring group formed by a $C_3$-$C_{60}$ aliphatic ring with a $C_6$-$C_{60}$ aromatic ring, and a $C_2$-$C_{60}$ heterocyclic group containing at least one heteroatom selected from the group consisting of O, N, S, Si, and P, and when the above $R^1$-$R^3$, $Ar^1$-$Ar^3$, $R_a$, $R_b$, $L^1$, $L^a$, $L^b$ and L' are each the aryl group, fluorenyl group, heterocyclic group, fused ring group, alkyl group, alkenyl group, alkynyl group, alkoxyl group, aryloxyl group, arylene group, or fluorenylene group, they are each optionally further substituted with one or more substituents selected from the group consisting of deuterium, halogen, a silane group substituted or unsubstituted with $C_1$-$C_{20}$ alkyl group or $C_6$-$C_{20}$ aryl group, a siloxane group, a boron group, a germanium group, a cyano group, a nitro group, a $C_1$-$C_{20}$ alkylthio group, a $C_1$-$C_{20}$ alkoxyl group, a $C_1$-$C_{20}$ alkyl group, a $C_2$-$C_{20}$ alkenyl group, a $C_2$-$C_{20}$ alkynyl group, a $C_6$-$C_{20}$ aryl group, a $C_6$-$C_{20}$ aryl group substituted with deuterium, a fluorenyl group, a $C_2$-$C_{20}$ heterocyclic group containing at least one heteroatom selected from the group consisting of O, N, S, Si, and P, a $C_3$-$C_{20}$ cycloalkyl group, a $C_7$-$C_{20}$ arylalkyl group and a $C_8$-$C_{20}$ arylalkenyl group.

2. The compound of claim 1, wherein Formula 1 is represented by one of the following Formulas 2, 3 and 5 to 11:

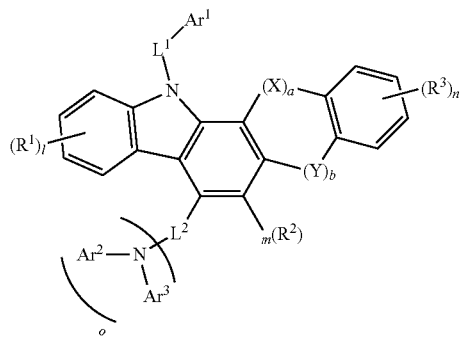

<Formula 2>

<Formula 3>
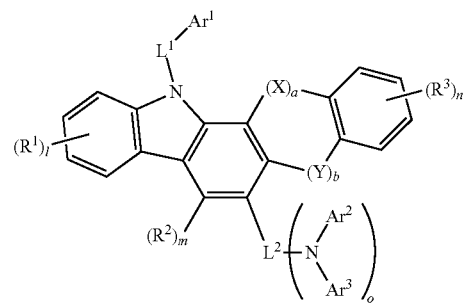
<Formula 5>
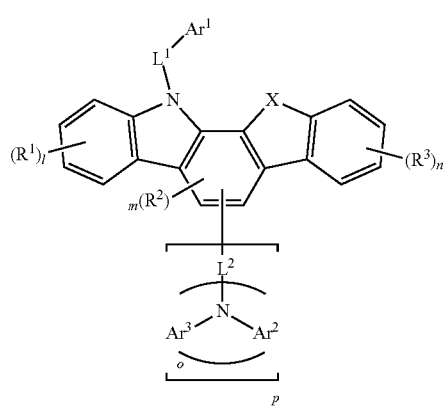
<Formula 6>
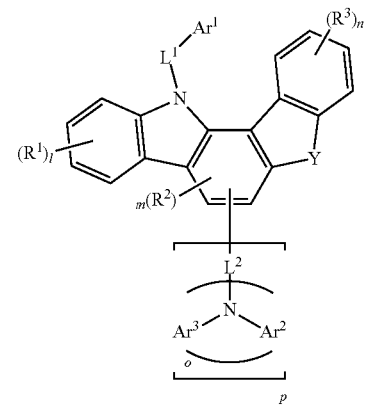
<Formula 7>
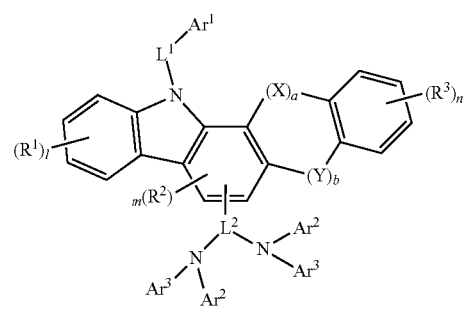
<Formula 8>
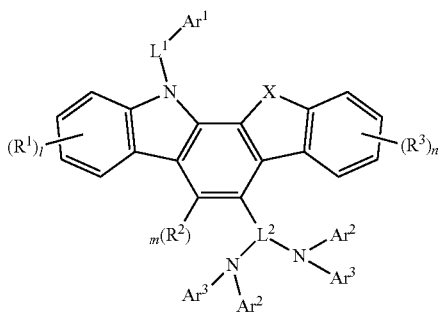
<Formula 9>
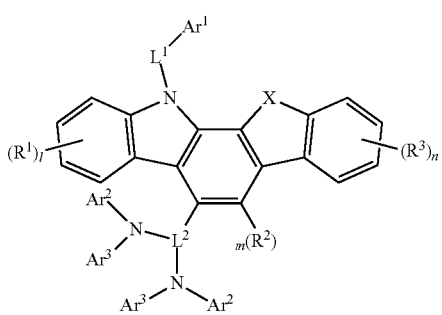
<Formula 10>
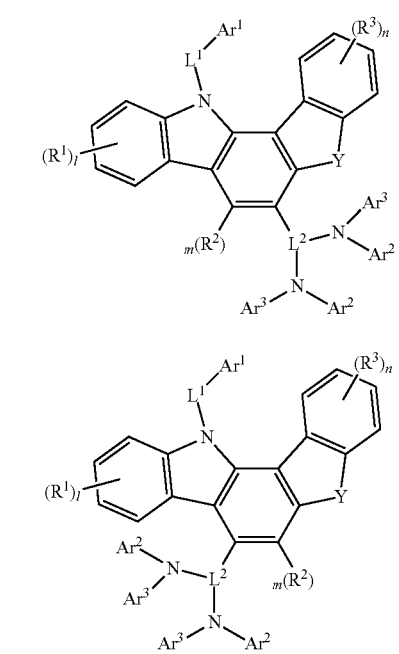
<Formula 11>
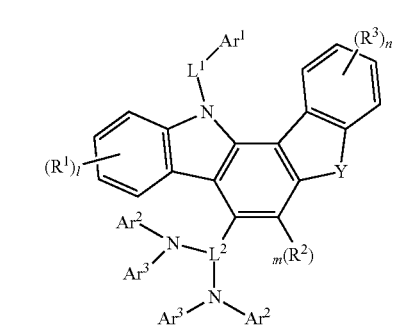
wherein X, Y, $R^1$-$R^3$, $Ar^1$-$Ar^3$, $L^1$, $L^2$, a, b, l, m, n, o and p are the same as defined in claim 1.
3. The compound of claim 1, wherein $L^1$ and $L^2$ are each independently selected from the following formulas (A-1) to (A-12):

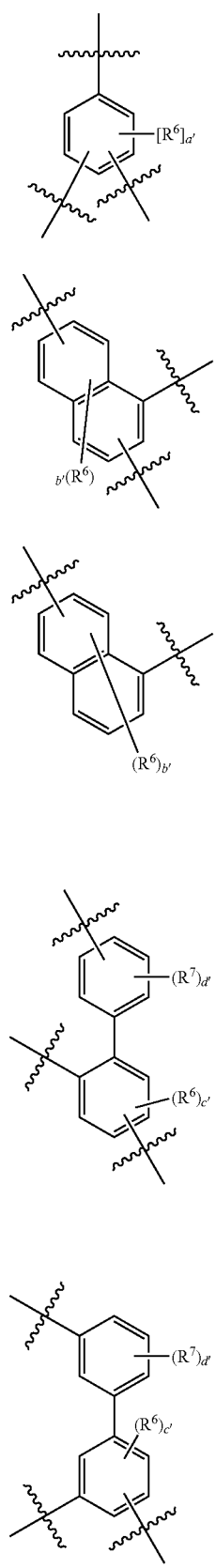
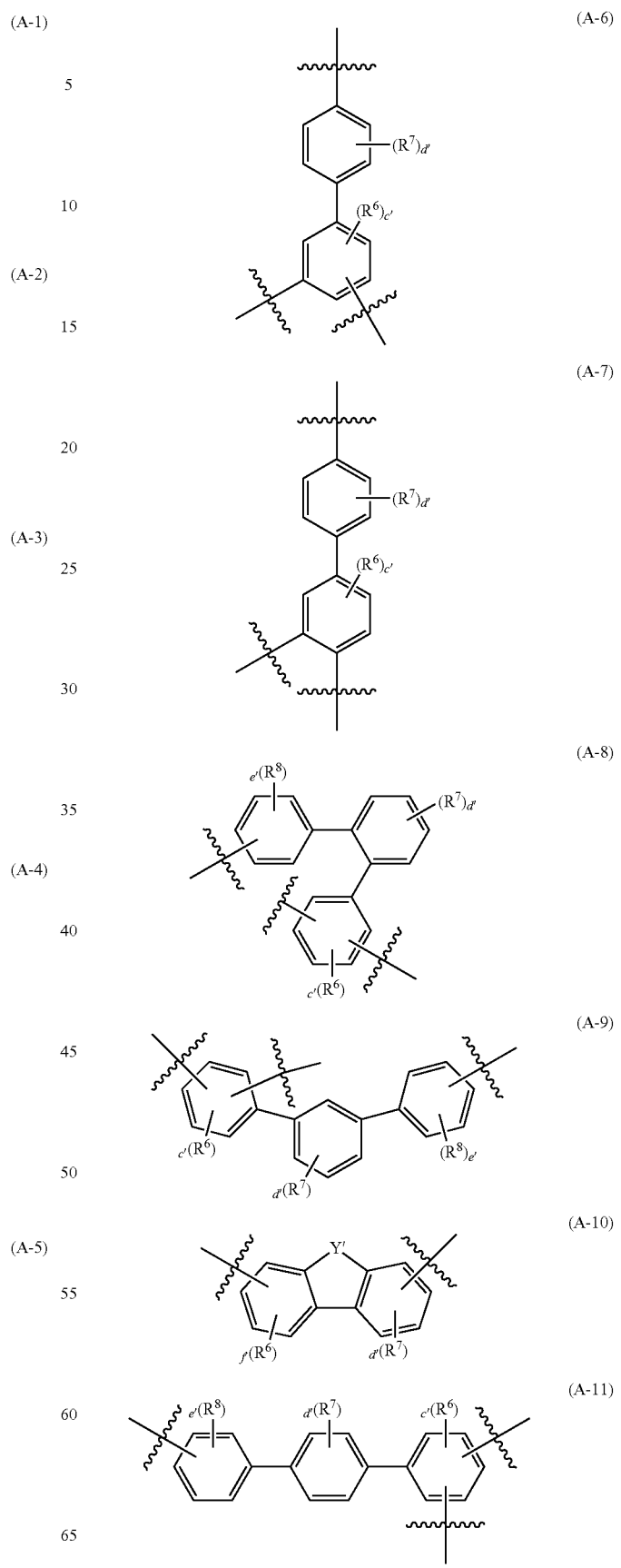

-continued

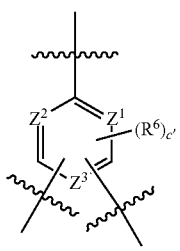
(A-12)

wherein, $R^6$-$R^8$ are defined the same as $R^1$-$R^3$ as defined in claim 1, a', c', d' and e' are each an integer 0 to 4, b' is an integer of 0 to 6, f' and g' are each an integer of 0 to 3, h' is 0 or 1, where a', c', d', e', f' and g' are each is an integer of 2 or more, adjacent $R^6$s, adjacent $R^7$s or adjacent $R^8$s may optionally be linked together to form a ring, in the Formula (A-10), Y' is N(R'), O, S or C(R')(R"), wherein $R^1$ is defined the same as in claim 1 and R' and R" are each independently selected from the group consisting of a $C_6$-$C_{60}$ aryl group, a fluorenyl group, a $C_2$-$C_{60}$ heterocyclic group containing at least one heteroatom selected from the group consisting of O, N, S, Si, and P, a fused ring group formed by a $C_3$-$C_{60}$ aliphatic ring with a $C_6$-$C_{60}$ aromatic ring, and a $C_1$-$C_{50}$ alkyl group, and R' and R" may optionally be linked together with C to which they are bonded to form a spiro-compound, and in the Formula (A-12), $Z^1$-$Z^3$ are each C($R^1$) or N, and at least one of $Z^1$-$Z^3$ is N.

4. The compound of claim 1, wherein Formula 1 is one of the following compounds:

P-1

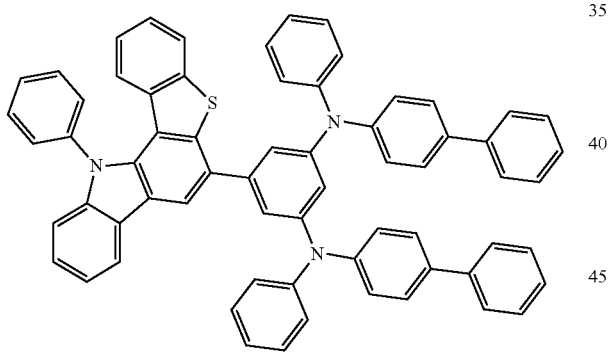

P-2

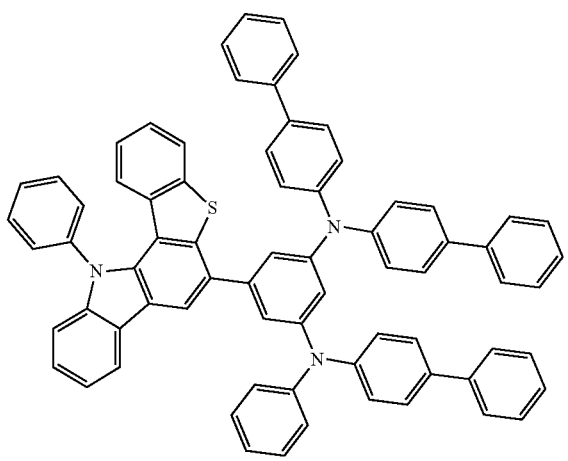

P-3

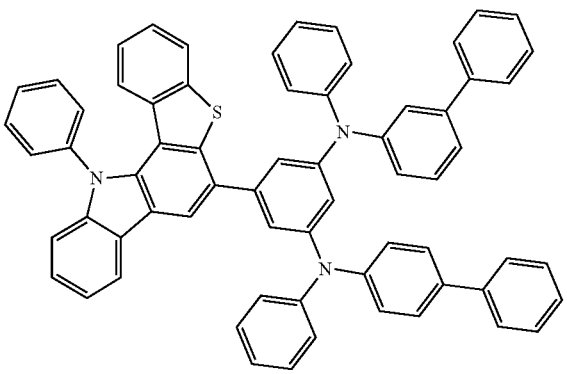

P-4

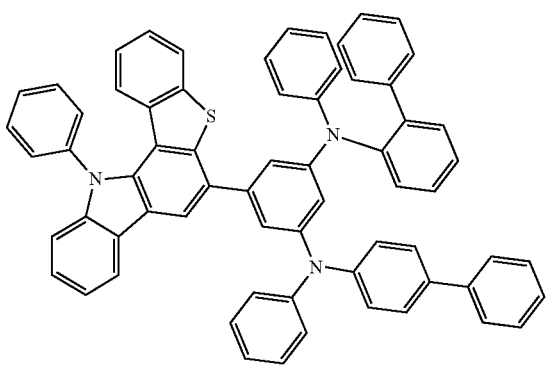

P-5

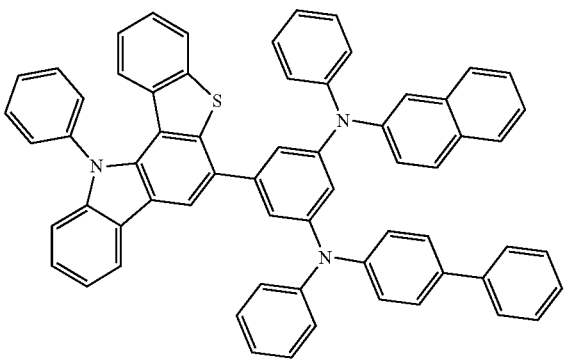

P-6

P-7
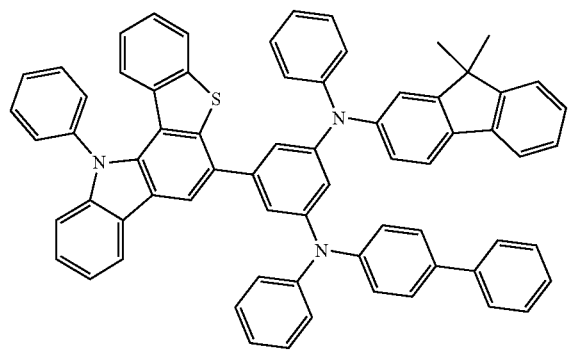
P-10
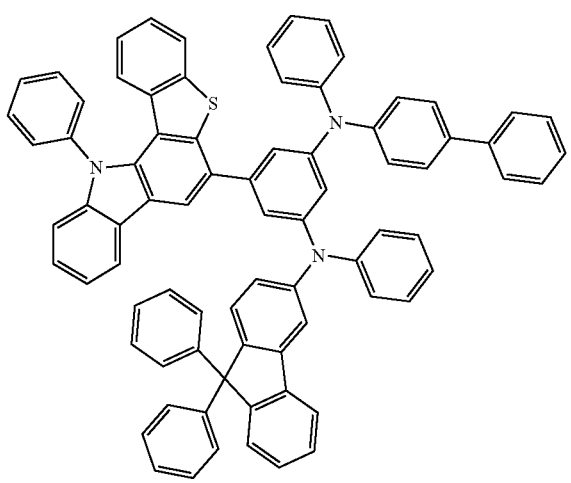
P-8
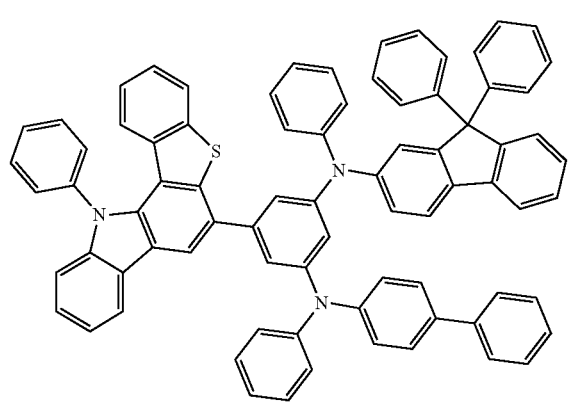
P-11
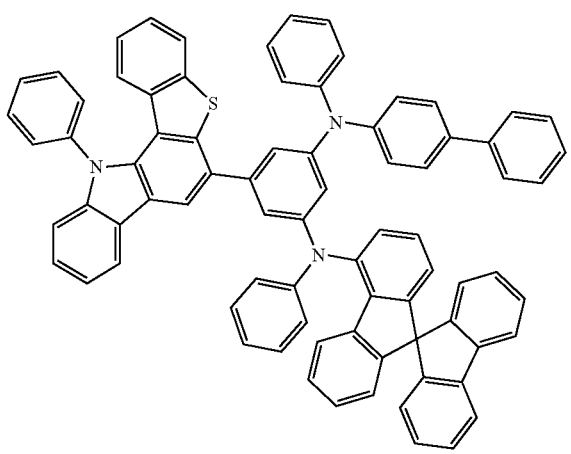
P-9
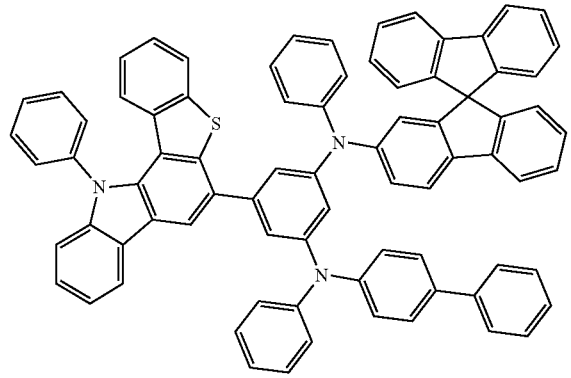
P-12
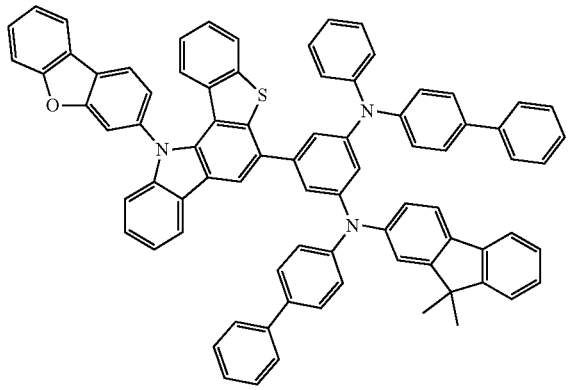

P-13
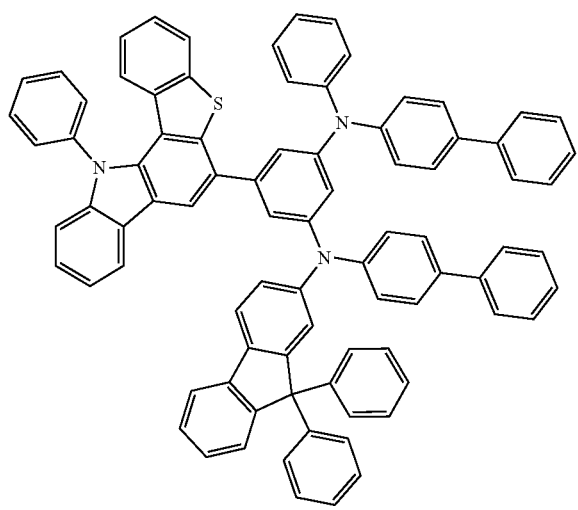
P-14
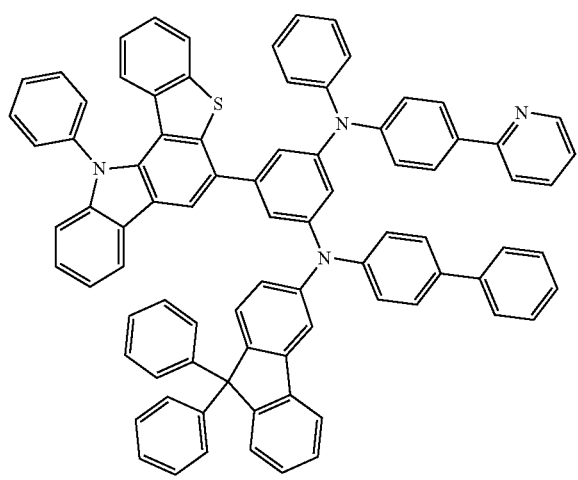
P-15
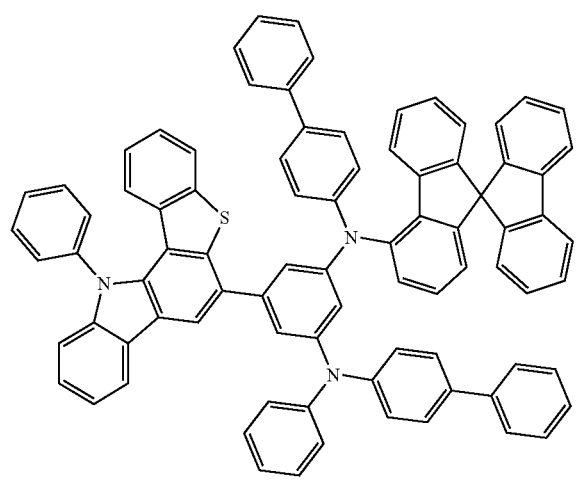
P-16
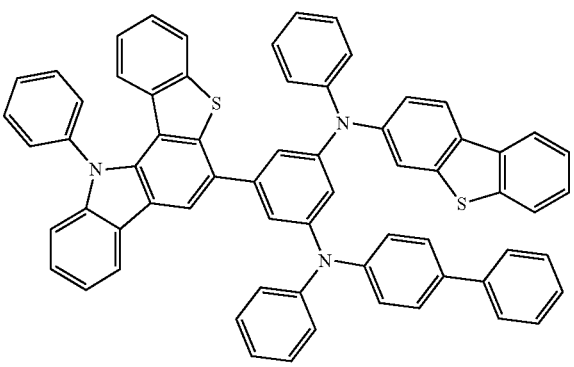
P-17
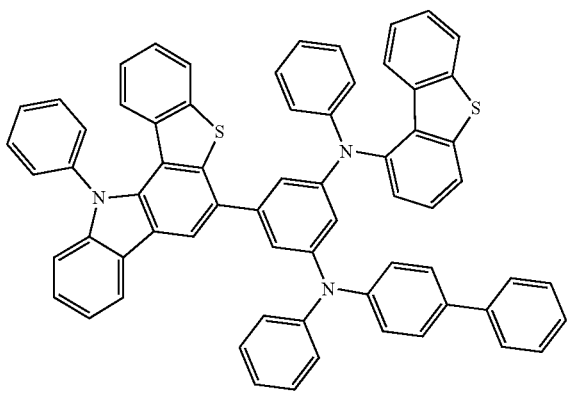
P-18
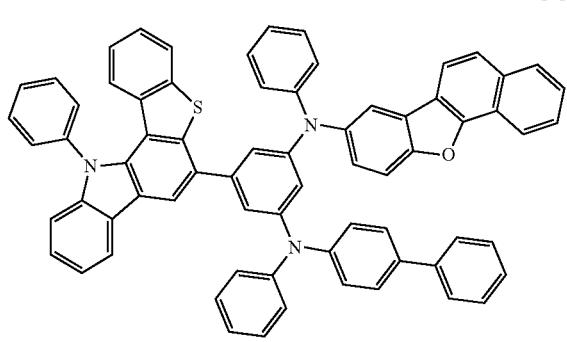
P-19
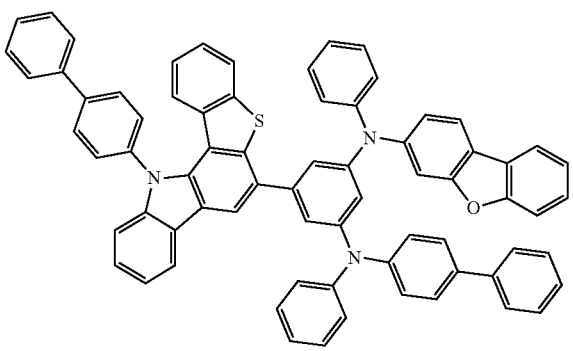

P-20
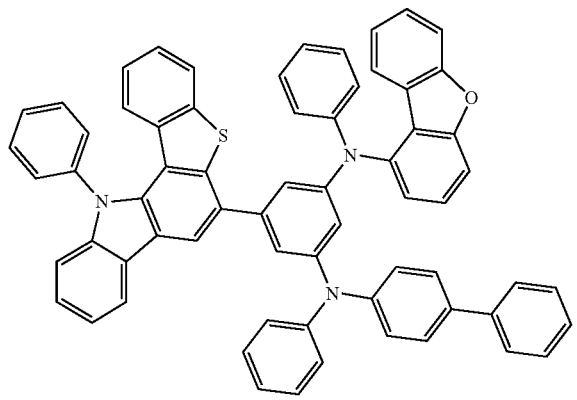
P-23
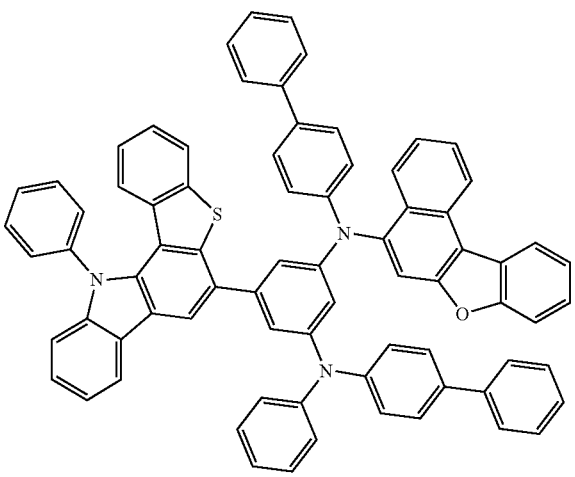
P-21
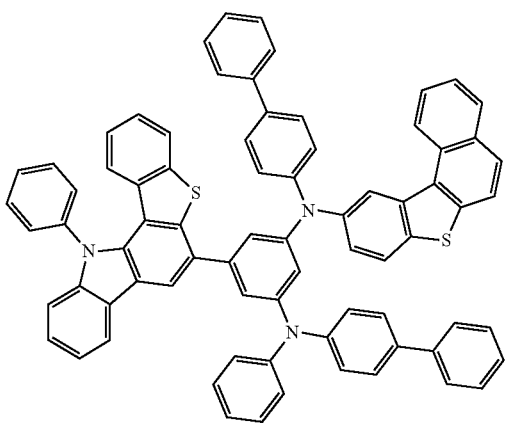
P-24
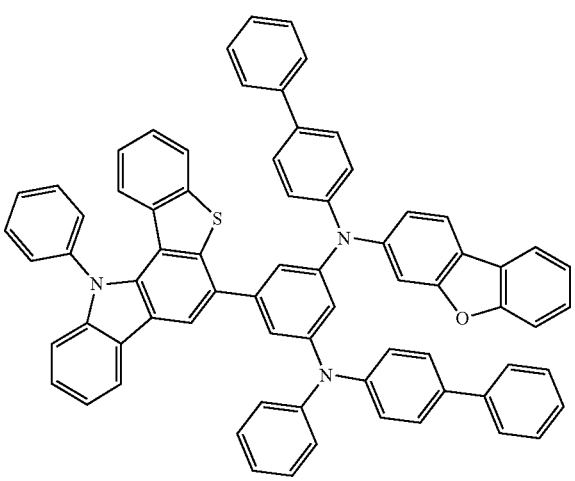
P-22
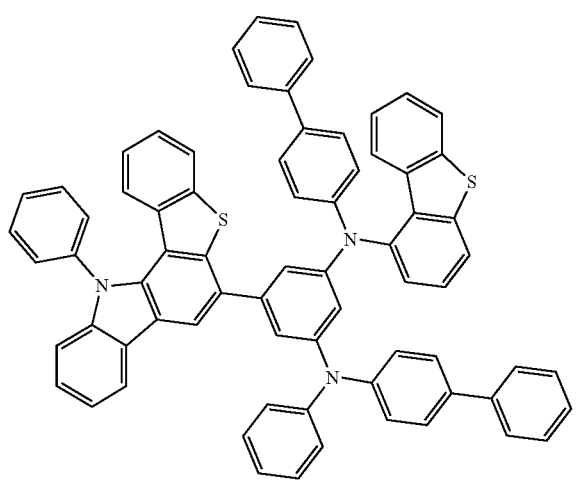
P-25
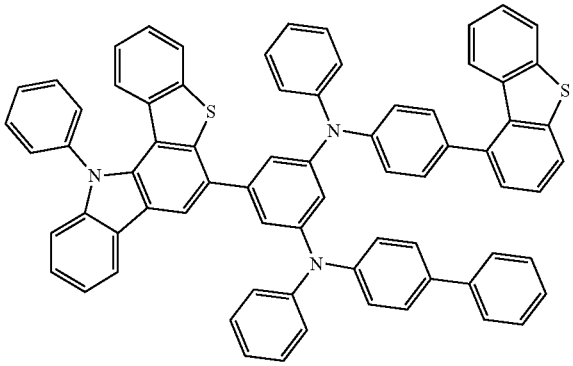

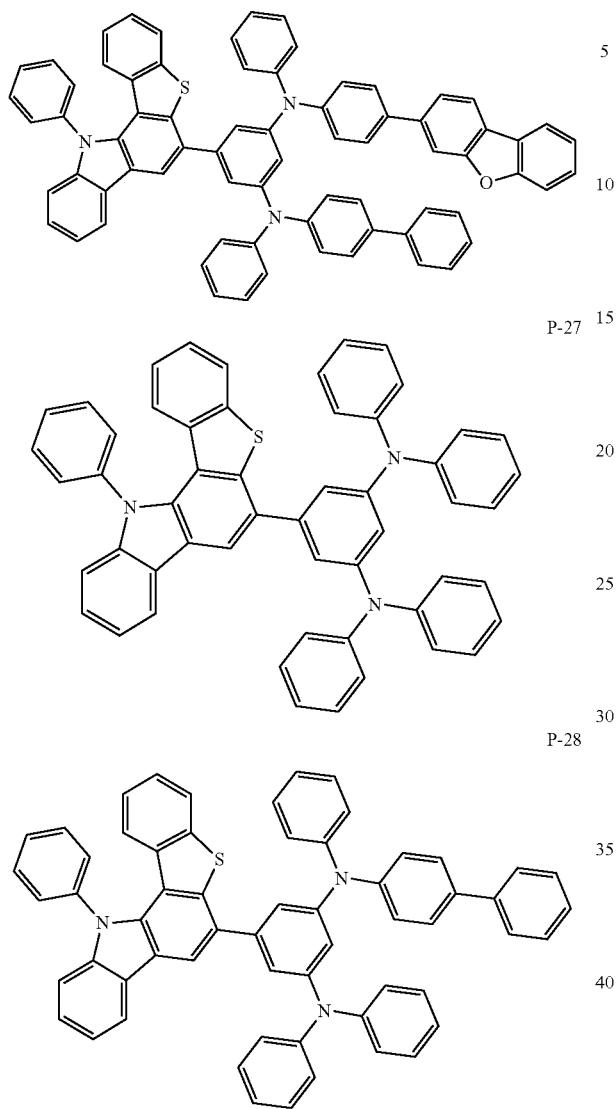
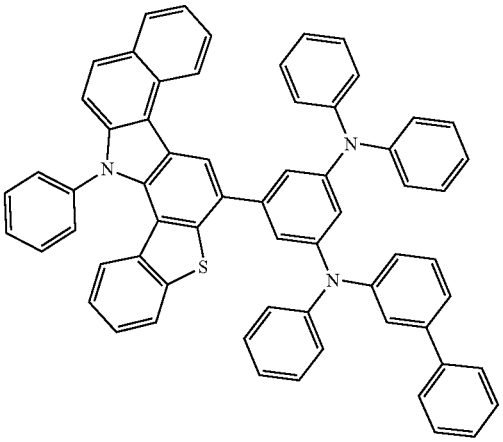
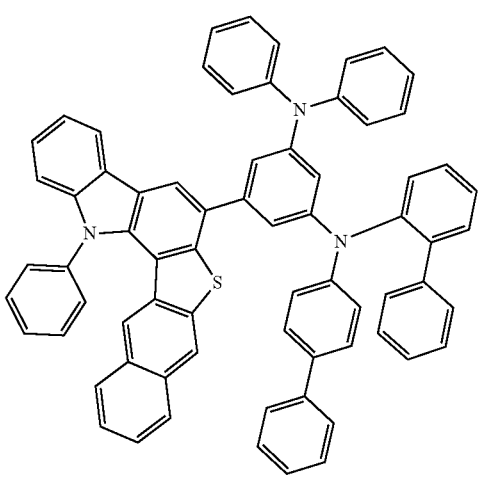
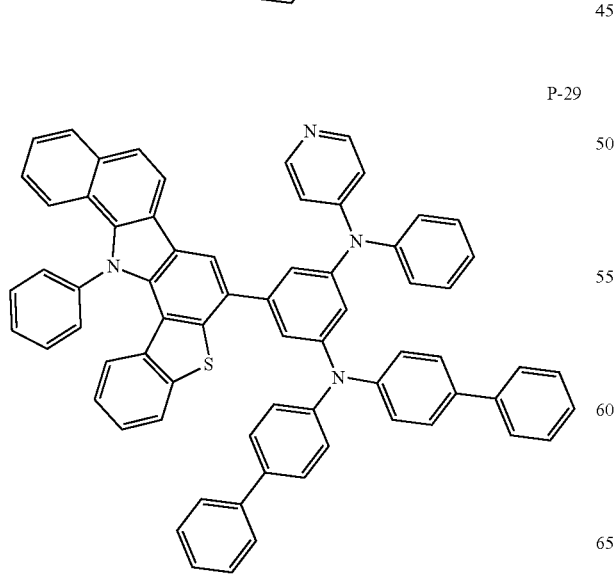
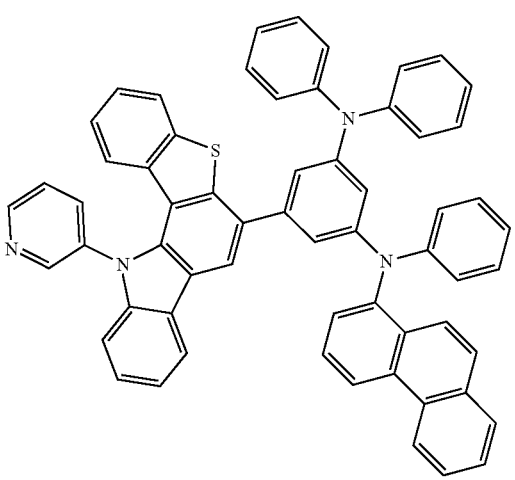

-continued
P-33
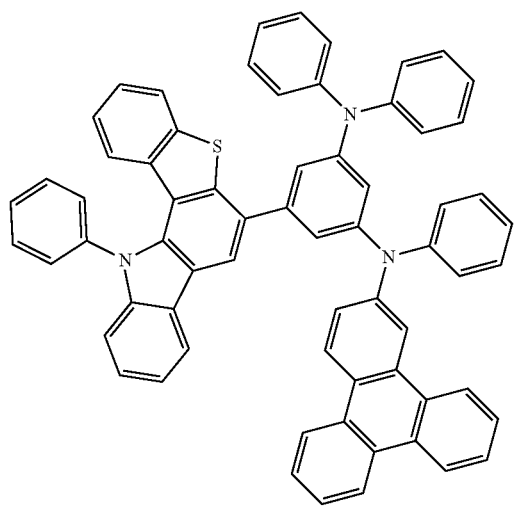
P-36
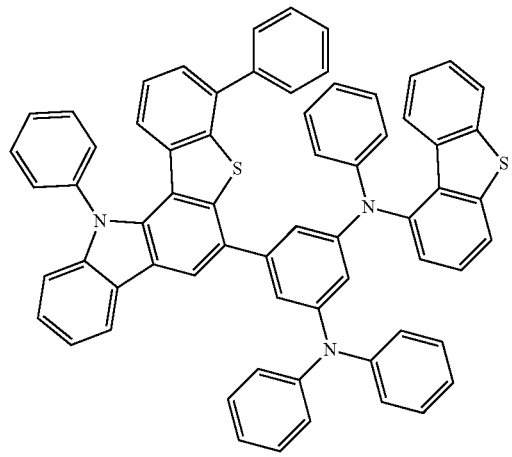
P-34
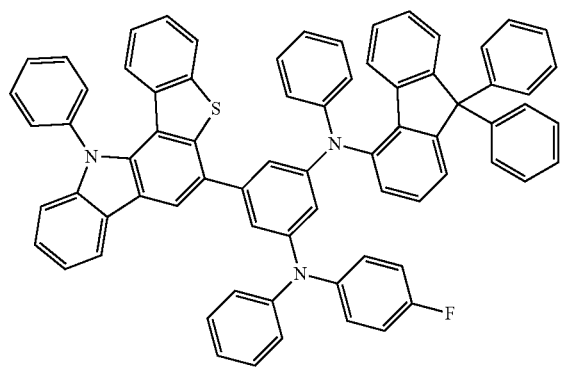
P-37
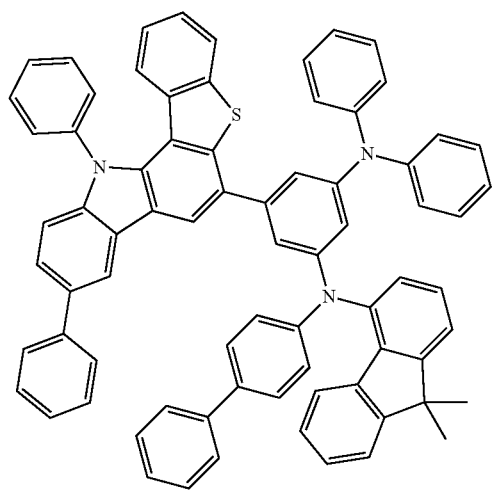
P-35
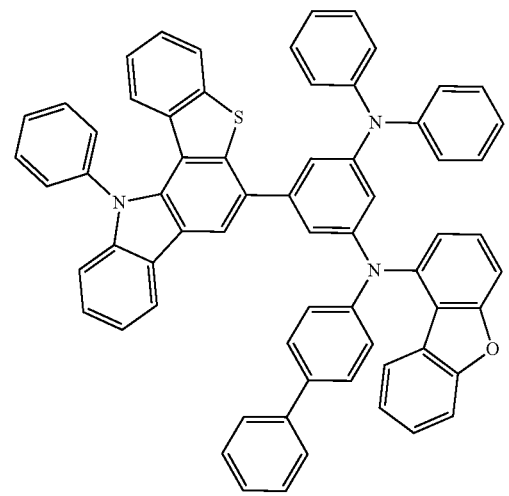
P-38

-continued
P-39
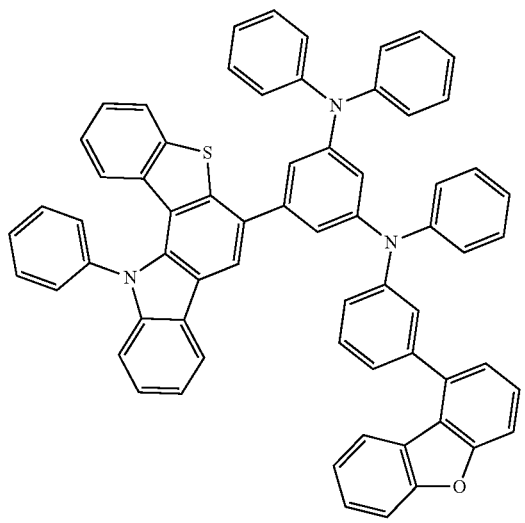
P-40
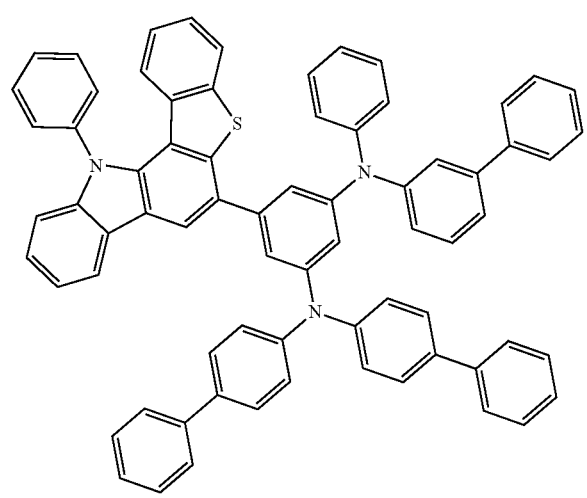
P-41
P-42
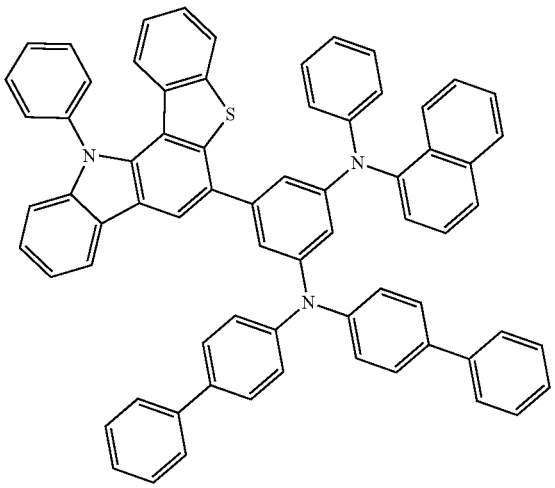
P-43
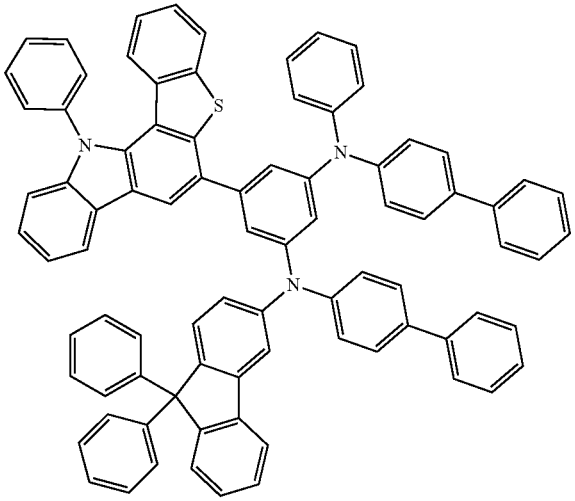

P-44
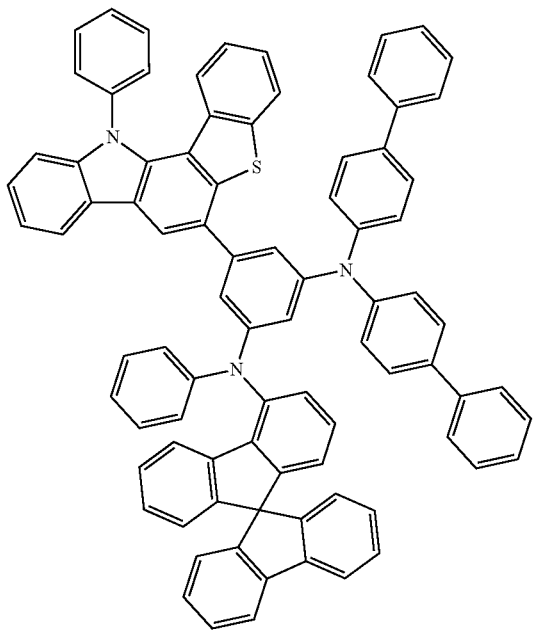
P-45
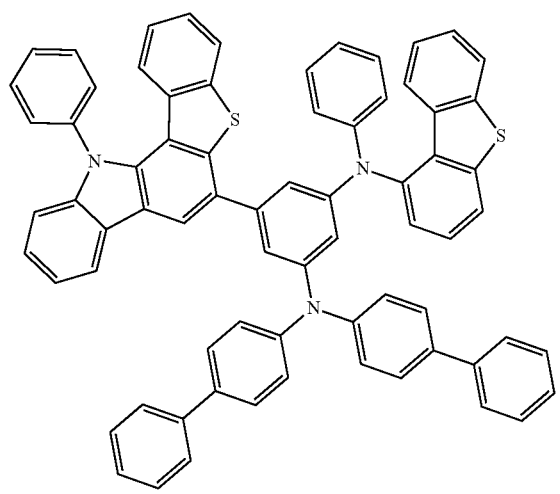
P-46
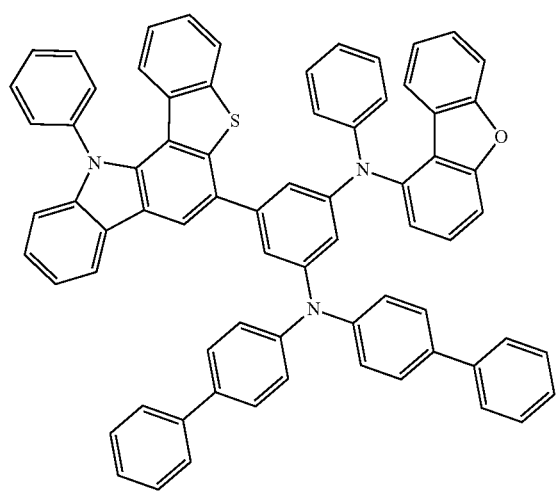
P-47
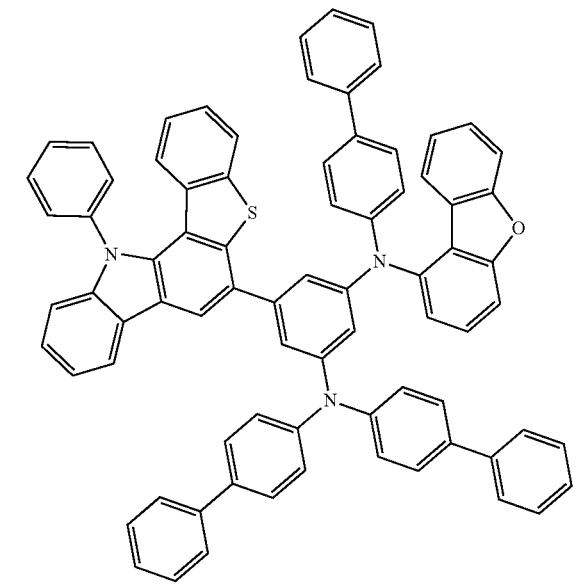
P-48
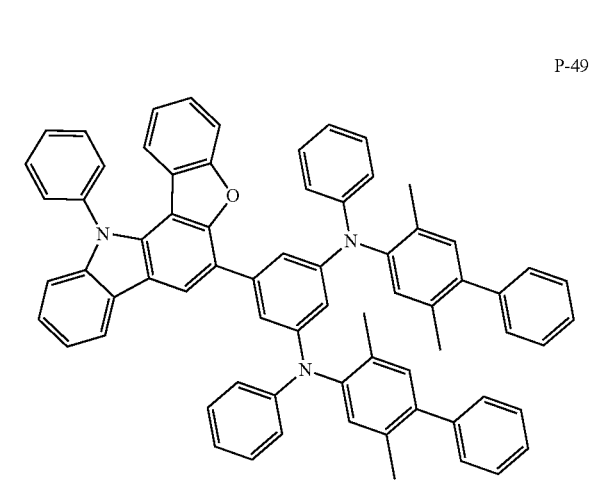
P-49

P-50
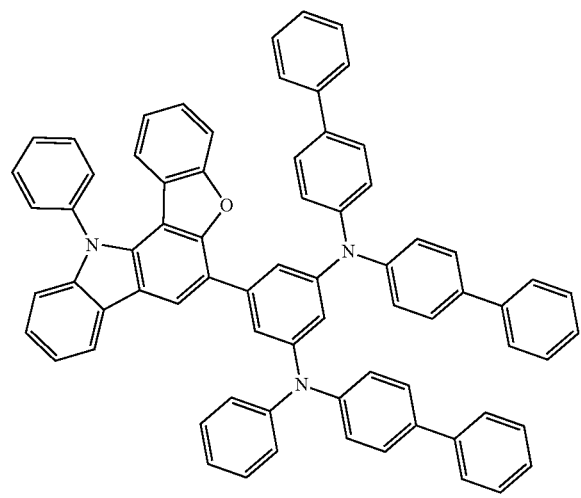
P-51
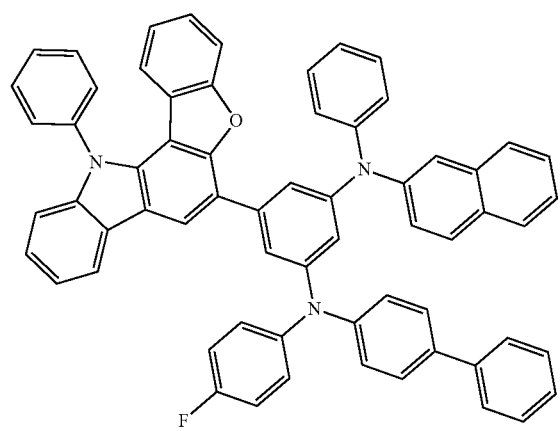
P-52
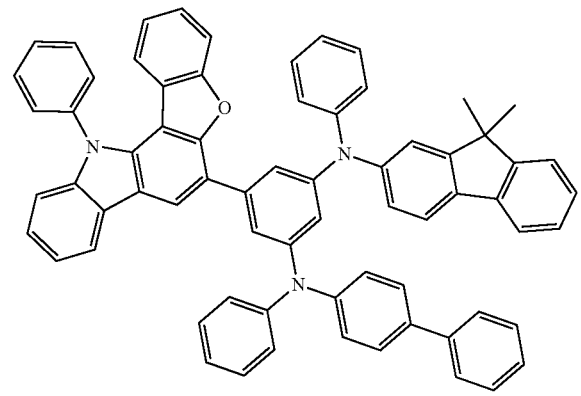
P-53
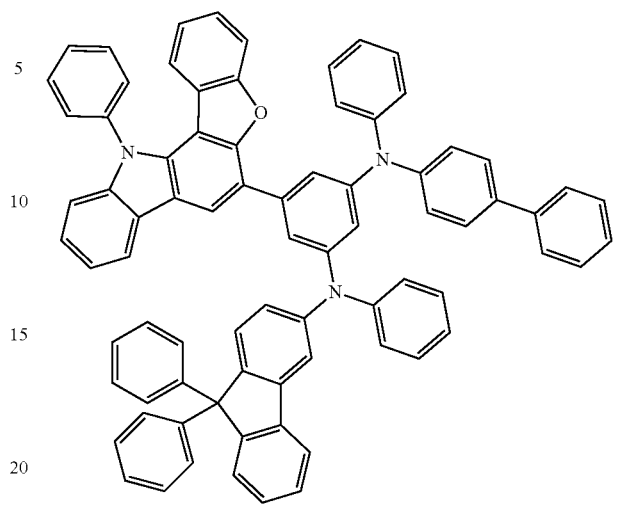
p-54
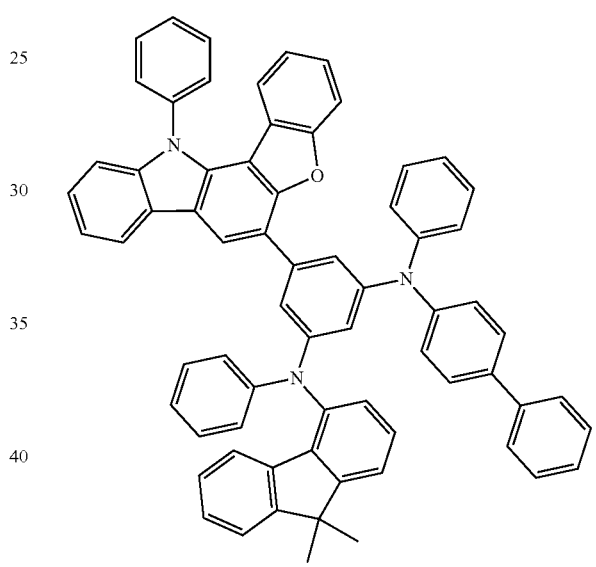
P-55
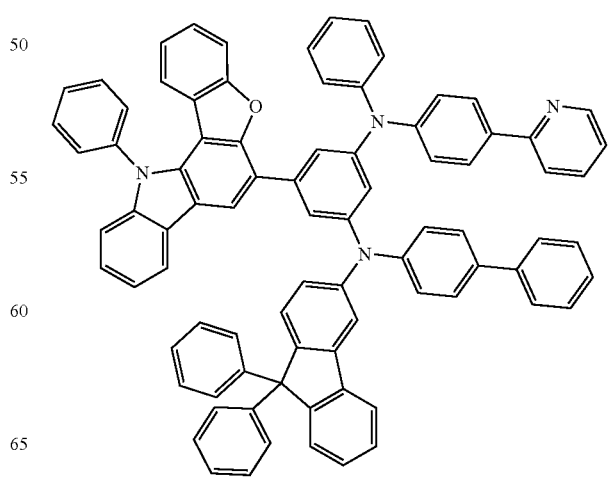

P-56
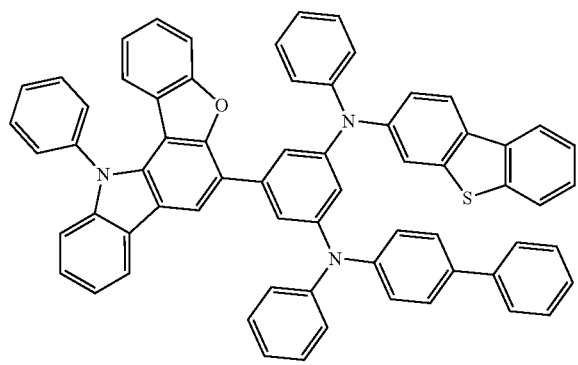
P-57
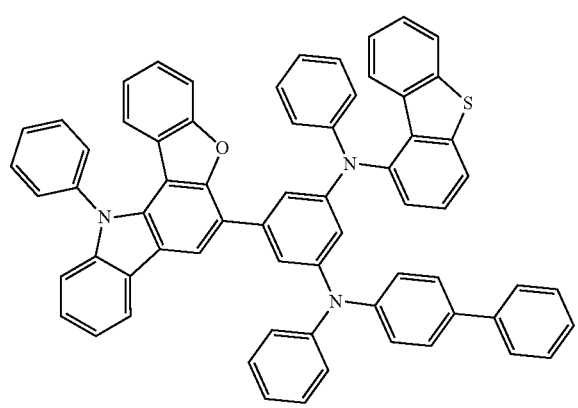
P-58
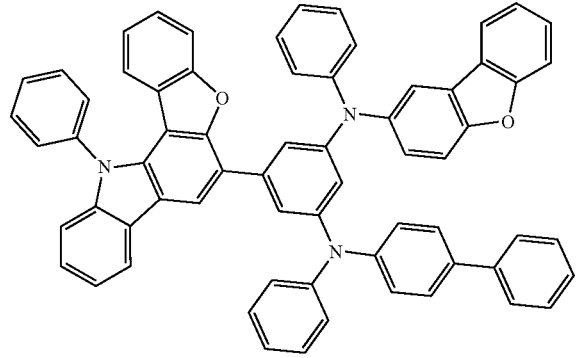
P-59
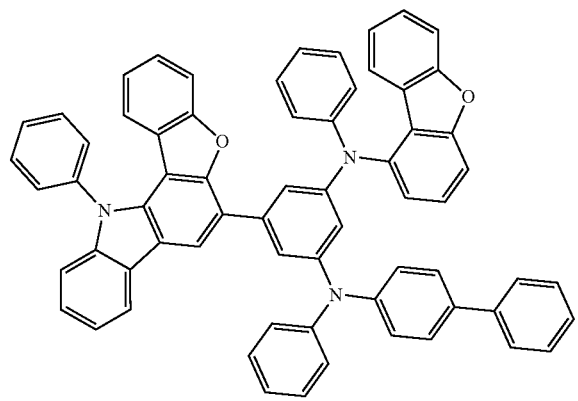
P-60
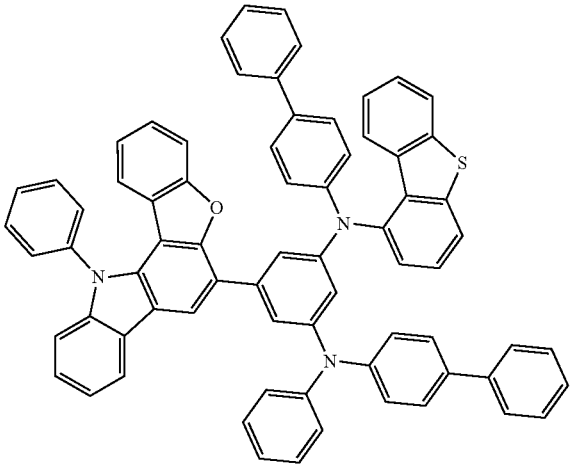
P-61
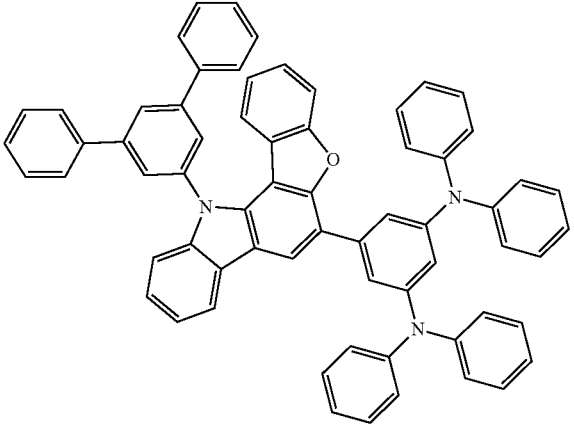
P-62
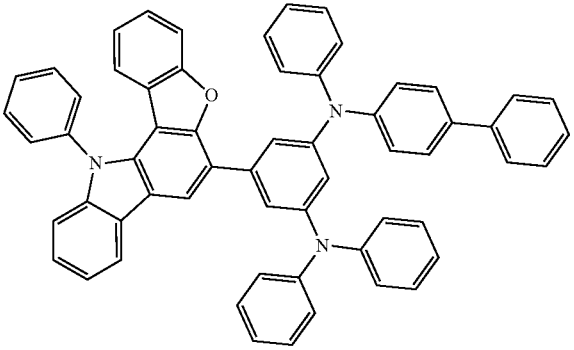

-continued
P-63
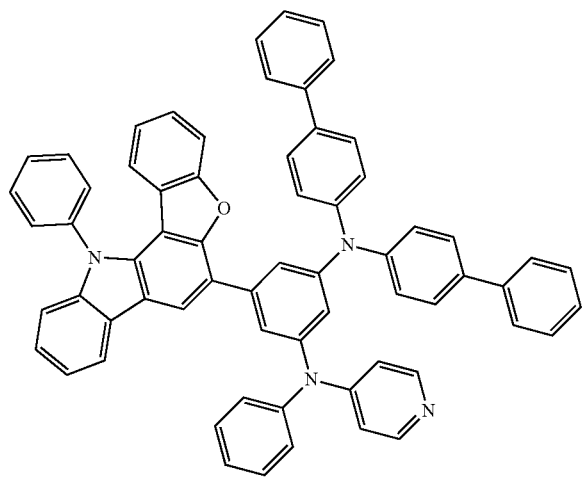
P-64
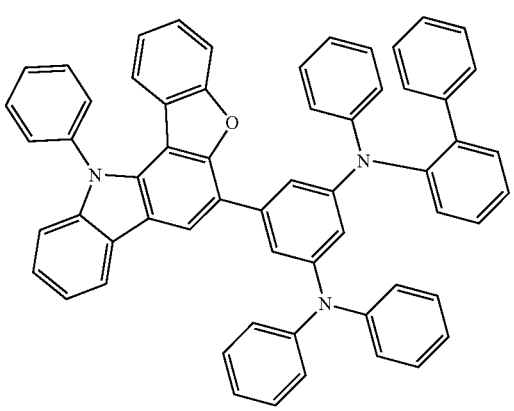
P-65
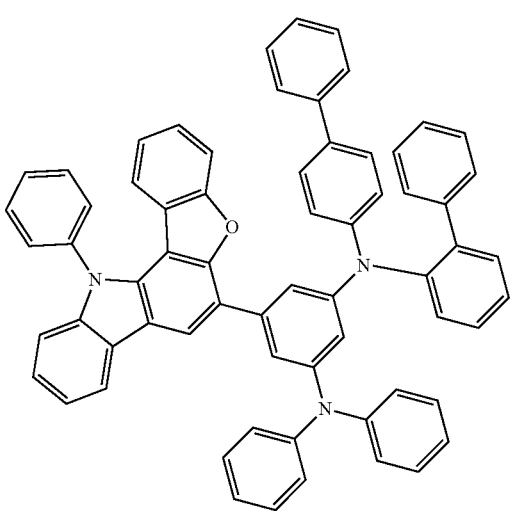
-continued
P-66
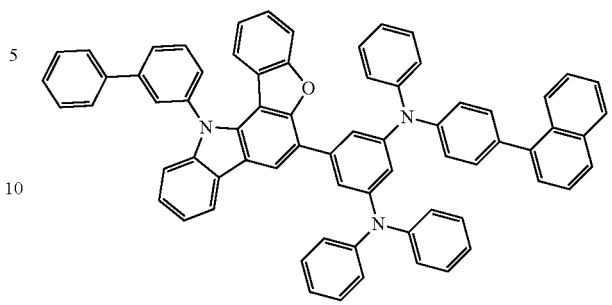
P-67
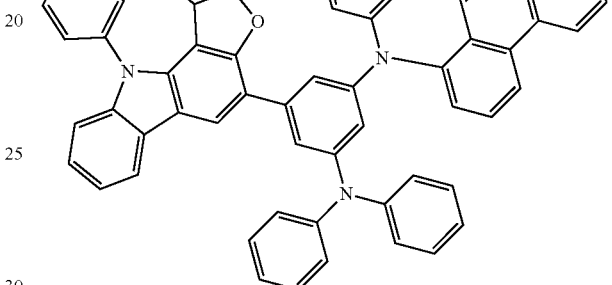
P-68
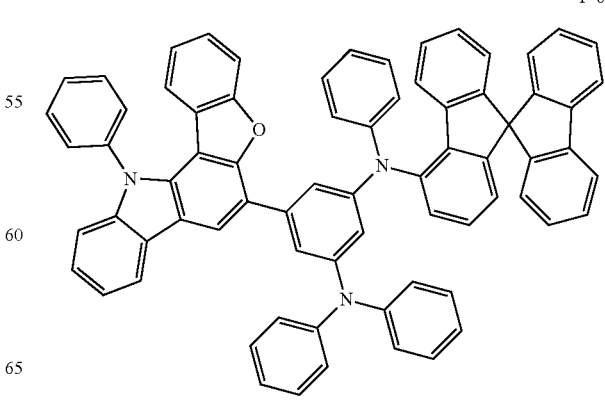
P-69

P-70
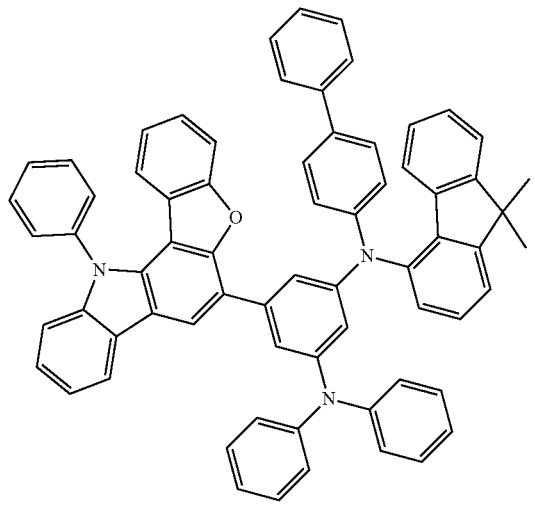
P-71
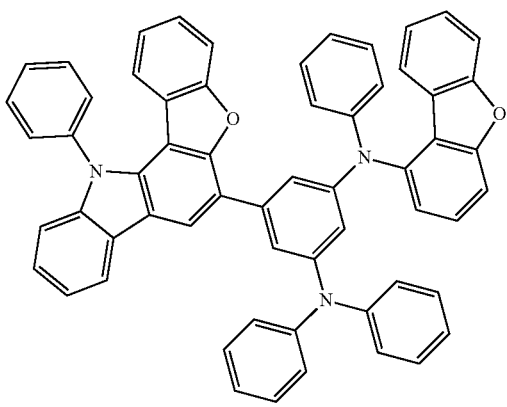
P-72
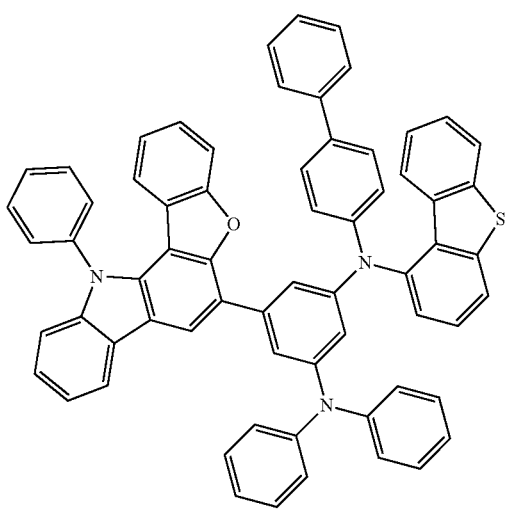
P-73
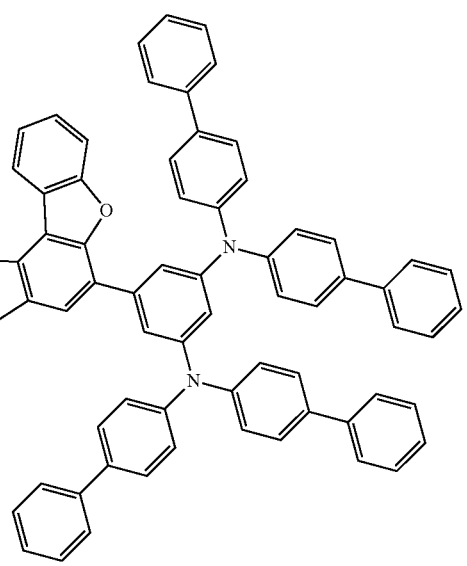
P-74
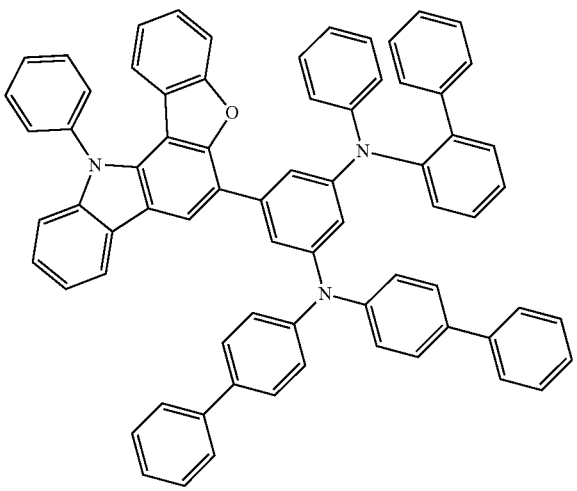

P-75
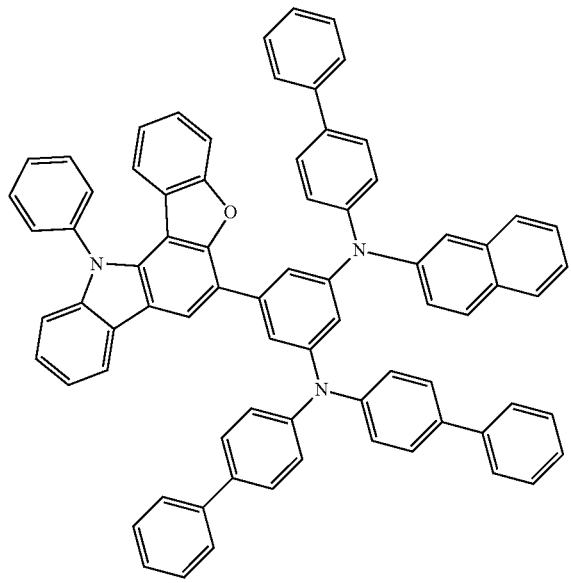
P-76
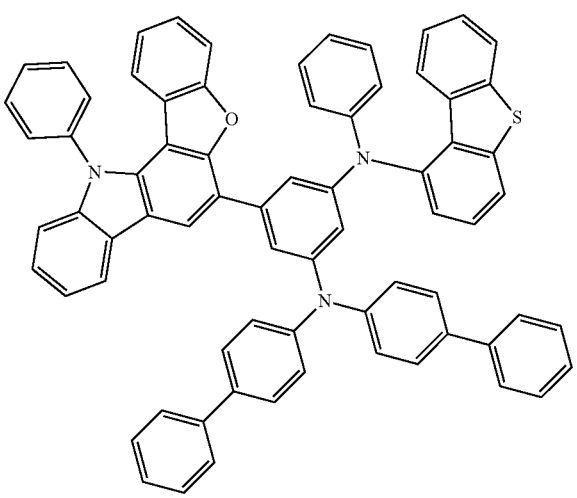
P-77
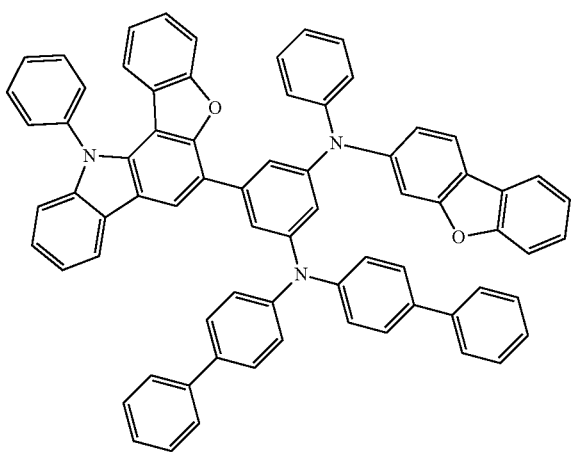
P-78
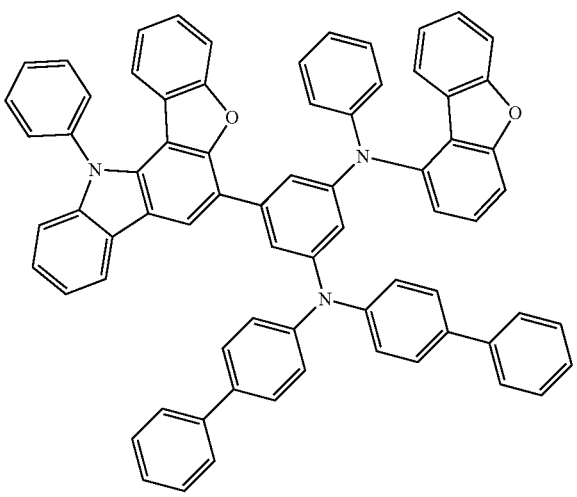
P-79
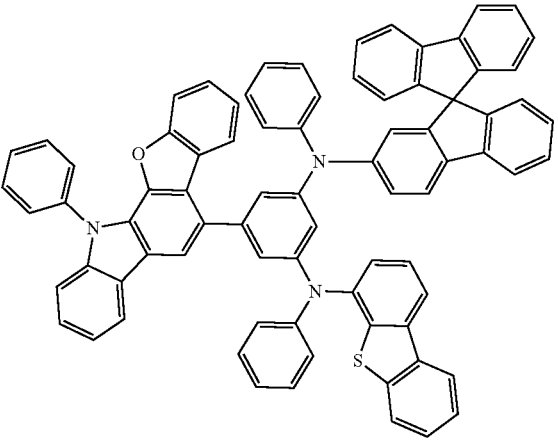
P-80

P-81
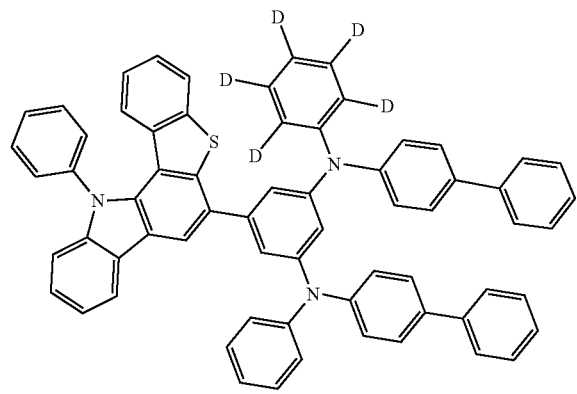
P-82
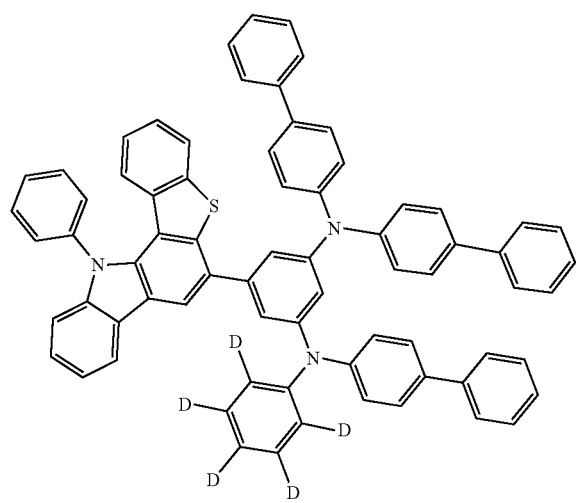
P-83
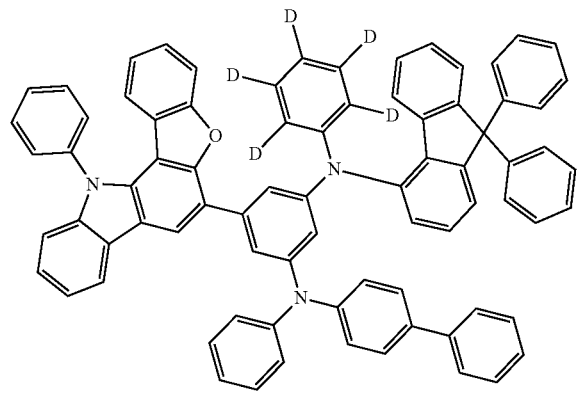
P-84
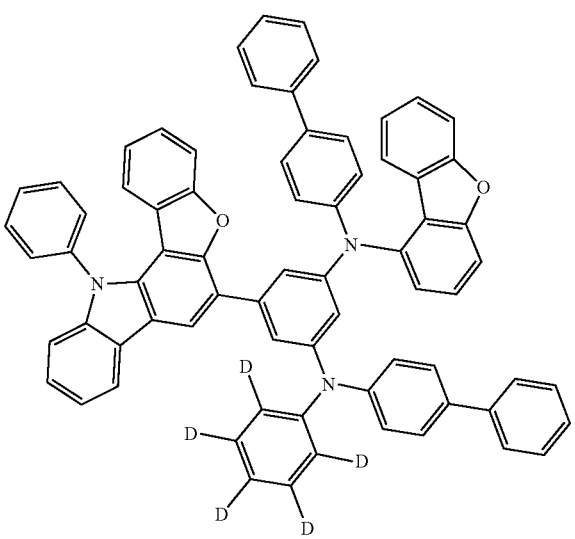
P-85
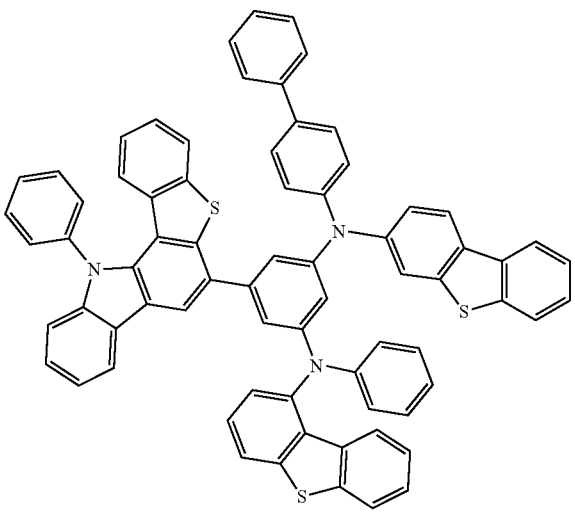
P-86
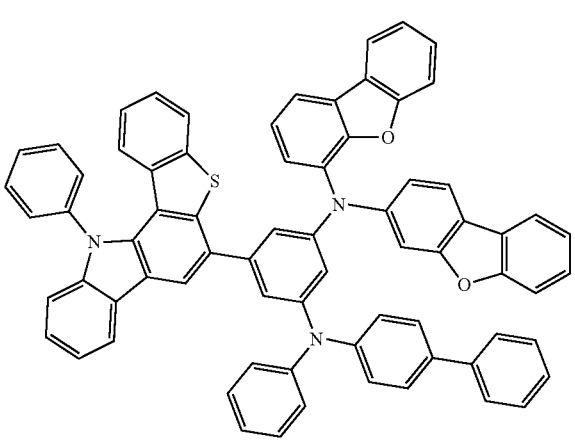

P-87
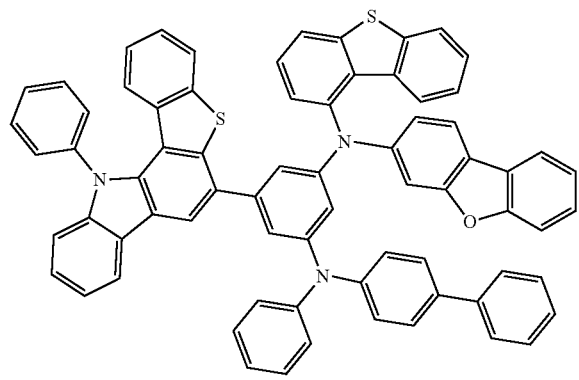
P-88
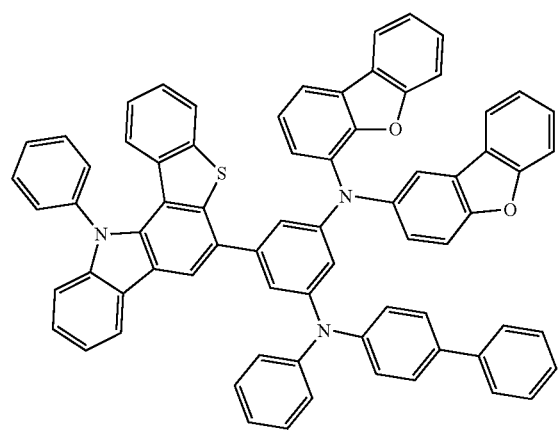
P-89
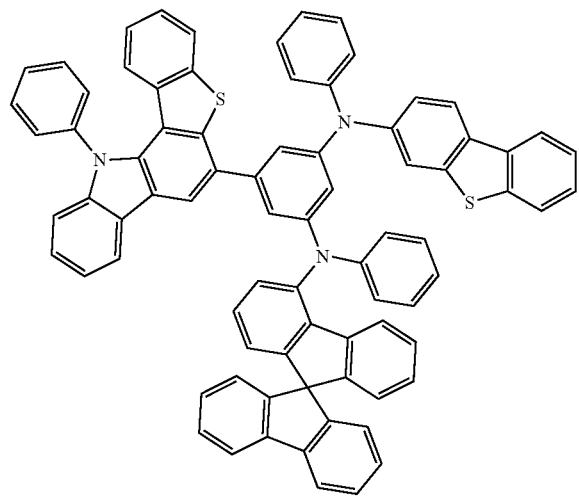
P-90
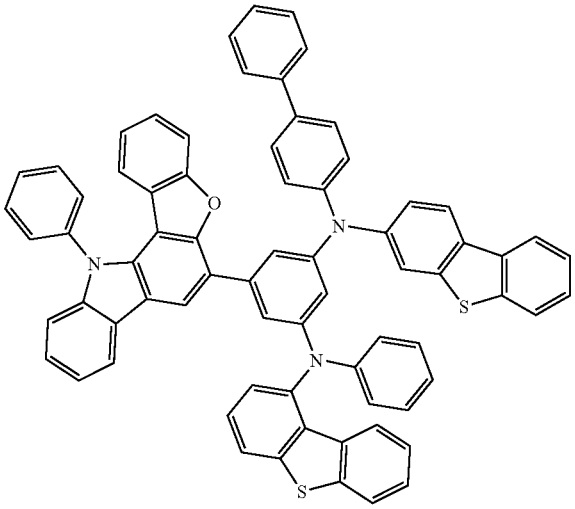
P-91
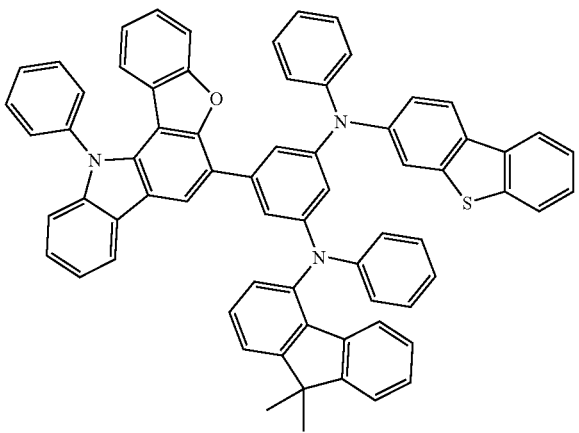
P-92

P-93
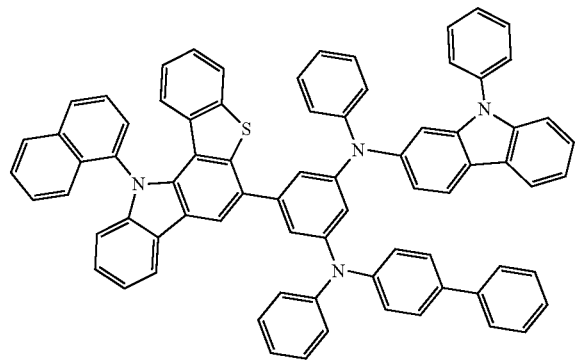
P-94
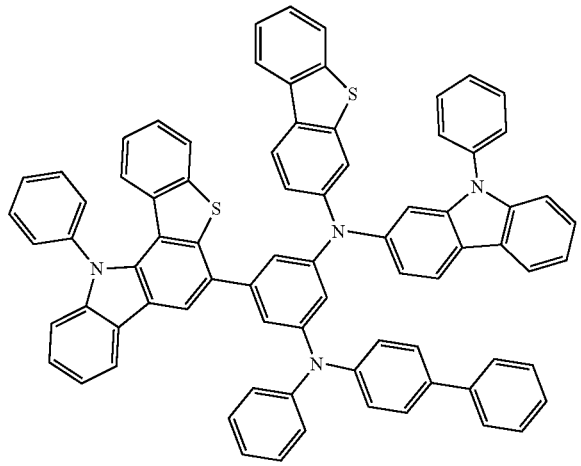
P-95
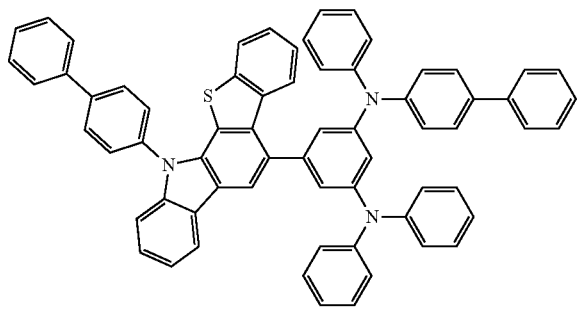
P-96
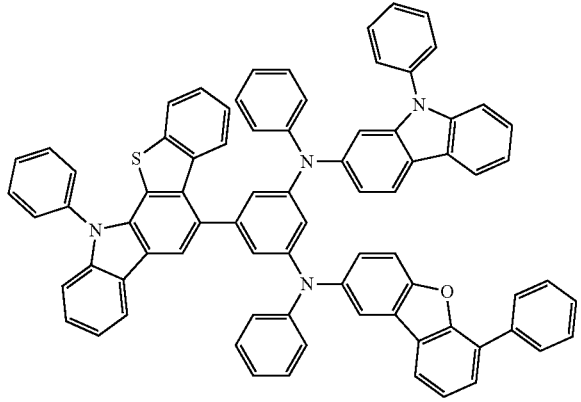
P-97
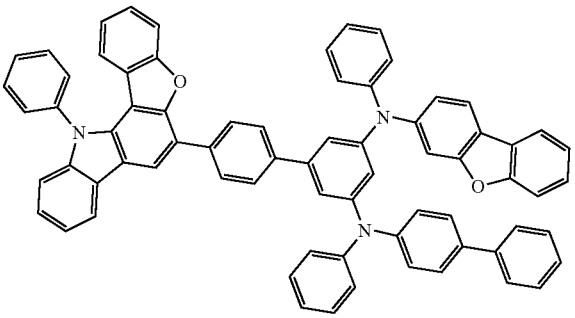
P-98
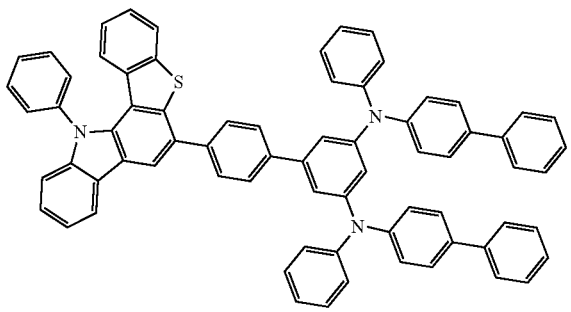
P-99
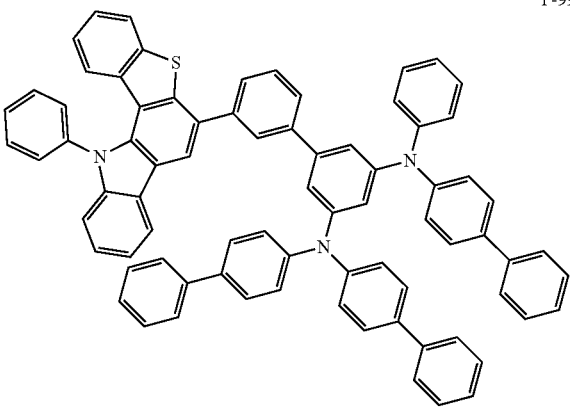
P-100
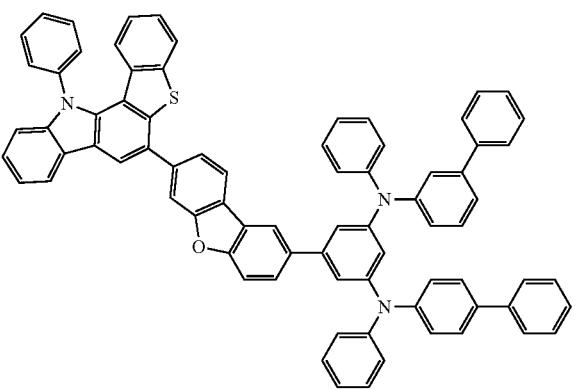

-continued
P-101
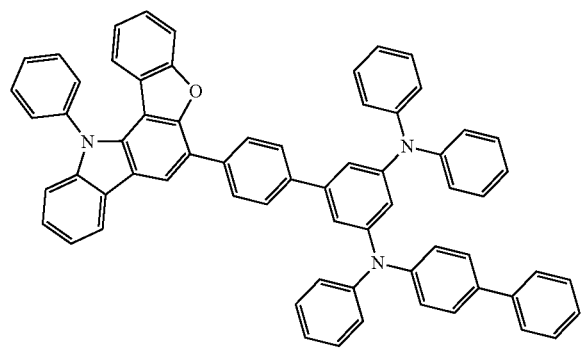
P-102
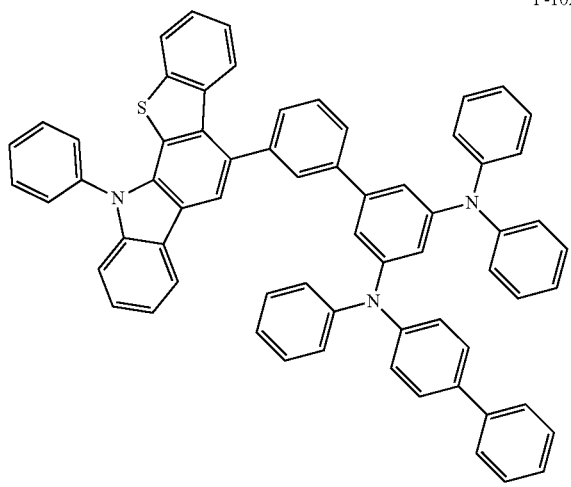
P-103
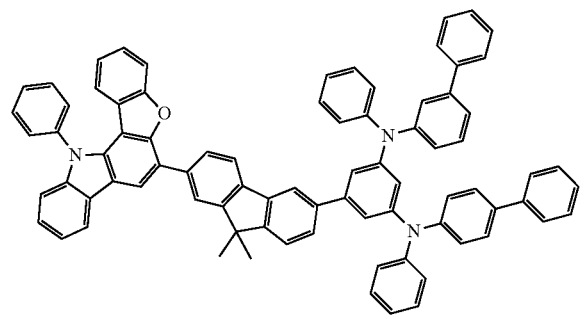
P-104
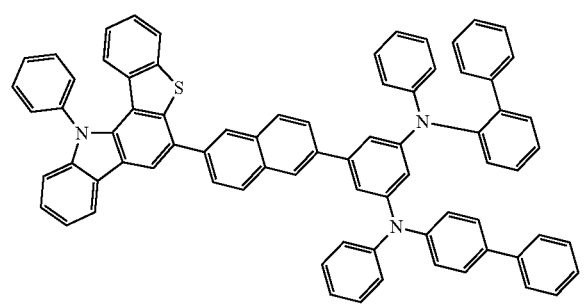
-continued
P-105
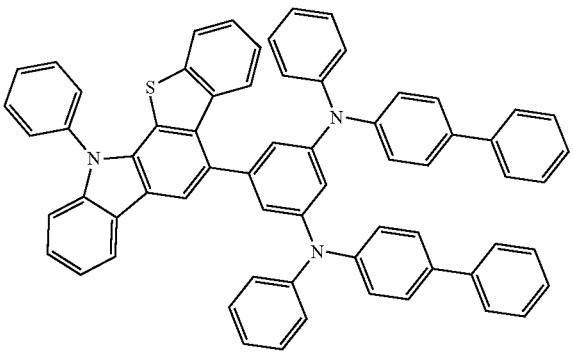
P-106
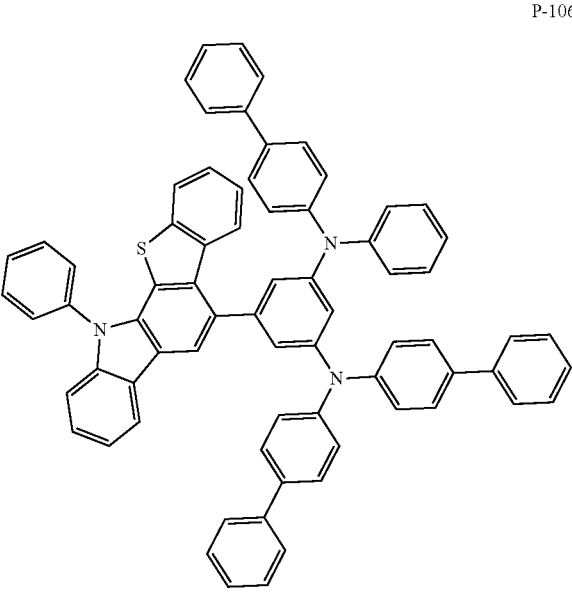
P-107
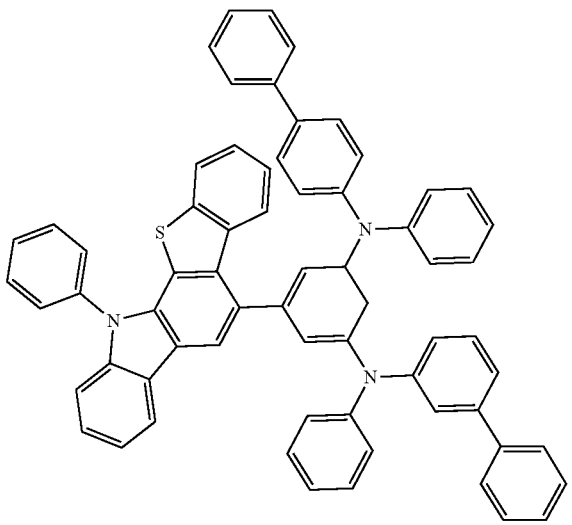

P-108
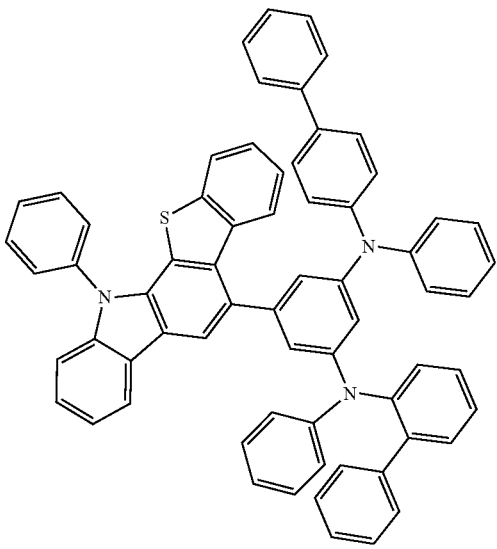
P-109
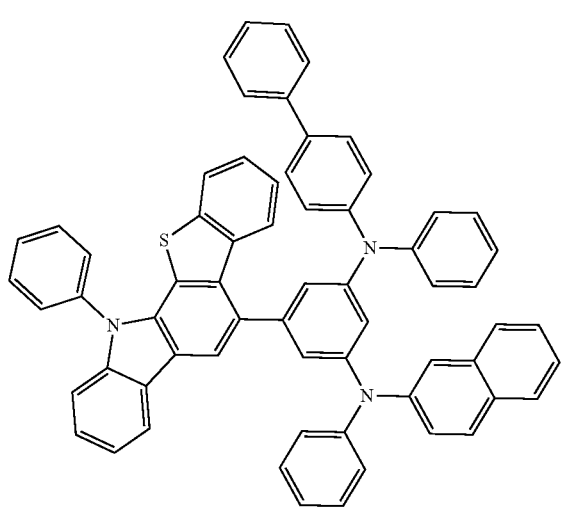
P-110
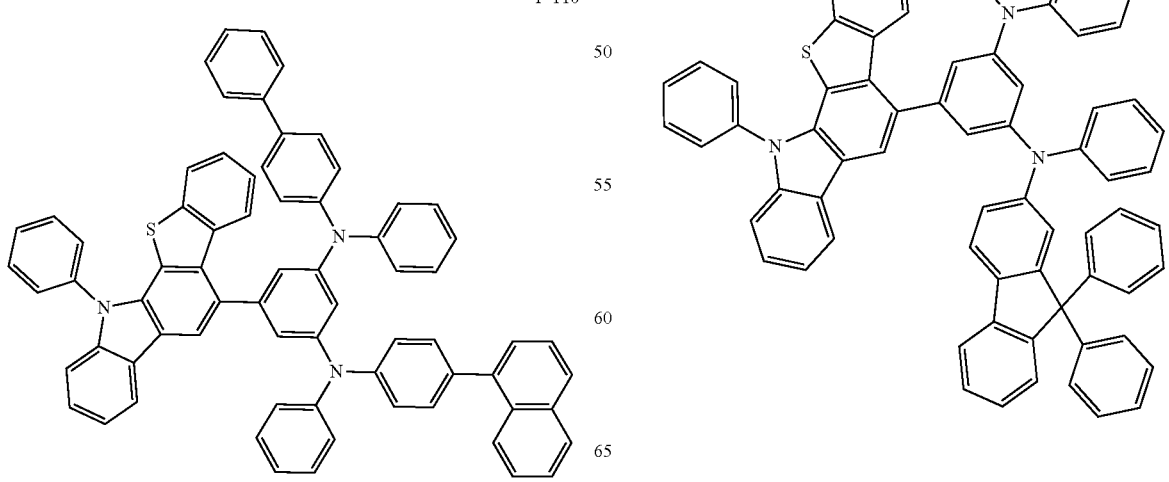
P-111
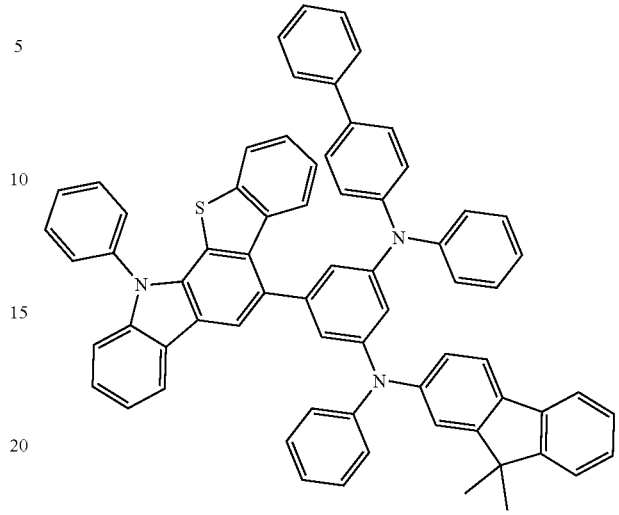
P-112

P-113
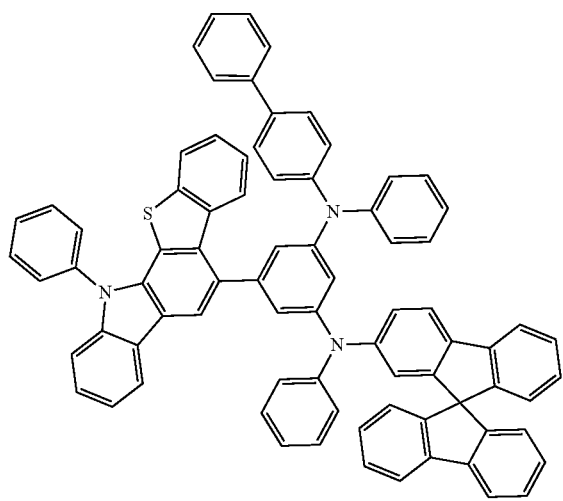
P-116
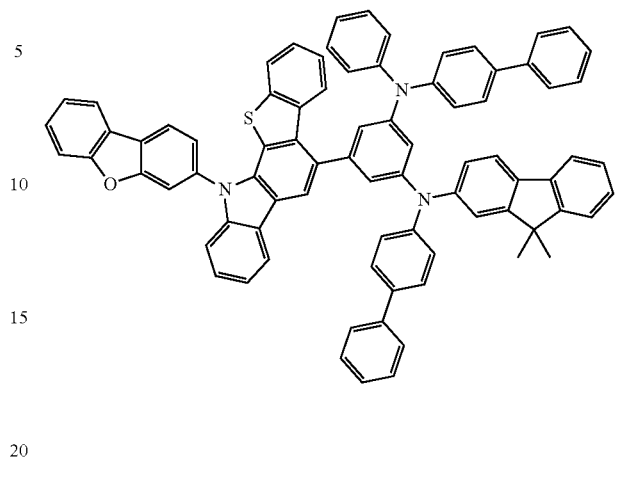
P-114
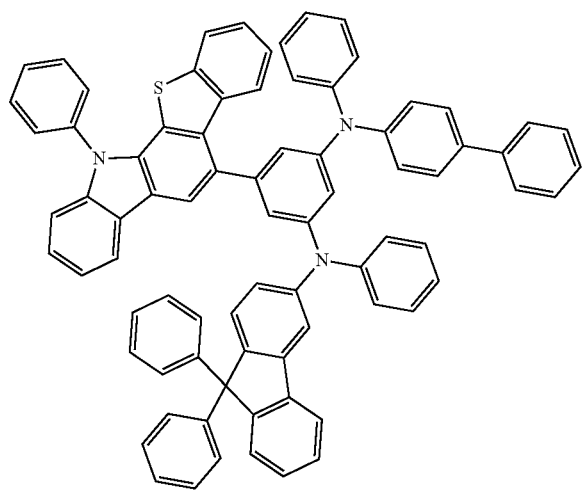
P-115
P-117
P-118
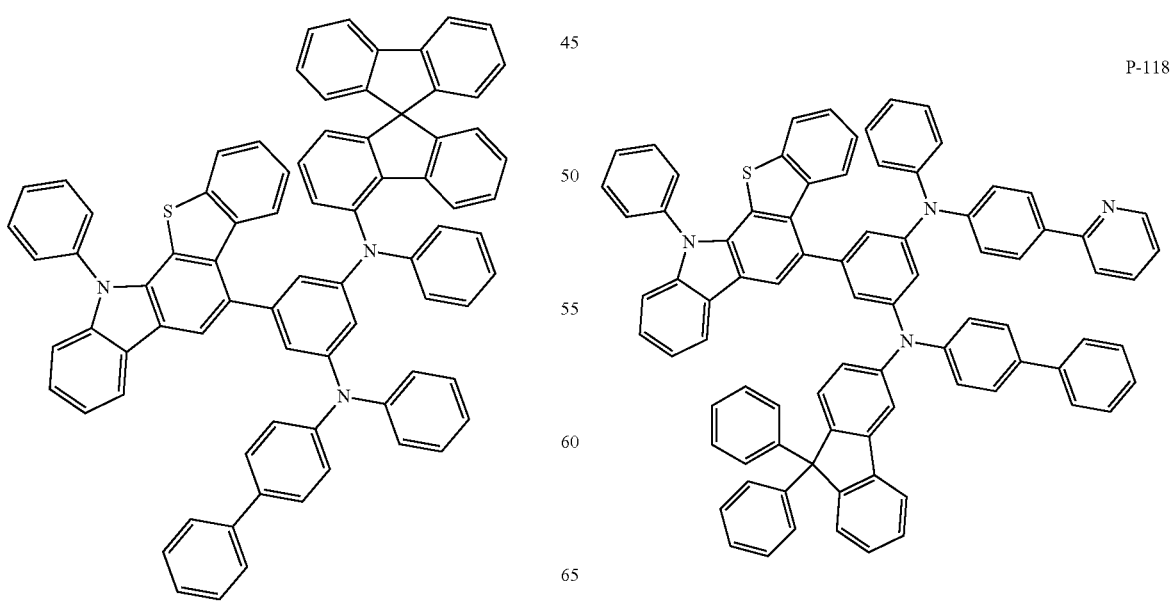

P-119
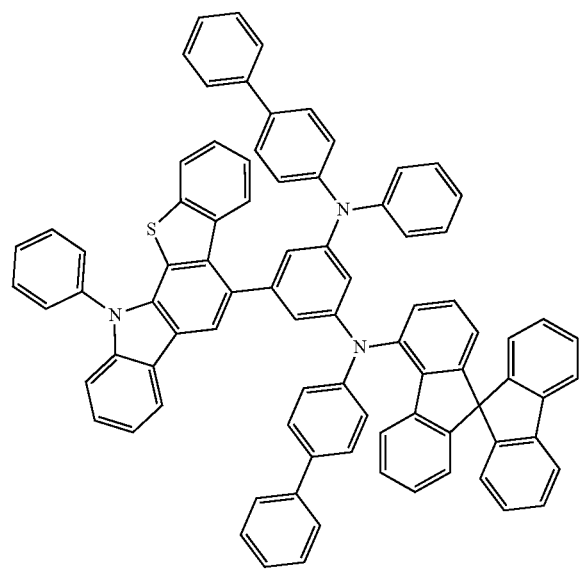
P-122
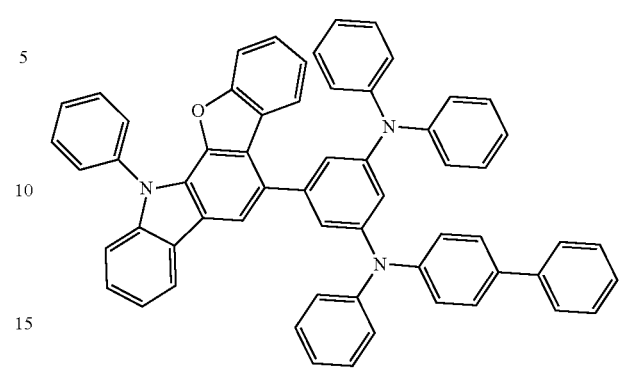
P-123
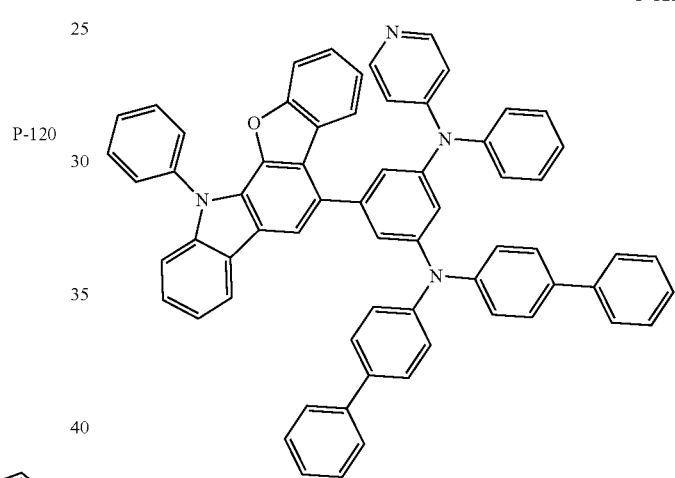
P-120
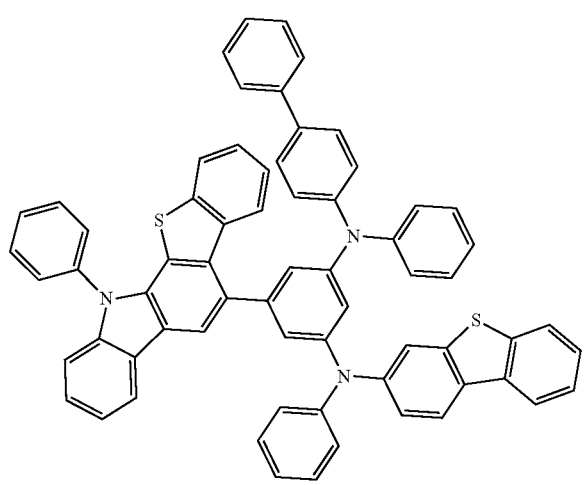
P-121
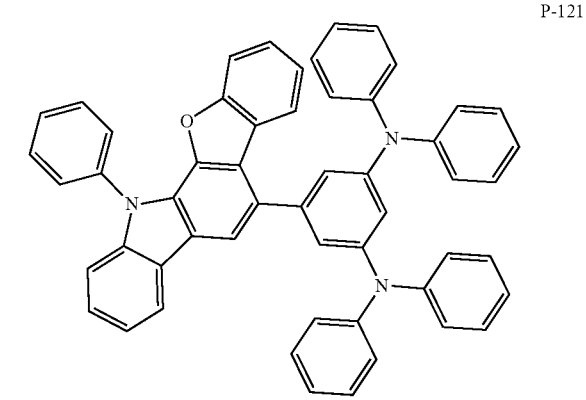
P-124
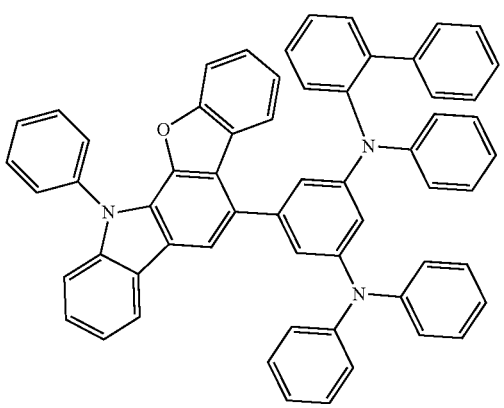

P-125
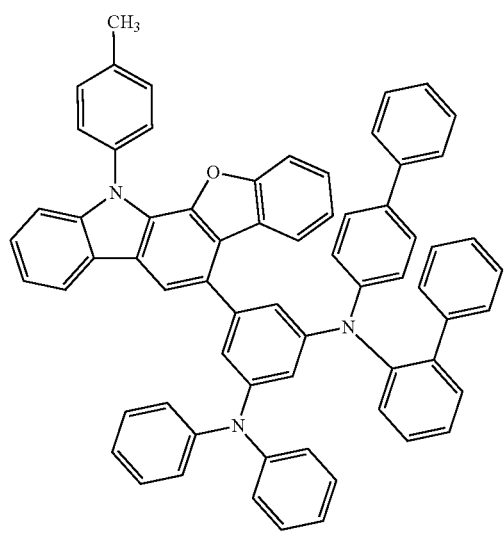
P-126
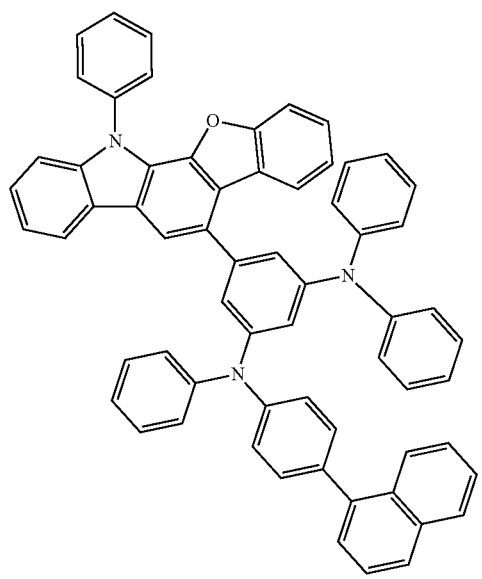
P-127
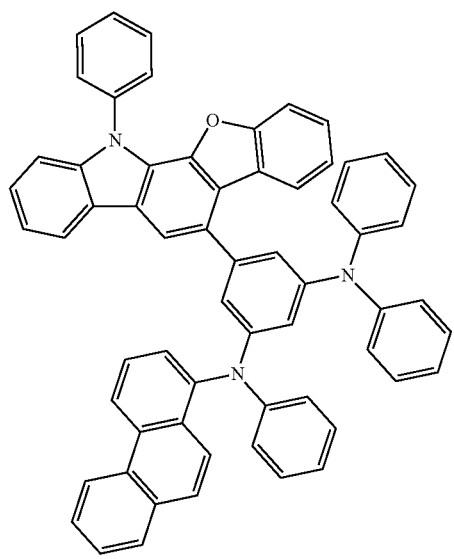
P-128
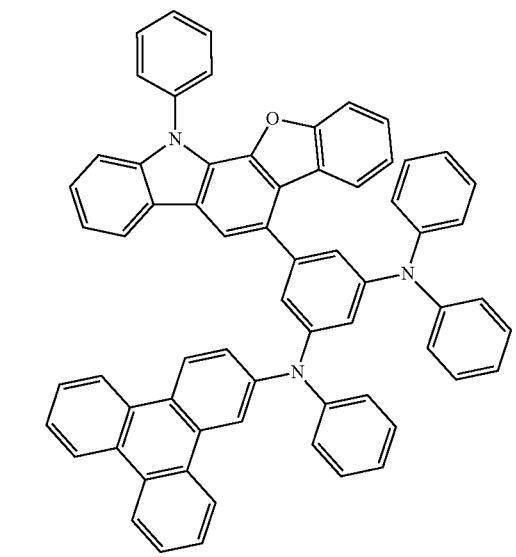
P-129
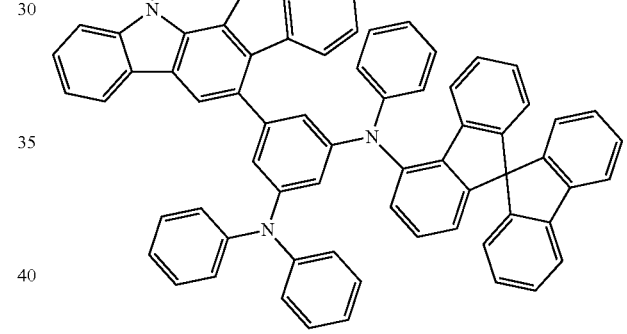
P-130
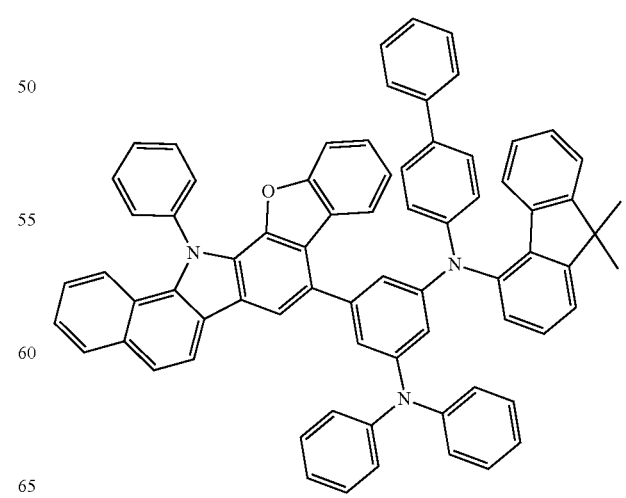

P-131
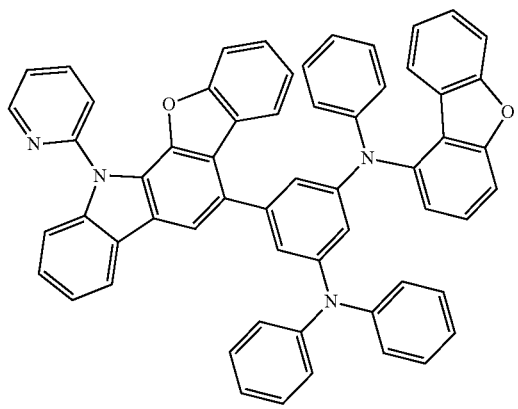
P-134
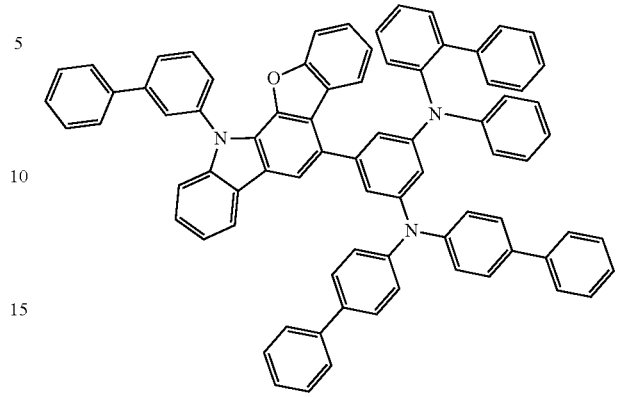
P-132
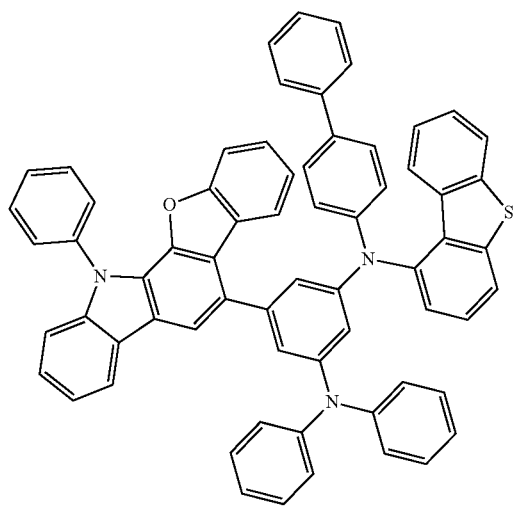
P-135
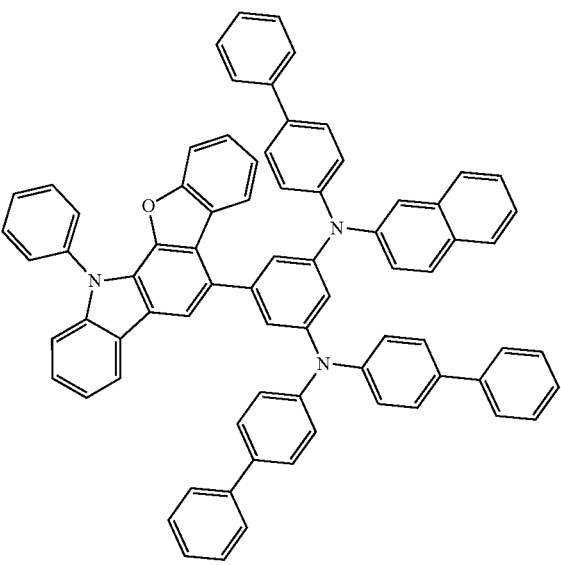
P-133
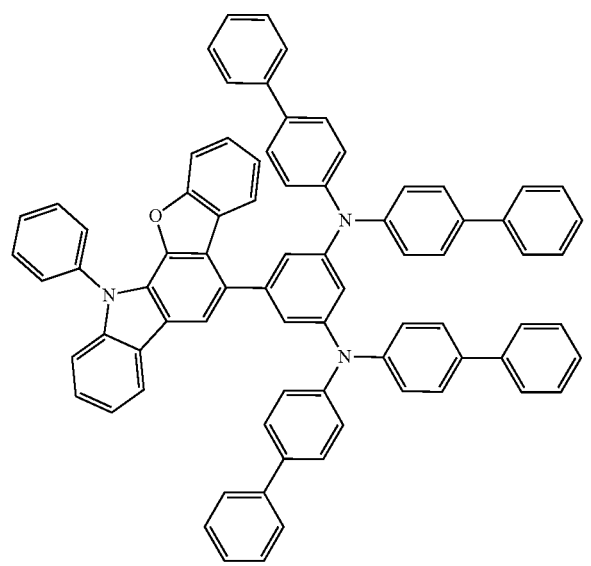
P-136
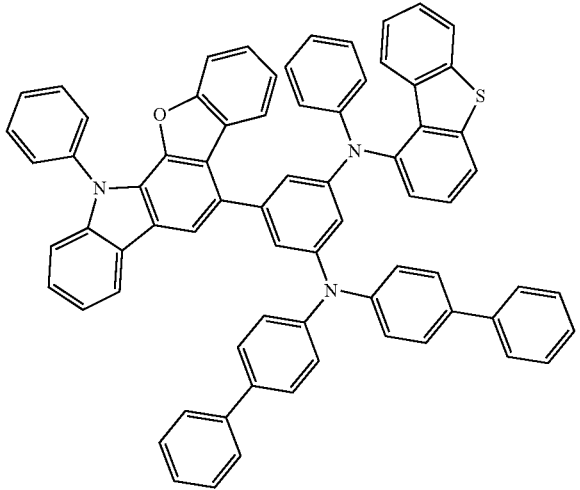

-continued
P-137
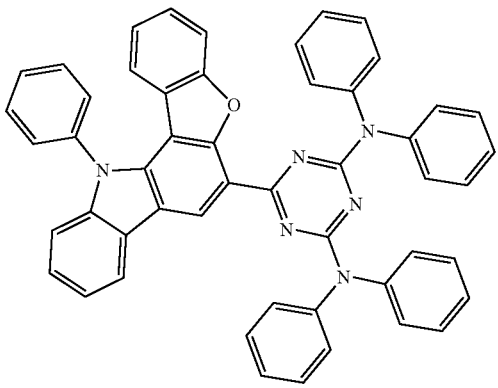
P-140
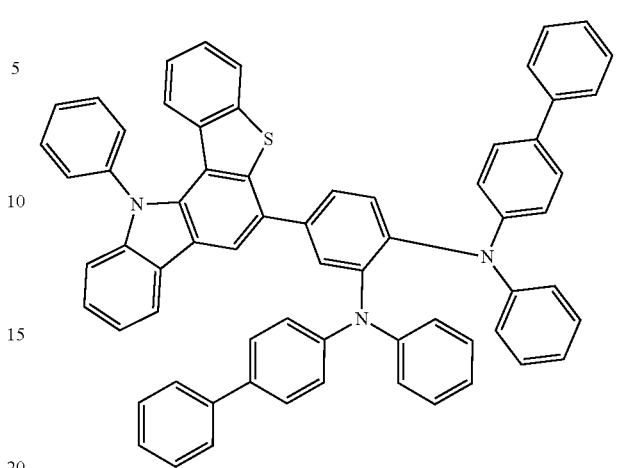
P-138
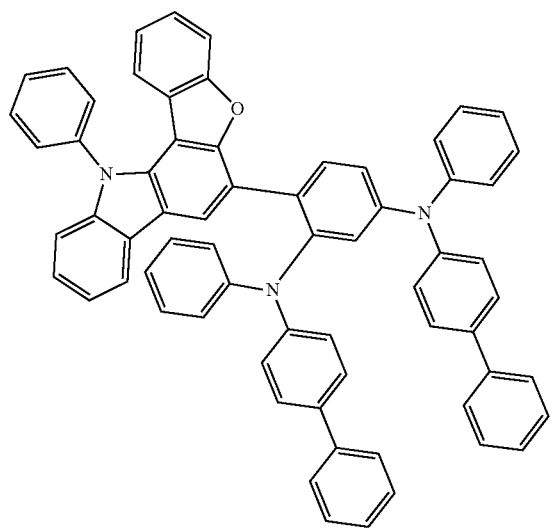
P-141
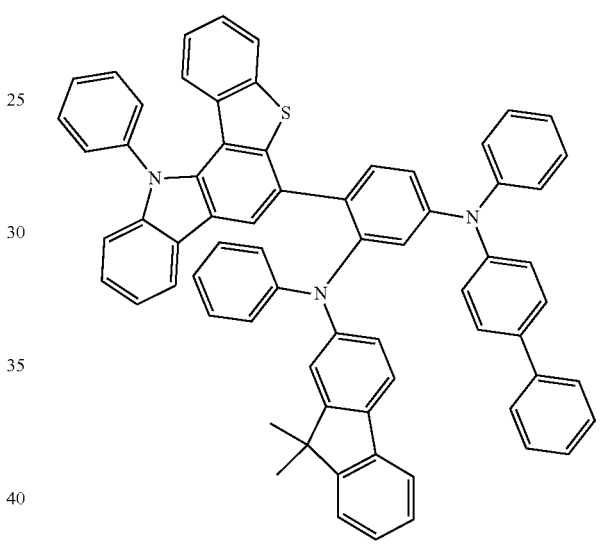
P-139
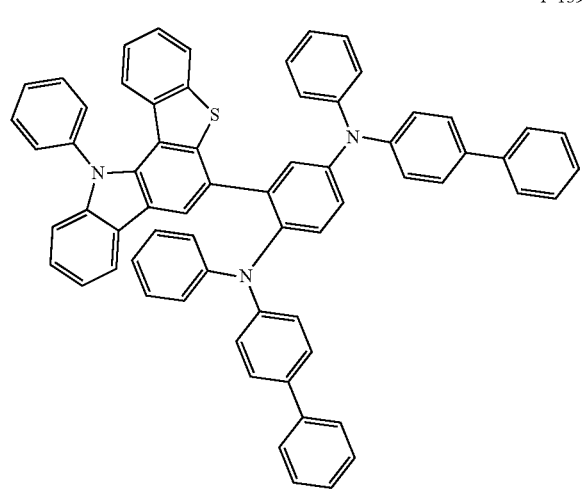
P-142
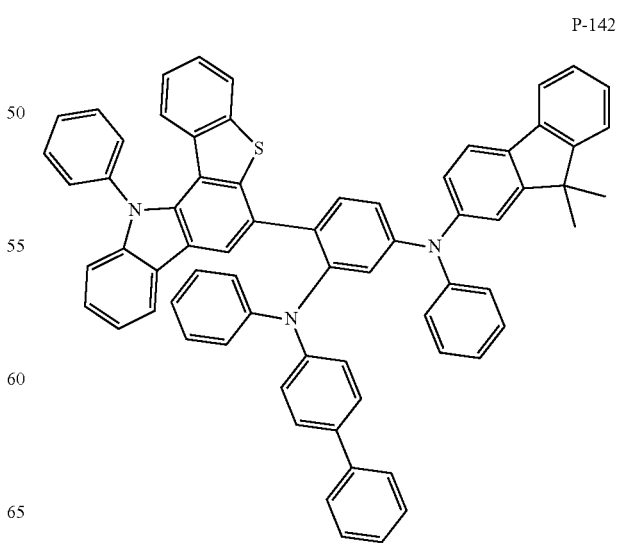

P-143
P-145
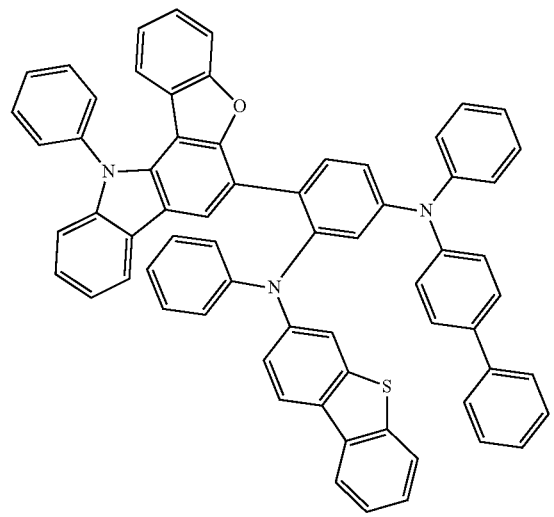
P-144
P-146
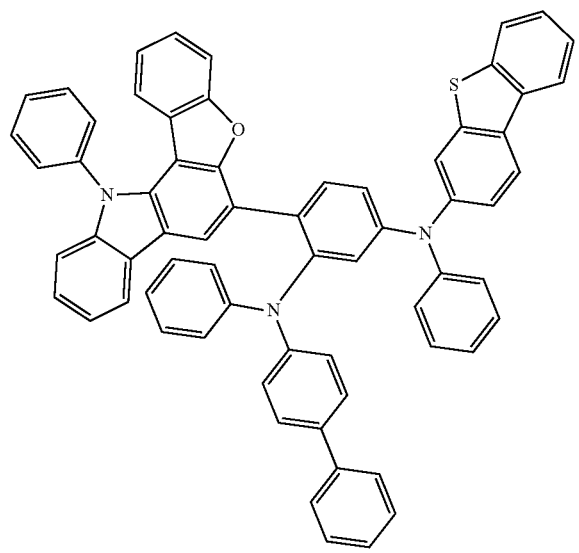

-continued
P-147
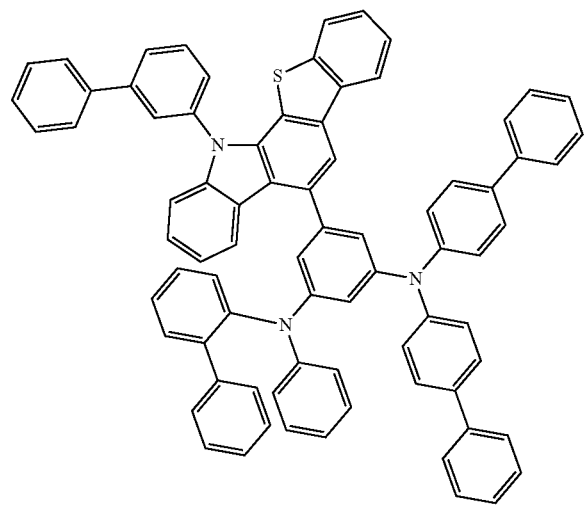
P-148
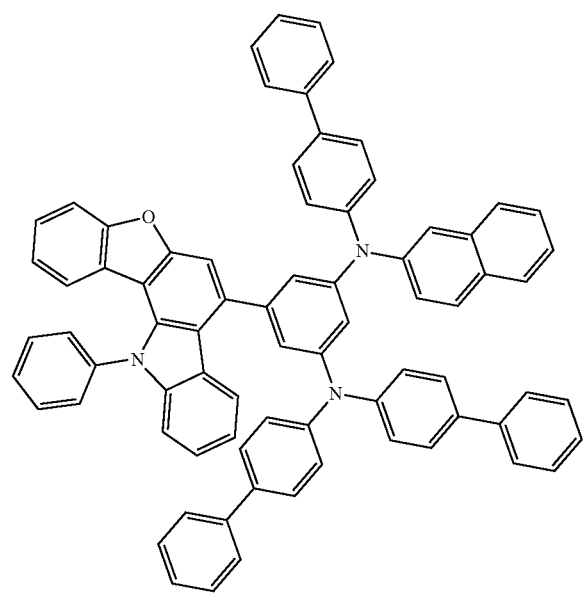
P-149
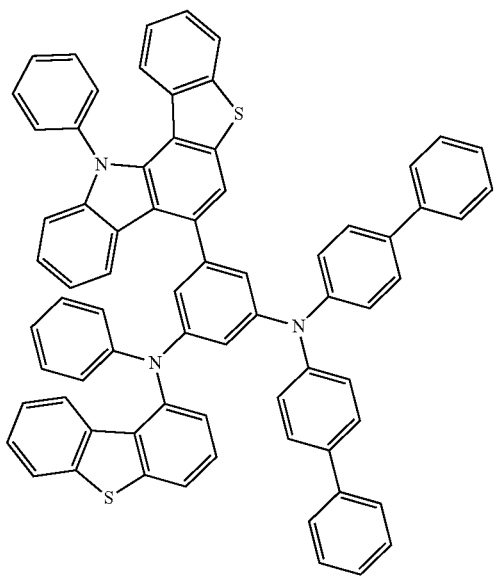
P-150
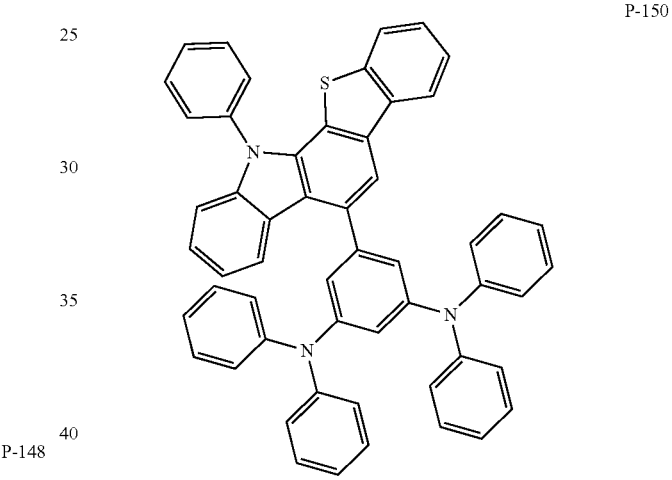
P-151
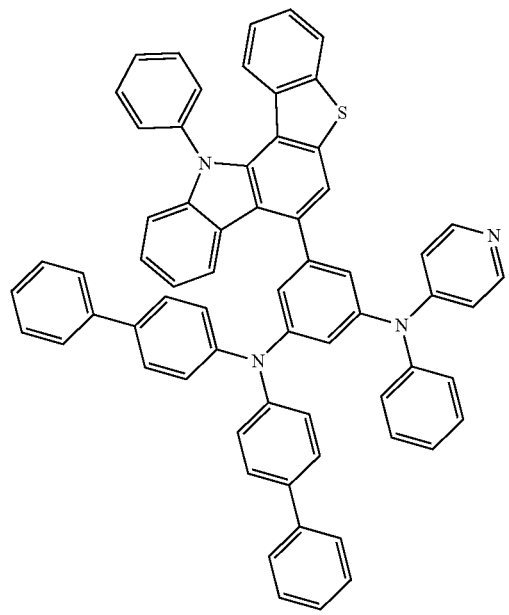

-continued

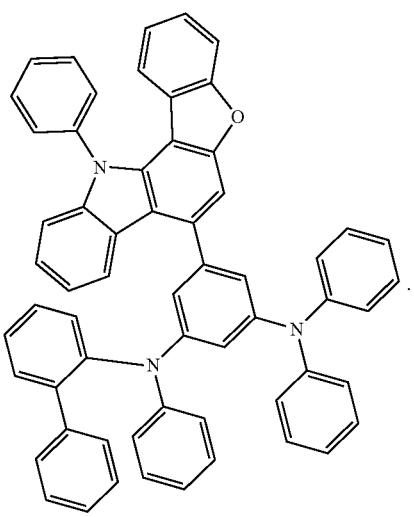

P-152

5. An organic electric element comprising a first electrode, a second electrode, and an organic material layer formed between the first electrode and the second electrode, wherein the organic material layer comprises the compound of claim 1.

6. The organic electric element of claim 5, wherein the compound is comprised in at least one layer of a hole injection layer, a hole transport layer, an emission-auxiliary layer, a light emitting layer, an electron transport auxiliary layer, an electron transport layer and an electron injection layer of the organic material layer, and the compound is used as a single compound or a mixture of two or more kinds.

7. The organic electric element of claim 6, wherein the compound is comprised in the emission-auxiliary layer of the organic material layer.

8. The organic electric element of claim 5, wherein the organic material layer is formed by a process of spin coating, nozzle printing, inkjet printing, slot coating, dip coating or roll-to-roll.

9. The organic electric element of claim 5, wherein the organic electric element further including a layer for improving luminous efficiency formed on a side of the first electrode or the second electrode, wherein the side is not facing the organic material layer.

10. An electronic device comprising a display device and a control unit for driving the display device, wherein the display device comprises the organic electric element of claim 5.

11. The electronic device of claim 10, wherein the organic electric element is one of an organic light emitting diode, an organic solar cell, an organic photo conductor, an organic transistor, and an element for monochromatic or white illumination.

* * * * *